(12) United States Patent
Robinson et al.

(10) Patent No.: US 10,967,045 B2
(45) Date of Patent: Apr. 6, 2021

(54) MULTICOMPONENT MENINGOCOCCAL VACCINE

(75) Inventors: Andrew Robinson; Margaret Robinson, legal representative, Salisbury (GB); Andrew Richard Gorringe, Salisbury (GB); Michael John Hudson, Salisbury (GB); Karen Margaret Reddin, Salisbury (GB)

(73) Assignee: Secretary of State for Health and Social Care, London (GB)

( * ) Notice: Subject to any disclaimer, the term of this patent is extended or adjusted under 35 U.S.C. 154(b) by 747 days.

(21) Appl. No.: 12/758,315

(22) Filed: Apr. 12, 2010

(65) Prior Publication Data

US 2011/0033491 A1 Feb. 10, 2011

Related U.S. Application Data

(63) Continuation-in-part of application No. 12/289,098, filed on Oct. 20, 2008, now abandoned, which is a continuation of application No. 10/320,800, filed on Dec. 17, 2002, now abandoned, which is a continuation-in-part of application No. 09/830,854, filed as application No. PCT/GB99/03626 on Nov. 2, 1999, now Pat. No. 6,821,521.

(30) Foreign Application Priority Data

Nov. 2, 1998 (GB) .................................. 9823978

(51) Int. Cl.
| | | |
|---|---|---|
| A61K 39/095 | (2006.01) | |
| C07K 14/22 | (2006.01) | |
| A61K 35/74 | (2015.01) | |
| A61K 38/16 | (2006.01) | |
| A61K 39/00 | (2006.01) | |

(52) U.S. Cl.
CPC ............ *A61K 38/164* (2013.01); *A61K 35/74* (2013.01); *A61K 39/095* (2013.01); *C07K 14/22* (2013.01); *A61K 2039/55572* (2013.01); *G01N 2333/22* (2013.01)

(58) Field of Classification Search
CPC .............. A61K 39/095; A61K 2300/00; A61K 2039/522; A61K 2039/575; A61K 31/56; A61K 38/164; A61K 2039/55555; A61K 9/127; A61K 2039/55566; A61K 39/00; A61K 2039/523; A61K 2039/55505; A61K 39/0258; A61K 2039/55572; A61K 45/06; A61K 2039/55561; A61K 2039/6018; A61K 2039/70; A61K 35/74; A61K 2039/55594; A61K 2039/6081; A61K 31/739; C07K 14/22; C07K 16/1217; C07K 14/245; C07K 2317/34; C07K 2319/00; Y10S 530/825; C12N 1/20; C12N 9/1051; C12N 15/74; C12N 1/38; C12N 9/1085; C12N 1/36; C12N 1/00; C12N 1/005; C12N 1/02; C12N 1/06; C12N 2800/60; Y02A 50/474; Y02A 50/478; C12Y 205/01072; B01D 2311/04; B01D 2311/2676; B01D 2311/16; B01D 61/145; B01D 61/147; B01D 61/16; C12R 1/01; C12R 1/36
See application file for complete search history.

(56) References Cited

U.S. PATENT DOCUMENTS

| | | |
|---|---|---|
| 4,707,543 A | 11/1987 | Zollinger et al. |
| 6,180,111 B1 | 1/2001 | Stein et al. |
| 6,287,574 B1 | 9/2001 | Brodeur et al. |
| 6,451,317 B1 | 9/2002 | Blake et al. |
| 6,558,677 B2 | 5/2003 | Zollinger et al. |
| 6,821,521 B1 | 11/2004 | Robinson et al. |
| 6,936,261 B2 | 8/2005 | Granoff et al. |
| 7,118,757 B1 * | 10/2006 | Seid et al. ................. 424/250.1 |
| 7,384,645 B2 | 6/2008 | Foster et al. |
| 2004/0249125 A1 * | 12/2004 | Pizza et al. .................. 530/350 |
| 2005/0013831 A1 * | 1/2005 | Foster ................. A61K 31/739 |
| | | 424/203.1 |
| 2005/0244436 A1 | 11/2005 | Giuliani et al. |
| 2006/0034854 A1 * | 2/2006 | Berthet et al. ............. 424/184.1 |
| 2006/0171957 A1 * | 8/2006 | Pizza ......................... 424/190.1 |
| 2006/0251670 A1 * | 11/2006 | Comanducci et al. ..... 424/190.1 |
| 2007/0059329 A1 * | 3/2007 | Norais et al. .............. 424/250.1 |
| 2007/0231342 A1 * | 10/2007 | Giuliani et al. ........... 424/190.1 |
| 2009/0035328 A1 * | 2/2009 | Granoff ...................... 424/200.1 |

(Continued)

FOREIGN PATENT DOCUMENTS

| | | |
|---|---|---|
| AU | 10569/00 | 6/2002 |
| BR | PI 991.4946-0 | 7/2009 |

(Continued)

OTHER PUBLICATIONS

Feavers IM. In: Methods in Molecular Medicine. volume 66, (Ed) Pollard AJ et al. Humana Press Inc., Totowa New Jersey, pp. 1-22, 2001.*

(Continued)

*Primary Examiner* — Sarvamangala Devi

(74) *Attorney, Agent, or Firm* — Evan Law Group LLC

(57) ABSTRACT

A composition is provided comprising *N. meningitidis* outer membrane vesicles, wherein said outer membrane vesicles are enriched with at least one antigenic component. The composition is suitable for use in vaccines and for treatment of infection, particularly meningococcal infection, demonstrating a broad spectrum of protection. A number of preferred antigenic components are described and include antigenic proteins and proteoglycans derived from *N. meningitidis*.

18 Claims, 13 Drawing Sheets

Specification includes a Sequence Listing.

(56) References Cited

U.S. PATENT DOCUMENTS

| | | |
|---|---|---|
| 2009/0148469 A1 | 6/2009 | Robinson et al. |
| 2011/0033491 A1 | 2/2011 | Robinson et al. |

FOREIGN PATENT DOCUMENTS

| | | |
|---|---|---|
| BR | PI 991.4946-0 | 12/2009 |
| BR | PI 991.4946-0 | 7/2010 |
| BR | PI 991.4946-0 | 11/2010 |
| CA | 2349331 | 3/2009 |
| CA | 2349331 | 2/2011 |
| EP | 0 586 266 A1 | 3/1994 |
| EP | 0 301 992 B1 | 5/1995 |
| EP | 0301992 | 5/1995 |
| EP | 0 560 968 B1 | 7/1996 |
| EP | 0 528 787 B1 | 12/1998 |
| EP | 02 025 569.1 | 4/2007 |
| EP | 02 025 569.1 | 5/2009 |
| EP | 02 025 569.1 | 4/2010 |
| EP | 10 171 629.8 | 2/2012 |
| GB | 9918319 | 8/1999 |
| JP | 2000-579250 | 12/2009 |
| JP | 2000-579250 | 5/2011 |
| WO | WO 87/06590 A1 | 11/1987 |
| WO | WO 90/06696 A2 | 6/1990 |
| WO | WO 90/06696 A3 | 6/1990 |
| WO | WO 90/12591 A1 | 11/1990 |
| WO | WO 93/06861 A1 | 4/1993 |
| WO | WO 94/08021 A1 | 4/1994 |
| WO | WO 98/56901 A2 | 12/1998 |
| WO | WO99/24578 | 5/1999 |
| WO | WO99/36544 | 7/1999 |
| WO | WO 00/25811 A2 | 5/2000 |
| WO | PCT/GB99/03626 | 8/2000 |
| WO | PCT/GB99/03626 | 1/2001 |
| WO | WO 01/09350 A2 | 2/2001 |
| WO | WO 01/52885 A1 * | 7/2001 |

OTHER PUBLICATIONS

Welsch et al. J. Immunol. 172: 5606-5615, 2004.*
Fredriksen et al. (NIPH Ann. 14: 67-79, 1991.*
Poolman JT. Infect. Agents and Diseases 4: 13-28, 1995.*
Zollinger WD. In: New Generation of Vaccines. (Ed) Levine et al. Marcel Dekker Inc., New York, Chapter 34, pp. 469-488, 1997.*
Piet et al. J. Infect. 69: 352-357, Jun. 13, 2014.*
Lehmann et al. Infect. Immun. 67: 2552-2560, 1999.*
Jones et al. J. Infect. Dis. 178: 451-459, 1998.*
Gerritzen et al. Biotechnol. Advances 35: 565-574, 2017.*
Tunheim et al. APMIS, John Wiley & Sons Ltd., 1-8, 2016.*
Acevedo et al. Front. Immunol. 5: 1-6, 2014.*
Van der Pol et al. Biotechnol. J. 10: 1689-17067, 2015, abstract.*
Ellis et al. Microbiol. Mol. Biol. Rev. 74: 81-94, 2010, abstract.*
Ko et al. J. Immunol. Nov. 23, 2016, abstract.*
Oftung et al. FEMS Immunol. Med. Microbiol. 26: 75-82, 1999.*
Dunn, K.L.R. et al., "Investigations into the molecular basis of meningococcal toxicity for human endothelial and epithelial cells: the synergistic effect of LPS and pili", Microbial Pathogenesis, vol. 18, pp. 81-96, (1995).
Martin, D. et al., "Highly conserved neisseria meningitides surface protein confers protection against experimental infection", The Journal of Experimental Medicine, vol. 185, No. 7, pp. 1173-1183, (1997).
Milagres, L.G. et al., "Antibody studies in mice of outer membrane antigens for use in an improved meningococcal B and C vaccine", FEMS Immunology and Medical Microbiology, vol. 13, pp. 9-17, (1996).
Moe, G.R. et al., "Differences in surface expression of NspA among neisseria meningitides group B strains", Infection and Immunity, vol. 67, No. 11, pp. 5664-5675, (1999).
Naess, L.M. et al., "Human T-Cell responses after vaccination with the Norwegian group B meningococcal outer membrane vesicle vaccine", Infection and Immunity, vol. 66, No. 3, pp. 959-965, (1998).

Ferron, L. et al., "Immunogenicity and antigenic heterogeneity of a human transferring-binding protein in neisseria meningitides", Infection and Immunity, vol. 60, No. 7, pp. 2887-2892, (1992).
Van Der Voort, E.R. et al. "Human B- and T-Cell responses after immunization with a hexavalent porA meningococcal outer membrane vesicle vaccine", Infection and Immunity, vol. 65, No. 12, pp. 5184-5190, (1997).
Ala'Aldeen, D.A.A., "Transferrin receptors of *Neisseria meningitidis*: promising candidates for a broadly cross-protective vaccine," *J. Med. Microbial.* 44:237-243, The Pathological Society of Great Britain and Ireland (1996).
Boulton, I.C. et al., "Transferrin-binding protein B isolated from *Neisseria meningitidis* discriminates between apo and diferric human transferrin," *Biochem. J.* 334:269-273, London Portland Press on Behalf of the Biochemical Society (Aug. 1998).
Ferreirós, C. M. et al., "Prevention of meningococcal disease: present and future," *Rev. Med. Microbiol.* 9(1):29-37, Chapman & Hall (Jan. 1998).
Frosch, M. et al., "Generation of capsule-deficient *Neisseria meningitidis* strains by homologous recombination," *Mol. Microbiol.* 4(7):1215-1218, Blackwell Scientific Publications (1990).
Gómez, J.A. et al., "Effect of adjuvants in the isotypes and bactericidal activity of antibodies against the transferrin-binding proteins of *Neisseria meningitidis*," *Vaccine* 16:1633-1639, Elsevier (Oct. 1998).
Gorringe, A.R. et al., "Human antibody response to meningococcal transferrin binding proteins: evidence for vaccine potential," *Vaccine* 13:1207-1212, Elsevier Science Ltd. (1995).
Gorringe, A.R., et al., "Vaccine potential of meningococcal transferring binding proteins: mouse protection studies," $10^{th}$ *Annu. Pathogenic Nesseria Conference Abstracts*, Chapter 3, Noncapsular Vaccines, Poster 46, (1996).
Grifantini, R., et al., "Previously unrecognized vaccine candidates against group B meningococcus identified by DNA microarrays," *Nat. Biotechnol.* 20:914-921, Nature America Publishing (Sep. 2002).
Legrain, M., et al., "Cloning and characterization of *Neisseria meningitidis* genes encoding the transferrin-binding proteins Tbp1 and Tbp2," *Gene* 130:73-80, Elsevier Science Publishers B.V. (1993).
Manning, D.S., et al., "Omp85 proteins of *Neisseria gonorrhoeae* and *Neisseria meningitidis* are similar to *Haemophilus influenzae* D-15-Ag and *Pasteurella multocida* Oma87," *Microb. Pathog.* 25:11-21, Academic Press (Jul. 1998).
Martin, D., et al., "Highly conserved *Neisseria meningitidis* Surface Protein Confers Protection against Experimental Infection," *J. Exp. Med.* 185:1173-1183, The Rockefeller University Press (Apr. 1997).
McGuinness, B., et al., "Deduced amino acid sequences of class 1 protein (PorA) from three strains of *Neisseria meningitidis*. Synthetic peptides define the epitopes responsible for serosubtype specificity," *J. Exp. Med.* 171:1871-1882, The Rockefeller University Press (1990).
Nassif, X., et al., "Transposition of Tn1545-Δ3 in the Pathogenic Neisseriae: a Genetic Tool for Mutagenesis," *J. Bacteriol.* 173:2147-2154, American Society for Microbiology (1991).
Pettersson, A., et al., "Molecular Characterization of FrpB, the 70-Kilodalton Iron-Regulated Outer Membrane Protein of *Neisseria meningitidis*," *Infect. Immun.* 63:4181-4184, American Society for Microbiology (1995).
Pizza, M., et al., "Identification of Vaccine Candidates Against Serogroup B Meningococcus by Whole-Genome Sequencing," *Science* 287:1816-1820, American Association for the Advancement of Science (Mar. 2000).
Van der Ley, P., et al., "Construction of *Neisseria meningitidis* strains carrying multiple chromosomal copies of the porA gene for use in the production of a multivalent outer membrane vesicle vaccine," *Vaccine* 13:401-407, Elsevier Science, Ltd. (1995).
Tabatabai, L.B. et al., "Modulation of immune responses in Balb/c mice vaccinated with *Brucella abortus* Cu—Zn superoxide dismutase synthetic peptide vaccine," *Vaccine* 12:919-924, Butterworth-Heinemann Ltd. (1994).

(56) References Cited

OTHER PUBLICATIONS

Wilks, K.E. et al., "Periplasmic Superoxide Dismutase in Meningococcal Pathogenicity," *Infect. Immun.* 66:213-217, American Society for Microbiology (Jan. 1998).
Ala'Aldeen, D.A.A., et al., "The meningococcal transferrin-binding proteins 1 and 2 are both surface exposed and generate bactericidal antibodies capable of killing homologous and heterologous strains," *Vaccine* 14:49-53, Elsevier Science, Ltd. (1996).
Ala'Aldeen, D.A.A., et al., "Immune Responses in Humans and Animals to Meningococcal Transferrin-Binding Proteins: Implications for Vaccine Design," *Infect. Immun.* 62:2984-2990, American Society for Microbiology (1994).
Claassen, I., et al., "Production, characterization and control of a *Neisseria meningitidis* hexavalent class 1 outer membrane protein containing vesicle vaccine," *Vaccine* 14:1001-1008, Elsevier Science, Ltd. (1996).
Peeters, C.C.A.M., et al., "Phase I clinical trial with a hexavalent PorA containing meningococcal outer membrane vesicle vaccine," *Vaccine* 14:1009-1015, Elsevier Science, Ltd. (1996).
European Search Report for European Patent Application No. EP 02 02 5569, completed on Apr. 29, 2003, European Patent Office, Netherlands.
Brandileone, M.C., et al., "Induction of Iron Regulated Proteins During Normal Growth of *Neisseria meningitidis* in a Chemically Defined Medium," *Rev. Inst. Med. Trop. São Paulo* 36:301-310, Instituto de Medicina Tropical de Sān Paulo (1994).
Legrain, M., et al., "Production of Lipidated Meningococcal Transferrin Binding Protein 2 in *Escherichia coli,*" *Prot. Expr. Purif.* 6:570-578, Academic Press Inc. (1995).
Lissolo, L., et al., "Evaluation of Transferrin-Binding Protein 2 within the Tranferrin-Binding Protein Complex as a Potential Antigen for Future Meningococcal Vaccines," *Infect. & Immun.* 63:884-890, American Society for Microbiology (1995).
Oftung, F., etal., "A mouse model utilising human transferrin to study protection against *Neisseria meningitidis* serogroup B induced by outer membrane vesicle vaccination," *FEMS Immunol. Med. Microbiol.* 26:75-82, Elsevier Science B.V. (Oct. 1999).
Pintor ,M., et al., "Blocking of iron uptake from transferrin by antibodies against the transferrin binding proteins in *Neisseria meningitidis,*" *Mircrobial Pathogen.* 20:127-139, Academic Press Ltd. (1996).
Rokbi, B., et al., "Evaluation of Recombinant Transferrin-Binding Protein B Variants from *Neisseria meningitidis* for Their Ability to Induce Cross-Reactive and Bactericidal Antibodies against a Genetically Diverse Collection of Serogroup B Strains," *Infect. Immun.* 65:55-63, American Society for Microbiology (Jan. 1997).
Schryvers, A.B. and Stojiljkovic, I., "MicroReview. Iron acquisition systems in the pathogenic *Neisseria,*" *Molec. Microbiol.* 32:1117-1123, Blackwell Science Ltd. (Jun. 1999).
Van der Ley, P. and Poolman, J.T., "Construction of a Multivalent Meningococcal Vaccine Strain Based on the Class 1 Outer Membrane Protein," *Infect. & Immun.* 60:3156-3161, American Society for Microbiology (1992).
Van der Ley, P., et al., "Use of Transformation to Construct Antigenic Hybrids of the Class 1 Outer Membrane Protein in *Neisseria meningitidis,*" *Infect. & Immun.* 61:4217-4224, American Society for Microbiology (1993).
Van der Voort, E.R., et al., "Specificity of Human Bactericidal Antibodies against PorA P1.7,16 Induced with a Hexavalent Meningococcal Outer Membrane Vesicle Vaccine," *Infect. & Immun.* 64:2745-2751, American Society for Microbiology (1996).
Van der Voort, E.R., of al., "Human B- and T-Cell Responses after Immunization with a Hexavalent PorA Meningococcal Outer Membrane Vesicle Vaccine," *Infect. & Immun.* 65:5184-5190, American Society for Microbiology (Dec. 1997).
English language translation of European Patent No. EP 0 560 968, Frank B. Dehn & Co., London, UK (1996).
Dialog File 351, Accession No. 9748403, Derwent WPI English language abstract for EP 0 586 266 A1.

Notice of Opposition for European Patent No. 1 126 874 (Mar. 2004).
Dunn, K.L. et al., "Investigations into the molecular basis of meningococcal toxicity for human endothelial and epithelial cells: the synergistic effect of LPS and pili," *Microbial Pathogenesis* 18:81-96, Academic Press Limited (1995).
Griffiths, E., et al., "Quality control of the Cuban and Norwegian serogroup B vaccines used in the Iceland study," *Proceedings of the Ninth International Pathogenic Neisseria Conference,* p. 437, (Sep. 26-30, 1994).
Moe, G.R. et al., "Differences in Surface Expression of NspA among *Neisseria meningitidis* Group B Strains," *Infect. Immun.* 67:5664-5675, American Society for Microbiology (1999).
Dalseg, R. et al., "Outer Membranes Vesicles from Group-B Meningococci Can Act as Mucosal Adjuvant for Influenza Virus Antigens," *Vaccines* 96:177-182, Cold Spring Harbor Laboratory Press (1996).
Naess, L.M. et al., "Human T-Cell Responses after Vaccination with the Norwegian Group B Meningococcal Outer Membrane Vesicle Vaccine," *Infect. Immun.* 66:959-965, American Society for Microbiology (1998).
Milagres, L.G. et al., Antibody studies in mice of outer membrane antigens for use in an improved meningococcal B and C vaccine, *FEMS Immunol. Med. Microbiol.* 13:9-17, Blackwell Pub. (1996).
Ferron, L., et al., "Immunogenicity and Antigenic Heterogeneity of a Human Transferrin-Binding Protein in *Neisseria meningitidis,"* *Infect. Immun.* 60:2887-2892, American Society for Microbiology, United States (1992).
Van der Voort, E.R., et al., "Human B- and T-Cell Responses after Immunization with a Hexavalent PorA Meningococcal Outer Membrane Vesicle Vaccine," *Infect. Immun.* 65:5184-5190, American Society for Microbiology, United States (1997).
Office Action dated Mar. 12, 2002, in U.S. Appl. No. 09/830,854, inventor Robinson, A., filed Aug. 29, 2001.
Office Action dated Oct. 21, 2002, in U.S. Appl. No. 09/830,854, inventor Robinson, A., filed Aug. 29, 2001.
Advisory Action dated Feb. 20, 2003, in U.S. Appl. No. 09/830,854, inventor Robinson, A., filed Aug. 29, 2001.
Office Action dated Jun. 17, 2003, in U.S. Appl. No. 09/830,854, inventor Robinson, A., filed Aug. 29, 2001.
Notice of Allowance dated Dec. 30, 2002, in U.S. Appl. No. 09/830,854, inventor Robinson, A., filed Aug. 29, 2001.
Office Action dated May 8, 2007, in U.S. Appl. No. 10/499,063, inventor Foster, K.A., filed Jun. 17, 2004.
Ala'Aldeen, D.A.A. and Cartwright, K.A.V., "*Neisseria meningitidis*: Vaccines and Vaccine Candidates," *J. Infect.* 33:153-157, W. B. Saunders (1996).
Dlawer et al., "The meningococcal transferring-binding proteins 1 and 2 are both surface exposed and generate bactericidal antibodies capable of killing homologous and heterologous strains", Vaccine, vol. 14, issue 1, pp. 49-53, (1996).
Dlawer et al., "Immune responses in humans and animals to meningococcal transferring-binding proteins: Implication for vaccine design", vol. 62, No. 7, pp. 2984-2990, (1994).
International Search Report of International Application No. PCT/GB99/03626, dated Jun. 13, 2000.
No. of Pages 19, Apr. 22, 2008, U.S. Appl. No. 10/320,800, US.
No. of Pages 11, Jun. 27, 2007, U.S. Appl. No. 10/320,800, US.
No. of Pages 9, Nov. 15, 2006, U.S. Appl. No. 10/320,800, US.
No. of Pages 26, Mar. 14, 2006, U.S. Appl. No. 10/320,800, US.
No. of Pages 6, Dec. 8, 2005, U.S. Appl. No. 10/320,800, US.
No. of Pages 19, Oct. 19, 2011, U.S. Appl. No. 12/289,098, US.
No. of Pages 33, Apr. 21, 2011, U.S. Appl. No. 12/289,098, US.
No. of Pages 10, Dec. 8, 2010, U.S. Appl. No. 12/289,098, US.
No. of Pages 8, Nov. 28, 2001, U.S. Appl. No. 09/830,854, US.
No. of Pages 11, Mar. 12, 2002, U.S. Appl. No. 09/830,854, US.
No. of Pages 10, Oct. 21, 2002, U.S. Appl. No. 09/830,854, US.
No. of Pages 6, Feb. 20, 2003, U.S. Appl. No. 09/830,854, US.
No. of Pages 9, Jun 17, 2003, U.S. Appl. No. 09/830,854, US.
No. of Pages 2, Jul. 23, 2003, U.S. Appl. No. 09/830,854, US.
No. of Pages 9, Dec. 30, 2003, U.S. Appl. No. 09/830,854, US.
No. of Pages 15, Jun. 30, 2004, U.S. Appl. No. 09/830,854, US.
No. of Pages 4, Apr. 1, 2014, U.S. Appl. No. 12/289,098, US.

(56) References Cited

OTHER PUBLICATIONS

No. of Pages 38, Aug. 20, 2014, U.S. Appl. No. 12/289,098, US.
No. of Pages 3, Apr. 18, 2014, U.S. Appl. No. 12/289,098, US.
No. of Pages 4, Aug. 18, 2014, U.S. Appl. No. 12/289,098, US.
No. of Pages 3, Sep. 3, 2014, U.S. Appl. No. 12/289,098, US.
No. of Pages 22, May 13, 2015, U.S. Appl. No. 12/289,098, US.
Beuvery, E.C. et al., "Preparation and physicochemical and immunological characterization of polysaccharide-outer membrane protein complexes of neisseria meningitidis", Infection and Immunity, vol. 40, No. 1, pp. 369-380, (1983).
Definition of "Adjuvant", printed from Wikipedia, the free encyclopedia on May 16, 2018, 3 pages, found at http://en.wikipedia.org/wiki/adjuvant.
Findlow, J. et al., "Multicenter, open-label, randomized phase II controlled trial of an investigational recombinant meningococcal serogroup B vaccine with and without outer membrane vesicles, administered in infancy", Clinical Infectious Diseases, vol. 51, No. 10, pp. 1127-1137, (2010).
Fransen, F. et al., "Agonists of toll-like receptors 3, 4, 7, and 9 are candidates for use as adjuvants in an outer membrane vaccine against *Neisseria meningitidis* serogroup B", Infection and Immunity, vol. 75, No. 12, pp. 5939-5946, (2007).
Holst, J. et al., "Properties and clinical performance of vaccines containing outer membrane vesicles from *Neisseria meningitidis*", Vaccine, vol. 275, pp. B3-B12, (2009).
Nagaputra, J.C. et al., "*Neisseria meningitidis* native outer membrane vesicles containing different lipopolysaccharide glycoforms as adjuvants for meningococcal and nonmeningococcal antigens", Clinical and Vaccine Immunology, vol. 21, No. 2, pp. 234-242, (2014).
Piet, J.R. et al., "Meningitis caused by a lipopolysaccharide deficient neisseria meningitidis", Journal of Infection, vol. 69, pp. 352-357, (2014).
Pizza, M. et al., "Identification of vaccine candidates against serogroup B meningococcus by whole-g-enome sequencing", Science, vol. 287, pp. 1816-1820, (2000).
Pratt, A.J. et al., "Structural, functional, and immunogenic insights on Cu,Zn superoxide dismutase pathogenic virulence factors from neisseria meningitidis and brucella abortus", Journal of Bacteriology, vol. 197, No. 24, pp. 3834-3847, (2015).
Sanders, H. et al., "Adjuvant properties of meningococcal outer membrane vesicles and the use of adjuvants in neisseria meningitidis protein vaccines", Expert Review of Vaccines, vol. 10, No. 3, pp. 323-334, (2011).
Wilks, K.E. et al., "Periplasmic superoxide dismutase in meningococcal pathogenicity", Infection and Immunity, vol. 66, No. 1, pp. 213-217, (1998).

\* cited by examiner

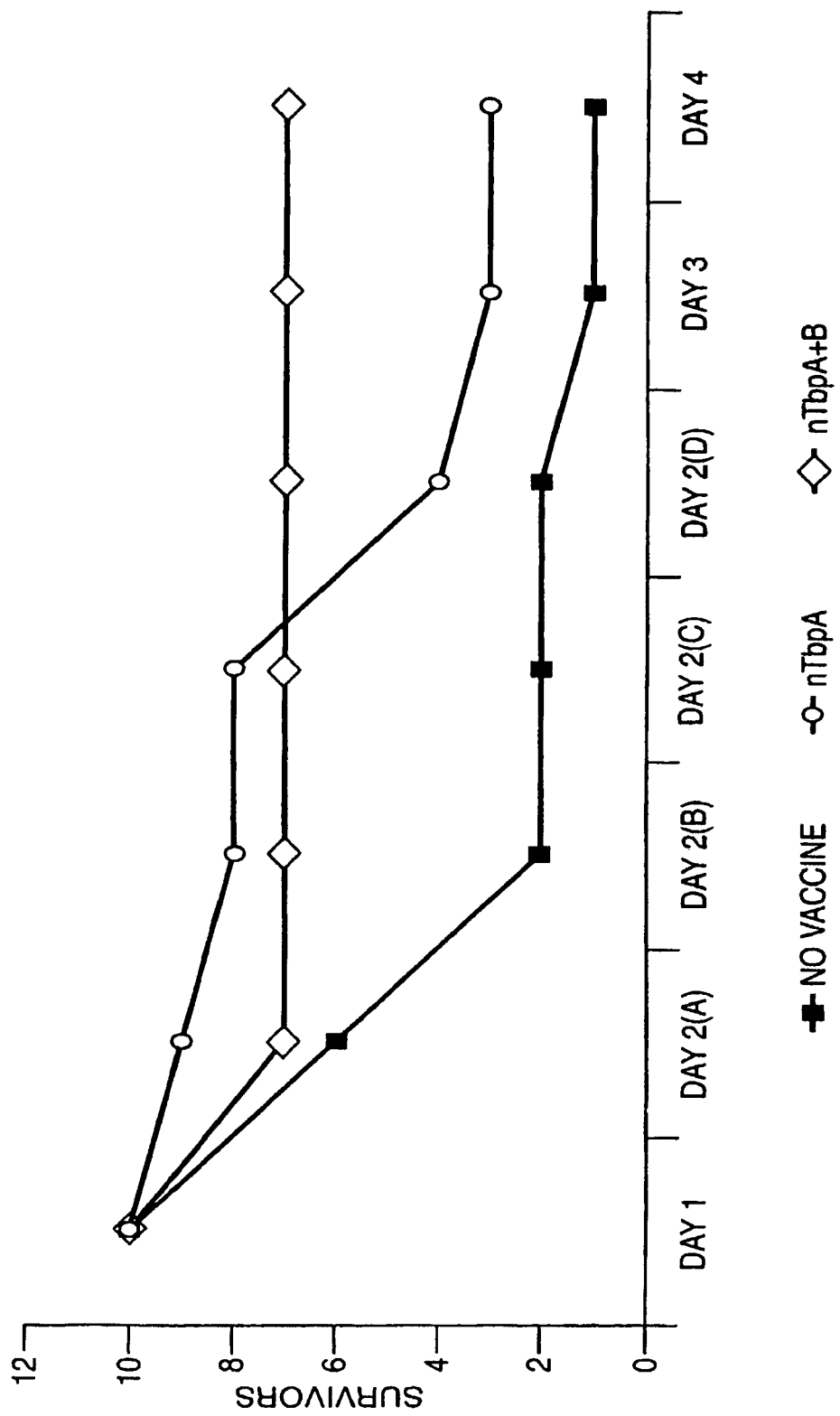

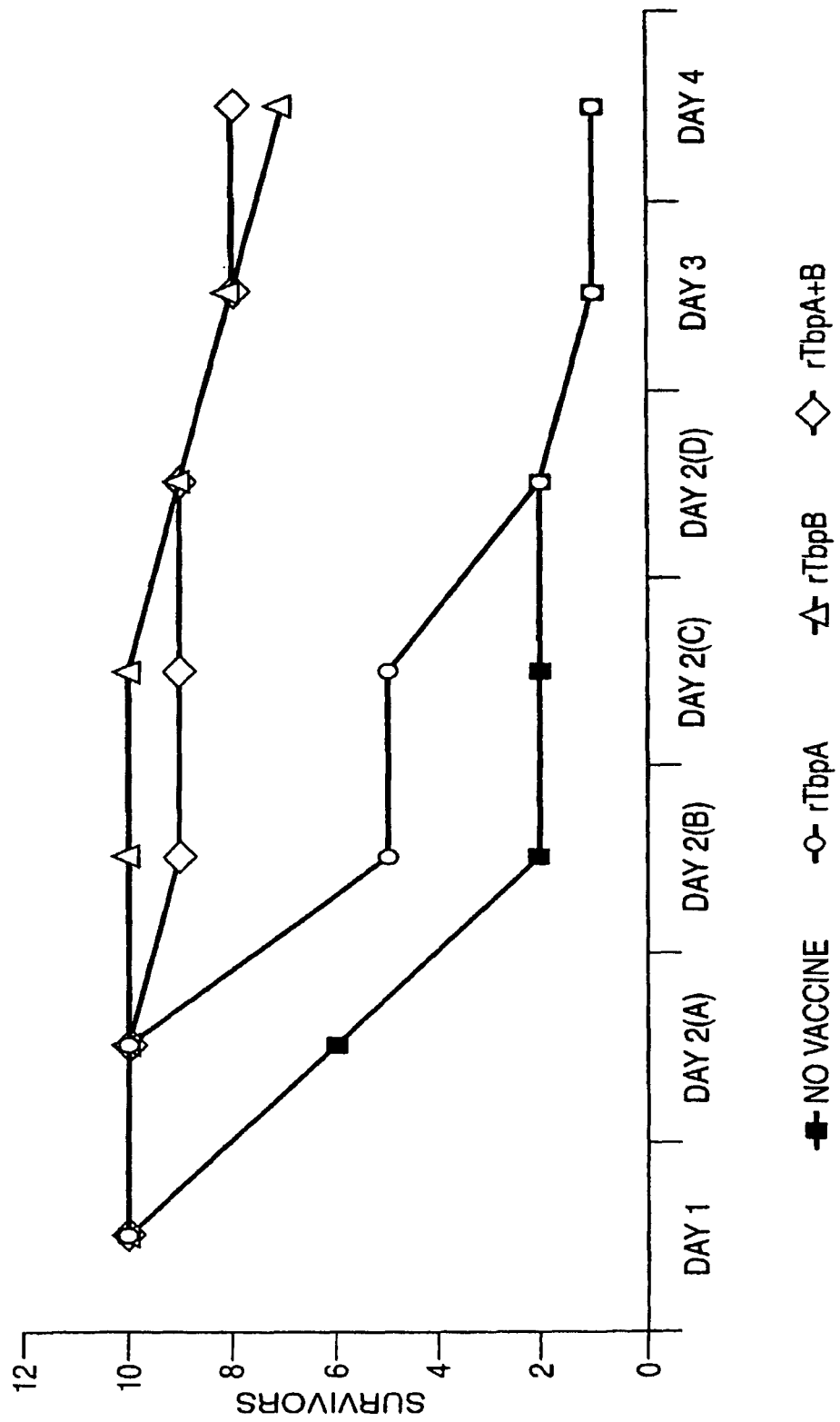

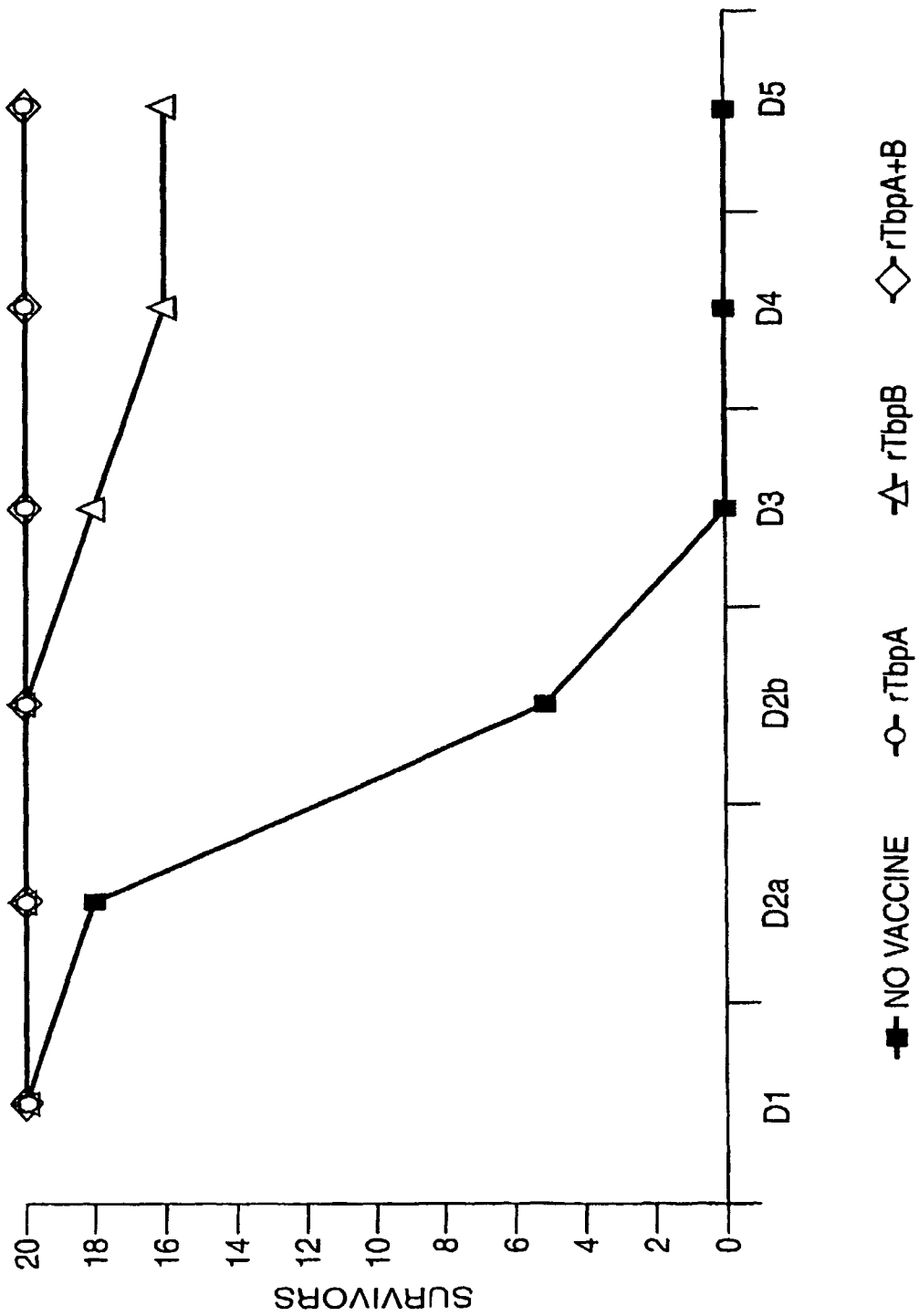

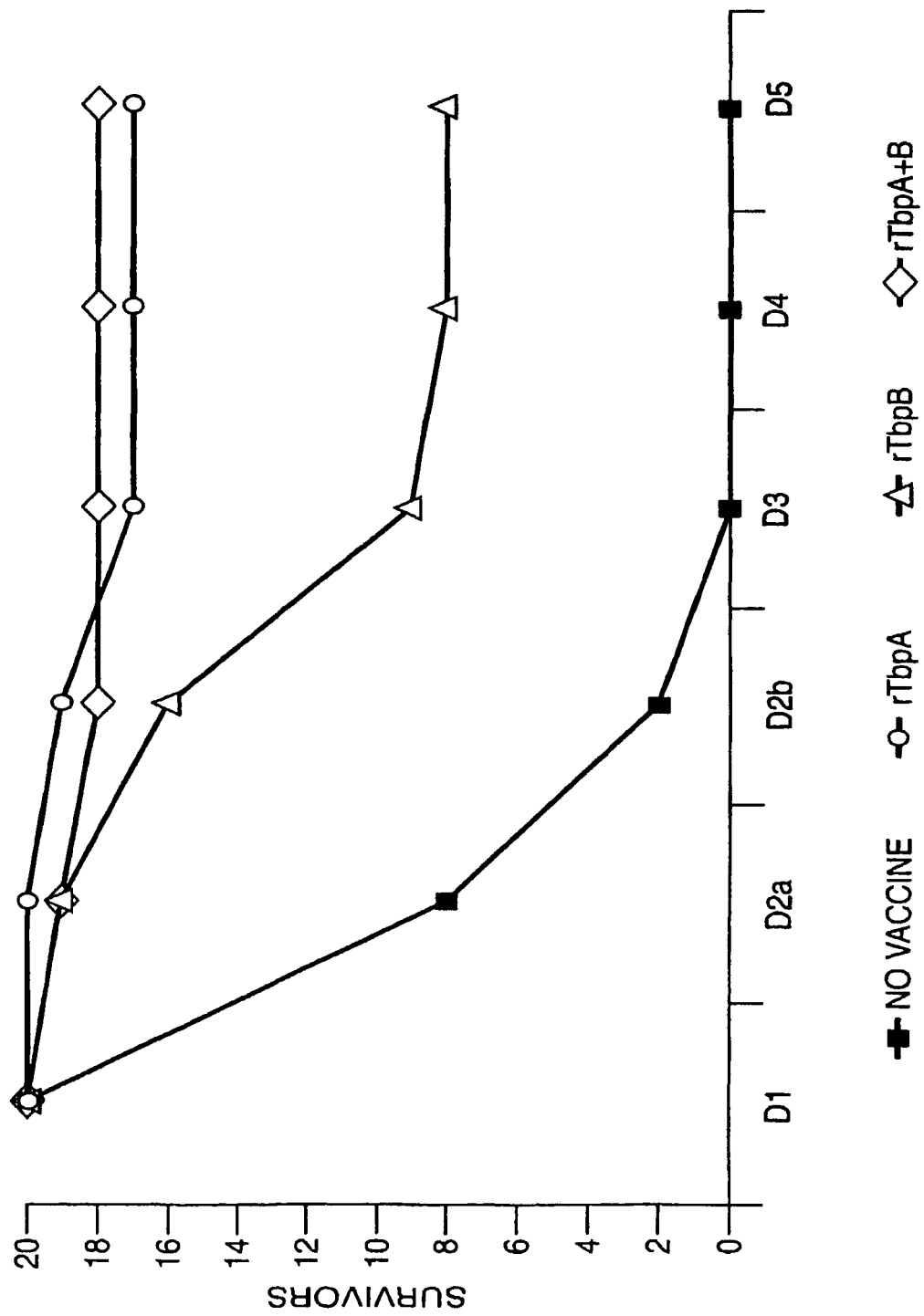

Fig. 10
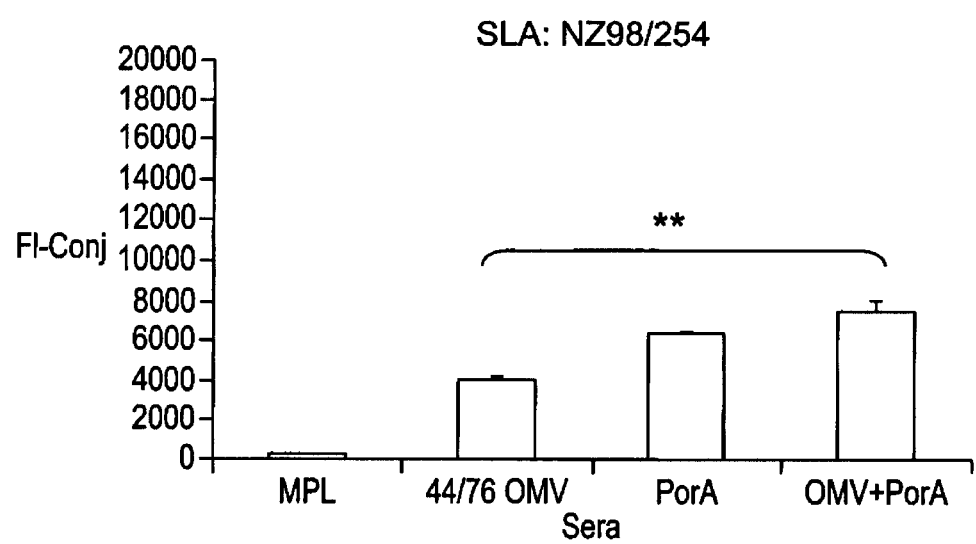
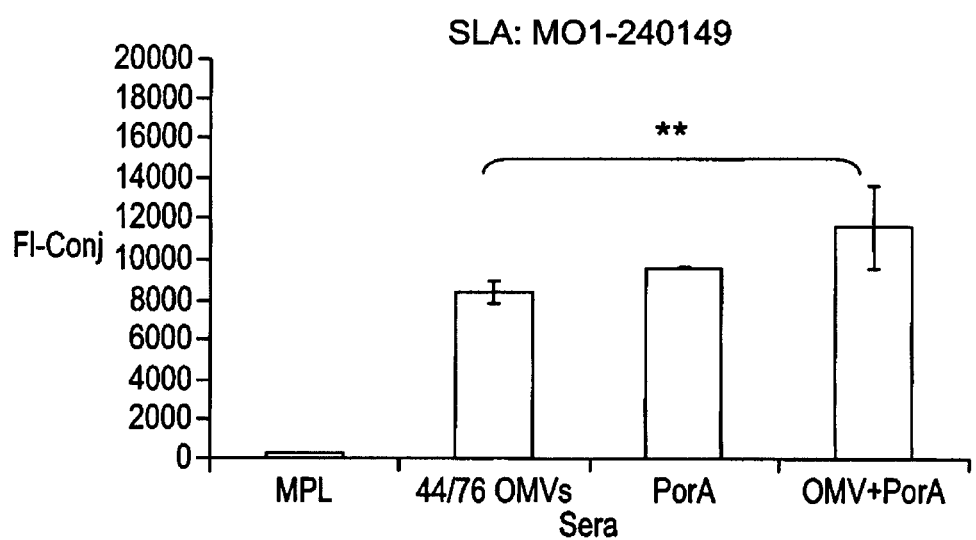

Fig. 11
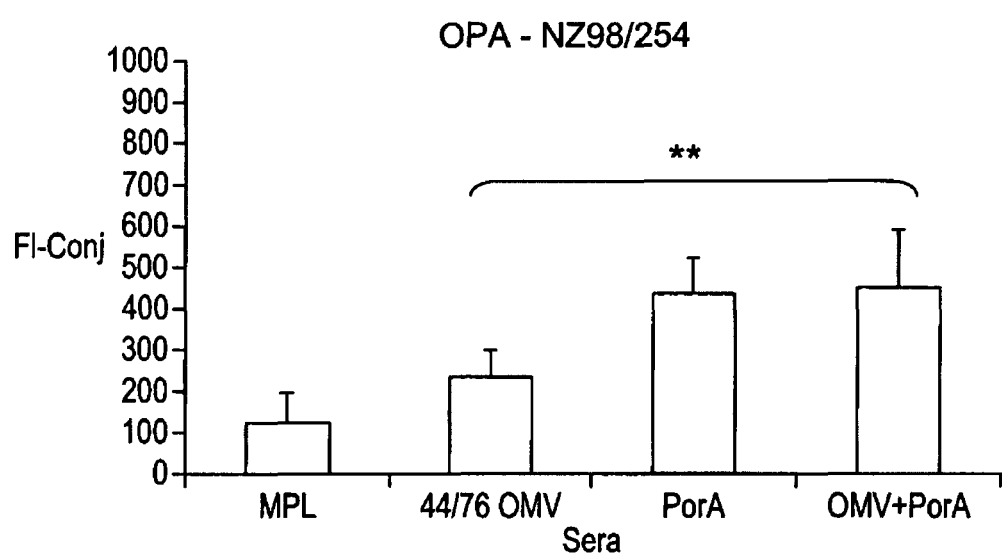
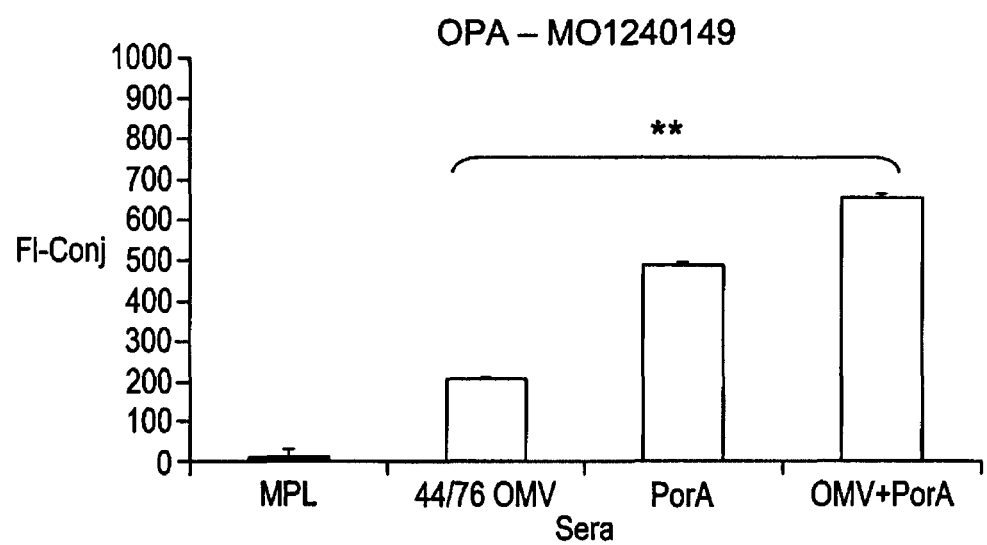

SEQUENCE LISTING

```
<160> NUMBER OF SEQ ID NOS: 75

<210> SEQ ID NO 1
<211> LENGTH: 1176
<212> TYPE: DNA
<213> ORGANISM: Neisseria meningitidis
<220> FEATURE:
<221> NAME/KEY: CDS
<222> LOCATION: (1)..(1176)
<223> OTHER INFORMATION: porA cds

<400> SEQUENCE: 1 atg cga aaa aaa ctt acc gcc ctc gta ttg tcc gca ctg ccg ctt gcg      48
Met Arg Lys Lys Leu Thr Ala Leu Val Leu Ser Ala Leu Pro Leu Ala
1               5                   10                  15 gcc gtt gcc gat gtc agc cta tac ggc gaa atc aaa gcc ggc gtg gaa      96
Ala Val Ala Asp Val Ser Leu Tyr Gly Glu Ile Lys Ala Gly Val Glu
            20                  25                  30 ggc agg aac tac cag ctg caa ttg act gaa gca caa gcc gct aac ggt     144
Gly Arg Asn Tyr Gln Leu Gln Leu Thr Glu Ala Gln Ala Ala Asn Gly
        35                  40                  45
```

-continued

| | | |
|---|---|---|
| gga gcg agc ggt cag gta aaa gtt act aaa gtt act aag gcc aaa agc<br>Gly Ala Ser Gly Gln Val Lys Val Thr Lys Val Thr Lys Ala Lys Ser<br>50      55            60 | 192 |
| cgc atc agg acg aaa atc agt gat ttc ggc tcg ttt atc ggc ttt aag<br>Arg Ile Arg Thr Lys Ile Ser Asp Phe Gly Ser Phe Ile Gly Phe Lys<br>65      70            75            80 | 240 |
| ggg agt gag gat ttg ggc gac ggg ctg aag gct gtt tgg cag ctt gag<br>Gly Ser Glu Asp Leu Gly Asp Gly Leu Lys Ala Val Trp Gln Leu Glu<br>         85            90            95 | 288 |
| caa gac gta tcc gtt gcc ggc ggc gcg acc cag tgg ggc aac agg<br>Gln Asp Val Ser Val Ala Gly Gly Ala Thr Gln Trp Gly Asn Arg<br>      100            105            110 | 336 |
| gaa tcc ttt atc ggc ttg gca ggc gaa ttc ggt acg ctg cgc gcc ggt<br>Glu Ser Phe Ile Gly Leu Ala Gly Glu Phe Gly Thr Leu Arg Ala Gly<br>      115            120            125 | 384 |
| cgc gtt gcg aat cag ttt gac gat gcc agc caa gcc att gat cct tgg<br>Arg Val Ala Asn Gln Phe Asp Asp Ala Ser Gln Ala Ile Asp Pro Trp<br>130            135            140 | 432 |
| gac agc aat aat gat gtg gct tcg caa ttg ggt att ttc aaa cgc cac<br>Asp Ser Asn Asn Asp Val Ala Ser Gln Leu Gly Ile Phe Lys Arg His<br>145            150            155            160 | 480 |
| gac gac atg ccg gtt tcc gta cgc tac gat tcc ccc gaa ttt tcc ggt<br>Asp Asp Met Pro Val Ser Val Arg Tyr Asp Ser Pro Glu Phe Ser Gly<br>            165            170            175 | 528 |
| ttc agc ggc agc gtt caa ttc gtt ccg atc caa aac agc aag tcc gcc<br>Phe Ser Gly Ser Val Gln Phe Val Pro Ile Gln Asn Ser Lys Ser Ala<br>         180            185            190 | 576 |
| tat acg ccg gct tat tat act aag aat aca aac aat aat ctt act ctc<br>Tyr Thr Pro Ala Tyr Tyr Thr Lys Asn Thr Asn Asn Asn Leu Thr Leu<br>      195            200            205 | 624 |
| gtt ccg gct gtt gtc ggc aag ccc gga tcg gat gtg tat tat gcc ggt<br>Val Pro Ala Val Val Gly Lys Pro Gly Ser Asp Val Tyr Tyr Ala Gly<br>210            215            220 | 672 |
| ctg aat tac aaa aat ggc ggt ttt gcc ggg aac tat gcc ttt aaa tat<br>Leu Asn Tyr Lys Asn Gly Gly Phe Ala Gly Asn Tyr Ala Phe Lys Tyr<br>225            230            235            240 | 720 |
| gcg aga cac gcc aat gtc gga cgt aat gct ttt gag ttg ttc ttg atc<br>Ala Arg His Ala Asn Val Gly Arg Asn Ala Phe Glu Leu Phe Leu Ile<br>            245            250            255 | 768 |
| ggc agc ggg agt gat caa gcc aaa ggt acc gat ccc ttg aaa aac cat<br>Gly Ser Gly Ser Asp Gln Ala Lys Gly Thr Asp Pro Leu Lys Asn His<br>         260            265            270 | 816 |
| cag gta cac cgt ctg acg ggc ggc tat gag gaa ggc ggc ttg aat ctc<br>Gln Val His Arg Leu Thr Gly Gly Tyr Glu Glu Gly Gly Leu Asn Leu<br>      275            280            285 | 864 |
| gcc ttg gcg gct cag ttg gat ttg tct gaa aat ggc gac aaa acc aaa<br>Ala Leu Ala Ala Gln Leu Asp Leu Ser Glu Asn Gly Asp Lys Thr Lys<br>290            295            300 | 912 |
| aac agt acg acc gaa att gcc gcc act gct tcc tac cgc ttc ggt aat<br>Asn Ser Thr Thr Glu Ile Ala Ala Thr Ala Ser Tyr Arg Phe Gly Asn<br>305            310            315            320 | 960 |
| gca gtt cca cgc atc agc tat gcc cat ggt ttc gac ttt atc gaa cgc<br>Ala Val Pro Arg Ile Ser Tyr Ala His Gly Phe Asp Phe Ile Glu Arg<br>            325            330            335 | 1008 |
| ggt aaa aaa ggc gaa aat acc agc tac gat caa atc atc gcc ggc gtt<br>Gly Lys Lys Gly Glu Asn Thr Ser Tyr Asp Gln Ile Ile Ala Gly Val<br>         340            345            350 | 1056 |
| gat tat gat ttt tcc aaa cgc act tcc gcc atc gtg tct ggc gct tgg<br>Asp Tyr Asp Phe Ser Lys Arg Thr Ser Ala Ile Val Ser Gly Ala Trp<br>      355            360            365 | 1104 |

```
ctg aaa cgc aat acc ggc atc ggc aac tac act caa att aat gcc gcc       1152
Leu Lys Arg Asn Thr Gly Ile Gly Asn Tyr Thr Gln Ile Asn Ala Ala
370                 375                 380 tcc gtc ggt ttg cgc cac aaa ttc                                       1176
Ser Val Gly Leu Arg His Lys Phe
385                 390

<210> SEQ ID NO 2
<211> LENGTH: 392
<212> TYPE: PRT
<213> ORGANISM: Neisseria meningitidis

<400> SEQUENCE: 2

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ala Gln Ala Ala Asn Gly
        35                  40                  45

Gly Ala Ser Gly Gln Val Lys Val Thr Lys Val Thr Lys Ala Lys Ser
    50                  55                  60

Arg Ile Arg Thr Lys Ile Ser Asp Phe Gly Ser Phe Ile Gly Phe Lys
65                  70                  75                  80

Gly Ser Glu Asp Leu Gly Asp Gly Leu Lys Ala Val Trp Gln Leu Glu
                85                  90                  95

Gln Asp Val Ser Val Ala Gly Gly Ala Thr Gln Trp Gly Asn Arg
            100                 105                 110

Glu Ser Phe Ile Gly Leu Ala Gly Glu Phe Gly Thr Leu Arg Ala Gly
        115                 120                 125

Arg Val Ala Asn Gln Phe Asp Asp Ala Ser Gln Ala Ile Asp Pro Trp
    130                 135                 140

Asp Ser Asn Asn Asp Val Ala Ser Gln Leu Gly Ile Phe Lys Arg His
145                 150                 155                 160

Asp Asp Met Pro Val Ser Val Arg Tyr Asp Ser Pro Glu Phe Ser Gly
                165                 170                 175

Phe Ser Gly Ser Val Gln Phe Val Pro Ile Gln Asn Ser Lys Ser Ala
            180                 185                 190

Tyr Thr Pro Ala Tyr Tyr Thr Lys Asn Thr Asn Asn Leu Thr Leu
        195                 200                 205

Val Pro Ala Val Val Gly Lys Pro Gly Ser Asp Val Tyr Tyr Ala Gly
    210                 215                 220

Leu Asn Tyr Lys Asn Gly Gly Phe Ala Gly Asn Tyr Ala Phe Lys Tyr
225                 230                 235                 240

Ala Arg His Ala Asn Val Gly Arg Asn Ala Phe Glu Leu Phe Leu Ile
                245                 250                 255

Gly Ser Gly Ser Asp Gln Ala Lys Gly Thr Asp Pro Leu Lys Asn His
            260                 265                 270

Gln Val His Arg Leu Thr Gly Gly Tyr Glu Glu Gly Leu Asn Leu
        275                 280                 285

Ala Leu Ala Ala Gln Leu Asp Leu Ser Glu Asn Gly Asp Lys Thr Lys
    290                 295                 300

Asn Ser Thr Thr Glu Ile Ala Ala Thr Ala Ser Tyr Arg Phe Gly Asn
305                 310                 315                 320

Ala Val Pro Arg Ile Ser Tyr Ala His Gly Phe Asp Phe Ile Glu Arg
                325                 330                 335
```

```
Gly Lys Lys Gly Glu Asn Thr Ser Tyr Asp Gln Ile Ile Ala Gly Val
            340                 345                 350

Asp Tyr Asp Phe Ser Lys Arg Thr Ser Ala Ile Val Ser Gly Ala Trp
        355                 360                 365

Leu Lys Arg Asn Thr Gly Ile Gly Asn Tyr Thr Gln Ile Asn Ala Ala
    370                 375                 380

Ser Val Gly Leu Arg His Lys Phe
385                 390

<210> SEQ ID NO 3
<211> LENGTH: 522
<212> TYPE: DNA
<213> ORGANISM: Neisseria meningitidis
<220> FEATURE:
<221> NAME/KEY: CDS
<222> LOCATION: (1)..(522)
<223> OTHER INFORMATION: NspA cds

<400> SEQUENCE: 3 atg aaa aaa gca ctt gcc aca ctg att gcc ctc gct ctc ccg gcc gcc      48
Met Lys Lys Ala Leu Ala Thr Leu Ile Ala Leu Ala Leu Pro Ala Ala
1               5                   10                  15 gca ctg gcg gaa ggc gca tcc ggc ttt tac gtc caa gcc gat gcc gca      96
Ala Leu Ala Glu Gly Ala Ser Gly Phe Tyr Val Gln Ala Asp Ala Ala
                20                  25                  30 cac gca aaa gcc tca agc tct tta ggt tct gcc aaa ggc ttc agc ccg     144
His Ala Lys Ala Ser Ser Ser Leu Gly Ser Ala Lys Gly Phe Ser Pro
            35                  40                  45 cgc atc tcc gca ggc tac cgc atc aac gac ctc cgc ttc gcc gtc gat     192
Arg Ile Ser Ala Gly Tyr Arg Ile Asn Asp Leu Arg Phe Ala Val Asp
        50                  55                  60 tac acg cgc tac aaa aac tat aaa gcc cca tcc acc gat ttc aaa ctt     240
Tyr Thr Arg Tyr Lys Asn Tyr Lys Ala Pro Ser Thr Asp Phe Lys Leu
65                  70                  75                  80 tac agc atc ggc gcg tcc gcc att tac gac ttc gac acc caa tcg ccc     288
Tyr Ser Ile Gly Ala Ser Ala Ile Tyr Asp Phe Asp Thr Gln Ser Pro
                85                  90                  95 gtc aaa ccg tat ctc ggc gcg cgc ttg agc ctc aac cgc gcc tcc gtc     336
Val Lys Pro Tyr Leu Gly Ala Arg Leu Ser Leu Asn Arg Ala Ser Val
                100                 105                 110 gac ttg ggc ggc agc gac agc ttc agc caa acc tcc atc ggc ctc ggc     384
Asp Leu Gly Gly Ser Asp Ser Phe Ser Gln Thr Ser Ile Gly Leu Gly
            115                 120                 125 gta ttg acg ggc gta agc tat gcc gtt acc ccg aat gtc gat ttg gat     432
Val Leu Thr Gly Val Ser Tyr Ala Val Thr Pro Asn Val Asp Leu Asp
        130                 135                 140 gcc ggc tac cgc tac aac tac atc ggc aaa gtc aac act gtc aaa aac     480
Ala Gly Tyr Arg Tyr Asn Tyr Ile Gly Lys Val Asn Thr Val Lys Asn
145                 150                 155                 160 gtc cgt tcc ggc gaa ctg tcc gcc ggt gtg cgc gtc aaa ttc                522
Val Arg Ser Gly Glu Leu Ser Ala Gly Val Arg Val Lys Phe
                165                 170

<210> SEQ ID NO 4
<211> LENGTH: 174
<212> TYPE: PRT
<213> ORGANISM: Neisseria meningitidis

<400> SEQUENCE: 4

Met Lys Lys Ala Leu Ala Thr Leu Ile Ala Leu Ala Leu Pro Ala Ala
1               5                   10                  15
```

```
Ala Leu Ala Glu Gly Ala Ser Gly Phe Tyr Val Gln Ala Asp Ala Ala
            20                  25                  30

His Ala Lys Ala Ser Ser Ser Leu Gly Ser Ala Lys Gly Phe Ser Pro
        35                  40                  45

Arg Ile Ser Ala Gly Tyr Arg Ile Asn Asp Leu Arg Phe Ala Val Asp
    50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
            100                 105                 110

Asp Leu Gly Gly Ser Asp Ser Phe Ser Gln Thr Ser Ile Gly Leu Gly
        115                 120                 125

Val Leu Thr Gly Val Ser Tyr Ala Val Thr Pro Asn Val Asp Leu Asp
    130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Ala Gly Val Arg Val Lys Phe
                165                 170
```

<210> SEQ ID NO 5
<211> LENGTH: 2391
<212> TYPE: DNA
<213> ORGANISM: Neisseria meningitidis
<220> FEATURE:
<221> NAME/KEY: CDS
<222> LOCATION: (1)..(2391)
<223> OTHER INFORMATION: OMP85 cds

<400> SEQUENCE: 5

```
atg aaa ctg aaa cag att gct tcc gca ctg atg atg ttg ggc ata tcg      48
Met Lys Leu Lys Gln Ile Ala Ser Ala Leu Met Met Leu Gly Ile Ser
1               5                   10                  15 cct ttg gca ctt gcc gac ttc acc atc caa gac atc cgc gtc gaa ggc      96
Pro Leu Ala Leu Ala Asp Phe Thr Ile Gln Asp Ile Arg Val Glu Gly
            20                  25                  30 ttg cag cgt acc gag ccg agt acc gta ttc aac tac ctg ccc gtc aaa     144
Leu Gln Arg Thr Glu Pro Ser Thr Val Phe Asn Tyr Leu Pro Val Lys
        35                  40                  45 gtc ggc gac acc tac aac gac aca cac ggc agt gcc atc atc aaa agc     192
Val Gly Asp Thr Tyr Asn Asp Thr His Gly Ser Ala Ile Ile Lys Ser
    50                  55                  60 ctg tac gcc acc ggt ttc ttt gac gac gta cgc gtc gaa act gcg gac     240
Leu Tyr Ala Thr Gly Phe Phe Asp Asp Val Arg Val Glu Thr Ala Asp
65                  70                  75                  80 ggg cag ctc ctg ctg acc gtt atc gaa cgc ccc acc atc ggc tcg ctc     288
Gly Gln Leu Leu Leu Thr Val Ile Glu Arg Pro Thr Ile Gly Ser Leu
                85                  90                  95 aac atc acc ggc gca aaa atg ctg caa aac gac gcc att aag aaa aac     336
Asn Ile Thr Gly Ala Lys Met Leu Gln Asn Asp Ala Ile Lys Lys Asn
            100                 105                 110 ctc gaa tcg ttc ggg ctg gcg cag tcg caa tac ttt aat cag gcg aca     384
Leu Glu Ser Phe Gly Leu Ala Gln Ser Gln Tyr Phe Asn Gln Ala Thr
        115                 120                 125 ctc aat cag gca gtc gcc ggc ctg aaa gaa gaa tac ctc ggg cgc ggc     432
Leu Asn Gln Ala Val Ala Gly Leu Lys Glu Glu Tyr Leu Gly Arg Gly
    130                 135                 140
```

-continued

| | | |
|---|---|---|
| aaa ctc aat atc caa atc acg ccc aaa gta acc aaa ctc gcc cgc aac<br>Lys Leu Asn Ile Gln Ile Thr Pro Lys Val Thr Lys Leu Ala Arg Asn<br>145                        150                    155                  160 | | 480 |
| cgc gtc gac atc gac atc acg att gac gag ggc aaa tcc gcc aaa atc<br>Arg Val Asp Ile Asp Ile Thr Ile Asp Glu Gly Lys Ser Ala Lys Ile<br>                    165                    170                    175 | | 528 |
| acc gac atc gaa ttt gaa ggc aac caa gtc tat tcc gac cgc aaa ctg<br>Thr Asp Ile Glu Phe Glu Gly Asn Gln Val Tyr Ser Asp Arg Lys Leu<br>          180                    185                    190 | | 576 |
| atg cgg caa atg tcc ctg acc gaa ggc ggt att tgg aca tgg ctg aca<br>Met Arg Gln Met Ser Leu Thr Glu Gly Gly Ile Trp Thr Trp Leu Thr<br>      195                    200                    205 | | 624 |
| cga agc aac caa ttc aac gag cag aaa ttt gcc caa gat atg gaa aaa<br>Arg Ser Asn Gln Phe Asn Glu Gln Lys Phe Ala Gln Asp Met Glu Lys<br>210                        215                    220 | | 672 |
| gta acc gac ttc tac caa aat aac ggc tac ttc gat ttc cgt atc ctc<br>Val Thr Asp Phe Tyr Gln Asn Asn Gly Tyr Phe Asp Phe Arg Ile Leu<br>225                        230                    235                  240 | | 720 |
| gat acc gac atc caa acc aac gaa gac aaa acc aag cag acc atc aaa<br>Asp Thr Asp Ile Gln Thr Asn Glu Asp Lys Thr Lys Gln Thr Ile Lys<br>                    245                    250                    255 | | 768 |
| atc acc gtc cac gaa ggc gga cgt ttc cgt tgg ggc aaa gtc tcc atc<br>Ile Thr Val His Glu Gly Gly Arg Phe Arg Trp Gly Lys Val Ser Ile<br>          260                    265                    270 | | 816 |
| gaa ggc gac acc aac gaa gtc ccc aaa gcc gaa ctg gaa aaa ctg ctg<br>Glu Gly Asp Thr Asn Glu Val Pro Lys Ala Glu Leu Glu Lys Leu Leu<br>      275                    280                    285 | | 864 |
| acc atg aag ccc ggc aaa tgg tac gaa cgc cag cag atg acc gcc gtt<br>Thr Met Lys Pro Gly Lys Trp Tyr Glu Arg Gln Gln Met Thr Ala Val<br>290                        295                    300 | | 912 |
| ttg ggt gag att cag aac cgc atg ggc tcg gca ggc tac gca tac agc<br>Leu Gly Glu Ile Gln Asn Arg Met Gly Ser Ala Gly Tyr Ala Tyr Ser<br>305                        310                    315                  320 | | 960 |
| gaa atc agc gta cag ccg ctg ccg aac gct gaa acc aaa acc gtc gat<br>Glu Ile Ser Val Gln Pro Leu Pro Asn Ala Glu Thr Lys Thr Val Asp<br>                    325                    330                    335 | | 1008 |
| ttc gtc ctg cac atc gaa ccg ggc cgg aaa atc tac gtc aac gaa ata<br>Phe Val Leu His Ile Glu Pro Gly Arg Lys Ile Tyr Val Asn Glu Ile<br>          340                    345                    350 | | 1056 |
| cac atc acc ggc aac aac aaa acc cgc gac gaa gtc gtc cgc cgt gaa<br>His Ile Thr Gly Asn Asn Lys Thr Arg Asp Glu Val Val Arg Arg Glu<br>      355                    360                    365 | | 1104 |
| tta cgc caa atg gaa tcc gca cct tac gac acc tcc aag ctg caa cgt<br>Leu Arg Gln Met Glu Ser Ala Pro Tyr Asp Thr Ser Lys Leu Gln Arg<br>370                        375                    380 | | 1152 |
| tcc aaa gag cgc gtc gag ctt ttg ggc tac ttc gac aat gtc cag ttt<br>Ser Lys Glu Arg Val Glu Leu Leu Gly Tyr Phe Asp Asn Val Gln Phe<br>385                        390                    395                  400 | | 1200 |
| gat gct gtc ccg ctt gcc ggc acg ccc gac aaa gtc gat ttg aac atg<br>Asp Ala Val Pro Leu Ala Gly Thr Pro Asp Lys Val Asp Leu Asn Met<br>                    405                    410                    415 | | 1248 |
| agt ctg acc gaa cgt tcc acc ggt tcc ctg gat ttg agc gcg ggt tgg<br>Ser Leu Thr Glu Arg Ser Thr Gly Ser Leu Asp Leu Ser Ala Gly Trp<br>          420                    425                    430 | | 1296 |
| gtt caa gat acc ggg ttg gtc atg tcc gca ggc gtt tcc caa gac aac<br>Val Gln Asp Thr Gly Leu Val Met Ser Ala Gly Val Ser Gln Asp Asn<br>      435                    440                    445 | | 1344 |
| ctg ttc ggt acg ggc aag tcg gcc gca ctg cgc gcc tcc agg agc aaa<br>Leu Phe Gly Thr Gly Lys Ser Ala Ala Leu Arg Ala Ser Arg Ser Lys<br>450                        455                    460 | | 1392 |

-continued

```
acc acg ctt aac ggc tcg ctg tcg ttt act gac ccg tac ttc acg gca    1440
Thr Thr Leu Asn Gly Ser Leu Ser Phe Thr Asp Pro Tyr Phe Thr Ala
465                 470                 475                 480 gac ggg gtc agc ctg ggc tac gat gtt tac gga aaa gcc ttc gac ccg    1488
Asp Gly Val Ser Leu Gly Tyr Asp Val Tyr Gly Lys Ala Phe Asp Pro
                        485                 490                 495 cgc aaa gca tcg acc agc atc aaa caa tat aaa acc acg gca ggc        1536
Arg Lys Ala Ser Thr Ser Ile Lys Gln Tyr Lys Thr Thr Ala Gly
                500                 505                 510 gca ggc atc cgc atg agc gtg cct gtt acc gaa tac gac cgc gtg aat    1584
Ala Gly Ile Arg Met Ser Val Pro Val Thr Glu Tyr Asp Arg Val Asn
            515                 520                 525 ttc ggt ttg gtg gca gaa cac ctg acc gtc aac acc tac aac aaa gcg    1632
Phe Gly Leu Val Ala Glu His Leu Thr Val Asn Thr Tyr Asn Lys Ala
        530                 535                 540 ccc aaa cac tat gcc gac ttt atc aag aaa tac ggc aaa acc gac ggc    1680
Pro Lys His Tyr Ala Asp Phe Ile Lys Lys Tyr Gly Lys Thr Asp Gly
545                 550                 555                 560 aca gac ggc agc ttc aaa ggc tgg ctg tac aaa ggt acc gtc ggc tgg    1728
Thr Asp Gly Ser Phe Lys Gly Trp Leu Tyr Lys Gly Thr Val Gly Trp
                    565                 570                 575 ggg cgc aac aaa acc gac agc gcg tta tgg ccg acg cgc ggc tac ctg    1776
Gly Arg Asn Lys Thr Asp Ser Ala Leu Trp Pro Thr Arg Gly Tyr Leu
                580                 585                 590 acg ggc gtg aac gcc gaa atc gcc ctg cct ggc agc aaa ctg caa tac    1824
Thr Gly Val Asn Ala Glu Ile Ala Leu Pro Gly Ser Lys Leu Gln Tyr
            595                 600                 605 tac tcc gcc acc cac aac caa acc tgg ttc ttc ccc ctg agc aaa acc    1872
Tyr Ser Ala Thr His Asn Gln Thr Trp Phe Phe Pro Leu Ser Lys Thr
        610                 615                 620 ttc acg ctg atg ctc ggc ggc gaa gtc ggc att gcg ggc ggc tac ggc    1920
Phe Thr Leu Met Leu Gly Gly Glu Val Gly Ile Ala Gly Gly Tyr Gly
625                 630                 635                 640 aga acc aaa gaa atc ccc ttc ttt gaa aac ttc tac ggc ggc ggc ctg    1968
Arg Thr Lys Glu Ile Pro Phe Phe Glu Asn Phe Tyr Gly Gly Gly Leu
                    645                 650                 655 ggt tcg gtg cgc gga tac gaa agc ggc acg ctc ggt ccg aaa gtc tat    2016
Gly Ser Val Arg Gly Tyr Glu Ser Gly Thr Leu Gly Pro Lys Val Tyr
                660                 665                 670 gac gaa tac ggc gaa aaa atc agc tac ggc ggc aac aaa aaa gcc aac    2064
Asp Glu Tyr Gly Glu Lys Ile Ser Tyr Gly Gly Asn Lys Lys Ala Asn
            675                 680                 685 gtc tcc gcc gag ctg ctc ttc ccg atg ccc ggc gcg aaa gac gcg cgc    2112
Val Ser Ala Glu Leu Leu Phe Pro Met Pro Gly Ala Lys Asp Ala Arg
        690                 695                 700 acc gtc cgc ctg agc ctg ttt gcc gac gca ggc agc gtg tgg gac ggc    2160
Thr Val Arg Leu Ser Leu Phe Ala Asp Ala Gly Ser Val Trp Asp Gly
705                 710                 715                 720 aaa acc tac gac gac aac agc agt tcc gcg acc ggc ggc agg gtt caa    2208
Lys Thr Tyr Asp Asp Asn Ser Ser Ser Ala Thr Gly Gly Arg Val Gln
                    725                 730                 735 aac att tac ggc gcc ggc aat acc cat aaa tcc acc ttt acc aac gaa    2256
Asn Ile Tyr Gly Ala Gly Asn Thr His Lys Ser Thr Phe Thr Asn Glu
                740                 745                 750 ttg cgc tat tcc gcc ggc ggc gcg gtt acc tgg ctc tcg cct tta ggc    2304
Leu Arg Tyr Ser Ala Gly Gly Ala Val Thr Trp Leu Ser Pro Leu Gly
            755                 760                 765 ccg atg aaa ttc agc tac gcc tac ccg ctg aag aaa aaa ccg gaa gac    2352
Pro Met Lys Phe Ser Tyr Ala Tyr Pro Leu Lys Lys Lys Pro Glu Asp
```

```
                770               775               780
gaa atc caa cgc ttc caa ttc caa ctc ggc acg acg ttc            2391
Glu Ile Gln Arg Phe Gln Phe Gln Leu Gly Thr Thr Phe
785                 790               795
```

<210> SEQ ID NO 6
<211> LENGTH: 797
<212> TYPE: PRT
<213> ORGANISM: Neisseria meningitidis

<400> SEQUENCE: 6

```
Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
                20                  25                  30

Leu Gln Arg Thr Glu Pro Ser Thr Val Phe Asn Tyr Leu Pro Val Lys
            35                  40                  45

Val Gly Asp Thr Tyr Asn Asp Thr His Gly Ser Ala Ile Ile Lys Ser
        50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asn Gln Phe Asn Glu Gln Lys Phe Ala Gln Asp Met Glu Lys
    210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
    290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
            340                 345                 350
```

```
His Ile Thr Gly Asn Asn Lys Thr Arg Asp Glu Val Val Arg Glu
        355                 360                 365
Leu Arg Gln Met Glu Ser Ala Pro Tyr Asp Thr Ser Lys Leu Gln Arg
    370                 375                 380
Ser Lys Glu Arg Val Glu Leu Leu Gly Tyr Phe Asp Asn Val Gln Phe
385                 390                 395                 400
Asp Ala Val Pro Leu Ala Gly Thr Pro Asp Lys Val Asp Leu Asn Met
                405                 410                 415
Ser Leu Thr Glu Arg Ser Thr Gly Ser Leu Asp Leu Ser Ala Gly Trp
            420                 425                 430
Val Gln Asp Thr Gly Leu Val Met Ser Ala Gly Val Ser Gln Asp Asn
            435                 440                 445
Leu Phe Gly Thr Gly Lys Ser Ala Ala Leu Arg Ala Ser Arg Ser Lys
        450                 455                 460
Thr Thr Leu Asn Gly Ser Leu Ser Phe Thr Asp Pro Tyr Phe Thr Ala
465                 470                 475                 480
Asp Gly Val Ser Leu Gly Tyr Asp Val Tyr Gly Lys Ala Phe Asp Pro
                485                 490                 495
Arg Lys Ala Ser Thr Ser Ile Lys Gln Tyr Lys Thr Thr Thr Ala Gly
                500                 505                 510
Ala Gly Ile Arg Met Ser Val Pro Val Thr Glu Tyr Asp Arg Val Asn
            515                 520                 525
Phe Gly Leu Val Ala Glu His Leu Thr Val Asn Thr Tyr Asn Lys Ala
        530                 535                 540
Pro Lys His Tyr Ala Asp Phe Ile Lys Lys Tyr Gly Lys Thr Asp Gly
545                 550                 555                 560
Thr Asp Gly Ser Phe Lys Gly Trp Leu Tyr Lys Gly Thr Val Gly Trp
                565                 570                 575
Gly Arg Asn Lys Thr Asp Ser Ala Leu Trp Pro Thr Arg Gly Tyr Leu
            580                 585                 590
Thr Gly Val Asn Ala Glu Ile Ala Leu Pro Gly Ser Lys Leu Gln Tyr
        595                 600                 605
Tyr Ser Ala Thr His Asn Gln Thr Trp Phe Phe Pro Leu Ser Lys Thr
    610                 615                 620
Phe Thr Leu Met Leu Gly Gly Glu Val Gly Ile Ala Gly Gly Tyr Gly
625                 630                 635                 640
Arg Thr Lys Glu Ile Pro Phe Phe Glu Asn Phe Tyr Gly Gly Gly Leu
                645                 650                 655
Gly Ser Val Arg Gly Tyr Glu Ser Gly Thr Leu Gly Pro Lys Val Tyr
                660                 665                 670
Asp Glu Tyr Gly Glu Lys Ile Ser Tyr Gly Asn Lys Lys Ala Asn
            675                 680                 685
Val Ser Ala Glu Leu Leu Phe Pro Met Pro Gly Ala Lys Asp Ala Arg
        690                 695                 700
Thr Val Arg Leu Ser Leu Phe Ala Asp Ala Gly Ser Val Trp Asp Gly
705                 710                 715                 720
Lys Thr Tyr Asp Asp Asn Ser Ser Ala Thr Gly Gly Arg Val Gln
                725                 730                 735
Asn Ile Tyr Gly Ala Gly Asn Thr His Lys Ser Thr Phe Thr Asn Glu
            740                 745                 750
Leu Arg Tyr Ser Ala Gly Gly Ala Val Thr Trp Leu Ser Pro Leu Gly
        755                 760                 765
```

```
Pro Met Lys Phe Ser Tyr Ala Tyr Pro Leu Lys Lys Lys Pro Glu Asp
    770                 775                 780

Glu Ile Gln Arg Phe Gln Phe Gln Leu Gly Thr Thr Phe
785                 790                 795

<210> SEQ ID NO 7
<211> LENGTH: 2142
<212> TYPE: DNA
<213> ORGANISM: Neisseria meningitidis
<220> FEATURE:
<221> NAME/KEY: CDS
<222> LOCATION: (1)..(2142)
<223> OTHER INFORMATION: FrpB cds

<400> SEQUENCE: 7 atg aat acc cca ttg ttc cgt ctc agc ctg ctc tcg ctt acc ctg gcg      48
Met Asn Thr Pro Leu Phe Arg Leu Ser Leu Leu Ser Leu Thr Leu Ala
1               5                   10                  15 gca ggt ttt gcc cat gcg gca gaa aat aat gcc aag gtc gta ctg gat      96
Ala Gly Phe Ala His Ala Ala Glu Asn Asn Ala Lys Val Val Leu Asp
            20                  25                  30 acc gtt acc gta aaa ggc gac cgc caa ggc agc aaa atc cgt acc aac     144
Thr Val Thr Val Lys Gly Asp Arg Gln Gly Ser Lys Ile Arg Thr Asn
        35                  40                  45 atc gtt acg ctg caa caa aaa gac gaa agc acc gca acc gat atg cgc     192
Ile Val Thr Leu Gln Gln Lys Asp Glu Ser Thr Ala Thr Asp Met Arg
    50                  55                  60 gaa ctc tta aaa gaa gag ccc tcc atc gat ttc ggc ggc ggc aac ggc     240
Glu Leu Leu Lys Glu Glu Pro Ser Ile Asp Phe Gly Gly Gly Asn Gly
65                  70                  75                  80 acg tcc caa ttc ctg acg ctg cgc ggc atg ggt caa aac tct gtc gac     288
Thr Ser Gln Phe Leu Thr Leu Arg Gly Met Gly Gln Asn Ser Val Asp
                85                  90                  95 atc aag gtg gac aac gcc tat tcc gac agc caa atc ctt tac cac caa     336
Ile Lys Val Asp Asn Ala Tyr Ser Asp Ser Gln Ile Leu Tyr His Gln
            100                 105                 110 ggc aga ttt att gtc gat ccc gct ttg gtt aaa gtc gtt tcc gta caa     384
Gly Arg Phe Ile Val Asp Pro Ala Leu Val Lys Val Val Ser Val Gln
        115                 120                 125 aaa ggc gcg ggt tcc gcc tct gcc ggt atc ggc gcg acc aac ggc gcg     432
Lys Gly Ala Gly Ser Ala Ser Ala Gly Ile Gly Ala Thr Asn Gly Ala
    130                 135                 140 atc atc acc aaa acc gtc gat gcc caa gac ctg ctc aaa ggc ttg gat     480
Ile Ile Thr Lys Thr Val Asp Ala Gln Asp Leu Leu Lys Gly Leu Asp
145                 150                 155                 160 aaa aac tgg ggc gtg cgc ctc aac agc ggc ttt gcc agc aac gaa ggc     528
Lys Asn Trp Gly Val Arg Leu Asn Ser Gly Phe Ala Ser Asn Glu Gly
                165                 170                 175 gta agc tac ggc gca agc gta ttc ggg aaa gag ggc aac ttc gac ggc     576
Val Ser Tyr Gly Ala Ser Val Phe Gly Lys Glu Gly Asn Phe Asp Gly
            180                 185                 190 ttg ttc tct tac aac cgc aac aat gaa aaa gat tac gaa gca ggt aaa     624
Leu Phe Ser Tyr Asn Arg Asn Asn Glu Lys Asp Tyr Glu Ala Gly Lys
        195                 200                 205 ggc ttc cgt aat aat ttc aac ggc ggc aaa acc gta ccg tac agc gcg     672
Gly Phe Arg Asn Asn Phe Asn Gly Gly Lys Thr Val Pro Tyr Ser Ala
    210                 215                 220 ctg gac aaa cgc agc tac ctc gcc aaa atc gga aca agc ttc ggc gac     720
Leu Asp Lys Arg Ser Tyr Leu Ala Lys Ile Gly Thr Ser Phe Gly Asp
225                 230                 235                 240 ggc gac cac cgc atc gta ttg agc cat atg aaa gac cag cac cgg ggc     768
```

| | | | | | | | | | | | | | |
|---|---|---|---|---|---|---|---|---|---|---|---|---|---|
| Gly | Asp | His | Arg | Ile | Val | Leu | Ser | His | Met | Lys | Asp | Gln | His | Arg | Gly |
| | | | 245 | | | | | 250 | | | | | 255 | | | atc cgt acc gtc cgt gaa gaa ttt acc gtc ggc ggc gat aaa gag cga    816
Ile Arg Thr Val Arg Glu Glu Phe Thr Val Gly Gly Asp Lys Glu Arg
             260                 265                 270 ata agt atg gaa cgc caa gcc cct gct tac cgc gaa acc aca caa tcc    864
Ile Ser Met Glu Arg Gln Ala Pro Ala Tyr Arg Glu Thr Thr Gln Ser
         275                 280                 285 aac acc aat ttg gcg tac acg ggt aaa aac ctg ggc ttt gtc gaa aaa    912
Asn Thr Asn Leu Ala Tyr Thr Gly Lys Asn Leu Gly Phe Val Glu Lys
     290                 295                 300 ctg gat gcc aac gcc tat gtg ttg gaa aaa gaa cgc tat tcc gcc gat    960
Leu Asp Ala Asn Ala Tyr Val Leu Glu Lys Glu Arg Tyr Ser Ala Asp
305                 310                 315                 320 gac agc ggc acc ggt tac gca ggc aat gta aaa ggc ccc aac cat acc   1008
Asp Ser Gly Thr Gly Tyr Ala Gly Asn Val Lys Gly Pro Asn His Thr
                 325                 330                 335 caa atc acc act cgg ggt atg aac ttc aac ttc gac agc cgc ctt gcc   1056
Gln Ile Thr Thr Arg Gly Met Asn Phe Asn Phe Asp Ser Arg Leu Ala
             340                 345                 350 gaa caa acc ctg ctg aaa tac ggt atc aac tac cgc cat cag gaa atc   1104
Glu Gln Thr Leu Leu Lys Tyr Gly Ile Asn Tyr Arg His Gln Glu Ile
         355                 360                 365 aaa ccg caa gcg ttt ttg aat tca caa ttt aaa att gaa gat aaa gaa   1152
Lys Pro Gln Ala Phe Leu Asn Ser Gln Phe Lys Ile Glu Asp Lys Glu
     370                 375                 380 aaa gca act gat gaa gag aaa aat aag aac cgt gaa aat gaa aaa att   1200
Lys Ala Thr Asp Glu Glu Lys Asn Lys Asn Arg Glu Asn Glu Lys Ile
385                 390                 395                 400 gcc aaa gcc tac cgt ctg acc aac ccg acc aaa acc gat acc ggc gcg   1248
Ala Lys Ala Tyr Arg Leu Thr Asn Pro Thr Lys Thr Asp Thr Gly Ala
                 405                 410                 415 tat atc gaa gcc att cac gag att gac ggc ttt acc ctg acc ggc ggg   1296
Tyr Ile Glu Ala Ile His Glu Ile Asp Gly Phe Thr Leu Thr Gly Gly
             420                 425                 430 ctg cgt tac gac cgc ttc aag gtg aaa acc cac gac ggc aaa acc gtt   1344
Leu Arg Tyr Asp Arg Phe Lys Val Lys Thr His Asp Gly Lys Thr Val
         435                 440                 445 tca agc aac aac ctt aac ccg agt ttc ggc gtg att tgg cag ccg cac   1392
Ser Ser Asn Asn Leu Asn Pro Ser Phe Gly Val Ile Trp Gln Pro His
     450                 455                 460 gaa cac tgg agc ttc agc gcg agc cac aac tac gcc agc cgc agc ccg   1440
Glu His Trp Ser Phe Ser Ala Ser His Asn Tyr Ala Ser Arg Ser Pro
465                 470                 475                 480 cgc ctg tat gac gcg ctg caa acc cac ggc aaa cgc ggc atc atc tcg   1488
Arg Leu Tyr Asp Ala Leu Gln Thr His Gly Lys Arg Gly Ile Ile Ser
                 485                 490                 495 att gcc gac ggc acg aaa gcc gaa cgc gcg cgc aat acc gaa atc ggc   1536
Ile Ala Asp Gly Thr Lys Ala Glu Arg Ala Arg Asn Thr Glu Ile Gly
             500                 505                 510 ttc aac tac aac gac ggc acg ttt gcc gca aac ggc agc tac ttc tgg   1584
Phe Asn Tyr Asn Asp Gly Thr Phe Ala Ala Asn Gly Ser Tyr Phe Trp
         515                 520                 525 cag acc atc aaa gac gcg ctt gcc aat ccg caa aac cgc cac gac tct   1632
Gln Thr Ile Lys Asp Ala Leu Ala Asn Pro Gln Asn Arg His Asp Ser
     530                 535                 540 gtc gcc gtc cgt gaa gcc gtc aat gcc ggt tac atc aaa aac cac ggt   1680
Val Ala Val Arg Glu Ala Val Asn Ala Gly Tyr Ile Lys Asn His Gly
545                 550                 555                 560

| | | | | | | | | | | | | | | | |
|---|---|---|---|---|---|---|---|---|---|---|---|---|---|---|---|
| tac | gaa | ttg | ggc | gcg | tcc | tac | cgc | acc | ggc | ggc | ctg | act | gcc | aaa | gtc | 1728 |
| Tyr | Glu | Leu | Gly | Ala | Ser | Tyr | Arg | Thr | Gly | Gly | Leu | Thr | Ala | Lys | Val | |
| | | | 565 | | | | 570 | | | | | 575 | | | | |

```
tac gaa ttg ggc gcg tcc tac cgc acc ggc ggc ctg act gcc aaa gtc    1728
Tyr Glu Leu Gly Ala Ser Tyr Arg Thr Gly Gly Leu Thr Ala Lys Val
            565                 570                 575 ggc gta agc cac agc aaa ccg cgc ttt tac gat acg cac aaa gac aag    1776
Gly Val Ser His Ser Lys Pro Arg Phe Tyr Asp Thr His Lys Asp Lys
            580                 585                 590 ctg ttg agc gcg aat cct gaa ttt ggc gca caa gtc ggc cgc act tgg    1824
Leu Leu Ser Ala Asn Pro Glu Phe Gly Ala Gln Val Gly Arg Thr Trp
            595                 600                 605 acg gct tcc ctt gcc tac cgc ttc caa aac ccg aat ctg gaa atc ggc    1872
Thr Ala Ser Leu Ala Tyr Arg Phe Gln Asn Pro Asn Leu Glu Ile Gly
            610                 615                 620 tgg cgc ggc cgt tat gtt caa aaa gcc gtg ggt tcg ata ttg gtg gca    1920
Trp Arg Gly Arg Tyr Val Gln Lys Ala Val Gly Ser Ile Leu Val Ala
625                 630                 635                 640 ggt caa aaa gac cgc aac ggc aaa ttg gaa aac gtt gta cgc aaa ggt    1968
Gly Gln Lys Asp Arg Asn Gly Lys Leu Glu Asn Val Val Arg Lys Gly
                    645                 650                 655 ttc ggt gtg aac gat gtc ttc gcc aac tgg aaa ccg ctg ggc aaa gac    2016
Phe Gly Val Asn Asp Val Phe Ala Asn Trp Lys Pro Leu Gly Lys Asp
                660                 665                 670 acg ctc aat gtt aat ctt tcg gtt aac aac gtg ttc aac acg ttc tac    2064
Thr Leu Asn Val Asn Leu Ser Val Asn Asn Val Phe Asn Thr Phe Tyr
            675                 680                 685 tat ccg cac agc caa cga tgg acc aat acc ctg ccg ggc gtg gga cgt    2112
Tyr Pro His Ser Gln Arg Trp Thr Asn Thr Leu Pro Gly Val Gly Arg
            690                 695                 700 gat gta cgc ttg ggc gtg aac tac aag ttc                            2142
Asp Val Arg Leu Gly Val Asn Tyr Lys Phe
705                 710
```

<210> SEQ ID NO 8
<211> LENGTH: 714
<212> TYPE: PRT
<213> ORGANISM: Neisseria meningitidis

<400> SEQUENCE: 8

```
Met Asn Thr Pro Leu Phe Arg Leu Ser Leu Leu Ser Leu Thr Leu Ala
1               5                   10                  15

Ala Gly Phe Ala His Ala Ala Glu Asn Asn Ala Lys Val Val Leu Asp
            20                  25                  30

Thr Val Thr Val Lys Gly Asp Arg Gln Gly Ser Lys Ile Arg Thr Asn
        35                  40                  45

Ile Val Thr Leu Gln Gln Lys Asp Glu Ser Thr Ala Thr Asp Met Arg
    50                  55                  60

Glu Leu Leu Lys Glu Glu Pro Ser Ile Asp Phe Gly Gly Gly Asn Gly
65                  70                  75                  80

Thr Ser Gln Phe Leu Thr Leu Arg Gly Met Gly Gln Asn Ser Val Asp
                85                  90                  95

Ile Lys Val Asp Asn Ala Tyr Ser Asp Ser Gln Ile Leu Tyr His Gln
            100                 105                 110

Gly Arg Phe Ile Val Asp Pro Ala Leu Val Lys Val Ser Val Gln
        115                 120                 125

Lys Gly Ala Gly Ser Ala Ser Ala Gly Ile Gly Ala Thr Asn Gly Ala
    130                 135                 140

Ile Ile Thr Lys Thr Val Asp Ala Gln Asp Leu Leu Lys Gly Leu Asp
145                 150                 155                 160

Lys Asn Trp Gly Val Arg Leu Asn Ser Gly Phe Ala Ser Asn Glu Gly
```

-continued

```
                165                 170                 175
Val Ser Tyr Gly Ala Ser Val Phe Gly Lys Glu Gly Asn Phe Asp Gly
            180                 185                 190

Leu Phe Ser Tyr Asn Arg Asn Asn Glu Lys Asp Tyr Glu Ala Gly Lys
            195                 200                 205

Gly Phe Arg Asn Asn Phe Asn Gly Gly Lys Thr Val Pro Tyr Ser Ala
210                 215                 220

Leu Asp Lys Arg Ser Tyr Leu Ala Lys Ile Gly Thr Ser Phe Gly Asp
225                 230                 235                 240

Gly Asp His Arg Ile Val Leu Ser His Met Lys Asp Gln His Arg Gly
            245                 250                 255

Ile Arg Thr Val Arg Glu Glu Phe Thr Val Gly Gly Asp Lys Glu Arg
            260                 265                 270

Ile Ser Met Glu Arg Gln Ala Pro Ala Tyr Arg Glu Thr Thr Gln Ser
            275                 280                 285

Asn Thr Asn Leu Ala Tyr Thr Gly Lys Asn Leu Gly Phe Val Glu Lys
            290                 295                 300

Leu Asp Ala Asn Ala Tyr Val Leu Glu Lys Glu Arg Tyr Ser Ala Asp
305                 310                 315                 320

Asp Ser Gly Thr Gly Tyr Ala Gly Asn Val Lys Gly Pro Asn His Thr
            325                 330                 335

Gln Ile Thr Thr Arg Gly Met Asn Phe Asn Phe Asp Ser Arg Leu Ala
            340                 345                 350

Glu Gln Thr Leu Leu Lys Tyr Gly Ile Asn Tyr Arg His Gln Glu Ile
            355                 360                 365

Lys Pro Gln Ala Phe Leu Asn Ser Gln Phe Lys Ile Glu Asp Lys Glu
            370                 375                 380

Lys Ala Thr Asp Glu Glu Lys Asn Lys Asn Arg Glu Asn Glu Lys Ile
385                 390                 395                 400

Ala Lys Ala Tyr Arg Leu Thr Asn Pro Thr Lys Thr Asp Thr Gly Ala
            405                 410                 415

Tyr Ile Glu Ala Ile His Glu Ile Asp Gly Phe Thr Leu Thr Gly Gly
            420                 425                 430

Leu Arg Tyr Asp Arg Phe Lys Val Lys Thr His Asp Gly Lys Thr Val
            435                 440                 445

Ser Ser Asn Asn Leu Asn Pro Ser Phe Gly Val Ile Trp Gln Pro His
450                 455                 460

Glu His Trp Ser Phe Ser Ala Ser His Asn Tyr Ala Ser Arg Ser Pro
465                 470                 475                 480

Arg Leu Tyr Asp Ala Leu Gln Thr His Gly Lys Arg Gly Ile Ile Ser
            485                 490                 495

Ile Ala Asp Gly Thr Lys Ala Glu Arg Ala Arg Asn Thr Glu Ile Gly
            500                 505                 510

Phe Asn Tyr Asn Asp Gly Thr Phe Ala Ala Asn Gly Ser Tyr Phe Trp
            515                 520                 525

Gln Thr Ile Lys Asp Ala Leu Ala Asn Pro Gln Asn Arg His Asp Ser
            530                 535                 540

Val Ala Val Arg Glu Ala Val Asn Ala Gly Tyr Ile Lys Asn His Gly
545                 550                 555                 560

Tyr Glu Leu Gly Ala Ser Tyr Arg Thr Gly Gly Leu Thr Ala Lys Val
            565                 570                 575

Gly Val Ser His Ser Lys Pro Arg Phe Tyr Asp Thr His Lys Asp Lys
            580                 585                 590
```

```
Leu Leu Ser Ala Asn Pro Glu Phe Gly Ala Gln Val Gly Arg Thr Trp
            595                 600                 605

Thr Ala Ser Leu Ala Tyr Arg Phe Gln Asn Pro Asn Leu Glu Ile Gly
        610                 615                 620

Trp Arg Gly Arg Tyr Val Gln Lys Ala Val Gly Ser Ile Leu Val Ala
625                 630                 635                 640

Gly Gln Lys Asp Arg Asn Gly Lys Leu Glu Asn Val Val Arg Lys Gly
                645                 650                 655

Phe Gly Val Asn Asp Val Phe Ala Asn Trp Lys Pro Leu Gly Lys Asp
            660                 665                 670

Thr Leu Asn Val Asn Leu Ser Val Asn Val Phe Asn Thr Phe Tyr
        675                 680                 685

Tyr Pro His Ser Gln Arg Trp Thr Asn Thr Leu Pro Gly Val Gly Arg
    690                 695                 700

Asp Val Arg Leu Gly Val Asn Tyr Lys Phe
705                 710

<210> SEQ ID NO 9
<211> LENGTH: 2307
<212> TYPE: DNA
<213> ORGANISM: Neisseria meningitidis
<220> FEATURE:
<221> NAME/KEY: CDS
<222> LOCATION: (1)..(2307)
<223> OTHER INFORMATION: PilQ cds

<400> SEQUENCE: 9
```

| | | |
|---|---|---|
| atg aat acc aaa ctg aca aaa atc att tcc ggt ctc ttt gtc gca acc | 48 | |
| Met Asn Thr Lys Leu Thr Lys Ile Ile Ser Gly Leu Phe Val Ala Thr | | |
| 1               5                   10                  15 | | |
| | | |
| gcc gcc ttt cag aca gca tcg gca gga aac att aca gac atc aaa gtt | 96 | |
| Ala Ala Phe Gln Thr Ala Ser Ala Gly Asn Ile Thr Asp Ile Lys Val | | |
|             20                  25                  30 | | |
| | | |
| tcc tcc ctg ccc aac aaa cag aaa atc gtc aaa gtc agc ttt gac aaa | 144 | |
| Ser Ser Leu Pro Asn Lys Gln Lys Ile Val Lys Val Ser Phe Asp Lys | | |
|         35                  40                  45 | | |
| | | |
| gag att gtc aac ccg acc ggc ttc gta acc tcc tca ccg gcc cgc atc | 192 | |
| Glu Ile Val Asn Pro Thr Gly Phe Val Thr Ser Ser Pro Ala Arg Ile | | |
|     50                  55                  60 | | |
| | | |
| gcc ttg gac ttt gaa caa acc ggc att tcc atg gat caa cag gta ctc | 240 | |
| Ala Leu Asp Phe Glu Gln Thr Gly Ile Ser Met Asp Gln Gln Val Leu | | |
| 65                  70                  75                  80 | | |
| | | |
| gaa tat gcc gat cct ctg ttg agc aaa atc agt gcc gca caa aac agc | 288 | |
| Glu Tyr Ala Asp Pro Leu Leu Ser Lys Ile Ser Ala Ala Gln Asn Ser | | |
|                 85                  90                  95 | | |
| | | |
| agc cgt gcg cgt ctg gtt ctg aat ctg aac aaa ccg ggc caa tac aat | 336 | |
| Ser Arg Ala Arg Leu Val Leu Asn Leu Asn Lys Pro Gly Gln Tyr Asn | | |
|             100                 105                 110 | | |
| | | |
| acc gaa gta cgc ggg aac aaa gtt tgg ata ttc att aac gaa tcg gac | 384 | |
| Thr Glu Val Arg Gly Asn Lys Val Trp Ile Phe Ile Asn Glu Ser Asp | | |
|         115                 120                 125 | | |
| | | |
| gat acc gtg tcc gcc ccc gca cgc ccc gcc gta aaa gcc gcg cct gcc | 432 | |
| Asp Thr Val Ser Ala Pro Ala Arg Pro Ala Val Lys Ala Ala Pro Ala | | |
|     130                 135                 140 | | |
| | | |
| gca ccg gca aaa caa cag gct gcc gca ccg tct acc aag tcc gca gta | 480 | |
| Ala Pro Ala Lys Gln Gln Ala Ala Ala Pro Ser Thr Lys Ser Ala Val | | |
| 145                 150                 155                 160 | | |
| | | |
| tcc gta tcc gaa ccc ttt acc ccg gca aaa caa cag gct gcc gca ccg | 528 | |
| Ser Val Ser Glu Pro Phe Thr Pro Ala Lys Gln Gln Ala Ala Ala Pro | | |

-continued

|     |     |     |     |     |     |     |     |     |     |     |     |     |     |     |     |     |
|---|---|---|---|---|---|---|---|---|---|---|---|---|---|---|---|---|
|     |     |     | 165 |     |     |     | 170 |     |     |     | 175 |     |     |     |     |     |
| ttt | acc | gag | tcc | gta | gta | tcc | gta | tcc | gca | ccg | ttc | agc | ccg | gca | aaa | 576 |
| Phe | Thr | Glu | Ser | Val | Val | Ser | Val | Ser | Ala | Pro | Phe | Ser | Pro | Ala | Lys |     |
|     |     | 180 |     |     |     |     | 185 |     |     |     |     | 190 |     |     |     |     |
| caa | cag | gcg | gcg | gca | tca | gca | aaa | caa | cag | gcg | gca | gca | cca | gca | aaa | 624 |
| Gln | Gln | Ala | Ala | Ala | Ser | Ala | Lys | Gln | Gln | Ala | Ala | Ala | Pro | Ala | Lys |     |
|     | 195 |     |     |     |     | 200 |     |     |     |     | 205 |     |     |     |     |     |
| caa | cag | gcg | gca | gca | cca | gca | aaa | caa | cag | gcg | gca | gca | cca | gca | aaa | 672 |
| Gln | Gln | Ala | Ala | Ala | Pro | Ala | Lys | Gln | Gln | Ala | Ala | Ala | Pro | Ala | Lys |     |
| 210 |     |     |     |     | 215 |     |     |     |     | 220 |     |     |     |     |     |     |
| caa | acc | aat | atc | gat | ttc | cgc | aaa | gac | ggc | aaa | aat | gcc | ggc | att | atc | 720 |
| Gln | Thr | Asn | Ile | Asp | Phe | Arg | Lys | Asp | Gly | Lys | Asn | Ala | Gly | Ile | Ile |     |
| 225 |     |     |     | 230 |     |     |     |     | 235 |     |     |     |     | 240 |     |     |
| gaa | ttg | gct | gca | ttg | ggc | ttt | gcc | ggg | cag | ccc | gac | atc | agc | caa | cag | 768 |
| Glu | Leu | Ala | Ala | Leu | Gly | Phe | Ala | Gly | Gln | Pro | Asp | Ile | Ser | Gln | Gln |     |
|     |     |     |     | 245 |     |     |     |     | 250 |     |     |     |     | 255 |     |     |
| cac | gac | cac | atc | atc | gtt | acg | ctg | aaa | aac | cat | acc | ctg | ccg | acc | acg | 816 |
| His | Asp | His | Ile | Ile | Val | Thr | Leu | Lys | Asn | His | Thr | Leu | Pro | Thr | Thr |     |
|     |     |     | 260 |     |     |     |     | 265 |     |     |     |     | 270 |     |     |     |
| ctc | caa | cgc | agt | ttg | gat | gtg | gca | gac | ttt | aaa | aca | ccg | gtt | caa | aag | 864 |
| Leu | Gln | Arg | Ser | Leu | Asp | Val | Ala | Asp | Phe | Lys | Thr | Pro | Val | Gln | Lys |     |
|     |     | 275 |     |     |     |     | 280 |     |     |     |     | 285 |     |     |     |     |
| gtt | acg | ctg | aaa | cgc | ctc | aat | aac | gac | acc | cag | ctg | att | atc | aca | aca | 912 |
| Val | Thr | Leu | Lys | Arg | Leu | Asn | Asn | Asp | Thr | Gln | Leu | Ile | Ile | Thr | Thr |     |
|     | 290 |     |     |     |     | 295 |     |     |     |     | 300 |     |     |     |     |     |
| gcc | ggc | aac | tgg | gaa | ctc | gtc | aac | aaa | tcc | gcc | gcg | ccc | gga | tac | ttt | 960 |
| Ala | Gly | Asn | Trp | Glu | Leu | Val | Asn | Lys | Ser | Ala | Ala | Pro | Gly | Tyr | Phe |     |
| 305 |     |     |     |     | 310 |     |     |     |     | 315 |     |     |     |     | 320 |     |
| acc | ttc | caa | gtc | ctg | ccg | aaa | aaa | caa | aac | ctc | gag | tca | ggc | ggc | gtg | 1008 |
| Thr | Phe | Gln | Val | Leu | Pro | Lys | Lys | Gln | Asn | Leu | Glu | Ser | Gly | Gly | Val |     |
|     |     |     |     | 325 |     |     |     |     | 330 |     |     |     |     | 335 |     |     |
| aac | aat | gcg | ccc | aaa | acc | ttc | aca | ggc | cgg | aaa | atc | tcc | ctt | gac | ttc | 1056 |
| Asn | Asn | Ala | Pro | Lys | Thr | Phe | Thr | Gly | Arg | Lys | Ile | Ser | Leu | Asp | Phe |     |
|     |     |     | 340 |     |     |     |     | 345 |     |     |     |     | 350 |     |     |     |
| caa | gat | gtc | gaa | atc | cgc | acc | atc | ctg | cag | att | ttg | gca | aaa | gaa | tcc | 1104 |
| Gln | Asp | Val | Glu | Ile | Arg | Thr | Ile | Leu | Gln | Ile | Leu | Ala | Lys | Glu | Ser |     |
|     |     | 355 |     |     |     |     | 360 |     |     |     |     | 365 |     |     |     |     |
| gga | atg | aac | att | gtt | gcc | agc | gac | tcc | gtc | aac | ggc | aaa | atg | acc | ctc | 1152 |
| Gly | Met | Asn | Ile | Val | Ala | Ser | Asp | Ser | Val | Asn | Gly | Lys | Met | Thr | Leu |     |
|     | 370 |     |     |     |     | 375 |     |     |     |     | 380 |     |     |     |     |     |
| tcc | ctc | aag | gat | gtg | cct | tgg | gat | cag | gct | ttg | gat | ttg | gtt | atg | cag | 1200 |
| Ser | Leu | Lys | Asp | Val | Pro | Trp | Asp | Gln | Ala | Leu | Asp | Leu | Val | Met | Gln |     |
| 385 |     |     |     | 390 |     |     |     |     | 395 |     |     |     |     | 400 |     |     |
| gcg | cgc | aac | ctc | gat | atg | cgc | cag | caa | ggg | aat | atc | gtc | aac | atc | gcg | 1248 |
| Ala | Arg | Asn | Leu | Asp | Met | Arg | Gln | Gln | Gly | Asn | Ile | Val | Asn | Ile | Ala |     |
|     |     |     | 405 |     |     |     |     | 410 |     |     |     |     | 415 |     |     |     |
| ccc | cgc | gac | gag | ctg | ctt | gcc | aaa | gac | aaa | gcc | ctc | tta | cag | gca | gaa | 1296 |
| Pro | Arg | Asp | Glu | Leu | Leu | Ala | Lys | Asp | Lys | Ala | Leu | Leu | Gln | Ala | Glu |     |
|     |     | 420 |     |     |     |     | 425 |     |     |     |     | 430 |     |     |     |     |
| aaa | gac | att | gcc | gat | ttg | ggt | gcg | ctg | tat | tcc | caa | aac | ttc | cag | ttg | 1344 |
| Lys | Asp | Ile | Ala | Asp | Leu | Gly | Ala | Leu | Tyr | Ser | Gln | Asn | Phe | Gln | Leu |     |
|     | 435 |     |     |     |     | 440 |     |     |     |     | 445 |     |     |     |     |     |
| aaa | tac | aaa | aat | gtg | gaa | gaa | ttc | cgc | agc | atc | ctg | cgt | ttg | gac | aat | 1392 |
| Lys | Tyr | Lys | Asn | Val | Glu | Glu | Phe | Arg | Ser | Ile | Leu | Arg | Leu | Asp | Asn |     |
| 450 |     |     |     |     | 455 |     |     |     |     | 460 |     |     |     |     |     |     |
| gcc | gac | acg | acc | gga | aac | cgc | aac | acg | ctt | atc | agc | ggc | agg | ggc | agc | 1440 |
| Ala | Asp | Thr | Thr | Gly | Asn | Arg | Asn | Thr | Leu | Ile | Ser | Gly | Arg | Gly | Ser |     |
| 465 |     |     |     | 470 |     |     |     |     | 475 |     |     |     |     | 480 |     |     |
| gtg | ctg | atc | gat | ccc | gcc | acc | aac | acc | ctg | att | gtt | acc | gac | acc | cgc | 1488 |

```
Val Leu Ile Asp Pro Ala Thr Asn Thr Leu Ile Val Thr Asp Thr Arg
                485                 490                 495 agc gtc atc gaa aaa ttc cgc aaa ctg att gac gaa ttg gac gta ccc      1536
Ser Val Ile Glu Lys Phe Arg Lys Leu Ile Asp Glu Leu Asp Val Pro
            500                 505                 510 gcg caa caa gtg atg att gag gcg cgt atc gtc gaa gcg gca gac ggc      1584
Ala Gln Gln Val Met Ile Glu Ala Arg Ile Val Glu Ala Ala Asp Gly
        515                 520                 525 ttc tcg cgc gat ttg ggc gtt aaa ttc ggc gcg aca ggc aag aaa aag      1632
Phe Ser Arg Asp Leu Gly Val Lys Phe Gly Ala Thr Gly Lys Lys Lys
    530                 535                 540 ctg aaa aat gat aca agc gca ttc ggc tgg ggg gta aac tcc ggc ttc      1680
Leu Lys Asn Asp Thr Ser Ala Phe Gly Trp Gly Val Asn Ser Gly Phe
545                 550                 555                 560 ggc ggc gac gat aaa tgg ggg gcc gaa acc aaa atc aac ctg ccg att      1728
Gly Gly Asp Asp Lys Trp Gly Ala Glu Thr Lys Ile Asn Leu Pro Ile
                565                 570                 575 acc gct gcc gca aac agc att tcg ctg gtg cgc gcg att tcc tcc ggt      1776
Thr Ala Ala Ala Asn Ser Ile Ser Leu Val Arg Ala Ile Ser Ser Gly
            580                 585                 590 gcc ttg aat ttg gaa ttg tcc gca tcc gaa tcg ctt tca aaa acc aaa      1824
Ala Leu Asn Leu Glu Leu Ser Ala Ser Glu Ser Leu Ser Lys Thr Lys
        595                 600                 605 acg ctt gcc aat ccg cgc gtg ctg acc caa aac cgc aaa gag gcc aaa      1872
Thr Leu Ala Asn Pro Arg Val Leu Thr Gln Asn Arg Lys Glu Ala Lys
    610                 615                 620 atc gaa tcc ggt tac gaa att cct ttc acc gta acc tca atc gcg aac      1920
Ile Glu Ser Gly Tyr Glu Ile Pro Phe Thr Val Thr Ser Ile Ala Asn
625                 630                 635                 640 ggc ggc agc agc acg aac acg gaa ctc aaa aaa gcc gtc ttg ggg ctg      1968
Gly Gly Ser Ser Thr Asn Thr Glu Leu Lys Lys Ala Val Leu Gly Leu
                645                 650                 655 acc gtt acg ccg aac atc acg ccc gac ggc caa atc att atg acc gtc      2016
Thr Val Thr Pro Asn Ile Thr Pro Asp Gly Gln Ile Ile Met Thr Val
            660                 665                 670 aaa atc aac aag gac tcg cct gcg caa tgt gcc tcc ggt aat cag acg      2064
Lys Ile Asn Lys Asp Ser Pro Ala Gln Cys Ala Ser Gly Asn Gln Thr
        675                 680                 685 atc ctg tgt att tcg acc aaa aac ctg aat acg cag gct atg gtt gaa      2112
Ile Leu Cys Ile Ser Thr Lys Asn Leu Asn Thr Gln Ala Met Val Glu
    690                 695                 700 aac ggc ggc aca ttg att gtc ggc ggt att tat gaa gaa gac aac ggc      2160
Asn Gly Gly Thr Leu Ile Val Gly Gly Ile Tyr Glu Glu Asp Asn Gly
705                 710                 715                 720 aat acg ctg acc aaa gtc ccc ctg ttg ggc gac atc ccc gtt atc ggc      2208
Asn Thr Leu Thr Lys Val Pro Leu Leu Gly Asp Ile Pro Val Ile Gly
                725                 730                 735 aac ctc ttt aaa aca cgc ggg aaa aaa acc gac cgc cgc gaa ctg ctg      2256
Asn Leu Phe Lys Thr Arg Gly Lys Lys Thr Asp Arg Arg Glu Leu Leu
            740                 745                 750 att ttc att acc ccg agg att atg ggt acg gcc ggc aac agc ctg cgc      2304
Ile Phe Ile Thr Pro Arg Ile Met Gly Thr Ala Gly Asn Ser Leu Arg
        755                 760                 765 tat                                                                   2307
Tyr

<210> SEQ ID NO 10
<211> LENGTH: 769
<212> TYPE: PRT
<213> ORGANISM: Neisseria meningitidis
```

<400> SEQUENCE: 10

```
Met Asn Thr Lys Leu Thr Lys Ile Ile Ser Gly Leu Phe Val Ala Thr
1               5                   10                  15

Ala Ala Phe Gln Thr Ala Ser Ala Gly Asn Ile Thr Asp Ile Lys Val
            20                  25                  30

Ser Ser Leu Pro Asn Lys Gln Lys Ile Val Lys Val Ser Phe Asp Lys
        35                  40                  45

Glu Ile Val Asn Pro Thr Gly Phe Val Thr Ser Ser Pro Ala Arg Ile
    50                  55                  60

Ala Leu Asp Phe Glu Gln Thr Gly Ile Ser Met Asp Gln Gln Val Leu
65                  70                  75                  80

Glu Tyr Ala Asp Pro Leu Leu Ser Lys Ile Ser Ala Ala Gln Asn Ser
                85                  90                  95

Ser Arg Ala Arg Leu Val Leu Asn Leu Asn Lys Pro Gly Gln Tyr Asn
            100                 105                 110

Thr Glu Val Arg Gly Asn Lys Val Trp Ile Phe Ile Asn Glu Ser Asp
        115                 120                 125

Asp Thr Val Ser Ala Pro Ala Arg Pro Ala Val Lys Ala Ala Pro Ala
130                 135                 140

Ala Pro Ala Lys Gln Gln Ala Ala Pro Ser Thr Lys Ser Ala Val
145                 150                 155                 160

Ser Val Ser Glu Pro Phe Thr Pro Ala Lys Gln Ala Ala Ala Pro
                165                 170                 175

Phe Thr Glu Ser Val Val Ser Val Ser Ala Pro Phe Ser Pro Ala Lys
            180                 185                 190

Gln Gln Ala Ala Ala Ser Ala Lys Gln Gln Ala Ala Ala Pro Ala Lys
            195                 200                 205

Gln Gln Ala Ala Pro Ala Lys Gln Gln Ala Ala Ala Pro Ala Lys
        210                 215                 220

Gln Thr Asn Ile Asp Phe Arg Lys Asp Gly Lys Asn Ala Gly Ile Ile
225                 230                 235                 240

Glu Leu Ala Ala Leu Gly Phe Ala Gly Gln Pro Asp Ile Ser Gln Gln
                245                 250                 255

His Asp His Ile Ile Val Thr Leu Lys Asn His Thr Leu Pro Thr Thr
            260                 265                 270

Leu Gln Arg Ser Leu Asp Val Ala Asp Phe Lys Thr Pro Val Gln Lys
        275                 280                 285

Val Thr Leu Lys Arg Leu Asn Asn Asp Thr Gln Leu Ile Ile Thr Thr
    290                 295                 300

Ala Gly Asn Trp Glu Leu Val Asn Lys Ser Ala Ala Pro Gly Tyr Phe
305                 310                 315                 320

Thr Phe Gln Val Leu Pro Lys Lys Gln Asn Leu Glu Ser Gly Gly Val
                325                 330                 335

Asn Asn Ala Pro Lys Thr Phe Thr Gly Arg Lys Ile Ser Leu Asp Phe
            340                 345                 350

Gln Asp Val Glu Ile Arg Thr Ile Leu Gln Ile Leu Ala Lys Glu Ser
        355                 360                 365

Gly Met Asn Ile Val Ala Ser Asp Ser Val Asn Gly Lys Met Thr Leu
    370                 375                 380

Ser Leu Lys Asp Val Pro Trp Asp Gln Ala Leu Asp Leu Val Met Gln
385                 390                 395                 400

Ala Arg Asn Leu Asp Met Arg Gln Gln Gly Asn Ile Val Asn Ile Ala
```

```
            405                 410                 415
Pro Arg Asp Glu Leu Ala Lys Asp Lys Ala Leu Leu Gln Ala Glu
        420                 425                 430

Lys Asp Ile Ala Asp Leu Gly Ala Leu Tyr Ser Gln Asn Phe Gln Leu
        435                 440                 445

Lys Tyr Lys Asn Val Glu Glu Phe Arg Ser Ile Leu Arg Leu Asp Asn
    450                 455                 460

Ala Asp Thr Thr Gly Asn Arg Asn Thr Leu Ile Ser Gly Arg Gly Ser
465                 470                 475                 480

Val Leu Ile Asp Pro Ala Thr Asn Thr Leu Ile Val Thr Asp Thr Arg
                485                 490                 495

Ser Val Ile Glu Lys Phe Arg Lys Leu Ile Asp Glu Leu Asp Val Pro
            500                 505                 510

Ala Gln Gln Val Met Ile Glu Ala Arg Ile Val Glu Ala Ala Asp Gly
        515                 520                 525

Phe Ser Arg Asp Leu Gly Val Lys Phe Gly Ala Thr Gly Lys Lys Lys
    530                 535                 540

Leu Lys Asn Asp Thr Ser Ala Phe Gly Trp Gly Val Asn Ser Gly Phe
545                 550                 555                 560

Gly Gly Asp Asp Lys Trp Gly Ala Glu Thr Lys Ile Asn Leu Pro Ile
                565                 570                 575

Thr Ala Ala Ala Asn Ser Ile Ser Leu Val Arg Ala Ile Ser Ser Gly
            580                 585                 590

Ala Leu Asn Leu Glu Leu Ser Ala Ser Glu Leu Ser Lys Thr Lys
        595                 600                 605

Thr Leu Ala Asn Pro Arg Val Leu Thr Gln Asn Arg Lys Glu Ala Lys
    610                 615                 620

Ile Glu Ser Gly Tyr Glu Ile Pro Phe Thr Val Thr Ser Ile Ala Asn
625                 630                 635                 640

Gly Gly Ser Ser Thr Asn Thr Glu Leu Lys Lys Ala Val Leu Gly Leu
                645                 650                 655

Thr Val Thr Pro Asn Ile Thr Pro Asp Gly Gln Ile Ile Met Thr Val
            660                 665                 670

Lys Ile Asn Lys Asp Ser Pro Ala Gln Cys Ala Ser Gly Asn Gln Thr
        675                 680                 685

Ile Leu Cys Ile Ser Thr Lys Asn Leu Asn Thr Gln Ala Met Val Glu
    690                 695                 700

Asn Gly Gly Thr Leu Ile Val Gly Ile Tyr Glu Glu Asp Asn Gly
705                 710                 715                 720

Asn Thr Leu Thr Lys Val Pro Leu Leu Gly Asp Ile Pro Val Ile Gly
                725                 730                 735

Asn Leu Phe Lys Thr Arg Gly Lys Lys Thr Asp Arg Arg Glu Leu Leu
            740                 745                 750

Ile Phe Ile Thr Pro Arg Ile Met Gly Thr Ala Gly Asn Ser Leu Arg
        755                 760                 765

Tyr

<210> SEQ ID NO 11
<211> LENGTH: 1773
<212> TYPE: DNA
<213> ORGANISM: Neisseria meningitidis
<220> FEATURE:
<221> NAME/KEY: CDS
<222> LOCATION: (1)..(1773)
<223> OTHER INFORMATION: Hsf cds
```

<400> SEQUENCE: 11

```
atg aac aaa ata tac cgc atc att tgg aat agt gcc ctc aat gcc tgg      48
Met Asn Lys Ile Tyr Arg Ile Ile Trp Asn Ser Ala Leu Asn Ala Trp
1               5                  10                  15 gtc gtc gta tcc gag ctc aca cgc aac cac acc aaa cgc gcc tcc gca      96
Val Val Val Ser Glu Leu Thr Arg Asn His Thr Lys Arg Ala Ser Ala
            20                  25                  30 acc gtg aag acc gcc gta ttg gcg aca ctg ttg ttt gca acg gtt cag     144
Thr Val Lys Thr Ala Val Leu Ala Thr Leu Leu Phe Ala Thr Val Gln
        35                  40                  45 gca agt gct aac aat gaa gag caa gaa gaa gat tta tat tta gac ccc     192
Ala Ser Ala Asn Asn Glu Glu Gln Glu Glu Asp Leu Tyr Leu Asp Pro
    50                  55                  60 gta caa cgc act gtt gcc gtg ttg ata gtc aat tcc gat aaa gaa ggc     240
Val Gln Arg Thr Val Ala Val Leu Ile Val Asn Ser Asp Lys Glu Gly
65                  70                  75                  80 acg gga gaa aaa gaa aaa gta gaa gaa aat tca gat tgg gca gta tat     288
Thr Gly Glu Lys Glu Lys Val Glu Glu Asn Ser Asp Trp Ala Val Tyr
                85                  90                  95 ttc aac gag aaa gga gta cta aca gcc aga gaa atc acc ctc aaa gcc     336
Phe Asn Glu Lys Gly Val Leu Thr Ala Arg Glu Ile Thr Leu Lys Ala
            100                 105                 110 ggc gac aac ctg aaa atc aaa caa aac ggc aca aac ttc acc tac tcg     384
Gly Asp Asn Leu Lys Ile Lys Gln Asn Gly Thr Asn Phe Thr Tyr Ser
        115                 120                 125 ctg aaa aaa gac ctc aca gat ctg acc agt gtt gga act gaa aaa tta     432
Leu Lys Lys Asp Leu Thr Asp Leu Thr Ser Val Gly Thr Glu Lys Leu
    130                 135                 140 tcg ttt agc gca aac ggc aat aaa gtc aac atc aca agc gac acc aaa     480
Ser Phe Ser Ala Asn Gly Asn Lys Val Asn Ile Thr Ser Asp Thr Lys
145                 150                 155                 160 ggc ttg aat ttt gcg aaa gaa acg gct ggg acg aac ggc gac acc acg     528
Gly Leu Asn Phe Ala Lys Glu Thr Ala Gly Thr Asn Gly Asp Thr Thr
                165                 170                 175 gtt cat ctg aac ggt att ggt tcg act ttg acc gat acg ctg ctg aat     576
Val His Leu Asn Gly Ile Gly Ser Thr Leu Thr Asp Thr Leu Leu Asn
            180                 185                 190 acc gga gcg acc aca aac gta acc aac gac aac gtt acc gat gac gag     624
Thr Gly Ala Thr Thr Asn Val Thr Asn Asp Asn Val Thr Asp Asp Glu
        195                 200                 205 aaa aaa cgt gcg gca agc gtt aaa gac gta tta aac gct ggc tgg aac     672
Lys Lys Arg Ala Ala Ser Val Lys Asp Val Leu Asn Ala Gly Trp Asn
    210                 215                 220 att aaa ggc gtt aaa ccc ggt aca aca gct tcc gat aac gtt gat ttc     720
Ile Lys Gly Val Lys Pro Gly Thr Thr Ala Ser Asp Asn Val Asp Phe
225                 230                 235                 240 gtc cgc act tac gac aca gtc gag ttc ttg agc gca gat acg aaa aca     768
Val Arg Thr Tyr Asp Thr Val Glu Phe Leu Ser Ala Asp Thr Lys Thr
                245                 250                 255 acg act gtt aat gtg gaa agc aaa gac aac ggc aag aaa acc gaa gtt     816
Thr Thr Val Asn Val Glu Ser Lys Asp Asn Gly Lys Lys Thr Glu Val
            260                 265                 270 aaa atc ggt gcg aag act tct gtt att aaa gaa aaa gac ggt aag ttg     864
Lys Ile Gly Ala Lys Thr Ser Val Ile Lys Glu Lys Asp Gly Lys Leu
        275                 280                 285 gtt act ggt aaa gac aaa ggc gag aat ggt tct tct aca gac gaa ggc     912
Val Thr Gly Lys Asp Lys Gly Glu Asn Gly Ser Ser Thr Asp Glu Gly
    290                 295                 300
```

-continued

```
gaa ggc tta gtg act gca aaa gaa gtg att gat gca gta aac aag gct      960
Glu Gly Leu Val Thr Ala Lys Glu Val Ile Asp Ala Val Asn Lys Ala
305                 310                 315                 320 ggt tgg aga atg aaa aca aca acc gct aat ggt caa aca ggt caa gct     1008
Gly Trp Arg Met Lys Thr Thr Thr Ala Asn Gly Gln Thr Gly Gln Ala
                325                 330                 335 gac aag ttt gaa acc gtt aca tca ggc aca aat gta acc ttt gct agt     1056
Asp Lys Phe Glu Thr Val Thr Ser Gly Thr Asn Val Thr Phe Ala Ser
            340                 345                 350 ggt aaa ggt aca act gcg act gta agt aaa gat gat caa ggc aac atc     1104
Gly Lys Gly Thr Thr Ala Thr Val Ser Lys Asp Asp Gln Gly Asn Ile
        355                 360                 365 act gtt atg tat gat gta aat gtc ggc gat gcc cta aac gtc aat cag     1152
Thr Val Met Tyr Asp Val Asn Val Gly Asp Ala Leu Asn Val Asn Gln
    370                 375                 380 ctg caa aac agc ggt tgg aat ttg gat tcc aaa gcg gtt gca ggt tct     1200
Leu Gln Asn Ser Gly Trp Asn Leu Asp Ser Lys Ala Val Ala Gly Ser
385                 390                 395                 400 tcg ggc aaa gtc atc agc ggc aat gtt tcg ccg agc aag gga aag atg     1248
Ser Gly Lys Val Ile Ser Gly Asn Val Ser Pro Ser Lys Gly Lys Met
                405                 410                 415 gat gaa acc gtc aac att aat gcc ggc aac aac atc gag att acc cgc     1296
Asp Glu Thr Val Asn Ile Asn Ala Gly Asn Asn Ile Glu Ile Thr Arg
            420                 425                 430 aac ggt aaa aat atc gac atc gcc act tcg atg acc ccg cag ttt tcc     1344
Asn Gly Lys Asn Ile Asp Ile Ala Thr Ser Met Thr Pro Gln Phe Ser
        435                 440                 445 agc gtt tcg ctc ggc gcg ggg gcg gat gcg ccc act ttg agc gtg gat     1392
Ser Val Ser Leu Gly Ala Gly Ala Asp Ala Pro Thr Leu Ser Val Asp
    450                 455                 460 ggg gac gca ttg aat gtc ggc agc aag aag gac aac aaa ccc gtc cgc     1440
Gly Asp Ala Leu Asn Val Gly Ser Lys Lys Asp Asn Lys Pro Val Arg
465                 470                 475                 480 att acc aat gtc gcc ccg ggc gtt aaa gag ggg gat gtt aca aac gtc     1488
Ile Thr Asn Val Ala Pro Gly Val Lys Glu Gly Asp Val Thr Asn Val
                485                 490                 495 gca caa ctt aaa ggc gtg gcg caa aac ttg aac aac cgc atc gac aat     1536
Ala Gln Leu Lys Gly Val Ala Gln Asn Leu Asn Asn Arg Ile Asp Asn
            500                 505                 510 gtg gac ggc aac gcg cgt gcg ggc atc gcc caa gcg att gca acc gca     1584
Val Asp Gly Asn Ala Arg Ala Gly Ile Ala Gln Ala Ile Ala Thr Ala
        515                 520                 525 ggt ctg gtt cag gcg tat ttg ccc ggc aag agt atg atg gcg atc ggc     1632
Gly Leu Val Gln Ala Tyr Leu Pro Gly Lys Ser Met Met Ala Ile Gly
    530                 535                 540 ggc ggc act tat cgc ggc gaa gcc ggt tac gcc atc ggc tac tcc agt     1680
Gly Gly Thr Tyr Arg Gly Glu Ala Gly Tyr Ala Ile Gly Tyr Ser Ser
545                 550                 555                 560 att tcc gac ggc gga aat tgg att atc aaa ggc acg gct tcc ggc aat     1728
Ile Ser Asp Gly Gly Asn Trp Ile Ile Lys Gly Thr Ala Ser Gly Asn
                565                 570                 575 tcg cgc ggc cat ttc ggt gct tcc gca tct gtc ggt tat cag tgg         1773
Ser Arg Gly His Phe Gly Ala Ser Ala Ser Val Gly Tyr Gln Trp
            580                 585                 590

<210> SEQ ID NO 12
<211> LENGTH: 591
<212> TYPE: PRT
<213> ORGANISM: Neisseria meningitidis

<400> SEQUENCE:

```
Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                      60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
            115                 120                 125

Leu Lys Lys Asp Leu Thr Asp Leu Thr Ser Val Gly Thr Glu Lys Leu
        130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415
```

```
Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
            435                 440                 445

Ser Val Ser Leu Gly Ala Gly Ala Asp Ala Pro Thr Leu Ser Val Asp
            450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
            515                 520                 525

Gly Leu Val Gln Ala Tyr Leu Pro Gly Lys Ser Met Met Ala Ile Gly
            530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 13
<211> LENGTH: 549
<212> TYPE: DNA
<213> ORGANISM: Neisseria meningitidis
<220> FEATURE:
<221> NAME/KEY: CDS
<222> LOCATION: (1)..(549)
<223> OTHER INFORMATION: NMA0174

<400> SEQUENCE: 13 atg aaa gtt ttg aac ggt tgg tcg gac agg aag atg tgg cgg gtt ttg      48
Met Lys Val Leu Asn Gly Trp Ser Asp Arg Lys Met Trp Arg Val Leu
1               5                   10                  15 agt gct ttg ccg ata ggc gtg gtg ttt ttt gat ttg atc tac ggt ttt      96
Ser Ala Leu Pro Ile Gly Val Val Phe Phe Asp Leu Ile Tyr Gly Phe
                20                  25                  30 gtg ttg aat gtg ttg cag ggt ttg gat ttg cag cgt gcc gtg ccg gat     144
Val Leu Asn Val Leu Gln Gly Leu Asp Leu Gln Arg Ala Val Pro Asp
            35                  40                  45 tcg gaa ggc gtg ttg gcg gtt acg ccc gat att gca ttc aac agt ttg     192
Ser Glu Gly Val Leu Ala Val Thr Pro Asp Ile Ala Phe Asn Ser Leu
        50                  55                  60 cag att gtc gcc aac ggc ggt atg gcg gcg gtg gtc tgt ttc ggg ttg     240
Gln Ile Val Ala Asn Gly Gly Met Ala Ala Val Val Cys Phe Gly Leu
65                  70                  75                  80 gcg gtt gtg ttt ttg ctc aac cgt tcg gtg cgg cgg cgg cag gtg ttg     288
Ala Val Val Phe Leu Leu Asn Arg Ser Val Arg Arg Arg Gln Val Leu
                85                  90                  95 gaa atc ggg gtg ttc cgg atg ttg ggg ctg gtg gcg gta ttg gcg ttc     336
Glu Ile Gly Val Phe Arg Met Leu Gly Leu Val Ala Val Leu Ala Phe
            100                 105                 110 agc gcg ccg tcg gtg tgg gag tgg gcg aac gcg ctg ccg ctg ctg ctg     384
Ser Ala Pro Ser Val Trp Glu Trp Ala Asn Ala Leu Pro Leu Leu Leu
        115                 120                 125 aag ggc gcg gac gtg gtc aat acg ggg aat gcg cgt tat gtg ctg acg     432
Lys Gly Ala Asp Val Val Asn Thr Gly Asn Ala Arg Tyr Val Leu Thr
```

| | | |
|---|---|---|
| gct ttg tgt atg ccc ttt cct gcg gtg tcg tgc gtc atc ggg ctg gtg<br>Ala Leu Cys Met Pro Phe Pro Ala Val Ser Cys Val Ile Gly Leu Val<br>145                         150                    155                      160 | 480 |

```
gct ttg tgt atg ccc ttt cct gcg gtg tcg tgc gtc atc ggg ctg gtg      480
Ala Leu Cys Met Pro Phe Pro Ala Val Ser Cys Val Ile Gly Leu Val
145                 150                 155                 160 ggg cgg ttc agg ctt cag acg gca tcg ggc agg gcg gca aag tca ggg      528
Gly Arg Phe Arg Leu Gln Thr Ala Ser Gly Arg Ala Ala Lys Ser Gly
                165                 170                 175 ggt gcg ggc aag gcg gac gga                                          549
Gly Ala Gly Lys Ala Asp Gly
            180
```

<210> SEQ ID NO 14
<211> LENGTH: 183
<212> TYPE: PRT
<213> ORGANISM: Neisseria meningitidis

<400> SEQUENCE: 14

```
Met Lys Val Leu Asn Gly Trp Ser Asp Arg Lys Met Trp Arg Val Leu
1               5                   10                  15

Ser Ala Leu Pro Ile Gly Val Val Phe Asp Leu Ile Tyr Gly Phe
                20                  25                  30

Val Leu Asn Val Leu Gln Gly Leu Asp Leu Gln Arg Ala Val Pro Asp
            35                  40                  45

Ser Glu Gly Val Leu Ala Val Thr Pro Asp Ile Ala Phe Asn Ser Leu
        50                  55                  60

Gln Ile Val Ala Asn Gly Gly Met Ala Ala Val Val Cys Phe Gly Leu
65                  70                  75                  80

Ala Val Val Phe Leu Leu Asn Arg Ser Val Arg Arg Gln Val Leu
                85                  90                  95

Glu Ile Gly Val Phe Arg Met Leu Gly Leu Val Ala Val Leu Ala Phe
            100                 105                 110

Ser Ala Pro Ser Val Trp Glu Trp Ala Asn Ala Leu Pro Leu Leu Leu
        115                 120                 125

Lys Gly Ala Asp Val Val Asn Thr Gly Asn Ala Arg Tyr Val Leu Thr
130                 135                 140

Ala Leu Cys Met Pro Phe Pro Ala Val Ser Cys Val Ile Gly Leu Val
145                 150                 155                 160

Gly Arg Phe Arg Leu Gln Thr Ala Ser Gly Arg Ala Ala Lys Ser Gly
                165                 170                 175

Gly Ala Gly Lys Ala Asp Gly
            180
```

<210> SEQ ID NO 15
<211> LENGTH: 2373
<212> TYPE: DNA
<213> ORGANISM: Neisseria meningitidis
<220> FEATURE:
<221> NAME/KEY: CDS
<222> LOCATION: (1)..(2373)
<223> OTHER INFORMATION: NMA1371

<400> SEQUENCE: 15

```
atg aat aaa aat att aaa tct tta aat tta cgg gaa aaa gac ccg ttt      48
Met Asn Lys Asn Ile Lys Ser Leu Asn Leu Arg Glu Lys Asp Pro Phe
1               5                   10                  15 tta agt cgt gaa aaa cag cgt tat gaa cat cct ttg ccc agt cgg gaa      96
Leu Ser Arg Glu Lys Gln Arg Tyr Glu His Pro Leu Pro Ser Arg Glu
                20                  25                  30 tgg ata atc gag ctg ctt gaa cgt aaa ggc gta cca tcc aag att gaa     144
Trp Ile Ile Glu Leu Leu Glu Arg Lys Gly Val Pro Ser Lys Ile Glu
```

```
            Trp Ile Ile Glu Leu Leu Glu Arg Lys Gly Val Pro Ser Lys Ile Glu
                         35                  40                  45 gct ttg gta cgc gaa ttg tcg att aag gaa gaa gag tac gaa ttt ttc      192
Ala Leu Val Arg Glu Leu Ser Ile Lys Glu Glu Glu Tyr Glu Phe Phe
         50                  55                  60 gaa cgt cgt ctg aag gcg atg gcg cgg gac ggt cag gtt tta atc aac      240
Glu Arg Arg Leu Lys Ala Met Ala Arg Asp Gly Gln Val Leu Ile Asn
 65                  70                  75                  80 cgt cgg ggc gcg gtt tgc gcg gcg gac aaa ttg gat ttg gtc aaa tgc      288
Arg Arg Gly Ala Val Cys Ala Ala Asp Lys Leu Asp Leu Val Lys Cys
                     85                  90                  95 cgt gtc gag gcg cac aaa gac ggc ttc ggt ttc gcc gtg ccg ctc acg      336
Arg Val Glu Ala His Lys Asp Gly Phe Gly Phe Ala Val Pro Leu Thr
                100                 105                 110 ccc gcc aaa gac ggt gat ttt gtt ttg tac gaa cgc cag atg cgc ggc      384
Pro Ala Lys Asp Gly Asp Phe Val Leu Tyr Glu Arg Gln Met Arg Gly
            115                 120                 125 att atg cac ggc gat att gtc act gtt cgt cct gcc ggc atg gac cgt      432
Ile Met His Gly Asp Ile Val Thr Val Arg Pro Ala Gly Met Asp Arg
        130                 135                 140 agg ggc cgc cgc gaa ggg acg gtt ctg gat att gtc gaa cgc gcg caa      480
Arg Gly Arg Arg Glu Gly Thr Val Leu Asp Ile Val Glu Arg Ala Gln
145                 150                 155                 160 agc aaa gtg gtc ggc cgt ttc tat atg gat agg ggc gtg gcg att ttg      528
Ser Lys Val Val Gly Arg Phe Tyr Met Asp Arg Gly Val Ala Ile Leu
                165                 170                 175 gag ccg gaa gac aag cgt ctg aac caa agc atc gta ttg gaa ccg gac      576
Glu Pro Glu Asp Lys Arg Leu Asn Gln Ser Ile Val Leu Glu Pro Asp
            180                 185                 190 ggc gtg gcg cgt ttc aaa cct gaa tcc ggt cag gtc atc gtc ggc gaa      624
Gly Val Ala Arg Phe Lys Pro Glu Ser Gly Gln Val Ile Val Gly Glu
        195                 200                 205 att gag gtt tat cct gag caa aac cgg ccg gca gtg gca aaa atc atc      672
Ile Glu Val Tyr Pro Glu Gln Asn Arg Pro Ala Val Ala Lys Ile Ile
    210                 215                 220 gaa gtt ttg ggc gat tat gcc gac agc ggc atg gag att gaa att gcc      720
Glu Val Leu Gly Asp Tyr Ala Asp Ser Gly Met Glu Ile Glu Ile Ala
225                 230                 235                 240 gtg cgc aag cat cat ttg ccg cac caa ttc agt gaa gcg tgt gcc aaa      768
Val Arg Lys His His Leu Pro His Gln Phe Ser Glu Ala Cys Ala Lys
                245                 250                 255 gcc gcg aaa aaa att ccc gac cat gta cgc aaa agc gat ttg aaa ggc      816
Ala Ala Lys Lys Ile Pro Asp His Val Arg Lys Ser Asp Leu Lys Gly
            260                 265                 270 cgc gtc gat ttg cgc gac ctg cct ttg gta acg ata gac ggc gaa acg      864
Arg Val Asp Leu Arg Asp Leu Pro Leu Val Thr Ile Asp Gly Glu Thr
        275                 280                 285 gct cga gat ttt gac gat gcg gtg ttt gcc gag aaa atc gga cgc aat      912
Ala Arg Asp Phe Asp Asp Ala Val Phe Ala Glu Lys Ile Gly Arg Asn
    290                 295                 300 tac cgt ctg gtc gtg gcg att gcc gat gtc agc cat tat gtc cgc ccc      960
Tyr Arg Leu Val Val Ala Ile Ala Asp Val Ser His Tyr Val Arg Pro
305                 310                 315                 320 gat gac gct atc gac acg gac gct cag gaa cgc agc acc agt gtt tac     1008
Asp Asp Ala Ile Asp Thr Asp Ala Gln Glu Arg Ser Thr Ser Val Tyr
                325                 330                 335 ttc ccg cgc cgc gtg att ccc atg ttg ccg gaa aac ctg tcc aac ggc     1056
Phe Pro Arg Arg Val Ile Pro Met Leu Pro Glu Asn Leu Ser Asn Gly
            340                 345                 350
```

| | | |
|---|---|---|
| atc tgc tcg ctc aat cct cat gtc gag cgt ttg tgt gtg gtg tgc gat<br>Ile Cys Ser Leu Asn Pro His Val Glu Arg Leu Cys Val Val Cys Asp<br>355 360 365 | | 1104 |
| atg gtt atc act tac gcg ggc aat atc aaa gaa tac cgc ttc tac ccc<br>Met Val Ile Thr Tyr Ala Gly Asn Ile Lys Glu Tyr Arg Phe Tyr Pro<br>370 375 380 | | 1152 |
| gcc gtg atg cgc tct cat gcc cgc ctg acc tac aac caa gtt tgg aaa<br>Ala Val Met Arg Ser His Ala Arg Leu Thr Tyr Asn Gln Val Trp Lys<br>385 390 395 400 | | 1200 |
| tgg ctt tca ggc ggc atc gag cat ccg ttc aaa acc caa atc gac acg<br>Trp Leu Ser Gly Gly Ile Glu His Pro Phe Lys Thr Gln Ile Asp Thr<br>405 410 415 | | 1248 |
| ctt tac aaa ctc ttc aaa atc ctt cag aaa aag cgt ttc gaa cgc ggg<br>Leu Tyr Lys Leu Phe Lys Ile Leu Gln Lys Lys Arg Phe Glu Arg Gly<br>420 425 430 | | 1296 |
| gcg gtg gag ttt gac agc atc gaa acc caa atg ctt ttc gac gac aac<br>Ala Val Glu Phe Asp Ser Ile Glu Thr Gln Met Leu Phe Asp Asp Asn<br>435 440 445 | | 1344 |
| ggt aaa att gaa aaa atc gtc ccc gtt gtc cgc aac gat gcc cac aag<br>Gly Lys Ile Glu Lys Ile Val Pro Val Val Arg Asn Asp Ala His Lys<br>450 455 460 | | 1392 |
| ctg att gaa gaa tgt atg ttg gcg gca aac gtt tgc gca gcg gat ttt<br>Leu Ile Glu Glu Cys Met Leu Ala Ala Asn Val Cys Ala Ala Asp Phe<br>465 470 475 480 | | 1440 |
| ctg ttg aaa aac aag cat acc gca ttg ttc cgc aac cat ttg ggg ccc<br>Leu Leu Lys Asn Lys His Thr Ala Leu Phe Arg Asn His Leu Gly Pro<br>485 490 495 | | 1488 |
| acg ccc gaa aaa ctc gcc gcc ttg cgc gag cag ctc ggt ctg ttg ggg<br>Thr Pro Glu Lys Leu Ala Ala Leu Arg Glu Gln Leu Gly Leu Leu Gly<br>500 505 510 | | 1536 |
| ctt caa ctt ggc ggc ggc gac aac ccg tcg ccg aaa gac tat gcc gcg<br>Leu Gln Leu Gly Gly Gly Asp Asn Pro Ser Pro Lys Asp Tyr Ala Ala<br>515 520 525 | | 1584 |
| ctt gcc gga cag ttc aaa ggc agg ccg gat gcc gaa ttg ctg caa gtc<br>Leu Ala Gly Gln Phe Lys Gly Arg Pro Asp Ala Glu Leu Leu Gln Val<br>530 535 540 | | 1632 |
| atg atg ttg cgc tcc atg caa cag gcg gtt tac gaa ccg cat tgc gac<br>Met Met Leu Arg Ser Met Gln Gln Ala Val Tyr Glu Pro His Cys Asp<br>545 550 555 560 | | 1680 |
| gga cac ttt ggt ctt gcc tac gaa gca tac gcc cac ttc acc tcg ccc<br>Gly His Phe Gly Leu Ala Tyr Glu Ala Tyr Ala His Phe Thr Ser Pro<br>565 570 575 | | 1728 |
| atc cgc cgc tat ccc gac ctg acc gta cac cgc gcc atc aaa gcc gtg<br>Ile Arg Arg Tyr Pro Asp Leu Thr Val His Arg Ala Ile Lys Ala Val<br>580 585 590 | | 1776 |
| ttg aat cag caa acc tac acg cca aaa aaa agc tgg cag gct ttg ggc<br>Leu Asn Gln Gln Thr Tyr Thr Pro Lys Lys Ser Trp Gln Ala Leu Gly<br>595 600 605 | | 1824 |
| gtg cat acc tcg ttc tgt gag cgc cgt gcc gac gac gcc agc cgc gac<br>Val His Thr Ser Phe Cys Glu Arg Arg Ala Asp Asp Ala Ser Arg Asp<br>610 615 620 | | 1872 |
| gtg gaa aac tgg ctg aaa acc tat tat atg cgc gat aag gtc ggc gaa<br>Val Glu Asn Trp Leu Lys Thr Tyr Tyr Met Arg Asp Lys Val Gly Glu<br>625 630 635 640 | | 1920 |
| gta ttc gaa ggt aaa atc tcc ggc atg acc agt ttt ggt atc ttt gta<br>Val Phe Glu Gly Lys Ile Ser Gly Met Thr Ser Phe Gly Ile Phe Val<br>645 650 655 | | 1968 |
| aca ctg gac ggc atc cac att gac ggc ttg gtg cat atc agc gat ttg<br>Thr Leu Asp Gly Ile His Ile Asp Gly Leu Val His Ile Ser Asp Leu<br>660 665 670 | | 2016 |

```
ggc gaa gac tat ttc aac ttc cgc ccc gaa atc atg gca atc gaa ggc     2064
Gly Glu Asp Tyr Phe Asn Phe Arg Pro Glu Ile Met Ala Ile Glu Gly
            675                 680                 685 gaa cgc agc ggc atc cgt ttc aac atg ggg gac agg gtt gcc gtc cgg     2112
Glu Arg Ser Gly Ile Arg Phe Asn Met Gly Asp Arg Val Ala Val Arg
        690                 695                 700 gtc gcc cgt gcc gat ttg gat gac gga aaa atc gat ttt gtc ctg att     2160
Val Ala Arg Ala Asp Leu Asp Asp Gly Lys Ile Asp Phe Val Leu Ile
705                 710                 715                 720 gcc ggg ggg agc ggc agg ggg cgg aaa gtt aaa tca tcc gcg tct gcc     2208
Ala Gly Gly Ser Gly Arg Gly Arg Lys Val Lys Ser Ser Ala Ser Ala
                725                 730                 735 aaa ccg gca ggg acg gcg ggg aaa ggg aag ccg aaa acc gcc gcc gag     2256
Lys Pro Ala Gly Thr Ala Gly Lys Gly Lys Pro Lys Thr Ala Ala Glu
            740                 745                 750 aaa aaa aca gcc cga ggc ggc aaa gta agg gga agg ggc gcg tct gcc     2304
Lys Lys Thr Ala Arg Gly Gly Lys Val Arg Gly Arg Gly Ala Ser Ala
        755                 760                 765 gcc gca gaa tcg agg aaa aag gca aag aaa ccg gtt ccg att aag gta     2352
Ala Ala Glu Ser Arg Lys Lys Ala Lys Lys Pro Val Pro Ile Lys Val
770                 775                 780 aaa aaa cgg aaa ggc aaa tca                                         2373
Lys Lys Arg Lys Gly Lys Ser
785                 790
```

<210> SEQ ID NO 16
<211> LENGTH: 791
<212> TYPE: PRT
<213> ORGANISM: Neisseria meningitidis

<400> SEQUENCE: 16

```
Met Asn Lys Asn Ile Lys Ser Leu Asn Leu Arg Glu Lys Asp Pro Phe
1               5                   10                  15

Leu Ser Arg Glu Lys Gln Arg Tyr Glu His Pro Leu Pro Ser Arg Glu
            20                  25                  30

Trp Ile Ile Glu Leu Leu Glu Arg Lys Gly Val Pro Ser Lys Ile Glu
        35                  40                  45

Ala Leu Val Arg Glu Leu Ser Ile Lys Glu Glu Tyr Glu Phe Phe
    50                  55                  60

Glu Arg Arg Leu Lys Ala Met Ala Arg Asp Gly Gln Val Leu Ile Asn
65                  70                  75                  80

Arg Arg Gly Ala Val Cys Ala Ala Asp Lys Leu Asp Leu Val Lys Cys
                85                  90                  95

Arg Val Glu Ala His Lys Asp Gly Phe Gly Phe Ala Val Pro Leu Thr
            100                 105                 110

Pro Ala Lys Asp Gly Asp Phe Val Leu Tyr Glu Arg Gln Met Arg Gly
        115                 120                 125

Ile Met His Gly Asp Ile Val Thr Val Arg Pro Ala Gly Met Asp Arg
    130                 135                 140

Arg Gly Arg Arg Glu Gly Thr Val Leu Asp Ile Val Glu Arg Ala Gln
145                 150                 155                 160

Ser Lys Val Val Gly Arg Phe Tyr Met Asp Arg Gly Val Ala Ile Leu
                165                 170                 175

Glu Pro Glu Asp Lys Arg Leu Asn Gln Ser Ile Val Leu Glu Pro Asp
            180                 185                 190

Gly Val Ala Arg Phe Lys Pro Glu Ser Gly Gln Val Ile Val Gly Glu
        195                 200                 205
```

```
Ile Glu Val Tyr Pro Glu Gln Asn Arg Pro Ala Val Ala Lys Ile Ile
210                 215                 220

Glu Val Leu Gly Asp Tyr Ala Asp Ser Gly Met Glu Ile Glu Ile Ala
225                 230                 235                 240

Val Arg Lys His His Leu Pro His Gln Phe Ser Glu Ala Cys Ala Lys
                245                 250                 255

Ala Ala Lys Lys Ile Pro Asp His Val Arg Lys Ser Asp Leu Lys Gly
            260                 265                 270

Arg Val Asp Leu Arg Asp Leu Pro Leu Val Thr Ile Asp Gly Glu Thr
        275                 280                 285

Ala Arg Asp Phe Asp Asp Ala Val Phe Ala Glu Lys Ile Gly Arg Asn
    290                 295                 300

Tyr Arg Leu Val Val Ala Ile Ala Asp Val Ser His Tyr Val Arg Pro
305                 310                 315                 320

Asp Asp Ala Ile Asp Thr Asp Ala Gln Glu Arg Ser Thr Ser Val Tyr
                325                 330                 335

Phe Pro Arg Arg Val Ile Pro Met Leu Pro Glu Asn Leu Ser Asn Gly
                340                 345                 350

Ile Cys Ser Leu Asn Pro His Val Glu Arg Leu Cys Val Val Cys Asp
            355                 360                 365

Met Val Ile Thr Tyr Ala Gly Asn Ile Lys Glu Tyr Arg Phe Tyr Pro
370                 375                 380

Ala Val Met Arg Ser His Ala Arg Leu Thr Tyr Asn Gln Val Trp Lys
385                 390                 395                 400

Trp Leu Ser Gly Gly Ile Glu His Pro Phe Lys Thr Gln Ile Asp Thr
                405                 410                 415

Leu Tyr Lys Leu Phe Lys Ile Leu Gln Lys Lys Arg Phe Glu Arg Gly
            420                 425                 430

Ala Val Glu Phe Asp Ser Ile Glu Thr Gln Met Leu Phe Asp Asp Asn
        435                 440                 445

Gly Lys Ile Glu Lys Ile Val Pro Val Val Arg Asn Asp Ala His Lys
    450                 455                 460

Leu Ile Glu Glu Cys Met Leu Ala Ala Asn Val Cys Ala Ala Asp Phe
465                 470                 475                 480

Leu Leu Lys Asn Lys His Thr Ala Leu Phe Arg Asn His Leu Gly Pro
                485                 490                 495

Thr Pro Glu Lys Leu Ala Ala Leu Arg Glu Gln Leu Gly Leu Leu Gly
            500                 505                 510

Leu Gln Leu Gly Gly Gly Asp Asn Pro Ser Pro Lys Asp Tyr Ala Ala
        515                 520                 525

Leu Ala Gly Gln Phe Lys Gly Arg Pro Asp Ala Glu Leu Leu Gln Val
    530                 535                 540

Met Met Leu Arg Ser Met Gln Gln Ala Val Tyr Glu Pro His Cys Asp
545                 550                 555                 560

Gly His Phe Gly Leu Ala Tyr Glu Ala Tyr Ala His Phe Thr Ser Pro
                565                 570                 575

Ile Arg Arg Tyr Pro Asp Leu Thr Val His Arg Ala Ile Lys Ala Val
            580                 585                 590

Leu Asn Gln Gln Thr Tyr Thr Pro Lys Lys Ser Trp Gln Ala Leu Gly
        595                 600                 605

Val His Thr Ser Phe Cys Glu Arg Arg Ala Asp Asp Ala Ser Arg Asp
610                 615                 620
```

```
Val Glu Asn Trp Leu Lys Thr Tyr Tyr Met Arg Asp Lys Val Gly Glu
625                 630                 635                 640

Val Phe Glu Gly Lys Ile Ser Gly Met Thr Ser Phe Gly Ile Phe Val
            645                 650                 655

Thr Leu Asp Gly Ile His Ile Asp Gly Leu Val His Ile Ser Asp Leu
                660                 665                 670

Gly Glu Asp Tyr Phe Asn Phe Arg Pro Glu Ile Met Ala Ile Glu Gly
            675                 680                 685

Glu Arg Ser Gly Ile Arg Phe Asn Met Gly Asp Arg Val Ala Val Arg
690                 695                 700

Val Ala Arg Ala Asp Leu Asp Asp Gly Lys Ile Asp Phe Val Leu Ile
705                 710                 715                 720

Ala Gly Gly Ser Gly Arg Gly Arg Lys Val Lys Ser Ser Ala Ser Ala
                725                 730                 735

Lys Pro Ala Gly Thr Ala Gly Lys Gly Lys Pro Lys Thr Ala Ala Glu
                740                 745                 750

Lys Lys Thr Ala Arg Gly Gly Lys Val Arg Gly Arg Gly Ala Ser Ala
            755                 760                 765

Ala Ala Glu Ser Arg Lys Lys Ala Lys Lys Pro Val Pro Ile Lys Val
770                 775                 780

Lys Lys Arg Lys Gly Lys Ser
785                 790

<210> SEQ ID NO 17
<211> LENGTH: 1605
<212> TYPE: DNA
<213> ORGANISM: Neisseria meningitidis
<220> FEATURE:
<221> NAME/KEY: CDS
<222> LOCATION: (1)..(1605)
<223> OTHER INFORMATION: NMA1555

<400> SEQUENCE: 17 atg agt atc gta gaa atc aaa gtc ccc gat atc ggc ggt cac gaa aac       48
Met Ser Ile Val Glu Ile Lys Val Pro Asp Ile Gly Gly His Glu Asn
1               5                   10                  15 gtc gac atc atc gcc gta gaa gtt aaa gcg ggc gac acc atc gcc gtt       96
Val Asp Ile Ile Ala Val Glu Val Lys Ala Gly Asp Thr Ile Ala Val
                20                  25                  30 gac gac acc ctg att aca ctg gaa acc gac aaa gcc acg atg gat gtg      144
Asp Asp Thr Leu Ile Thr Leu Glu Thr Asp Lys Ala Thr Met Asp Val
            35                  40                  45 cct gcc gat gcg gcc ggt gtc gtg aaa gaa gtg aaa gtc aaa gtc ggc      192
Pro Ala Asp Ala Ala Gly Val Val Lys Glu Val Lys Val Lys Val Gly
50                  55                  60 gac aaa atc tcc gaa ggc ggc gta att ctg acc gtt gaa acc ggt gcc      240
Asp Lys Ile Ser Glu Gly Gly Val Ile Leu Thr Val Glu Thr Gly Ala
65                  70                  75                  80 gcc gcc gcc gaa gcc gcc ccg gct gct gcc gaa gca caa cct gca cct      288
Ala Ala Ala Glu Ala Ala Pro Ala Ala Ala Glu Ala Gln Pro Ala Pro
                85                  90                  95 gct gcc gca ccc gct gcc gca ggc ggt gca acc gtt caa gta gcc gtt      336
Ala Ala Ala Pro Ala Ala Ala Gly Gly Ala Thr Val Gln Val Ala Val
            100                 105                 110 ccc gat atc ggc ggc cat acc gat gtg gat gta atc gcc gtt gaa atc      384
Pro Asp Ile Gly Gly His Thr Asp Val Asp Val Ile Ala Val Glu Ile
        115                 120                 125 aaa gtg ggc gac acc gtt gcc gaa gac gac acg ctg att act ttg gaa      432
Lys Val Gly Asp Thr Val Ala Glu Asp Asp Thr Leu Ile Thr Leu Glu
```

-continued

|  |  |  |  |  |  |  |  |  |  |  |  |  |  |  |  |
|---|---|---|---|---|---|---|---|---|---|---|---|---|---|---|---|
|  |  | 130 |  |  |  | 135 |  |  |  | 140 |  |  |  |  |  |

```
acc gat aaa gcg aca atg gac gta cct tgt acc gct gcc ggt gtc gtt    480
Thr Asp Lys Ala Thr Met Asp Val Pro Cys Thr Ala Ala Gly Val Val
145             150                 155                 160 aaa gcc gta ttc tta aaa gtc ggc gac aaa gta tcc gaa ggc tct gcc    528
Lys Ala Val Phe Leu Lys Val Gly Asp Lys Val Ser Glu Gly Ser Ala
            165                 170                 175 att atc gaa gta gaa acc gtc ggc tct gcc gca gca gcc cct gct caa    576
Ile Ile Glu Val Glu Thr Val Gly Ser Ala Ala Ala Pro Ala Gln
        180                 185                 190 gcc gct caa gct gcc gca ccg gct gcc gct ccg cct ccg act gct gcc    624
Ala Ala Gln Ala Ala Ala Pro Ala Ala Ala Pro Pro Pro Thr Ala Ala
                195                 200                 205 gcc gca ccc gcc gcc gcg cct gca cct tct gca cct gcc gct gcc aaa    672
Ala Ala Pro Ala Ala Ala Pro Ala Pro Ser Ala Pro Ala Ala Ala Lys
    210                 215                 220 atc gac gag gcc gct ttc gcc aaa gca cac gcc ggc cct tcc gca cgc    720
Ile Asp Glu Ala Ala Phe Ala Lys Ala His Ala Gly Pro Ser Ala Arg
225                 230                 235                 240 aaa ctg gcg cgc gaa ttg ggc gtg gat ttg ggc caa gtc aaa ggt acc    768
Lys Leu Ala Arg Glu Leu Gly Val Asp Leu Gly Gln Val Lys Gly Thr
            245                 250                 255 ggc ttg aaa ggc cgc atc gtg ggc gac gac atc aaa gcc ttt gtg aaa    816
Gly Leu Lys Gly Arg Ile Val Gly Asp Asp Ile Lys Ala Phe Val Lys
        260                 265                 270 tcc gta atg cag ggc ggc gcg gca aaa cct gcc gca gtc ggc gcg tct    864
Ser Val Met Gln Gly Gly Ala Ala Lys Pro Ala Ala Val Gly Ala Ser
                275                 280                 285 tta ggc ggc ggt ctg gac ttg ctg ccc tgg cct aaa gtg gac ttc tcc    912
Leu Gly Gly Gly Leu Asp Leu Leu Pro Trp Pro Lys Val Asp Phe Ser
    290                 295                 300 aaa ttc ggt aat gtc gaa gtt aaa gaa ttg tcc cgc att aag aaa att    960
Lys Phe Gly Asn Val Glu Val Lys Glu Leu Ser Arg Ile Lys Lys Ile
305                 310                 315                 320 tcc ggt caa aac ctg tct cgc aac tgg gtg gtg att ccc cac gtt acc   1008
Ser Gly Gln Asn Leu Ser Arg Asn Trp Val Val Ile Pro His Val Thr
            325                 330                 335 gta cac gaa gaa gca gat atg acc gag ctg gaa gaa ttc cgc aaa caa   1056
Val His Glu Glu Ala Asp Met Thr Glu Leu Glu Glu Phe Arg Lys Gln
        340                 345                 350 ctg aac aaa gaa tgg gaa cgc gaa ggc gtg aaa ctg tca ccg ttg gcg   1104
Leu Asn Lys Glu Trp Glu Arg Glu Gly Val Lys Leu Ser Pro Leu Ala
                355                 360                 365 ttc atc atc aaa gcc tcc gtt tcc gcg ctg aaa gcc ttc ccc gaa ttc   1152
Phe Ile Ile Lys Ala Ser Val Ser Ala Leu Lys Ala Phe Pro Glu Phe
    370                 375                 380 aac gct tct ctg gac ggc gac aac ttg gtg ctg aaa aac tac ttc aac   1200
Asn Ala Ser Leu Asp Gly Asp Asn Leu Val Leu Lys Asn Tyr Phe Asn
385                 390                 395                 400 atc ggt ttc gca gca gac acg ccg aac ggc ttg gtt gtt cca gta atc   1248
Ile Gly Phe Ala Ala Asp Thr Pro Asn Gly Leu Val Val Pro Val Ile
            405                 410                 415 aaa gac gtg gat caa aaa ggc ttg aaa caa atc agc caa gag ctg acc   1296
Lys Asp Val Asp Gln Lys Gly Leu Lys Gln Ile Ser Gln Glu Leu Thr
        420                 425                 430 gaa ttg tct aaa aaa gcc cgc gaa ggc aag ctc aaa cca caa gaa atg   1344
Glu Leu Ser Lys Lys Ala Arg Glu Gly Lys Leu Lys Pro Gln Glu Met
                435                 440                 445 caa ggc gca tgc ttt acc att tcc agc ttg ggc ggc atc ggc ggc aca   1392
Gln Gly Ala Cys Phe Thr Ile Ser Ser Leu Gly Gly Ile Gly Gly Thr
```

-continued

```
                Gln Gly Ala Cys Phe Thr Ile Ser Ser Leu Gly Ile Gly Gly Thr
                    450                 455                 460 ggt ttc acg ccg att gtg aac gct ccc gaa gtc gcc atc ttg ggc gtg         1440
Gly Phe Thr Pro Ile Val Asn Ala Pro Glu Val Ala Ile Leu Gly Val
465                 470                 475                 480 tgc aaa tcc caa atc aaa ccg gtt tgg aac ggc aaa gaa ttc gct cct         1488
Cys Lys Ser Gln Ile Lys Pro Val Trp Asn Gly Lys Glu Phe Ala Pro
                    485                 490                 495 cgc ctg atg tgc cca ttg agc ctg tcc ttt gac cac cgt gtc atc gac         1536
Arg Leu Met Cys Pro Leu Ser Leu Ser Phe Asp His Arg Val Ile Asp
                500                 505                 510 ggc gcg gcc ggt atg cgc ttc acc gta ttc ctg gcc aac ctg ttg aaa         1584
Gly Ala Ala Gly Met Arg Phe Thr Val Phe Leu Ala Asn Leu Leu Lys
            515                 520                 525 gac ttc cgc cgc att act ctg                                              1605
Asp Phe Arg Arg Ile Thr Leu
        530                 535

<210> SEQ ID NO 18
<211> LENGTH: 535
<212> TYPE: PRT
<213> ORGANISM: Neisseria meningitidis

<400> SEQUENCE: 18

Met Ser Ile Val Glu Ile Lys Val Pro Asp Ile Gly Gly His Glu Asn
1               5                   10                  15

Val Asp Ile Ile Ala Val Glu Val Lys Ala Gly Asp Thr Ile Ala Val
                20                  25                  30

Asp Asp Thr Leu Ile Thr Leu Glu Thr Asp Lys Ala Thr Met Asp Val
            35                  40                  45

Pro Ala Asp Ala Ala Gly Val Val Lys Glu Val Lys Val Lys Val Gly
    50                  55                  60

Asp Lys Ile Ser Glu Gly Gly Val Ile Leu Thr Val Glu Thr Gly Ala
65                  70                  75                  80

Ala Ala Ala Glu Ala Ala Pro Ala Ala Glu Ala Gln Pro Ala Pro
                85                  90                  95

Ala Ala Ala Pro Ala Ala Ala Gly Gly Ala Thr Val Gln Val Ala Val
                100                 105                 110

Pro Asp Ile Gly Gly His Thr Asp Val Asp Val Ile Ala Val Glu Ile
            115                 120                 125

Lys Val Gly Asp Thr Val Ala Glu Asp Asp Thr Leu Ile Thr Leu Glu
    130                 135                 140

Thr Asp Lys Ala Thr Met Asp Val Pro Cys Thr Ala Ala Gly Val Val
145                 150                 155                 160

Lys Ala Val Phe Leu Lys Val Gly Asp Lys Val Ser Glu Gly Ser Ala
                165                 170                 175

Ile Ile Glu Val Glu Thr Val Gly Ser Ala Ala Ala Pro Ala Gln
                180                 185                 190

Ala Ala Gln Ala Ala Ala Pro Ala Ala Pro Pro Thr Ala Ala
            195                 200                 205

Ala Ala Pro Ala Ala Pro Ala Pro Ser Ala Pro Ala Ala Ala Lys
    210                 215                 220

Ile Asp Glu Ala Ala Phe Ala Lys Ala His Ala Gly Pro Ser Ala Arg
225                 230                 235                 240

Lys Leu Ala Arg Glu Leu Gly Val Asp Leu Gly Gln Val Lys Gly Thr
                245                 250                 255
```

```
Gly Leu Lys Gly Arg Ile Val Gly Asp Asp Ile Lys Ala Phe Val Lys
                260                 265                 270

Ser Val Met Gln Gly Gly Ala Ala Lys Pro Ala Ala Val Gly Ala Ser
            275                 280                 285

Leu Gly Gly Gly Leu Asp Leu Leu Pro Trp Pro Lys Val Asp Phe Ser
        290                 295                 300

Lys Phe Gly Asn Val Glu Val Lys Glu Leu Ser Arg Ile Lys Lys Ile
305                 310                 315                 320

Ser Gly Gln Asn Leu Ser Arg Asn Trp Val Val Ile Pro His Val Thr
                325                 330                 335

Val His Glu Glu Ala Asp Met Thr Glu Leu Glu Glu Phe Arg Lys Gln
            340                 345                 350

Leu Asn Lys Glu Trp Glu Arg Glu Gly Val Lys Leu Ser Pro Leu Ala
        355                 360                 365

Phe Ile Ile Lys Ala Ser Val Ser Ala Leu Lys Ala Phe Pro Glu Phe
    370                 375                 380

Asn Ala Ser Leu Asp Gly Asp Asn Leu Val Leu Lys Asn Tyr Phe Asn
385                 390                 395                 400

Ile Gly Phe Ala Ala Asp Thr Pro Asn Gly Leu Val Val Pro Val Ile
                405                 410                 415

Lys Asp Val Asp Gln Lys Gly Leu Lys Gln Ile Ser Gln Glu Leu Thr
            420                 425                 430

Glu Leu Ser Lys Lys Ala Arg Glu Gly Lys Leu Lys Pro Gln Glu Met
        435                 440                 445

Gln Gly Ala Cys Phe Thr Ile Ser Ser Leu Gly Gly Ile Gly Gly Thr
    450                 455                 460

Gly Phe Thr Pro Ile Val Asn Ala Pro Glu Val Ala Ile Leu Gly Val
465                 470                 475                 480

Cys Lys Ser Gln Ile Lys Pro Val Trp Asn Gly Lys Glu Phe Ala Pro
                485                 490                 495

Arg Leu Met Cys Pro Leu Ser Leu Ser Phe Asp His Arg Val Ile Asp
            500                 505                 510

Gly Ala Ala Gly Met Arg Phe Thr Val Phe Leu Ala Asn Leu Leu Lys
        515                 520                 525

Asp Phe Arg Arg Ile Thr Leu
        530                 535

<210> SEQ ID NO 19
<211> LENGTH: 321
<212> TYPE: DNA
<213> ORGANISM: Neisseria meningitidis
<220> FEATURE:
<221> NAME/KEY: CDS
<222> LOCATION: (1)..(321)
<223> OTHER INFORMATION: NMA0039

<400> SEQUENCE: 19 atg ttt aag gac gaa cta aat gaa ttt atc cga ttg ata tcc gat ccg      48
Met Phe Lys Asp Glu Leu Asn Glu Phe Ile Arg Leu Ile Ser Asp Pro
1               5                   10                  15 gaa agt gaa ttg gat gaa tgg tat ttg agt gat ttt aaa gat gaa cat      96
Glu Ser Glu Leu Asp Glu Trp Tyr Leu Ser Asp Phe Lys Asp Glu His
            20                  25                  30 ata tgg gaa atg caa agt tac gaa gca ttt tca tgt ttg cgg gaa gca     144
Ile Trp Glu Met Gln Ser Tyr Glu Ala Phe Ser Cys Leu Arg Glu Ala
        35                  40                  45 gtc ccc tat ttg ttt gct tat ccc cga tac ggg tat gaa ctg ttg gag     192
```

```
Val Pro Tyr Leu Phe Ala Tyr Pro Arg Tyr Gly Tyr Glu Leu Leu Glu
     50                  55                  60 ata att tcc gcg tta aaa gaa aca tct gat acg aca gaa tta ttt tat      240
Ile Ile Ser Ala Leu Lys Glu Thr Ser Asp Thr Thr Glu Leu Phe Tyr
 65                  70                  75                  80 gag ccg ggt atc gtg cct ttg ctg att gct tta tat aaa gaa gat agt      288
Glu Pro Gly Ile Val Pro Leu Leu Ile Ala Leu Tyr Lys Glu Asp Ser
                     85                  90                  95 tat ctg gta aat atg gtc aaa cgg ata ttc aaa                          321
Tyr Leu Val Asn Met Val Lys Arg Ile Phe Lys
                100                 105

<210> SEQ ID NO 20
<211> LENGTH: 107
<212> TYPE: PRT
<213> ORGANISM: Neisseria meningitidis

<400> SEQUENCE: 20

Met Phe Lys Asp Glu Leu Asn Glu Phe Ile Arg Leu Ile Ser Asp Pro
 1               5                  10                  15

Glu Ser Glu Leu Asp Glu Trp Tyr Leu Ser Asp Phe Lys Asp Glu His
                20                  25                  30

Ile Trp Glu Met Gln Ser Tyr Glu Ala Phe Ser Cys Leu Arg Glu Ala
             35                  40                  45

Val Pro Tyr Leu Phe Ala Tyr Pro Arg Tyr Gly Tyr Glu Leu Leu Glu
     50                  55                  60

Ile Ile Ser Ala Leu Lys Glu Thr Ser Asp Thr Thr Glu Leu Phe Tyr
 65                  70                  75                  80

Glu Pro Gly Ile Val Pro Leu Leu Ile Ala Leu Tyr Lys Glu Asp Ser
                     85                  90                  95

Tyr Leu Val Asn Met Val Lys Arg Ile Phe Lys
                100                 105

<210> SEQ ID NO 21
<211> LENGTH: 279
<212> TYPE: DNA
<213> ORGANISM: Neisseria meningitidis
<220> FEATURE:
<221> NAME/KEY: CDS
<222> LOCATION: (1)..(279)
<223> OTHER INFORMATION: NMA0038

<400> SEQUENCE: 21 atg gaa aac ggg caa cgg aat aac cgg ttt cct ttg gaa aaa cga att       48
Met Glu Asn Gly Gln Arg Asn Asn Arg Phe Pro Leu Glu Lys Arg Ile
 1               5                  10                  15 ttt tat ctg gag cat tcg ggg cgg tat ctg atg att tgc gcc tta tcg       96
Phe Tyr Leu Glu His Ser Gly Arg Tyr Leu Met Ile Cys Ala Leu Ser
                20                  25                  30 gat tat tcc caa aac aaa cat act gtc gtt atg gca aat ttc atc tat      144
Asp Tyr Ser Gln Asn Lys His Thr Val Val Met Ala Asn Phe Ile Tyr
             35                  40                  45 ccg gat gaa aaa acg gat tgg cgg aat ttg gat gat tta ttc aat gag      192
Pro Asp Glu Lys Thr Asp Trp Arg Asn Leu Asp Asp Leu Phe Asn Glu
     50                  55                  60 ttg gtt tta gag gaa ttg cag gct tca ttt atg gat tgg cat ccg act      240
Leu Val Leu Glu Glu Leu Gln Ala Ser Phe Met Asp Trp His Pro Thr
 65                  70                  75                  80 gtt gaa gag gca atc agc cgt cat ttg gaa gac ttt tcg                  279
Val Glu Glu Ala Ile Ser Arg His Leu Glu Asp Phe Ser
                     85                  90
```

<210> SEQ ID NO 22
<211> LENGTH: 93
<212> TYPE: PRT
<213> ORGANISM: Neisseria meningitidis

<400> SEQUENCE: 22

```
Met Glu Asn Gly Gln Arg Asn Asn Arg Phe Pro Leu Glu Lys Arg Ile
1               5                   10                  15

Phe Tyr Leu Glu His Ser Gly Arg Tyr Leu Met Ile Cys Ala Leu Ser
            20                  25                  30

Asp Tyr Ser Gln Asn Lys His Thr Val Val Met Ala Asn Phe Ile Tyr
        35                  40                  45

Pro Asp Glu Lys Thr Asp Trp Arg Asn Leu Asp Asp Leu Phe Asn Glu
    50                  55                  60

Leu Val Leu Glu Glu Leu Gln Ala Ser Phe Met Asp Trp His Pro Thr
65                  70                  75                  80

Val Glu Glu Ala Ile Ser Arg His Leu Glu Asp Phe Ser
                85                  90
```

<210> SEQ ID NO 23
<211> LENGTH: 471
<212> TYPE: DNA
<213> ORGANISM: Neisseria meningitidis
<220> FEATURE:
<221> NAME/KEY: CDS
<222> LOCATION: (1)..(471)
<223> OTHER INFORMATION: NMB0222

<400> SEQUENCE: 23

```
atg aac ctt gat tta acc gcg caa aaa gtc cgt ctt tct tgg aag gat      48
Met Asn Leu Asp Leu Thr Ala Gln Lys Val Arg Leu Ser Trp Lys Asp
1               5                   10                  15 att ctg tgg ggg tat ggg aat aaa tac ttg ggt tgg gct gat gtg gca      96
Ile Leu Trp Gly Tyr Gly Asn Lys Tyr Leu Gly Trp Ala Asp Val Ala
            20                  25                  30 gct tat gcc cga aaa atg acg ctt tca gat cat gat gaa cgt gtg ttc     144
Ala Tyr Ala Arg Lys Met Thr Leu Ser Asp His Asp Glu Arg Val Phe
        35                  40                  45 aaa cta tct tta atc aac aaa tcc aat att ctt gaa tta aag cct gtt     192
Lys Leu Ser Leu Ile Asn Lys Ser Asn Ile Leu Glu Leu Lys Pro Val
    50                  55                  60 ctg gaa gat ttg gct tcg gaa atg agg gat tat tcc cct aaa aat tgg     240
Leu Glu Asp Leu Ala Ser Glu Met Arg Asp Tyr Ser Pro Lys Asn Trp
65                  70                  75                  80 ctg tac gtc ctc tta agc gat gta ttc cat aga aaa gaa gaa ttt gag     288
Leu Tyr Val Leu Leu Ser Asp Val Phe His Arg Lys Glu Glu Phe Glu
                85                  90                  95 gat cct ttg ggg gaa gtt gaa aaa att tat gca gat ttt gat tat ccg     336
Asp Pro Leu Gly Glu Val Glu Lys Ile Tyr Ala Asp Phe Asp Tyr Pro
            100                 105                 110 gaa gaa ata gaa tca ttt gtc agg tat atg ccg ccc aaa gac ggt tat     384
Glu Glu Ile Glu Ser Phe Val Arg Tyr Met Pro Pro Lys Asp Gly Tyr
        115                 120                 125 att cct tct gcc cac acc tat gaa gaa aat att gcc cgg tta tat tct     432
Ile Pro Ser Ala His Thr Tyr Glu Glu Asn Ile Ala Arg Leu Tyr Ser
    130                 135                 140 cac tgg gaa cac tat ttg aac aac ggc gga ggg cag ggt                 471
His Trp Glu His Tyr Leu Asn Asn Gly Gly Gly Gln Gly
145                 150                 155
```

<210> SEQ ID NO 24
<211> LENGTH: 157
<212> TYPE: PRT
<213> ORGANISM: Neisseria meningitidis

<400> SEQUENCE: 24

Met Asn Leu Asp Leu Thr Ala Gln Lys Val Arg Leu Ser Trp Lys Asp
1               5                   10                  15

Ile Leu Trp Gly Tyr Gly Asn Lys Tyr Leu Gly Trp Ala Asp Val Ala
            20                  25                  30

Ala Tyr Ala Arg Lys Met Thr Leu Ser Asp His Asp Glu Arg Val Phe
        35                  40                  45

Lys Leu Ser Leu Ile Asn Lys Ser Asn Ile Leu Glu Leu Lys Pro Val
    50                  55                  60

Leu Glu Asp Leu Ala Ser Glu Met Arg Asp Tyr Ser Pro Lys Asn Trp
65                  70                  75                  80

Leu Tyr Val Leu Leu Ser Asp Val Phe His Arg Lys Glu Glu Phe Glu
                85                  90                  95

Asp Pro Leu Gly Glu Val Glu Lys Ile Tyr Ala Asp Phe Asp Tyr Pro
            100                 105                 110

Glu Glu Ile Glu Ser Phe Val Arg Tyr Met Pro Pro Lys Asp Gly Tyr
        115                 120                 125

Ile Pro Ser Ala His Thr Tyr Glu Glu Asn Ile Ala Arg Leu Tyr Ser
    130                 135                 140

His Trp Glu His Tyr Leu Asn Asn Gly Gly Gly Gln Gly
145                 150                 155

<210> SEQ ID NO 25
<211> LENGTH: 333
<212> TYPE: DNA
<213> ORGANISM: Neisseria meningitidis
<220> FEATURE:
<221> NAME/KEY: CDS
<222> LOCATION: (1)..(333)
<223> OTHER INFORMATION: NMA0036

<400> SEQUENCE: 25 atg acg gtt gat aag gaa caa gta gaa aag atg att tat tct gaa aat    48
Met Thr Val Asp Lys Glu Gln Val Glu Lys Met Ile Tyr Ser Glu Asn
1               5                   10                  15 aaa cag agt gtt att gac ggt atg ctc ggt atg acc ttc agc tcg gag    96
Lys Gln Ser Val Ile Asp Gly Met Leu Gly Met Thr Phe Ser Ser Glu
            20                  25                  30 gag gat gaa atc ccc tgg att tcc gag aag ttg acg gag ttg tcg aaa   144
Glu Asp Glu Ile Pro Trp Ile Ser Glu Lys Leu Thr Glu Leu Ser Lys
        35                  40                  45 cat aaa gac ttg gat att gcc aga ttg tca tta acc tgt ttc gga cat   192
His Lys Asp Leu Asp Ile Ala Arg Leu Ser Leu Thr Cys Phe Gly His
    50                  55                  60 ctc gcc agg atg cat gaa aat atc ggc gat tgc gat aaa gtg att gct   240
Leu Ala Arg Met His Glu Asn Ile Gly Asp Cys Asp Lys Val Ile Ala
65                  70                  75                  80 tta ttg ctc tca aaa caa ggt gat ccg gat ttt caa ggt ttt gcc gaa   288
Leu Leu Leu Ser Lys Gln Gly Asp Pro Asp Phe Gln Gly Phe Ala Glu
                85                  90                  95 gat gcg tta gac gag att tct tta ttt ata ttt aaa aag cgt ccg        333
Asp Ala Leu Asp Glu Ile Ser Leu Phe Ile Phe Lys Lys Arg Pro
            100                 105                 110

```
<210> SEQ ID NO 26
<211> LENGTH: 111
<212> TYPE: PRT
<213> ORGANISM: Neisseria meningitidis

<400> SEQUENCE: 26

Met Thr Val Asp Lys Glu Gln Val Glu Lys Met Ile Tyr Ser Glu Asn
1               5                   10                  15

Lys Gln Ser Val Ile Asp Gly Met Leu Gly Met Thr Phe Ser Ser Glu
            20                  25                  30

Glu Asp Glu Ile Pro Trp Ile Ser Glu Lys Leu Thr Glu Leu Ser Lys
        35                  40                  45

His Lys Asp Leu Asp Ile Ala Arg Leu Ser Leu Thr Cys Phe Gly His
    50                  55                  60

Leu Ala Arg Met His Glu Asn Ile Gly Asp Cys Asp Lys Val Ile Ala
65                  70                  75                  80

Leu Leu Leu Ser Lys Gln Gly Asp Pro Asp Phe Gln Gly Phe Ala Glu
                85                  90                  95

Asp Ala Leu Asp Glu Ile Ser Leu Phe Ile Phe Lys Lys Arg Pro
            100                 105                 110

<210> SEQ ID NO 27
<211> LENGTH: 1338
<212> TYPE: DNA
<213> ORGANISM: Neisseria meningitidis
<220> FEATURE:
<221> NAME/KEY: CDS
<222> LOCATION: (1)..(1338)
<223> OTHER INFORMATION: NMB1645

<400> SEQUENCE: 27
```

| | | | | | | | | | | | | | | | | |
|---|---|---|---|---|---|---|---|---|---|---|---|---|---|---|---|---|
| atg | ttg | aat | cca | tcc | cga | aaa | ctg | gtt | gag | ctg | gtc | cgt | att | ttg | gac | 48 |
| Met | Leu | Asn | Pro | Ser | Arg | Lys | Leu | Val | Glu | Leu | Val | Arg | Ile | Leu | Asp | |
| 1 | | | | 5 | | | | | 10 | | | | | 15 | | |
| gaa | ggc | ggt | ttt | att | ttc | agc | ggc | gat | ccc | gta | cag | gcg | acg | gag | gct | 96 |
| Glu | Gly | Gly | Phe | Ile | Phe | Ser | Gly | Asp | Pro | Val | Gln | Ala | Thr | Glu | Ala | |
| | | | 20 | | | | | 25 | | | | | 30 | | | |
| ttg | cgc | cgc | gtg | gac | ggc | agt | acg | gag | gaa | aaa | atc | atc | cgt | cgg | gcg | 144 |
| Leu | Arg | Arg | Val | Asp | Gly | Ser | Thr | Glu | Glu | Lys | Ile | Ile | Arg | Arg | Ala | |
| | 35 | | | | | 40 | | | | | 45 | | | | | |
| gag | atg | att | gac | agg | aac | cgt | atg | ctg | cgg | gag | acg | ttg | gaa | cgt | gtg | 192 |
| Glu | Met | Ile | Asp | Arg | Asn | Arg | Met | Leu | Arg | Glu | Thr | Leu | Glu | Arg | Val | |
| | 50 | | | | | 55 | | | | | 60 | | | | | |
| cgt | gcg | ggg | tcg | ttc | tgg | ttg | tgg | gtg | gtg | gcg | gcg | acg | ttt | gca | ttt | 240 |
| Arg | Ala | Gly | Ser | Phe | Trp | Leu | Trp | Val | Val | Ala | Ala | Thr | Phe | Ala | Phe | |
| 65 | | | | 70 | | | | | 75 | | | | | 80 | | |
| ttt | acc | ggt | ttt | tca | gtc | act | tat | ctt | cta | atg | gac | aat | cag | ggt | ctg | 288 |
| Phe | Thr | Gly | Phe | Ser | Val | Thr | Tyr | Leu | Leu | Met | Asp | Asn | Gln | Gly | Leu | |
| | | | | 85 | | | | | 90 | | | | | 95 | | |
| aat | ttc | ttt | ttg | gtt | ttg | gcg | ggc | gtg | ttg | ggc | atg | aat | acg | ctg | atg | 336 |
| Asn | Phe | Phe | Leu | Val | Leu | Ala | Gly | Val | Leu | Gly | Met | Asn | Thr | Leu | Met | |
| | | | 100 | | | | | 105 | | | | | 110 | | | |
| ctg | gca | gta | tgg | ttg | gca | atg | ttg | ttc | ctg | cgt | gtg | aaa | gtg | ggg | cgt | 384 |
| Leu | Ala | Val | Trp | Leu | Ala | Met | Leu | Phe | Leu | Arg | Val | Lys | Val | Gly | Arg | |
| | | 115 | | | | | 120 | | | | | 125 | | | | |
| ttt | ttc | agc | agt | ccg | gcg | acg | tgg | ttt | cgg | ggc | aaa | gac | cct | gta | aat | 432 |
| Phe | Phe | Ser | Ser | Pro | Ala | Thr | Trp | Phe | Arg | Gly | Lys | Asp | Pro | Val | Asn | |
| | | 130 | | | | | 135 | | | | | 140 | | | | |
| cag | gcg | gtg | ttg | cgg | ctg | tat | gcg | gac | gag | tgg | cgg | caa | cct | tcg | gta | 480 |
| Gln | Ala | Val | Leu | Arg | Leu | Tyr | Ala | Asp | Glu | Trp | Arg | Gln | Pro | Ser | Val | |
| 145 | | | | 150 | | | | | 155 | | | | | 160 | | |

```
cgt tgg aaa ata ggc gca acg tcg cac agc ctg tgg ctc tgc acg ctg      528
Arg Trp Lys Ile Gly Ala Thr Ser His Ser Leu Trp Leu Cys Thr Leu
            165                 170                 175 ctc gga atg ctg gtg tcg gta ttg ttg ctg ctt ttg gtg cgg caa tat      576
Leu Gly Met Leu Val Ser Val Leu Leu Leu Leu Val Arg Gln Tyr
            180                 185                 190 acg ttc aac tgg gaa agc acg ctg ttg agc aat gcc gct tcg gta cgc      624
Thr Phe Asn Trp Glu Ser Thr Leu Leu Ser Asn Ala Ala Ser Val Arg
            195                 200                 205 gcg gtg gaa atg ttg gca tgg ctg ccg tcg aaa ctc ggt ttc cct gtc      672
Ala Val Glu Met Leu Ala Trp Leu Pro Ser Lys Leu Gly Phe Pro Val
    210                 215                 220 ccc gat gcg cgg gcg gtc atc gaa ggc cgt ctg aac ggc aat att gcc      720
Pro Asp Ala Arg Ala Val Ile Glu Gly Arg Leu Asn Gly Asn Ile Ala
225                 230                 235                 240 gat gcg cgg gct tgg tcg ggg ctg ctg gtc ggc agt atc gcc tgc tac      768
Asp Ala Arg Ala Trp Ser Gly Leu Leu Val Gly Ser Ile Ala Cys Tyr
            245                 250                 255 ggc atc ctg ccg cgc ctg ctg gct tgg gta gtg tgt aaa atc ctt ttg      816
Gly Ile Leu Pro Arg Leu Leu Ala Trp Val Val Cys Lys Ile Leu Leu
            260                 265                 270 aaa aca agc gaa aac gga ttg gat ttg gaa aag ccc tat tat cag gcg      864
Lys Thr Ser Glu Asn Gly Leu Asp Leu Glu Lys Pro Tyr Tyr Gln Ala
            275                 280                 285 gtc atc cgc cgc tgg cag aac aaa atc acc gat gcg gat acg cgt cgg      912
Val Ile Arg Arg Trp Gln Asn Lys Ile Thr Asp Ala Asp Thr Arg Arg
            290                 295                 300 gaa acc gtg tcc gcc gtt tca ccg aaa atc atc ttg aac gat gcg ccg      960
Glu Thr Val Ser Ala Val Ser Pro Lys Ile Ile Leu Asn Asp Ala Pro
305                 310                 315                 320 aaa tgg gcg gtc atg ctg gag acc gag tgg cag gac ggc gaa tgg ttc     1008
Lys Trp Ala Val Met Leu Glu Thr Glu Trp Gln Asp Gly Glu Trp Phe
            325                 330                 335 gag ggc agg ctg gcg cag gaa tgg ctg gat aag ggc gtt gcc acc aat     1056
Glu Gly Arg Leu Ala Gln Glu Trp Leu Asp Lys Gly Val Ala Thr Asn
            340                 345                 350 cgg gaa cag gtt gcc gcg ctg gag aca gag ctg aag cag aaa ccg gcg     1104
Arg Glu Gln Val Ala Ala Leu Glu Thr Glu Leu Lys Gln Lys Pro Ala
            355                 360                 365 caa ctg ctt atc ggc gtg cgc gcc caa act gtg ccg gac cgc ggc gtg     1152
Gln Leu Leu Ile Gly Val Arg Ala Gln Thr Val Pro Asp Arg Gly Val
            370                 375                 380 ttg cgg cag att gtc cga ctc tcg gaa gcg gcg cag ggc ggc gcg gtg     1200
Leu Arg Gln Ile Val Arg Leu Ser Glu Ala Ala Gln Gly Gly Ala Val
385                 390                 395                 400 gtg cag ctt ttg gcg gaa cag ggg ctt tca gac gac ctt tcg gaa aag     1248
Val Gln Leu Leu Ala Glu Gln Gly Leu Ser Asp Asp Leu Ser Glu Lys
            405                 410                 415 ctg gaa cat tgg cgt aac gcg ctg gcc gaa tgc ggc gcg gcg tgg ctt     1296
Leu Glu His Trp Arg Asn Ala Leu Ala Glu Cys Gly Ala Ala Trp Leu
            420                 425                 430 gag cct gac agg gcg gcg cag gaa ggg cgt ttg aaa gac caa             1338
Glu Pro Asp Arg Ala Ala Gln Glu Gly Arg Leu Lys Asp Gln
            435                 440                 445

<210> SEQ ID NO 28
<211> LENGTH: 446
<212> TYPE: PRT
<213> ORGANISM: Neisseria meningitidis
```

<400> SEQUENCE: 28

```
Met Leu Asn Pro Ser Arg Lys Leu Val Glu Leu Val Arg Ile Leu Asp
1               5                   10                  15

Glu Gly Gly Phe Ile Phe Ser Gly Asp Pro Val Gln Ala Thr Glu Ala
            20                  25                  30

Leu Arg Arg Val Asp Gly Ser Thr Glu Glu Lys Ile Ile Arg Arg Ala
        35                  40                  45

Glu Met Ile Asp Arg Asn Arg Met Leu Arg Glu Thr Leu Glu Arg Val
50                  55                  60

Arg Ala Gly Ser Phe Trp Leu Trp Val Val Ala Ala Thr Phe Ala Phe
65                  70                  75                  80

Phe Thr Gly Phe Ser Val Thr Tyr Leu Leu Met Asp Asn Gln Gly Leu
                85                  90                  95

Asn Phe Phe Leu Val Leu Ala Gly Val Leu Gly Met Asn Thr Leu Met
            100                 105                 110

Leu Ala Val Trp Leu Ala Met Leu Phe Leu Arg Val Lys Val Gly Arg
        115                 120                 125

Phe Phe Ser Ser Pro Ala Thr Trp Phe Arg Gly Lys Asp Pro Val Asn
130                 135                 140

Gln Ala Val Leu Arg Leu Tyr Ala Asp Glu Trp Arg Gln Pro Ser Val
145                 150                 155                 160

Arg Trp Lys Ile Gly Ala Thr Ser His Ser Leu Trp Leu Cys Thr Leu
                165                 170                 175

Leu Gly Met Leu Val Ser Val Leu Leu Leu Leu Val Arg Gln Tyr
        180                 185                 190

Thr Phe Asn Trp Glu Ser Thr Leu Leu Ser Asn Ala Ala Ser Val Arg
                195                 200                 205

Ala Val Glu Met Leu Ala Trp Leu Pro Ser Lys Leu Gly Phe Pro Val
        210                 215                 220

Pro Asp Ala Arg Ala Val Ile Glu Gly Arg Leu Asn Gly Asn Ile Ala
225                 230                 235                 240

Asp Ala Arg Ala Trp Ser Gly Leu Leu Val Gly Ser Ile Ala Cys Tyr
                245                 250                 255

Gly Ile Leu Pro Arg Leu Leu Ala Trp Val Val Cys Lys Ile Leu Leu
            260                 265                 270

Lys Thr Ser Glu Asn Gly Leu Asp Leu Glu Lys Pro Tyr Tyr Gln Ala
        275                 280                 285

Val Ile Arg Arg Trp Gln Asn Lys Ile Thr Asp Ala Asp Thr Arg Arg
290                 295                 300

Glu Thr Val Ser Ala Val Ser Pro Lys Ile Ile Leu Asn Asp Ala Pro
305                 310                 315                 320

Lys Trp Ala Val Met Leu Glu Thr Glu Trp Gln Asp Gly Glu Trp Phe
                325                 330                 335

Glu Gly Arg Leu Ala Gln Glu Trp Leu Asp Lys Gly Val Ala Thr Asn
            340                 345                 350

Arg Glu Gln Val Ala Ala Leu Glu Thr Glu Leu Lys Gln Lys Pro Ala
        355                 360                 365

Gln Leu Leu Ile Gly Val Arg Ala Gln Thr Val Pro Asp Arg Gly Val
370                 375                 380

Leu Arg Gln Ile Val Arg Leu Ser Glu Ala Ala Gln Gly Gly Ala Val
385                 390                 395                 400

Val Gln Leu Leu Ala Glu Gln Gly Leu Ser Asp Asp Leu Ser Glu Lys
                405                 410                 415
```

```
Leu Glu His Trp Arg Asn Ala Leu Ala Glu Cys Gly Ala Ala Trp Leu
            420                 425                 430
Glu Pro Asp Arg Ala Ala Gln Glu Gly Arg Leu Lys Asp Gln
            435                 440                 445

<210> SEQ ID NO 29
<211> LENGTH: 1392
<212> TYPE: DNA
<213> ORGANISM: Neisseria meningitidis
<220> FEATURE:
<221> NAME/KEY: CDS
<222> LOCATION: (1)..(1392)
<223> OTHER INFORMATION: NMA1898

<400> SEQUENCE: 29 atg aac aaa caa ccc ctt tcc ctc gcc gtc gtc ggg cat acc aat acc      48
Met Asn Lys Gln Pro Leu Ser Leu Ala Val Val Gly His Thr Asn Thr
1               5                   10                  15 ggc aaa acc tcg ctc ctg cgc acc cta ttg cgc gac agc ggc ttc ggc      96
Gly Lys Thr Ser Leu Leu Arg Thr Leu Leu Arg Asp Ser Gly Phe Gly
            20                  25                  30 gaa gtc aaa aat gcc ccg tcc act acg cgc cat gtc gaa gaa gcc gcc     144
Glu Val Lys Asn Ala Pro Ser Thr Thr Arg His Val Glu Glu Ala Ala
        35                  40                  45 atc agc gac ggc gca gac acg ctg gtt ttc ctg tat gac acg ccc gga     192
Ile Ser Asp Gly Ala Asp Thr Leu Val Phe Leu Tyr Asp Thr Pro Gly
    50                  55                  60 ctc gaa gac gcg ggc ggt gtt ttg gaa tgg ctg gaa acc cat acg gat     240
Leu Glu Asp Ala Gly Gly Val Leu Glu Trp Leu Glu Thr His Thr Asp
65                  70                  75                  80 acg cgt tca gac ggc atc gaa cgg ctg caa cag ttt ctc ggc agc cac     288
Thr Arg Ser Asp Gly Ile Glu Arg Leu Gln Gln Phe Leu Gly Ser His
                85                  90                  95 ggc gcg cac cat gat ttc aat cag gaa gcc aaa gtc tta cgg caa gtc     336
Gly Ala His His Asp Phe Asn Gln Glu Ala Lys Val Leu Arg Gln Val
            100                 105                 110 ttg caa agc gat atg gca atg tac gtc atc gac gcg cgc gaa ccc gtc     384
Leu Gln Ser Asp Met Ala Met Tyr Val Ile Asp Ala Arg Glu Pro Val
        115                 120                 125 ctc gac aaa tac agg gac gag ttg acc atc ctt tca tgg tgt gcc aaa     432
Leu Asp Lys Tyr Arg Asp Glu Leu Thr Ile Leu Ser Trp Cys Ala Lys
    130                 135                 140 ccg gtt atg ccc gtg ttc aac ttt acc ggc gga cag cct ccc gaa tcg     480
Pro Val Met Pro Val Phe Asn Phe Thr Gly Gly Gln Pro Pro Glu Ser
145                 150                 155                 160 tgg aca acc atg ctg gcg agg aga aac ctg cac gtt ttc gca ggg ttc     528
Trp Thr Thr Met Leu Ala Arg Arg Asn Leu His Val Phe Ala Gly Phe
                165                 170                 175 gac acc gtc gcc ttt gat ttt gaa ggc gaa cta cgc ctg tgg gaa aac     576
Asp Thr Val Ala Phe Asp Phe Glu Gly Glu Leu Arg Leu Trp Glu Asn
            180                 185                 190 ctc gcc acc atg ttg ccc gaa cgc agc aca ctt gac cgc ctg aca gcc     624
Leu Ala Thr Met Leu Pro Glu Arg Ser Thr Leu Asp Arg Leu Thr Ala
        195                 200                 205 atg cgc cgg cgc gaa tgg cag cgg ctg gac ggc gaa gcg cgc cgc gaa     672
Met Arg Arg Arg Glu Trp Gln Arg Leu Asp Gly Glu Ala Arg Arg Glu
    210                 215                 220 atc gcc gac ttt tta att gat gcc gcc gcc ttc agg cag gaa gtg gac     720
Ile Ala Asp Phe Leu Ile Asp Ala Ala Ala Phe Arg Gln Glu Val Asp
225                 230                 235                 240
```

```
gaa aac gag gat acc gcc acc gtg ccg caa acc atg cag gcg gaa ata     768
Glu Asn Glu Asp Thr Ala Thr Val Pro Gln Thr Met Gln Ala Glu Ile
                245                 250                 255 cgc caa ctc gaa cgg cag atg cag cag cgg ctg ttt gcc ctt tac cgt     816
Arg Gln Leu Glu Arg Gln Met Gln Gln Arg Leu Phe Ala Leu Tyr Arg
            260                 265                 270 ttc tac cac agc gaa atc gac ggc ggc gac tgg atg ccg caa gcc ttc     864
Phe Tyr His Ser Glu Ile Asp Gly Gly Asp Trp Met Pro Gln Ala Phe
        275                 280                 285 cgc caa gac ccg ttc gac agc gaa ttg ctc aaa caa tac ggc atc cgc     912
Arg Gln Asp Pro Phe Asp Ser Glu Leu Leu Lys Gln Tyr Gly Ile Arg
    290                 295                 300 acc ggc acg ggc gcg gca acc ggc gcg ctc atc ggc ttg ggg ctg gac     960
Thr Gly Thr Gly Ala Ala Thr Gly Ala Leu Ile Gly Leu Gly Leu Asp
305                 310                 315                 320 atc gcc aca ctc ggc ggc tcg ctc gga ttg ggt acg gca atc ggc ggc    1008
Ile Ala Thr Leu Gly Gly Ser Leu Gly Leu Gly Thr Ala Ile Gly Gly
                325                 330                 335 ttt ttg ggc ggc atc ctg ccc aat acc cgc acc att tct gac aaa ctc    1056
Phe Leu Gly Gly Ile Leu Pro Asn Thr Arg Thr Ile Ser Asp Lys Leu
            340                 345                 350 gcc ggc cgt caa acc ctg cac acc gac ccc gaa acc ctg acc ctg ctc    1104
Ala Gly Arg Gln Thr Leu His Thr Asp Pro Glu Thr Leu Thr Leu Leu
        355                 360                 365 gcc gcc cgc gcc ctc gat ctg ctc cac gtc ctg caa acg cgc gga cac    1152
Ala Ala Arg Ala Leu Asp Leu Leu His Val Leu Gln Thr Arg Gly His
    370                 375                 380 gcg gca cag tcg gat atc gag ctg cac agc cgc aaa gtc ccg tgg gat    1200
Ala Ala Gln Ser Asp Ile Glu Leu His Ser Arg Lys Val Pro Trp Asp
385                 390                 395                 400 gcc gcc aga ctc ccg ccc gaa ctc aac aaa gcc cgc agt cat tgg aaa    1248
Ala Ala Arg Leu Pro Pro Glu Leu Asn Lys Ala Arg Ser His Trp Lys
                405                 410                 415 tgg tcg tcg ctc aat acg cac cgc ccg gaa acc agc cgc gcc gaa cgc    1296
Trp Ser Ser Leu Asn Thr His Arg Pro Glu Thr Ser Arg Ala Glu Arg
            420                 425                 430 gcc gga tat gtg gag aaa ctt caa atc cgc ctg tcg gga aaa tat agt    1344
Ala Gly Tyr Val Glu Lys Leu Gln Ile Arg Leu Ser Gly Lys Tyr Ser
        435                 440                 445 gaa tta aat tta aat cag gac aag gcg gcg agc cgc aga cag tac aaa    1392
Glu Leu Asn Leu Asn Gln Asp Lys Ala Ala Ser Arg Arg Gln Tyr Lys
    450                 455                 460

<210> SEQ ID NO 30
<211> LENGTH: 464
<212> TYPE: PRT
<213> ORGANISM: Neisseria meningitidis

<400> SEQUENCE: 30

Met Asn Lys Gln Pro Leu Ser Leu Ala Val Val Gly His Thr Asn Thr
1               5                   10                  15

Gly Lys Thr Ser Leu Leu Arg Thr Leu Leu Arg Asp Ser Gly Phe Gly
                20                  25                  30

Glu Val Lys Asn Ala Pro Ser Thr Thr Arg His Val Glu Glu Ala Ala
            35                  40                  45

Ile Ser Asp Gly Ala Asp Thr Leu Val Phe Leu Tyr Asp Thr Pro Gly
        50                  55                  60

Leu Glu Asp Ala Gly Gly Val Leu Glu Trp Leu Glu Thr His Thr Asp
65                  70                  75                  80
```

-continued

```
Thr Arg Ser Asp Gly Ile Glu Arg Leu Gln Gln Phe Leu Gly Ser His
                 85                  90                  95

Gly Ala His His Asp Phe Asn Gln Glu Ala Lys Val Leu Arg Gln Val
            100                 105                 110

Leu Gln Ser Asp Met Ala Met Tyr Val Ile Asp Ala Arg Glu Pro Val
        115                 120                 125

Leu Asp Lys Tyr Arg Asp Glu Leu Thr Ile Leu Ser Trp Cys Ala Lys
    130                 135                 140

Pro Val Met Pro Val Phe Asn Phe Thr Gly Gly Gln Pro Pro Glu Ser
145                 150                 155                 160

Trp Thr Thr Met Leu Ala Arg Arg Asn Leu His Val Phe Ala Gly Phe
                165                 170                 175

Asp Thr Val Ala Phe Asp Phe Glu Gly Glu Leu Arg Leu Trp Glu Asn
            180                 185                 190

Leu Ala Thr Met Leu Pro Glu Arg Ser Thr Leu Asp Arg Leu Thr Ala
        195                 200                 205

Met Arg Arg Arg Glu Trp Gln Arg Leu Asp Gly Glu Ala Arg Arg Glu
    210                 215                 220

Ile Ala Asp Phe Leu Ile Asp Ala Ala Ala Phe Arg Gln Glu Val Asp
225                 230                 235                 240

Glu Asn Glu Asp Thr Ala Thr Val Pro Gln Thr Met Gln Ala Glu Ile
                245                 250                 255

Arg Gln Leu Glu Arg Gln Met Gln Gln Arg Leu Phe Ala Leu Tyr Arg
            260                 265                 270

Phe Tyr His Ser Glu Ile Asp Gly Gly Asp Trp Met Pro Gln Ala Phe
        275                 280                 285

Arg Gln Asp Pro Phe Asp Ser Glu Leu Leu Lys Gln Tyr Gly Ile Arg
    290                 295                 300

Thr Gly Thr Gly Ala Ala Thr Gly Ala Leu Ile Gly Leu Gly Leu Asp
305                 310                 315                 320

Ile Ala Thr Leu Gly Gly Ser Leu Gly Leu Gly Thr Ala Ile Gly Gly
                325                 330                 335

Phe Leu Gly Gly Ile Leu Pro Asn Thr Arg Thr Ile Ser Asp Lys Leu
            340                 345                 350

Ala Gly Arg Gln Thr Leu His Thr Asp Pro Glu Thr Leu Thr Leu Leu
        355                 360                 365

Ala Ala Arg Ala Leu Asp Leu Leu His Val Leu Gln Thr Arg Gly His
    370                 375                 380

Ala Ala Gln Ser Asp Ile Glu Leu His Ser Arg Lys Val Pro Trp Asp
385                 390                 395                 400

Ala Ala Arg Leu Pro Pro Glu Leu Asn Lys Ala Arg Ser His Trp Lys
                405                 410                 415

Trp Ser Ser Leu Asn Thr His Arg Pro Glu Thr Ser Arg Ala Glu Arg
            420                 425                 430

Ala Gly Tyr Val Glu Lys Leu Gln Ile Arg Leu Ser Gly Lys Tyr Ser
        435                 440                 445

Glu Leu Asn Leu Asn Gln Asp Lys Ala Ala Ser Arg Arg Gln Tyr Lys
    450                 455                 460

<210> SEQ ID NO 31
<211> LENGTH: 2622
<212> TYPE: DNA
<213> ORGANISM: Neisseria meningitidis
<220> FEATURE:
<221> NAME/KEY: CDS
```

<222> LOCATION: (1)..(2622)
<223> OTHER INFORMATION: NMB1595

<400> SEQUENCE: 31

```
atg aaa acc tcc gaa ctg cgc caa aaa ttc cta aaa ttt ttt gaa acc      48
Met Lys Thr Ser Glu Leu Arg Gln Lys Phe Leu Lys Phe Phe Glu Thr
1               5                   10                  15 aaa ggc cac acc gtc gtc cgc tct tcc agc ctc gtg ccg cac gac gac      96
Lys Gly His Thr Val Val Arg Ser Ser Ser Leu Val Pro His Asp Asp
            20                  25                  30 ccg acc ctg ctg ttt acc aac gcg ggc atg aac cag ttt aaa gac gta     144
Pro Thr Leu Leu Phe Thr Asn Ala Gly Met Asn Gln Phe Lys Asp Val
        35                  40                  45 ttc tta ggt ttc gac aaa cgc ccg tac agc cgc gcc acc acc gcg caa     192
Phe Leu Gly Phe Asp Lys Arg Pro Tyr Ser Arg Ala Thr Thr Ala Gln
50                  55                  60 aaa tgc gta cgc gca ggc ggc aaa cac aac gac ttg gaa aac gtc ggc     240
Lys Cys Val Arg Ala Gly Gly Lys His Asn Asp Leu Glu Asn Val Gly
65                  70                  75                  80 tac acc gcc cgc cac cac acc ttc ttt gaa atg atg ggc aac ttc tcc     288
Tyr Thr Ala Arg His His Thr Phe Phe Glu Met Met Gly Asn Phe Ser
                85                  90                  95 ttc ggc gac tac ttc aaa cgc gac gcc atc cac ttc gct tgg gaa ttt     336
Phe Gly Asp Tyr Phe Lys Arg Asp Ala Ile His Phe Ala Trp Glu Phe
            100                 105                 110 ctg act tcc ccc gaa tgg ctc aac atc cct aaa gac aaa ctg ttg gcg     384
Leu Thr Ser Pro Glu Trp Leu Asn Ile Pro Lys Asp Lys Leu Leu Ala
        115                 120                 125 acc gtt tac gcg gaa gac gac gaa gcc tac aac atc tgg ttg aac gaa     432
Thr Val Tyr Ala Glu Asp Asp Glu Ala Tyr Asn Ile Trp Leu Asn Glu
    130                 135                 140 atc ggt atg ccg tcc gag cgc atc gtc cgc atc ggc gac aac aaa ggc     480
Ile Gly Met Pro Ser Glu Arg Ile Val Arg Ile Gly Asp Asn Lys Gly
145                 150                 155                 160 gcg aaa tac gca tcc gac aac ttc tgg caa atg ggc gac acc ggc cct     528
Ala Lys Tyr Ala Ser Asp Asn Phe Trp Gln Met Gly Asp Thr Gly Pro
                165                 170                 175 tgc ggc ccc tgc tcc gaa att ttc tac gac cac ggc gaa gaa atc tgg     576
Cys Gly Pro Cys Ser Glu Ile Phe Tyr Asp His Gly Glu Glu Ile Trp
            180                 185                 190 ggc ggc att ccc ggc agt ccc gaa gaa gac ggc gac cgc tgg atc gaa     624
Gly Gly Ile Pro Gly Ser Pro Glu Glu Asp Gly Asp Arg Trp Ile Glu
        195                 200                 205 att tgg aac tgc gta ttt atg cag ttc aac cgc gac gaa caa ggc aat     672
Ile Trp Asn Cys Val Phe Met Gln Phe Asn Arg Asp Glu Gln Gly Asn
    210                 215                 220 atg aac ccg ctt ccc aaa cct tcc gtc gat acc ggt atg ggc ttg gaa     720
Met Asn Pro Leu Pro Lys Pro Ser Val Asp Thr Gly Met Gly Leu Glu
225                 230                 235                 240 cgc ata gcc gcc gtc atg cag cat gtt cac agc aac tac gaa atc gac     768
Arg Ile Ala Ala Val Met Gln His Val His Ser Asn Tyr Glu Ile Asp
                245                 250                 255 ttg ttc caa gac ctg ctc aaa gcc gtt gcc cgc gaa acc ggc gcg ccg     816
Leu Phe Gln Asp Leu Leu Lys Ala Val Ala Arg Glu Thr Gly Ala Pro
            260                 265                 270 ttc aga atg gaa gaa ccc agc ctg aaa gtc atc gcc gac cac atc cgc     864
Phe Arg Met Glu Glu Pro Ser Leu Lys Val Ile Ala Asp His Ile Arg
        275                 280                 285 tcc tgc tcg ttc ctg att gca gac ggc gtc ttg cct tcc aac gaa ggc     912
Ser Cys Ser Phe Leu Ile Ala Asp Gly Val Leu Pro Ser Asn Glu Gly
```

```
                 290                 295                 300
cgc ggc tac gta ttg cgc cgc att atc cgc cgc gcc gtg cgc cac ggt        960
Arg Gly Tyr Val Leu Arg Arg Ile Ile Arg Arg Ala Val Arg His Gly
305                 310                 315                 320 tac aaa ctg ggt caa agc aaa ccg ttc ttc cac aaa ctc gtt gcc gat       1008
Tyr Lys Leu Gly Gln Ser Lys Pro Phe Phe His Lys Leu Val Ala Asp
                325                 330                 335 ttg gtc aaa gag atg ggc ggt gcc tac cct gaa ttg aaa gaa aaa caa       1056
Leu Val Lys Glu Met Gly Gly Ala Tyr Pro Glu Leu Lys Glu Lys Gln
            340                 345                 350 gcc caa atc gaa gaa gca ttg aaa aac gaa gaa agc cgt ttt gcc caa       1104
Ala Gln Ile Glu Glu Ala Leu Lys Asn Glu Glu Ser Arg Phe Ala Gln
        355                 360                 365 acg ctg gaa acc ggt atg gct ttg ttg gaa aac gcg ctg gtc aaa ggc       1152
Thr Leu Glu Thr Gly Met Ala Leu Leu Glu Asn Ala Leu Val Lys Gly
    370                 375                 380 ggc aaa aca ctc ggc ggc gaa atc atc ttc aaa ctc tac gat acc tac       1200
Gly Lys Thr Leu Gly Gly Glu Ile Ile Phe Lys Leu Tyr Asp Thr Tyr
385                 390                 395                 400 ggt ttc cca tac gac ttg act gcc gac atc tgc cgc gaa cgc aat atc       1248
Gly Phe Pro Tyr Asp Leu Thr Ala Asp Ile Cys Arg Glu Arg Asn Ile
                405                 410                 415 gaa ccg gac gaa gca ggc ttc gag cgc gaa atg gaa gcc caa cgc gca       1296
Glu Pro Asp Glu Ala Gly Phe Glu Arg Glu Met Glu Ala Gln Arg Ala
            420                 425                 430 cgc gca cgc gcc gcc caa agc ttc aaa gcc aac gcc caa ctg cct tat       1344
Arg Ala Arg Ala Ala Gln Ser Phe Lys Ala Asn Ala Gln Leu Pro Tyr
        435                 440                 445 gac ggt caa gac acc gag ttt aaa ggt tat agc gaa cgc caa acc gaa       1392
Asp Gly Gln Asp Thr Glu Phe Lys Gly Tyr Ser Glu Arg Gln Thr Glu
    450                 455                 460 tcc aaa gtc ctc gcc ctc tac aaa gac ggc gag caa gtc aac gaa ttg       1440
Ser Lys Val Leu Ala Leu Tyr Lys Asp Gly Glu Gln Val Asn Glu Leu
465                 470                 475                 480 aac gaa ggc gac agc ggc gca gtc gtc atc gac ttt acc ccg ttc tat       1488
Asn Glu Gly Asp Ser Gly Ala Val Val Ile Asp Phe Thr Pro Phe Tyr
                485                 490                 495 gca gaa tcc ggc ggc caa gtc ggc gat gtc ggc tat atc ttc tca ggc       1536
Ala Glu Ser Gly Gly Gln Val Gly Asp Val Gly Tyr Ile Phe Ser Gly
            500                 505                 510 gaa aac cgc ttt gaa gta cgc gat acc caa aaa atc aaa gcg gcc gta       1584
Glu Asn Arg Phe Glu Val Arg Asp Thr Gln Lys Ile Lys Ala Ala Val
        515                 520                 525 ttc ggt caa ttc ggc gta caa act tca ggc cgt ctg aaa gtc ggc gac       1632
Phe Gly Gln Phe Gly Val Gln Thr Ser Gly Arg Leu Lys Val Gly Asp
    530                 535                 540 agc gtt acc gcc aaa gtg gac gac gaa atc cgc aat gcc aat atg cgc       1680
Ser Val Thr Ala Lys Val Asp Asp Glu Ile Arg Asn Ala Asn Met Arg
545                 550                 555                 560 aac cac agc gca acc cac ttg atg cac aaa gcc ctg cgc gat gta ttg       1728
Asn His Ser Ala Thr His Leu Met His Lys Ala Leu Arg Asp Val Leu
                565                 570                 575 ggc aga cac gtc gaa caa aaa ggc tct ttg gtt acc gcc gaa tcc acc       1776
Gly Arg His Val Glu Gln Lys Gly Ser Leu Val Thr Ala Glu Ser Thr
            580                 585                 590 cgt ttc gac att tcc cat ccc caa gcg gta act gcc gaa gaa att gcc       1824
Arg Phe Asp Ile Ser His Pro Gln Ala Val Thr Ala Glu Glu Ile Ala
        595                 600                 605 gaa gta gaa cgc cgc gtc aac gaa gcc att ttg gcg aac gtt gcc gtc       1872
```

```
Glu Val Glu Arg Arg Val Asn Glu Ala Ile Leu Ala Asn Val Ala Val
    610             615                 620 aat gca gcc att atg agc atg gaa gac gcg caa aaa acc ggc gcg atg    1920
Asn Ala Ala Ile Met Ser Met Glu Asp Ala Gln Lys Thr Gly Ala Met
625             630                 635                 640 atg ctc ttc ggc gaa aaa tac ggc gaa gaa gtg cgc gta ctg caa atg    1968
Met Leu Phe Gly Glu Lys Tyr Gly Glu Glu Val Arg Val Leu Gln Met
                645                 650                 655 ggc ggt ttc tct acc gaa ttg tgc ggc ggc aca cac gtt tca cgc acc    2016
Gly Gly Phe Ser Thr Glu Leu Cys Gly Gly Thr His Val Ser Arg Thr
            660                 665                 670 ggc gac atc ggc ctc ttc aaa atc atc agc gaa ggc ggt att gcc gca    2064
Gly Asp Ile Gly Leu Phe Lys Ile Ile Ser Glu Gly Gly Ile Ala Ala
        675                 680                 685 ggc gtg cgc cgt atc gaa gcc atc acc ggc ctg aac gca ctc aaa tgg    2112
Gly Val Arg Arg Ile Glu Ala Ile Thr Gly Leu Asn Ala Leu Lys Trp
    690                 695                 700 gcg caa gag caa gag cgt ttg gtg aaa gac att att gcc gaa acc aaa    2160
Ala Gln Glu Gln Glu Arg Leu Val Lys Asp Ile Ile Ala Glu Thr Lys
705                 710                 715                 720 gcc caa acc gaa aaa gac gta ctg gca aaa atc caa gca ggc gcg gca    2208
Ala Gln Thr Glu Lys Asp Val Leu Ala Lys Ile Gln Ala Gly Ala Ala
                725                 730                 735 cac gcc aaa gca ttg gaa aaa gaa ttg gca cgc gcc aaa gcc gaa ctc    2256
His Ala Lys Ala Leu Glu Lys Glu Leu Ala Arg Ala Lys Ala Glu Leu
            740                 745                 750 gcc gtc cac gca ggc gcc aaa ctc ttg gac gat gca aaa gac ttg ggc    2304
Ala Val His Ala Gly Ala Lys Leu Leu Asp Asp Ala Lys Asp Leu Gly
        755                 760                 765 gca gcc aaa ctc gtt gcc gcc caa atc gaa gcc gac gca gcc gcc ctg    2352
Ala Ala Lys Leu Val Ala Ala Gln Ile Glu Ala Asp Ala Ala Ala Leu
    770                 775                 780 cgc gaa atc gtt acc gat tta acc ggt aaa tcc gac aac gcc gtg att    2400
Arg Glu Ile Val Thr Asp Leu Thr Gly Lys Ser Asp Asn Ala Val Ile
785                 790                 795                 800 ctt tta gcg gca gta aac gac ggc aaa gtc tcc ctg tgc gcc ggc gta    2448
Leu Leu Ala Ala Val Asn Asp Gly Lys Val Ser Leu Cys Ala Gly Val
                805                 810                 815 tcc aaa ccg ttg acc ggc aaa gtg aaa gca ggc gat ctg gtt aaa ttt    2496
Ser Lys Pro Leu Thr Gly Lys Val Lys Ala Gly Asp Leu Val Lys Phe
            820                 825                 830 gca gcc gaa caa gtc ggc ggc aaa ggc ggc ggc aga cca gat ttg gcg    2544
Ala Ala Glu Gln Val Gly Gly Lys Gly Gly Gly Arg Pro Asp Leu Ala
        835                 840                 845 caa gcc ggc ggc acg gat gcc gac aaa ttg ccc gcc gtg ttg gat agc    2592
Gln Ala Gly Gly Thr Asp Ala Asp Lys Leu Pro Ala Val Leu Asp Ser
    850                 855                 860 gtg aaa gac tgg gtc ggc gcg aag ctg gtt                            2622
Val Lys Asp Trp Val Gly Ala Lys Leu Val
865                 870

<210> SEQ ID NO 32
<211> LENGTH: 874
<212> TYPE: PRT
<213> ORGANISM: Neisseria meningitidis

<400> SEQUENCE: 32

Met Lys Thr Ser Glu Leu Arg Gln Lys Phe Leu Lys Phe Phe Glu Thr
1               5                   10                  15

Lys Gly His Thr Val Val Arg Ser Ser Ser Leu Val Pro His Asp Asp
```

```
                20              25              30
Pro Thr Leu Leu Phe Thr Asn Ala Gly Met Asn Gln Phe Lys Asp Val
            35                  40                  45
Phe Leu Gly Phe Asp Lys Arg Pro Tyr Ser Arg Ala Thr Thr Ala Gln
        50                  55                  60
Lys Cys Val Arg Ala Gly Lys His Asn Asp Leu Glu Asn Val Gly
65                  70                  75                  80
Tyr Thr Ala Arg His His Thr Phe Phe Glu Met Met Gly Asn Phe Ser
                85                  90                  95
Phe Gly Asp Tyr Phe Lys Arg Asp Ala Ile His Phe Ala Trp Glu Phe
            100                 105                 110
Leu Thr Ser Pro Glu Trp Leu Asn Ile Pro Lys Asp Lys Leu Leu Ala
        115                 120                 125
Thr Val Tyr Ala Glu Asp Asp Glu Ala Tyr Asn Ile Trp Leu Asn Glu
        130                 135                 140
Ile Gly Met Pro Ser Glu Arg Ile Val Arg Ile Gly Asp Asn Lys Gly
145                 150                 155                 160
Ala Lys Tyr Ala Ser Asp Asn Phe Trp Gln Met Gly Asp Thr Gly Pro
                165                 170                 175
Cys Gly Pro Cys Ser Glu Ile Phe Tyr Asp His Gly Glu Glu Ile Trp
            180                 185                 190
Gly Gly Ile Pro Gly Ser Pro Glu Glu Asp Gly Asp Arg Trp Ile Glu
        195                 200                 205
Ile Trp Asn Cys Val Phe Met Gln Phe Asn Arg Asp Glu Gln Gly Asn
        210                 215                 220
Met Asn Pro Leu Pro Lys Pro Ser Val Asp Thr Gly Met Gly Leu Glu
225                 230                 235                 240
Arg Ile Ala Ala Val Met Gln His Val His Ser Asn Tyr Glu Ile Asp
                245                 250                 255
Leu Phe Gln Asp Leu Leu Lys Ala Val Ala Arg Glu Thr Gly Ala Pro
            260                 265                 270
Phe Arg Met Glu Glu Pro Ser Leu Lys Val Ile Ala Asp His Ile Arg
        275                 280                 285
Ser Cys Ser Phe Leu Ile Ala Asp Gly Val Leu Pro Ser Asn Glu Gly
        290                 295                 300
Arg Gly Tyr Val Leu Arg Arg Ile Ile Arg Arg Ala Val Arg His Gly
305                 310                 315                 320
Tyr Lys Leu Gly Gln Ser Lys Pro Phe Phe His Lys Leu Val Ala Asp
                325                 330                 335
Leu Val Lys Glu Met Gly Gly Ala Tyr Pro Glu Leu Lys Glu Lys Gln
            340                 345                 350
Ala Gln Ile Glu Glu Ala Leu Lys Asn Glu Glu Ser Arg Phe Ala Gln
        355                 360                 365
Thr Leu Glu Thr Gly Met Ala Leu Leu Glu Asn Ala Leu Val Lys Gly
        370                 375                 380
Gly Lys Thr Leu Gly Gly Glu Ile Ile Phe Lys Leu Tyr Asp Thr Tyr
385                 390                 395                 400
Gly Phe Pro Tyr Asp Leu Thr Ala Asp Ile Cys Arg Glu Arg Asn Ile
                405                 410                 415
Glu Pro Asp Glu Ala Gly Phe Glu Arg Glu Met Glu Ala Gln Arg Ala
            420                 425                 430
Arg Ala Arg Ala Ala Gln Ser Phe Lys Ala Asn Ala Gln Leu Pro Tyr
        435                 440                 445
```

```
Asp Gly Gln Asp Thr Glu Phe Lys Gly Tyr Ser Glu Arg Gln Thr Glu
            450                 455                 460

Ser Lys Val Leu Ala Leu Tyr Lys Asp Gly Glu Gln Val Asn Glu Leu
465                 470                 475                 480

Asn Glu Gly Asp Ser Gly Ala Val Val Ile Asp Phe Thr Pro Phe Tyr
                485                 490                 495

Ala Glu Ser Gly Gly Gln Val Gly Asp Val Gly Tyr Ile Phe Ser Gly
                500                 505                 510

Glu Asn Arg Phe Glu Val Arg Asp Thr Gln Lys Ile Lys Ala Ala Val
            515                 520                 525

Phe Gly Gln Phe Gly Val Gln Thr Ser Gly Arg Leu Lys Val Gly Asp
530                 535                 540

Ser Val Thr Ala Lys Val Asp Asp Glu Ile Arg Asn Ala Asn Met Arg
545                 550                 555                 560

Asn His Ser Ala Thr His Leu Met His Lys Ala Leu Arg Asp Val Leu
                565                 570                 575

Gly Arg His Val Glu Gln Lys Gly Ser Leu Val Thr Ala Glu Ser Thr
            580                 585                 590

Arg Phe Asp Ile Ser His Pro Gln Ala Val Thr Ala Glu Glu Ile Ala
            595                 600                 605

Glu Val Glu Arg Arg Val Asn Glu Ala Ile Leu Ala Asn Val Ala Val
610                 615                 620

Asn Ala Ala Ile Met Ser Met Glu Asp Ala Gln Lys Thr Gly Ala Met
625                 630                 635                 640

Met Leu Phe Gly Glu Lys Tyr Gly Glu Glu Val Arg Val Leu Gln Met
                645                 650                 655

Gly Gly Phe Ser Thr Glu Leu Cys Gly Gly Thr His Val Ser Arg Thr
                660                 665                 670

Gly Asp Ile Gly Leu Phe Lys Ile Ile Ser Glu Gly Gly Ile Ala Ala
            675                 680                 685

Gly Val Arg Arg Ile Glu Ala Ile Thr Gly Leu Asn Ala Leu Lys Trp
690                 695                 700

Ala Gln Glu Gln Glu Arg Leu Val Lys Asp Ile Ile Ala Glu Thr Lys
705                 710                 715                 720

Ala Gln Thr Glu Lys Asp Val Leu Ala Lys Ile Gln Ala Gly Ala Ala
                725                 730                 735

His Ala Lys Ala Leu Glu Lys Glu Leu Ala Arg Ala Lys Ala Glu Leu
            740                 745                 750

Ala Val His Ala Gly Ala Lys Leu Leu Asp Asp Ala Lys Asp Leu Gly
            755                 760                 765

Ala Ala Lys Leu Val Ala Ala Gln Ile Glu Ala Asp Ala Ala Ala Leu
770                 775                 780

Arg Glu Ile Val Thr Asp Leu Thr Gly Lys Ser Asp Asn Ala Val Ile
785                 790                 795                 800

Leu Leu Ala Ala Val Asn Asp Gly Lys Val Ser Leu Cys Ala Gly Val
                805                 810                 815

Ser Lys Pro Leu Thr Gly Lys Val Lys Ala Gly Asp Leu Val Lys Phe
                820                 825                 830

Ala Ala Glu Gln Val Gly Gly Lys Gly Gly Arg Pro Asp Leu Ala
            835                 840                 845

Gln Ala Gly Gly Thr Asp Ala Asp Lys Leu Pro Ala Val Leu Asp Ser
850                 855                 860
```

Val Lys Asp Trp Val Gly Ala Lys Leu Val
865                 870

<210> SEQ ID NO 33
<211> LENGTH: 774
<212> TYPE: DNA
<213> ORGANISM: Neisseria meningitidis
<220> FEATURE:
<221> NAME/KEY: CDS
<222> LOCATION: (1)..(774)
<223> OTHER INFORMATION: NMA0750

<400> SEQUENCE: 33

| | | | | | | | | | | | | | | | | |
|---|---|---|---|---|---|---|---|---|---|---|---|---|---|---|---|---|
| atg | gct | aag | aaa | ttc | gat | aaa | gac | agc | ttc | agc | ggc | acg | ctg | att | gtc | 48 |
| Met | Ala | Lys | Lys | Phe | Asp | Lys | Asp | Ser | Phe | Ser | Gly | Thr | Leu | Ile | Val | |
| 1 | | | | 5 | | | | | 10 | | | | | 15 | | |
| gtg | ttg | gcg | gtc | agc | ctg | att | tgc | tcg | gtc | atc | gtt | gcc | ggt | gcg | gtc | 96 |
| Val | Leu | Ala | Val | Ser | Leu | Ile | Cys | Ser | Val | Ile | Val | Ala | Gly | Ala | Val | |
| | | | | 20 | | | | | 25 | | | | | 30 | | |
| gtc | ggc | ttg | aaa | ccc | atc | caa | gag | aaa | caa | aaa | ctc | caa | gac | aaa | caa | 144 |
| Val | Gly | Leu | Lys | Pro | Ile | Gln | Glu | Lys | Gln | Lys | Leu | Gln | Asp | Lys | Gln | |
| | | 35 | | | | | 40 | | | | | 45 | | | | |
| ggc | tat | atc | ttg | agc | gta | gcc | ggt | ttg | atg | gat | aag | gac | acc | gac | atc | 192 |
| Gly | Tyr | Ile | Leu | Ser | Val | Ala | Gly | Leu | Met | Asp | Lys | Asp | Thr | Asp | Ile | |
| | 50 | | | | | 55 | | | | | 60 | | | | | |
| ggt | aaa | act | ttt | gcc | gag | cgt | atc | gag | caa | cgc | gtg | gtc | gat | ttg | gcg | 240 |
| Gly | Lys | Thr | Phe | Ala | Glu | Arg | Ile | Glu | Gln | Arg | Val | Val | Asp | Leu | Ala | |
| 65 | | | | | 70 | | | | | 75 | | | | | 80 | |
| acc | ggc | gaa | tat | gtg | aaa | gac | gcg | ccg | aaa | gac | ttc | agt | gcg | cgc | atc | 288 |
| Thr | Gly | Glu | Tyr | Val | Lys | Asp | Ala | Pro | Lys | Asp | Phe | Ser | Ala | Arg | Ile | |
| | | | | 85 | | | | | 90 | | | | | 95 | | |
| gca | ggc | aaa | gac | ccc | gcg | caa | agc | atc | cgc | atc | aaa | ccc | gaa | gac | gat | 336 |
| Ala | Gly | Lys | Asp | Pro | Ala | Gln | Ser | Ile | Arg | Ile | Lys | Pro | Glu | Asp | Asp | |
| | | | 100 | | | | | 105 | | | | | 110 | | | |
| ttg | gca | ggc | atc | aaa | agc | cgt | gcc | aaa | tac | acc | gag | gtt | tac | ttg | gta | 384 |
| Leu | Ala | Gly | Ile | Lys | Ser | Arg | Ala | Lys | Tyr | Thr | Glu | Val | Tyr | Leu | Val | |
| | | 115 | | | | | 120 | | | | | 125 | | | | |
| aaa | ggt | gaa | gac | ggc | aaa | atc | ggc | caa | atc | atc | ctg | cct | atg | cac | ggt | 432 |
| Lys | Gly | Glu | Asp | Gly | Lys | Ile | Gly | Gln | Ile | Ile | Leu | Pro | Met | His | Gly | |
| | 130 | | | | | 135 | | | | | 140 | | | | | |
| aac | ggt | ttg | tgg | tcg | gtc | atg | tac | ggc | ttt | gtc | gcc | atc | caa | ccc | gac | 480 |
| Asn | Gly | Leu | Trp | Ser | Val | Met | Tyr | Gly | Phe | Val | Ala | Ile | Gln | Pro | Asp | |
| 145 | | | | | 150 | | | | | 155 | | | | | 160 | |
| ggc | aac | acc | atc | aac | ggc | att | acc | tac | tac | gag | caa | ggc | gaa | acc | ccg | 528 |
| Gly | Asn | Thr | Ile | Asn | Gly | Ile | Thr | Tyr | Tyr | Glu | Gln | Gly | Glu | Thr | Pro | |
| | | | | 165 | | | | | 170 | | | | | 175 | | |
| ggc | tta | ggc | ggc | gaa | atc | ggc | aat | cct | ttg | tgg | cag | caa | aaa | ttc | gtc | 576 |
| Gly | Leu | Gly | Gly | Glu | Ile | Gly | Asn | Pro | Leu | Trp | Gln | Gln | Lys | Phe | Val | |
| | | | 180 | | | | | 185 | | | | | 190 | | | |
| ggc | aaa | aaa | ctg | ttt | gac | gga | caa | ggc | aaa | ctc | gcc | ctg | cac | gtc | ggc | 624 |
| Gly | Lys | Lys | Leu | Phe | Asp | Gly | Gln | Gly | Lys | Leu | Ala | Leu | His | Val | Gly | |
| | | 195 | | | | | 200 | | | | | 205 | | | | |
| aaa | ggc | gcg | ggt | tcg | gac | aaa | gaa | cac | ggc | gta | gat | gcc | ctc | tcc | ggc | 672 |
| Lys | Gly | Ala | Gly | Ser | Asp | Lys | Glu | His | Gly | Val | Asp | Ala | Leu | Ser | Gly | |
| | 210 | | | | | 215 | | | | | 220 | | | | | |
| gcg | tcg | ctg | aca | tcc | aaa | ggc | gta | caa | ggt | tcg | ttc | gcc | tac | tgg | ttc | 720 |
| Ala | Ser | Leu | Thr | Ser | Lys | Gly | Val | Gln | Gly | Ser | Phe | Ala | Tyr | Trp | Phe | |
| 225 | | | | | 230 | | | | | 235 | | | | | 240 | |
| ggc | gaa | aac | ggc | tat | atc | ccc | tac | ctg | aac | aaa | ttg | aaa | tca | gca | gga | 768 |
| Gly | Glu | Asn | Gly | Tyr | Ile | Pro | Tyr | Leu | Asn | Lys | Leu | Lys | Ser | Ala | Gly | |
| | | | | 245 | | | | | 250 | | | | | 255 | | |

```
gcg caa                                                              774
Ala Gln
```

<210> SEQ ID NO 34
<211> LENGTH: 258
<212> TYPE: PRT
<213> ORGANISM: Neisseria meningitidis

<400> SEQUENCE: 34

```
Met Ala Lys Lys Phe Asp Lys Asp Ser Phe Ser Gly Thr Leu Ile Val
1               5                   10                  15

Val Leu Ala Val Ser Leu Ile Cys Ser Val Ile Val Ala Gly Ala Val
            20                  25                  30

Val Gly Leu Lys Pro Ile Gln Glu Lys Gln Lys Leu Gln Asp Lys Gln
        35                  40                  45

Gly Tyr Ile Leu Ser Val Ala Gly Leu Met Asp Lys Asp Thr Asp Ile
    50                  55                  60

Gly Lys Thr Phe Ala Glu Arg Ile Glu Gln Arg Val Val Asp Leu Ala
65                  70                  75                  80

Thr Gly Glu Tyr Val Lys Asp Ala Pro Lys Asp Phe Ser Ala Arg Ile
                85                  90                  95

Ala Gly Lys Asp Pro Ala Gln Ser Ile Arg Ile Lys Pro Glu Asp Asp
            100                 105                 110

Leu Ala Gly Ile Lys Ser Arg Ala Lys Tyr Thr Glu Val Tyr Leu Val
        115                 120                 125

Lys Gly Glu Asp Gly Lys Ile Gly Gln Ile Ile Leu Pro Met His Gly
    130                 135                 140

Asn Gly Leu Trp Ser Val Met Tyr Gly Phe Val Ala Ile Gln Pro Asp
145                 150                 155                 160

Gly Asn Thr Ile Asn Gly Ile Thr Tyr Tyr Glu Gln Gly Glu Thr Pro
                165                 170                 175

Gly Leu Gly Gly Glu Ile Gly Asn Pro Leu Trp Gln Gln Lys Phe Val
            180                 185                 190

Gly Lys Lys Leu Phe Asp Gly Gln Gly Lys Leu Ala Leu His Val Gly
        195                 200                 205

Lys Gly Ala Gly Ser Asp Lys Glu His Gly Val Asp Ala Leu Ser Gly
    210                 215                 220

Ala Ser Leu Thr Ser Lys Gly Val Gln Gly Ser Phe Ala Tyr Trp Phe
225                 230                 235                 240

Gly Glu Asn Gly Tyr Ile Pro Tyr Leu Asn Lys Leu Lys Ser Ala Gly
                245                 250                 255

Ala Gln
```

<210> SEQ ID NO 35
<211> LENGTH: 624
<212> TYPE: DNA
<213> ORGANISM: Neisseria meningitidis
<220> FEATURE:
<221> NAME/KEY: CDS
<222> LOCATION: (1)..(624)
<223> OTHER INFORMATION: NMA0749

<400> SEQUENCE: 35

```
atg gct gat atg aaa cgc ttg aaa cat ttg atg ttt tca ccc ttt atc    48
Met Ala Asp Met Lys Arg Leu Lys His Leu Met Phe Ser Pro Phe Ile
1               5                   10                  15 gac aac aac ccg att gcc ttg cag gtt ttg ggt att tgt tcg gct ttg    96
Asp Asn Asn Pro Ile Ala Leu Gln Val Leu Gly Ile Cys Ser Ala Leu
```

```
                  20                  25                  30
gcg gtt acc acc aaa ctt cag acg gcc atc gtg atg ggt att tcc gta        144
Ala Val Thr Thr Lys Leu Gln Thr Ala Ile Val Met Gly Ile Ser Val
         35                  40                  45 gct ttg gta acc ggt ttt tcc agc ttc ttc att tcg ctg gta cgc aac        192
Ala Leu Val Thr Gly Phe Ser Ser Phe Phe Ile Ser Leu Val Arg Asn
     50                  55                  60 tac atc ccc aac agc atc cgc atc atc gtg caa atg gcg att atc gcg        240
Tyr Ile Pro Asn Ser Ile Arg Ile Ile Val Gln Met Ala Ile Ile Ala
 65                  70                  75                  80 tcg ctg gtt acg ctg gtc gac caa ctc ttg cag gca ttt gcc tac gaa        288
Ser Leu Val Thr Leu Val Asp Gln Leu Leu Gln Ala Phe Ala Tyr Glu
                 85                  90                  95 ttg tcc aaa cag ctt tcc gta ttc gtc ggt ctg att att acc aac tgt        336
Leu Ser Lys Gln Leu Ser Val Phe Val Gly Leu Ile Ile Thr Asn Cys
            100                 105                 110 atc gtg atg ggc cgc gcc gaa gca ttt gcg atg aaa gag ccg ccg ctg        384
Ile Val Met Gly Arg Ala Glu Ala Phe Ala Met Lys Glu Pro Pro Leu
        115                 120                 125 gaa agc ctg atc gac ggc atc ggc aac ggc gcg ggc tac ggg atg atg        432
Glu Ser Leu Ile Asp Gly Ile Gly Asn Gly Ala Gly Tyr Gly Met Met
    130                 135                 140 ctg ctt gtc gtc gcc acc gtc cgc gaa ctg att ggc tcg ggc aaa ctc        480
Leu Leu Val Val Ala Thr Val Arg Glu Leu Ile Gly Ser Gly Lys Leu
145                 150                 155                 160 ttg ggc tac acc gtt ttc caa acc gtg cag gac ggc ggc tgg tat cag        528
Leu Gly Tyr Thr Val Phe Gln Thr Val Gln Asp Gly Gly Trp Tyr Gln
                165                 170                 175 acc aac ggc ttg ttc ctg ctc gcc ccc agc gcg ttc ttc atc atc ggc        576
Thr Asn Gly Leu Phe Leu Leu Ala Pro Ser Ala Phe Phe Ile Ile Gly
            180                 185                 190 ttt ttg att tgg gga ctg cgt acc tgg aaa ccc gaa cag gcg gag gaa        624
Phe Leu Ile Trp Gly Leu Arg Thr Trp Lys Pro Glu Gln Ala Glu Glu
        195                 200                 205

<210> SEQ ID NO 36
<211> LENGTH: 208
<212> TYPE: PRT
<213> ORGANISM: Neisseria meningitidis

<400> SEQUENCE: 36

Met Ala Asp Met Lys Arg Leu Lys His Leu Met Phe Ser Pro Phe Ile
1               5                   10                  15

Asp Asn Asn Pro Ile Ala Leu Gln Val Leu Gly Ile Cys Ser Ala Leu
            20                  25                  30

Ala Val Thr Thr Lys Leu Gln Thr Ala Ile Val Met Gly Ile Ser Val
        35                  40                  45

Ala Leu Val Thr Gly Phe Ser Ser Phe Phe Ile Ser Leu Val Arg Asn
    50                  55                  60

Tyr Ile Pro Asn Ser Ile Arg Ile Ile Val Gln Met Ala Ile Ile Ala
65                  70                  75                  80

Ser Leu Val Thr Leu Val Asp Gln Leu Leu Gln Ala Phe Ala Tyr Glu
                85                  90                  95

Leu Ser Lys Gln Leu Ser Val Phe Val Gly Leu Ile Ile Thr Asn Cys
            100                 105                 110

Ile Val Met Gly Arg Ala Glu Ala Phe Ala Met Lys Glu Pro Pro Leu
        115                 120                 125

Glu Ser Leu Ile Asp Gly Ile Gly Asn Gly Ala Gly Tyr Gly Met Met
```

```
                130                 135                 140
Leu Leu Val Val Ala Thr Val Arg Glu Leu Ile Gly Ser Gly Lys Leu
145                 150                 155                 160

Leu Gly Tyr Thr Val Phe Gln Thr Val Gln Asp Gly Gly Trp Tyr Gln
                165                 170                 175

Thr Asn Gly Leu Phe Leu Leu Ala Pro Ser Ala Phe Phe Ile Ile Gly
            180                 185                 190

Phe Leu Ile Trp Gly Leu Arg Thr Trp Lys Pro Glu Gln Ala Glu Glu
        195                 200                 205

<210> SEQ ID NO 37
<211> LENGTH: 630
<212> TYPE: DNA
<213> ORGANISM: Neisseria meningitidis
<220> FEATURE:
<221> NAME/KEY: CDS
<222> LOCATION: (1)..(630)
<223> OTHER INFORMATION: NMA0387

<400> SEQUENCE: 37 atg acc cta cgt tac gaa atc ctc tcc gtt acc ccc ttc cgc caa aac    48
Met Thr Leu Arg Tyr Glu Ile Leu Ser Val Thr Pro Phe Arg Gln Asn
1               5                   10                  15 tgc acc ctg att tgg gac gac gaa agc ggc gaa gcc gtc ctg acc gat    96
Cys Thr Leu Ile Trp Asp Asp Glu Ser Gly Glu Ala Val Leu Thr Asp
            20                  25                  30 gtc ggc ggc gac gtg ccg ttc ctg ctg caa gcg ttg gca aac cgc aaa   144
Val Gly Gly Asp Val Pro Phe Leu Leu Gln Ala Leu Ala Asn Arg Lys
        35                  40                  45 ctt acg ctc acg gca atc tgg ctg acg cac ggc cat ctc gat cac gcg   192
Leu Thr Leu Thr Ala Ile Trp Leu Thr His Gly His Leu Asp His Ala
    50                  55                  60 ggc ggc gtg gtc gaa atg ttg aaa acg cat aaa gtc cct gtc ctc ggg   240
Gly Gly Val Val Glu Met Leu Lys Thr His Lys Val Pro Val Leu Gly
65                  70                  75                  80 ccg cat ccg gac gat gaa ttc ctg ctc caa tcg ctg ccg caa acc acc   288
Pro His Pro Asp Asp Glu Phe Leu Leu Gln Ser Leu Pro Gln Thr Thr
                85                  90                  95 gcg caa tac gga ttt cct gtc tcg ccc gcc ttt gcg ccg aac cgt tgg   336
Ala Gln Tyr Gly Phe Pro Val Ser Pro Ala Phe Ala Pro Asn Arg Trp
            100                 105                 110 ctc gaa gaa ggc gaa acg ctc acg gtc gga cgc tat gcc ttt caa gtg   384
Leu Glu Glu Gly Glu Thr Leu Thr Val Gly Arg Tyr Ala Phe Gln Val
        115                 120                 125 ctg cat att ccg ggc cat acg ccg gga cat atc gtc ttt tat tgt gcc   432
Leu His Ile Pro Gly His Thr Pro Gly His Ile Val Phe Tyr Cys Ala
    130                 135                 140 gag gcg gaa ttg ctg att gcg ggc gac gtg ctg ttt tac gaa acc ata   480
Glu Ala Glu Leu Leu Ile Ala Gly Asp Val Leu Phe Tyr Glu Thr Ile
145                 150                 155                 160 ggc aga acc gat ttt ccg cgc ggc aac cac gcc gac tta atc aat aat   528
Gly Arg Thr Asp Phe Pro Arg Gly Asn His Ala Asp Leu Ile Asn Asn
                165                 170                 175 atc cgc aac aaa tta ttc gcc ctc ccc gaa acc gtg caa gtt gtc gcc   576
Ile Arg Asn Lys Leu Phe Ala Leu Pro Glu Thr Val Gln Val Val Ala
            180                 185                 190 gga cac ggg cgt atg act tcc atc gga cac gaa aaa cgg cac aat ccg   624
Gly His Gly Arg Met Thr Ser Ile Gly His Glu Lys Arg His Asn Pro
        195                 200                 205 ttt ttc                                                           630
```

```
Phe Phe
    210

<210> SEQ ID NO 38
<211> LENGTH: 210
<212> TYPE: PRT
<213> ORGANISM: Neisseria meningitidis

<400> SEQUENCE: 38

Met Thr Leu Arg Tyr Glu Ile Leu Ser Val Thr Pro Phe Arg Gln Asn
1               5                   10                  15

Cys Thr Leu Ile Trp Asp Asp Glu Ser Gly Glu Ala Val Leu Thr Asp
            20                  25                  30

Val Gly Gly Asp Val Pro Phe Leu Leu Gln Ala Leu Ala Asn Arg Lys
        35                  40                  45

Leu Thr Leu Thr Ala Ile Trp Leu Thr His Gly His Leu Asp His Ala
    50                  55                  60

Gly Gly Val Val Glu Met Leu Lys Thr His Lys Val Pro Val Leu Gly
65                  70                  75                  80

Pro His Pro Asp Asp Glu Phe Leu Leu Gln Ser Leu Pro Gln Thr Thr
                85                  90                  95

Ala Gln Tyr Gly Phe Pro Val Ser Pro Ala Phe Ala Pro Asn Arg Trp
            100                 105                 110

Leu Glu Glu Gly Glu Thr Leu Thr Val Gly Arg Tyr Ala Phe Gln Val
        115                 120                 125

Leu His Ile Pro Gly His Thr Pro Gly His Ile Val Phe Tyr Cys Ala
    130                 135                 140

Glu Ala Glu Leu Leu Ile Ala Gly Asp Val Leu Phe Tyr Glu Thr Ile
145                 150                 155                 160

Gly Arg Thr Asp Phe Pro Arg Gly Asn His Ala Asp Leu Ile Asn Asn
                165                 170                 175

Ile Arg Asn Lys Leu Phe Ala Leu Pro Glu Thr Val Gln Val Val Ala
            180                 185                 190

Gly His Gly Arg Met Thr Ser Ile Gly His Glu Lys Arg His Asn Pro
        195                 200                 205

Phe Phe
    210

<210> SEQ ID NO 39
<211> LENGTH: 7542
<212> TYPE: DNA
<213> ORGANISM: Neisseria meningitidis
<220> FEATURE:
<221> NAME/KEY: CDS
<222> LOCATION: (1)..(7542)
<223> OTHER INFORMATION: NMA1768

<400> SEQUENCE: 39 atg aat aaa act ctc tat cgt gta att ttc aac cgc aaa cgt ggg gct        48
Met Asn Lys Thr Leu Tyr Arg Val Ile Phe Asn Arg Lys Arg Gly Ala
1               5                   10                  15 gtg gta gcc gtt gct gaa act acc aag cgc gaa ggt aaa agc tgt gcc        96
Val Val Ala Val Ala Glu Thr Thr Lys Arg Glu Gly Lys Ser Cys Ala
            20                  25                  30 gat agt gat tca ggc agc gct cat gtg aaa tct gtt cct ttt ggt act       144
Asp Ser Asp Ser Gly Ser Ala His Val Lys Ser Val Pro Phe Gly Thr
        35                  40                  45 act cat gca cct gtt tgt cgt tca aat atc ttt tct ttt tct tta ttg       192
Thr His Ala Pro Val Cys Arg Ser Asn Ile Phe Ser Phe Ser Leu Leu
```

|  |  |  |  |  |  |  |  |  |  |  |  |  |  |  |  |
|---|---|---|---|---|---|---|---|---|---|---|---|---|---|---|---|
| | | 50 | | | | 55 | | | | 60 | | | | | |
| ggc | ttt | tct | tta | tgt | ttg | gct | gta | ggt | acg | gcc | aat | att | gct | ttt | gct | 240 |
| Gly | Phe | Ser | Leu | Cys | Leu | Ala | Val | Gly | Thr | Ala | Asn | Ile | Ala | Phe | Ala |
| 65 | | | | 70 | | | | | 75 | | | | | 80 | gat ggc att att gct gat aaa gct gct cct aaa act caa caa gcc acg   288
Asp Gly Ile Ile Ala Asp Lys Ala Ala Pro Lys Thr Gln Gln Ala Thr
              85                  90                  95 att ctg caa aca ggt aac ggc ata ccg caa gtc aat att caa acc cct   336
Ile Leu Gln Thr Gly Asn Gly Ile Pro Gln Val Asn Ile Gln Thr Pro
        100                 105                 110 act tcg gca ggg gtt tct gtt aat caa tac gcc cag ttt gat gtg ggt   384
Thr Ser Ala Gly Val Ser Val Asn Gln Tyr Ala Gln Phe Asp Val Gly
            115                 120                 125 aat cgc ggg gcg att tta aac aac agc cgc agc aac acc caa aca cag   432
Asn Arg Gly Ala Ile Leu Asn Asn Ser Arg Ser Asn Thr Gln Thr Gln
130                 135                 140 cta ggc ggt tgg att caa ggt aat cct tgg ttg gca agg ggc gaa gca   480
Leu Gly Gly Trp Ile Gln Gly Asn Pro Trp Leu Ala Arg Gly Glu Ala
145                 150                 155                 160 cgt gtg gtt gta aac caa atc aac agc agc cat tct tca caa atg aat   528
Arg Val Val Val Asn Gln Ile Asn Ser Ser His Ser Ser Gln Met Asn
                165                 170                 175 ggc tat att gaa gtg ggc gga cga cgt gca gaa gtc gtt att gcc aat   576
Gly Tyr Ile Glu Val Gly Gly Arg Arg Ala Glu Val Val Ile Ala Asn
            180                 185                 190 ccg gca ggg att gca gtc aat ggt ggt ggt ttt atc aat gct tcc cgt   624
Pro Ala Gly Ile Ala Val Asn Gly Gly Gly Phe Ile Asn Ala Ser Arg
        195                 200                 205 gcc act ttg acg aca ggc caa ccg caa tat caa gca gga gac ctt agc   672
Ala Thr Leu Thr Thr Gly Gln Pro Gln Tyr Gln Ala Gly Asp Leu Ser
    210                 215                 220 ggc ttt aag ata agg caa ggc aat gtt gta atc gcc gga cac ggt ttg   720
Gly Phe Lys Ile Arg Gln Gly Asn Val Val Ile Ala Gly His Gly Leu
225                 230                 235                 240 gat gcc cgt gat acc gat ttc aca cgt att ctc agt tat cat tcc aaa   768
Asp Ala Arg Asp Thr Asp Phe Thr Arg Ile Leu Ser Tyr His Ser Lys
                245                 250                 255 att gat gca ccc gta tgg gga caa gat gtt cgt gtc gtc gcg gga caa   816
Ile Asp Ala Pro Val Trp Gly Gln Asp Val Arg Val Val Ala Gly Gln
            260                 265                 270 aac gat gtg gtc gca aca ggt aat gca cat tcg cct att ctc aat aat   864
Asn Asp Val Val Ala Thr Gly Asn Ala His Ser Pro Ile Leu Asn Asn
        275                 280                 285 gct gct gcc aat acg tca aac aat aca gcc aac aac ggc aca cat atc   912
Ala Ala Ala Asn Thr Ser Asn Asn Thr Ala Asn Asn Gly Thr His Ile
    290                 295                 300 cct tta ttt gcg att gat aca ggc aaa tta gga ggt atg tat gcc aac   960
Pro Leu Phe Ala Ile Asp Thr Gly Lys Leu Gly Gly Met Tyr Ala Asn
305                 310                 315                 320 aaa atc acc ttg atc agt acg gcc gag caa gca ggc att cgt aat caa   1008
Lys Ile Thr Leu Ile Ser Thr Ala Glu Gln Ala Gly Ile Arg Asn Gln
                325                 330                 335 ggg cag ttg ttt gct tct tcc ggt aat gtg gcg att gat gca aat ggc   1056
Gly Gln Leu Phe Ala Ser Ser Gly Asn Val Ala Ile Asp Ala Asn Gly
            340                 345                 350 cgt tta gtc aat agt ggc acg atg gct gcc gcc aat gcg aaa gat acg   1104
Arg Leu Val Asn Ser Gly Thr Met Ala Ala Ala Asn Ala Lys Asp Thr
        355                 360                 365 gat aat aca gcg gaa cac aaa gtc aat atc cgc agt cag ggc gtt gaa   1152
Asp Asn Thr Ala Glu His Lys Val Asn Ile Arg Ser Gln Gly Val Glu

```
Asp Asn Thr Ala Glu His Lys Val Asn Ile Arg Ser Gln Gly Val Glu
    370             375                 380 aac agc ggt acg gcg gta tcg caa caa ggc act caa att cac agt cag      1200
Asn Ser Gly Thr Ala Val Ser Gln Gln Gly Thr Gln Ile His Ser Gln
385                 390                 395                 400 tcg att caa aac act ggc aca tta ttg tcc tca ggc gaa ata ttg att      1248
Ser Ile Gln Asn Thr Gly Thr Leu Leu Ser Ser Gly Glu Ile Leu Ile
                405                 410                 415 cac aat tcg ggc agc ctg aaa aat gaa aca tca ggc acc att gaa gcc      1296
His Asn Ser Gly Ser Leu Lys Asn Glu Thr Ser Gly Thr Ile Glu Ala
                420                 425                 430 gct cgt ttg gct att gat acc gac aca ctt aat aat caa ggc aaa ctc      1344
Ala Arg Leu Ala Ile Asp Thr Asp Thr Leu Asn Asn Gln Gly Lys Leu
                435                 440                 445 tct caa aca ggt tca caa aaa ctc cat att gat gca caa ggc aaa atg      1392
Ser Gln Thr Gly Ser Gln Lys Leu His Ile Asp Ala Gln Gly Lys Met
        450                 455                 460 gat aac cgt ggc cgc atg ggt tta caa gat acc gca cca acc gcg tca      1440
Asp Asn Arg Gly Arg Met Gly Leu Gln Asp Thr Ala Pro Thr Ala Ser
465                 470                 475                 480 aat ggt tca agc aat caa acc ggc aat agt tac aat gca tct ttc cat      1488
Asn Gly Ser Ser Asn Gln Thr Gly Asn Ser Tyr Asn Ala Ser Phe His
                485                 490                 495 tca tcc act acc aca cca aca acg gca aca ggt acg ggt act gca acc      1536
Ser Ser Thr Thr Thr Pro Thr Thr Ala Thr Gly Thr Gly Thr Ala Thr
                500                 505                 510 gtt tct ata tca aac ata act gcg cct acc ttt gct gat ggg aca att      1584
Val Ser Ile Ser Asn Ile Thr Ala Pro Thr Phe Ala Asp Gly Thr Ile
                515                 520                 525 cgc act cat ggt gca ctg gat aat tca ggc agt att att gcc aat ggt      1632
Arg Thr His Gly Ala Leu Asp Asn Ser Gly Ser Ile Ile Ala Asn Gly
530                 535                 540 caa aca gat gtt agt gcg caa caa ggt tta aat aat gca gga caa ata      1680
Gln Thr Asp Val Ser Ala Gln Gln Gly Leu Asn Asn Ala Gly Gln Ile
545                 550                 555                 560 gac att cat cag tta aat gca aaa ggt tcg gcg ttt gac aat cac aat      1728
Asp Ile His Gln Leu Asn Ala Lys Gly Ser Ala Phe Asp Asn His Asn
                565                 570                 575 gga aca att atc agt gat gcg gtc cac att caa gcc ggc agc ctg aat      1776
Gly Thr Ile Ile Ser Asp Ala Val His Ile Gln Ala Gly Ser Leu Asn
                580                 585                 590 aat caa aat ggc aac atc aca aca cgc caa cag tta gag att gaa acc      1824
Asn Gln Asn Gly Asn Ile Thr Thr Arg Gln Gln Leu Glu Ile Glu Thr
                595                 600                 605 gat caa ctg gat aac gct cat ggc aag tta tta tca gca gaa ata gcg      1872
Asp Gln Leu Asp Asn Ala His Gly Lys Leu Leu Ser Ala Glu Ile Ala
        610                 615                 620 gat tta gcc gtt tca ggc agc ctg aac aat caa aat ggc gaa ata gcg      1920
Asp Leu Ala Val Ser Gly Ser Leu Asn Asn Gln Asn Gly Glu Ile Ala
625                 630                 635                 640 acc aat caa caa ctg att att cac gat ggt cag caa tct acc gct gtc      1968
Thr Asn Gln Gln Leu Ile Ile His Asp Gly Gln Gln Ser Thr Ala Val
                645                 650                 655 att gat aat acg aat ggc acg ata caa tca ggc cgt gat gtt gct att      2016
Ile Asp Asn Thr Asn Gly Thr Ile Gln Ser Gly Arg Asp Val Ala Ile
                660                 665                 670 cag gca aaa tcg tta tcc aac aac ggc aca ctt gcc gct gat aat aaa      2064
Gln Ala Lys Ser Leu Ser Asn Asn Gly Thr Leu Ala Ala Asp Asn Lys
                675                 680                 685
```

```
                                          -continued ctg gat att gcg tta caa gat gat ttt tat gta gaa cgc aat atc gtg       2112
Leu Asp Ile Ala Leu Gln Asp Asp Phe Tyr Val Glu Arg Asn Ile Val
        690             695                 700 gcg ggc aat gaa ttg tcg ctc agt aca cga ggc agc ctg aaa aat tca       2160
Ala Gly Asn Glu Leu Ser Leu Ser Thr Arg Gly Ser Leu Lys Asn Ser
705             710                 715                 720 cat act ttg caa gca gga aaa cgc att cgg att aaa gca aat aac ctt       2208
His Thr Leu Gln Ala Gly Lys Arg Ile Arg Ile Lys Ala Asn Asn Leu
            725                 730                 735 gat aat gca gca caa ggc aac att caa tcc ggc ggt acg aca gac att       2256
Asp Asn Ala Ala Gln Gly Asn Ile Gln Ser Gly Gly Thr Thr Asp Ile
740             745                 750 ggc acg cag cac aat tta acc aat aga ggc ttg att gac gga caa caa       2304
Gly Thr Gln His Asn Leu Thr Asn Arg Gly Leu Ile Asp Gly Gln Gln
        755             760                 765 acc aaa atc caa gcc ggg caa atg aat aat atc ggt aca ggt cgg att       2352
Thr Lys Ile Gln Ala Gly Gln Met Asn Asn Ile Gly Thr Gly Arg Ile
770             775                 780 tat ggc gac aat atc gct att gcg gct acc cgc tta gac aat caa gat       2400
Tyr Gly Asp Asn Ile Ala Ile Ala Ala Thr Arg Leu Asp Asn Gln Asp
785             790                 795                 800 gaa aac ggt aca ggt gcc gcc att gcg gca cgt gaa aac ctg aat tta       2448
Glu Asn Gly Thr Gly Ala Ala Ile Ala Ala Arg Glu Asn Leu Asn Leu
            805                 810                 815 ggc atc gga caa tta aac aac cgt gaa aac agt ctg att tac agc ggt       2496
Gly Ile Gly Gln Leu Asn Asn Arg Glu Asn Ser Leu Ile Tyr Ser Gly
        820                 825                 830 aac gat atg gcg gtt ggc ggc gca tta gat acc aat ggc caa gcc aca       2544
Asn Asp Met Ala Val Gly Gly Ala Leu Asp Thr Asn Gly Gln Ala Thr
835             840                 845 ggc aaa gcc caa agg ata cac aat gcc ggc gca acc att gaa gct gca       2592
Gly Lys Ala Gln Arg Ile His Asn Ala Gly Ala Thr Ile Glu Ala Ala
        850                 855                 860 ggc aaa atg cgt tta ggt gta gaa aag ctg cac aat acc aat gag cat       2640
Gly Lys Met Arg Leu Gly Val Glu Lys Leu His Asn Thr Asn Glu His
865             870                 875                 880 ttg aaa acg cag ttg gta gaa aca ggg cgc gag cat att gtt gat tac       2688
Leu Lys Thr Gln Leu Val Glu Thr Gly Arg Glu His Ile Val Asp Tyr
            885                 890                 895 gaa gca ttt gga cga cac gaa tta ttg cga gaa ggc acg caa cat gaa       2736
Glu Ala Phe Gly Arg His Glu Leu Leu Arg Glu Gly Thr Gln His Glu
        900                 905                 910 tta ggc tgg tct gtc tat aac gat gaa tca gac cac tta cgc acc cct       2784
Leu Gly Trp Ser Val Tyr Asn Asp Glu Ser Asp His Leu Arg Thr Pro
915             920                 925 gat gga gcg gcg cat gaa aat tgg cat aaa tac gat tat gaa aaa gtc       2832
Asp Gly Ala Ala His Glu Asn Trp His Lys Tyr Asp Tyr Glu Lys Val
        930                 935                 940 acc caa aaa acc caa gtt acc caa act gcg cca gcc aaa atc att tca       2880
Thr Gln Lys Thr Gln Val Thr Gln Thr Ala Pro Ala Lys Ile Ile Ser
945             950                 955                 960 ggt aat gat tta acc att gat ggt aaa gaa gta ttt aat acc gat agc       2928
Gly Asn Asp Leu Thr Ile Asp Gly Lys Glu Val Phe Asn Thr Asp Ser
            965                 970                 975 caa atc att gct ggt ggc aat ctc att gta caa aca gaa aaa gac ggt       2976
Gln Ile Ile Ala Gly Gly Asn Leu Ile Val Gln Thr Glu Lys Asp Gly
        980                 985                 990 ttg cat aac gag caa acc ttt ggc  gaa aag aaa gta ttc  agt gaa aat    3024
Leu His Asn Glu Gln Thr Phe Gly  Glu Lys Lys Val Phe  Ser Glu Asn
995                 1000                1005
```

```
ggc aaa tta cac agc tat tgg cgt gag aaa cat aaa gga cga gac      3069
Gly Lys Leu His Ser Tyr Trp Arg Glu Lys His Lys Gly Arg Asp
    1010                1015                1020 tca acg gga cat agc gaa caa aat tac act ttg ccg gag gaa atc      3114
Ser Thr Gly His Ser Glu Gln Asn Tyr Thr Leu Pro Glu Glu Ile
1025                1030                1035 aca cgc aac att tca ctg ggt tca ttt gcc tat gaa tcg cat cgc      3159
Thr Arg Asn Ile Ser Leu Gly Ser Phe Ala Tyr Glu Ser His Arg
        1040                1045                1050 aaa gca tta agc cat cat gcg ccc agc caa ggc act gag ttg ccg      3204
Lys Ala Leu Ser His His Ala Pro Ser Gln Gly Thr Glu Leu Pro
            1055                1060                1065 caa agc aac ggt att tcg cta ccc tat acg tcc aat tct ttt acc      3249
Gln Ser Asn Gly Ile Ser Leu Pro Tyr Thr Ser Asn Ser Phe Thr
1070                1075                1080 cca tta ccc agc agc agc tta tac att atc aat cct gtc aat aaa      3294
Pro Leu Pro Ser Ser Ser Leu Tyr Ile Ile Asn Pro Val Asn Lys
    1085                1090                1095 ggc tat ctt gtt gaa acc gat cca cgc ttt gcc aac tac cgt caa      3339
Gly Tyr Leu Val Glu Thr Asp Pro Arg Phe Ala Asn Tyr Arg Gln
        1100                1105                1110 tgg ttg ggt agt gac tat atg ctg gac agc ctc aaa cta gac cca      3384
Trp Leu Gly Ser Asp Tyr Met Leu Asp Ser Leu Lys Leu Asp Pro
            1115                1120                1125 aac aat tta cat aaa cgt ttg ggt gat ggt tat tac gag caa cgt      3429
Asn Asn Leu His Lys Arg Leu Gly Asp Gly Tyr Tyr Glu Gln Arg
1130                1135                1140 tta atc aat gaa caa atc gca gag ctg aca ggg cat cgt cgt tta      3474
Leu Ile Asn Glu Gln Ile Ala Glu Leu Thr Gly His Arg Arg Leu
    1145                1150                1155 gac ggt tat caa aac gac gaa gaa caa ttt aaa gcc tta atg gat      3519
Asp Gly Tyr Gln Asn Asp Glu Glu Gln Phe Lys Ala Leu Met Asp
        1160                1165                1170 aat ggc gcg act gcg gca cgt tcg atg aat ctc agc gtt ggc att      3564
Asn Gly Ala Thr Ala Ala Arg Ser Met Asn Leu Ser Val Gly Ile
            1175                1180                1185 gca tta agt gcc gag caa gta gcg caa ctg acc agc gat att gtt      3609
Ala Leu Ser Ala Glu Gln Val Ala Gln Leu Thr Ser Asp Ile Val
1190                1195                1200 tgg ttg gta caa aaa gaa gtt aag ctt cct gat ggc ggc aca caa      3654
Trp Leu Val Gln Lys Glu Val Lys Leu Pro Asp Gly Gly Thr Gln
    1205                1210                1215 acc gta ttg gtg cca cag gtt tat gta cgc gtt aaa aat ggc gac      3699
Thr Val Leu Val Pro Gln Val Tyr Val Arg Val Lys Asn Gly Asp
        1220                1225                1230 ata gac ggt aaa ggt gca ttg ttg tca ggc agc aat aca caa atc      3744
Ile Asp Gly Lys Gly Ala Leu Leu Ser Gly Ser Asn Thr Gln Ile
            1235                1240                1245 aat gtt tca ggc agc ctg aaa aac tca ggc acg att gca ggg cgc      3789
Asn Val Ser Gly Ser Leu Lys Asn Ser Gly Thr Ile Ala Gly Arg
1250                1255                1260 aat gcg ctt att atc aat acc gat acg cta gac aat atc ggt ggg      3834
Asn Ala Leu Ile Ile Asn Thr Asp Thr Leu Asp Asn Ile Gly Gly
    1265                1270                1275 cgt att cat gcg caa aaa tca gcg gtt acg gcc aca caa gac atc      3879
Arg Ile His Ala Gln Lys Ser Ala Val Thr Ala Thr Gln Asp Ile
        1280                1285                1290 aat aat att ggc ggc atg ctt tct gcc gaa cag aca tta ttg ctc      3924
Asn Asn Ile Gly Gly Met Leu Ser Ala Glu Gln Thr Leu Leu Leu
```

|                     | 1295              | 1300              | 1305              |      |
|---------------------|-------------------|-------------------|-------------------|------|
| aac gca ggc aac aac atc aac agc caa agc acc acc gcc agc agt | | | | 3969 |
| Asn Ala Gly Asn Asn Ile Asn Ser Gln Ser Thr Thr Ala Ser Ser | | | | |
| 1310 | | 1315 | | 1320 | |

```
        1295                1300                1305 aac gca ggc aac aac atc aac agc caa agc acc acc gcc agc agt      3969
Asn Ala Gly Asn Asn Ile Asn Ser Gln Ser Thr Thr Ala Ser Ser
        1310                1315                1320 caa aat aca caa ggc agc agc acc tac cta gac cga atg gca ggt      4014
Gln Asn Thr Gln Gly Ser Ser Thr Tyr Leu Asp Arg Met Ala Gly
        1325                1330                1335 att tat atc aca ggc aaa gaa aaa ggt gtt tta gca gcg cag gca      4059
Ile Tyr Ile Thr Gly Lys Glu Lys Gly Val Leu Ala Ala Gln Ala
        1340                1345                1350 gga aaa gac atc aac atc att gcc ggt caa atc agc aat caa tca      4104
Gly Lys Asp Ile Asn Ile Ile Ala Gly Gln Ile Ser Asn Gln Ser
        1355                1360                1365 gag caa ggg caa acc cgg ctg caa gca ggg cgc gac att aac cta      4149
Glu Gln Gly Gln Thr Arg Leu Gln Ala Gly Arg Asp Ile Asn Leu
        1370                1375                1380 gat acg gta caa acc agc aaa cat caa gca acc cat ttt gat gcc      4194
Asp Thr Val Gln Thr Ser Lys His Gln Ala Thr His Phe Asp Ala
        1385                1390                1395 gat aac cat gtt att cgc ggt tca acg aac gaa gtc ggc agc agc      4239
Asp Asn His Val Ile Arg Gly Ser Thr Asn Glu Val Gly Ser Ser
        1400                1405                1410 att caa aca aaa ggc gat gtt acc cta ttg tca ggg aat aac ctc      4284
Ile Gln Thr Lys Gly Asp Val Thr Leu Leu Ser Gly Asn Asn Leu
        1415                1420                1425 aat gcc aaa gct gcc gaa gtc agc agc gca aac ggt aca ctc gct      4329
Asn Ala Lys Ala Ala Glu Val Ser Ser Ala Asn Gly Thr Leu Ala
        1430                1435                1440 gtg tct gcc aaa aat gac atc aac atc agc gca ggc atc aac acg      4374
Val Ser Ala Lys Asn Asp Ile Asn Ile Ser Ala Gly Ile Asn Thr
        1445                1450                1455 acc cat gtt gat gat gcg tcc aaa cac aca ggc aga agc ggt ggt      4419
Thr His Val Asp Asp Ala Ser Lys His Thr Gly Arg Ser Gly Gly
        1460                1465                1470 ggc aat aaa tta gtc att acc gat aaa gcc caa agt cat cac gaa      4464
Gly Asn Lys Leu Val Ile Thr Asp Lys Ala Gln Ser His His Glu
        1475                1480                1485 acc gcc caa agc agc acc ttt gaa ggc aag caa gtt gta ttg cag      4509
Thr Ala Gln Ser Ser Thr Phe Glu Gly Lys Gln Val Val Leu Gln
        1490                1495                1500 gca gga aac gat gcc aac atc ctt ggc agc aat gtt att tcc gat      4554
Ala Gly Asn Asp Ala Asn Ile Leu Gly Ser Asn Val Ile Ser Asp
        1505                1510                1515 aat ggc acc cag att caa gca ggc aat cat gtt cgc att ggt aca      4599
Asn Gly Thr Gln Ile Gln Ala Gly Asn His Val Arg Ile Gly Thr
        1520                1525                1530 acc caa act caa agc caa agc gaa acc tat cat caa acc cag aaa      4644
Thr Gln Thr Gln Ser Gln Ser Glu Thr Tyr His Gln Thr Gln Lys
        1535                1540                1545 tca gga ttg atg agt gca ggt atc ggc ttc act att ggc agc aag      4689
Ser Gly Leu Met Ser Ala Gly Ile Gly Phe Thr Ile Gly Ser Lys
        1550                1555                1560 aca aac aca caa gaa aac caa tcc caa agc aac gaa cat aca ggc      4734
Thr Asn Thr Gln Glu Asn Gln Ser Gln Ser Asn Glu His Thr Gly
        1565                1570                1575 agt acc gta ggc agc ttg aaa ggc gat acc acc att gtt gca ggc      4779
Ser Thr Val Gly Ser Leu Lys Gly Asp Thr Thr Ile Val Ala Gly
        1580                1585                1590 aaa cac tac gaa caa atc ggc agt acc gtt tcc agc ccg gaa ggc      4824
```

```
Lys His Tyr Glu Gln Ile Gly Ser Thr Val Ser Ser Pro Glu Gly
    1595                1600                1605 aac aat acc atc tat gcc caa agc ata gac att caa gcg gca cac           4869
Asn Asn Thr Ile Tyr Ala Gln Ser Ile Asp Ile Gln Ala Ala His
    1610                1615                1620 aac aaa tta aac agt aat acc acc caa acc tat gaa caa aaa ggc           4914
Asn Lys Leu Asn Ser Asn Thr Thr Gln Thr Tyr Glu Gln Lys Gly
    1625                1630                1635 cta acg gtg gca ttc agt tcg ccc gtt acc gat ttg gca caa caa           4959
Leu Thr Val Ala Phe Ser Ser Pro Val Thr Asp Leu Ala Gln Gln
    1640                1645                1650 gcg att gcc gta gca caa agc agc aaa caa gtc gga caa agc aaa           5004
Ala Ile Ala Val Ala Gln Ser Ser Lys Gln Val Gly Gln Ser Lys
    1655                1660                1665 aac gac cgc gtt aat gcc atg gcg gct gcc aat gca ggc tgg caa           5049
Asn Asp Arg Val Asn Ala Met Ala Ala Ala Asn Ala Gly Trp Gln
    1670                1675                1680 gcc tat caa aca ggt aag agt gca caa aac tta gcc aat ggt aca           5094
Ala Tyr Gln Thr Gly Lys Ser Ala Gln Asn Leu Ala Asn Gly Thr
    1685                1690                1695 acc aat gcc aaa caa gtc agc atc tcc ata acc tac ggc gaa cag           5139
Thr Asn Ala Lys Gln Val Ser Ile Ser Ile Thr Tyr Gly Glu Gln
    1700                1705                1710 caa aac cga caa acc acc caa gtt caa gcc aat caa gcc caa gcg           5184
Gln Asn Arg Gln Thr Thr Gln Val Gln Ala Asn Gln Ala Gln Ala
    1715                1720                1725 agt caa att caa gca ggt ggt aaa acc aca tta atc gcc aca ggc           5229
Ser Gln Ile Gln Ala Gly Gly Lys Thr Thr Leu Ile Ala Thr Gly
    1730                1735                1740 gca gca gaa caa tcc aat atc aac atc gca ggc tca gat gtt gcc           5274
Ala Ala Glu Gln Ser Asn Ile Asn Ile Ala Gly Ser Asp Val Ala
    1745                1750                1755 ggc aaa gca ggc aca atc ctg att gcc gat aac gac atc aca ctc           5319
Gly Lys Ala Gly Thr Ile Leu Ile Ala Asp Asn Asp Ile Thr Leu
    1760                1765                1770 caa tca gcc gag caa agc aat acc gaa cgc ggc caa aac aaa tcg           5364
Gln Ser Ala Glu Gln Ser Asn Thr Glu Arg Gly Gln Asn Lys Ser
    1775                1780                1785 gca ggc tgg aac gca ggt gct gcc gta tca ttc gga caa gga ggc           5409
Ala Gly Trp Asn Ala Gly Ala Ala Val Ser Phe Gly Gln Gly Gly
    1790                1795                1800 tgg tca tta ggc gtt acc gca ggc ggt aat gtc ggc aaa ggc tac           5454
Trp Ser Leu Gly Val Thr Ala Gly Gly Asn Val Gly Lys Gly Tyr
    1805                1810                1815 ggc aat ggc gac agc atc acc cac cgc cat agc cat atc ggc gac           5499
Gly Asn Gly Asp Ser Ile Thr His Arg His Ser His Ile Gly Asp
    1820                1825                1830 aaa ggc agc caa acc ctt atc caa agc ggt ggc gac act acc atc           5544
Lys Gly Ser Gln Thr Leu Ile Gln Ser Gly Gly Asp Thr Thr Ile
    1835                1840                1845 aaa ggc gcg caa gta cgc ggc aaa ggc gta caa gtc aat gcc aaa           5589
Lys Gly Ala Gln Val Arg Gly Lys Gly Val Gln Val Asn Ala Lys
    1850                1855                1860 aac cta agt att caa agc gta caa gat aga gaa acc tat caa agc           5634
Asn Leu Ser Ile Gln Ser Val Gln Asp Arg Glu Thr Tyr Gln Ser
    1865                1870                1875 aaa caa caa aac gcc agt gca caa gtt acc gta ggt tat ggc ttc           5679
Lys Gln Gln Asn Ala Ser Ala Gln Val Thr Val Gly Tyr Gly Phe
    1880                1885                1890
```

```
agt gcc ggt ggc gat tac agc caa agc aaa atc cga gcc gac cat      5724
Ser Ala Gly Gly Asp Tyr Ser Gln Ser Lys Ile Arg Ala Asp His
    1895            1900                1905 gtt tca gta acc gag caa agc ggt att tat gcc gga gaa gac ggc      5769
Val Ser Val Thr Glu Gln Ser Gly Ile Tyr Ala Gly Glu Asp Gly
1910            1915                1920 tat caa atc aag gtc gga aac cat aca gac ctc aaa ggc ggc atc      5814
Tyr Gln Ile Lys Val Gly Asn His Thr Asp Leu Lys Gly Gly Ile
    1925            1930                1935 atc acc agt acc caa agc gca gaa gac aag ggt aaa aac cgc ttt      5859
Ile Thr Ser Thr Gln Ser Ala Glu Asp Lys Gly Lys Asn Arg Phe
1940            1945                1950 cag acg gcc acc ctc acc cat agc gac atc aaa aac cac agc caa      5904
Gln Thr Ala Thr Leu Thr His Ser Asp Ile Lys Asn His Ser Gln
    1955            1960                1965 tac aaa ggc gaa agt ttt gga ttg ggc gca agt gcg tcc ata agc      5949
Tyr Lys Gly Glu Ser Phe Gly Leu Gly Ala Ser Ala Ser Ile Ser
1970            1975                1980 ggc aaa aca ctg gga cag ggc gca caa aat aaa cct caa aac aaa      5994
Gly Lys Thr Leu Gly Gln Gly Ala Gln Asn Lys Pro Gln Asn Lys
    1985            1990                1995 cac ctg aca agc gta gcc gat aaa aac agc gca agt tca tca gtg      6039
His Leu Thr Ser Val Ala Asp Lys Asn Ser Ala Ser Ser Ser Val
2000            2005                2010 ggt tat ggc agc gac agc gac agt caa agc agc atc aca aaa agc      6084
Gly Tyr Gly Ser Asp Ser Asp Ser Gln Ser Ser Ile Thr Lys Ser
    2015            2020                2025 ggc atc aac acc cgc aac att caa atc acc gac gaa gcc gca caa      6129
Gly Ile Asn Thr Arg Asn Ile Gln Ile Thr Asp Glu Ala Ala Gln
2030            2035                2040 atc cgg ctg aca ggc aaa aca gcg gca caa acc aaa gcc gat att      6174
Ile Arg Leu Thr Gly Lys Thr Ala Ala Gln Thr Lys Ala Asp Ile
    2045            2050                2055 gat aca aac gta acc aca gac acc gcc gaa cga cat tcg ggc agc      6219
Asp Thr Asn Val Thr Thr Asp Thr Ala Glu Arg His Ser Gly Ser
2060            2065                2070 ttg aag aac acc ttc aac aaa gaa gcg gtg caa agt gaa ctg gat      6264
Leu Lys Asn Thr Phe Asn Lys Glu Ala Val Gln Ser Glu Leu Asp
    2075            2080                2085 tta caa aga acc gtc agc caa gat ttt agt aaa aat gtt caa caa      6309
Leu Gln Arg Thr Val Ser Gln Asp Phe Ser Lys Asn Val Gln Gln
2090            2095                2100 gcc aat acc gag att aac caa cat tta gac aaa ctc aaa gca gac      6354
Ala Asn Thr Glu Ile Asn Gln His Leu Asp Lys Leu Lys Ala Asp
    2105            2110                2115 aaa gaa gca gcc gaa aca gca gca gcc gag gca tta gcc aat ggc      6399
Lys Glu Ala Ala Glu Thr Ala Ala Ala Glu Ala Leu Ala Asn Gly
2120            2125                2130 gat atg gaa act gcc aaa cgc aaa gcc cat gaa gct caa gat gcg      6444
Asp Met Glu Thr Ala Lys Arg Lys Ala His Glu Ala Gln Asp Ala
    2135            2140                2145 gca gca aaa gca gat aat tgg caa caa ggc aaa gtc att ctc aac      6489
Ala Ala Lys Ala Asp Asn Trp Gln Gln Gly Lys Val Ile Leu Asn
2150            2155                2160 atg tta gcc tca ggt tta gct gcg ccg acc caa agc gga gcg ggc      6534
Met Leu Ala Ser Gly Leu Ala Ala Pro Thr Gln Ser Gly Ala Gly
    2165            2170                2175 atc gct gcg gct acc gca tcg cca gcc gta tcg tat gcg att gga      6579
Ile Ala Ala Ala Thr Ala Ser Pro Ala Val Ser Tyr Ala Ile Gly
2180            2185                2190
```

| | | | | | | | | | | | |
|---|---|---|---|---|---|---|---|---|---|---|---|
| cag | cac | ttt | aaa | gat | tta | gcc | ggt | caa | aac | gcg | aat | ggt | aaa | cta | 6624 |
| Gln | His | Phe | Lys | Asp | Leu | Ala | Gly | Gln | Asn | Ala | Asn | Gly | Lys | Leu | |
| | 2195 | | | | 2200 | | | | | 2205 | | | | | |
| acc | gcc | agt | caa | gaa | acc | gca | cac | gtt | ctt | gcc | cac | gcg | gta | tta | 6669 |
| Thr | Ala | Ser | Gln | Glu | Thr | Ala | His | Val | Leu | Ala | His | Ala | Val | Leu | |
| | 2210 | | | | 2215 | | | | | 2220 | | | | | |
| gga | gca | gcg | gtt | gcc | gca | gta | gga | gac | aac | aat | gct | cta | gca | gga | 6714 |
| Gly | Ala | Ala | Val | Ala | Ala | Val | Gly | Asp | Asn | Asn | Ala | Leu | Ala | Gly | |
| | 2225 | | | | 2230 | | | | | 2235 | | | | | |
| gca | ttg | agt | gcg | ggc | ggg | tcg | gaa | gcg | gct | gcg | cct | tac | atc | agc | 6759 |
| Ala | Leu | Ser | Ala | Gly | Gly | Ser | Glu | Ala | Ala | Ala | Pro | Tyr | Ile | Ser | |
| | 2240 | | | | 2245 | | | | | 2250 | | | | | |
| aaa | tgg | tta | tac | ggc | aaa | gaa | aaa | gga | agc | gac | tta | acg | gcg | gaa | 6804 |
| Lys | Trp | Leu | Tyr | Gly | Lys | Glu | Lys | Gly | Ser | Asp | Leu | Thr | Ala | Glu | |
| | 2255 | | | | 2260 | | | | | 2265 | | | | | |
| gag | aaa | gag | act | gta | aca | gcg | att | aca | aat | gta | ttg | ggt | acg | gct | 6849 |
| Glu | Lys | Glu | Thr | Val | Thr | Ala | Ile | Thr | Asn | Val | Leu | Gly | Thr | Ala | |
| | 2270 | | | | 2275 | | | | | 2280 | | | | | |
| acg | ggt | gcg | gca | gtc | ggc | aac | agc | gca | aca | gat | gca | gcg | caa | ggc | 6894 |
| Thr | Gly | Ala | Ala | Val | Gly | Asn | Ser | Ala | Thr | Asp | Ala | Ala | Gln | Gly | |
| | 2285 | | | | 2290 | | | | | 2295 | | | | | |
| agc | ctg | aat | gcg | caa | agt | gcg | gtg | gag | aat | aat | gat | act | gta | gag | 6939 |
| Ser | Leu | Asn | Ala | Gln | Ser | Ala | Val | Glu | Asn | Asn | Asp | Thr | Val | Glu | |
| | 2300 | | | | 2305 | | | | | 2310 | | | | | |
| caa | gtg | aaa | ttt | gct | ctt | agg | cac | cct | aga | att | gct | att | gca | att | 6984 |
| Gln | Val | Lys | Phe | Ala | Leu | Arg | His | Pro | Arg | Ile | Ala | Ile | Ala | Ile | |
| | 2315 | | | | 2320 | | | | | 2325 | | | | | |
| gga | tct | gta | cat | aaa | gat | cct | ggc | tct | aca | tta | gag | cct | aat | att | 7029 |
| Gly | Ser | Val | His | Lys | Asp | Pro | Gly | Ser | Thr | Leu | Glu | Pro | Asn | Ile | |
| | 2330 | | | | 2335 | | | | | 2340 | | | | | |
| tca | aca | att | gct | tca | act | ttt | caa | tta | aat | tta | ttt | cct | aat | agt | 7074 |
| Ser | Thr | Ile | Ala | Ser | Thr | Phe | Gln | Leu | Asn | Leu | Phe | Pro | Asn | Ser | |
| | 2345 | | | | 2350 | | | | | 2355 | | | | | |
| gaa | ttt | ggt | ggt | gaa | ggt | gga | gtt | ggc | aat | gca | ttc | agg | cac | gtt | 7119 |
| Glu | Phe | Gly | Gly | Glu | Gly | Gly | Val | Gly | Asn | Ala | Phe | Arg | His | Val | |
| | 2360 | | | | 2365 | | | | | 2370 | | | | | |
| tta | tgg | caa | gca | acc | atc | aca | cga | gaa | ttt | ggc | aaa | gat | att | gct | 7164 |
| Leu | Trp | Gln | Ala | Thr | Ile | Thr | Arg | Glu | Phe | Gly | Lys | Asp | Ile | Ala | |
| | 2375 | | | | 2380 | | | | | 2385 | | | | | |
| gtt | aaa | gta | gga | aat | agt | cat | gaa | agt | ggg | gaa | aaa | att | aat | tat | 7209 |
| Val | Lys | Val | Gly | Asn | Ser | His | Glu | Ser | Gly | Glu | Lys | Ile | Asn | Tyr | |
| | 2390 | | | | 2395 | | | | | 2400 | | | | | |
| tct | ata | aga | cgt | aat | ctt | tca | tta | gat | aaa | gca | gat | gaa | atg | att | 7254 |
| Ser | Ile | Arg | Arg | Asn | Leu | Ser | Leu | Asp | Lys | Ala | Asp | Glu | Met | Ile | |
| | 2405 | | | | 2410 | | | | | 2415 | | | | | |
| gat | caa | cta | aat | aac | gaa | ata | gga | aga | gaa | ata | gca | tta | aat | acc | 7299 |
| Asp | Gln | Leu | Asn | Asn | Glu | Ile | Gly | Arg | Glu | Ile | Ala | Leu | Asn | Thr | |
| | 2420 | | | | 2425 | | | | | 2430 | | | | | |
| aat | agg | tta | aac | aca | aaa | gag | tta | gtt | gga | tta | att | ctg | gaa | act | 7344 |
| Asn | Arg | Leu | Asn | Thr | Lys | Glu | Leu | Val | Gly | Leu | Ile | Leu | Glu | Thr | |
| | 2435 | | | | 2440 | | | | | 2445 | | | | | |
| tat | aaa | aat | aat | ggt | ttt | tat | caa | gca | gaa | aga | aac | agt | aat | gga | 7389 |
| Tyr | Lys | Asn | Asn | Gly | Phe | Tyr | Gln | Ala | Glu | Arg | Asn | Ser | Asn | Gly | |
| | 2450 | | | | 2455 | | | | | 2460 | | | | | |
| aat | tat | gat | gtt | gta | aga | aaa | aga | tta | tct | gaa | aaa | gat | tac | cag | 7434 |
| Asn | Tyr | Asp | Val | Val | Arg | Lys | Arg | Leu | Ser | Glu | Lys | Asp | Tyr | Gln | |
| | 2465 | | | | 2470 | | | | | 2475 | | | | | |
| aat | aca | agc | aat | ata | ttg | att | cac | tta | gat | aat | act | ggt | gcc | gga | 7479 |
| Asn | Thr | Ser | Asn | Ile | Leu | Ile | His | Leu | Asp | Asn | Thr | Gly | Ala | Gly | |

```
                2480                2485                2490
ttt aaa att cag cag agg aga aaa caa atc aga gca caa att tca      7524
Phe Lys Ile Gln Gln Arg Arg Lys Gln Ile Arg Ala Gln Ile Ser
    2495                2500                2505 gcc aga caa tgg aga aga                                           7542
Ala Arg Gln Trp Arg Arg
    2510

<210> SEQ ID NO 40
<211> LENGTH: 2514
<212> TYPE: PRT
<213> ORGANISM: Neisseria meningitidis

<400> SEQUENCE: 40
```

Met Asn Lys Thr Leu Tyr Arg Val Ile Phe Asn Arg Lys Arg Gly Ala
1               5                   10                  15

Val Val Ala Val Ala Glu Thr Thr Lys Arg Glu Gly Lys Ser Cys Ala
                20                  25                  30

Asp Ser Asp Ser Gly Ser Ala His Val Lys Ser Val Pro Phe Gly Thr
            35                  40                  45

Thr His Ala Pro Val Cys Arg Ser Asn Ile Phe Ser Phe Ser Leu Leu
        50                  55                  60

Gly Phe Ser Leu Cys Leu Ala Val Gly Thr Ala Asn Ile Ala Phe Ala
65                  70                  75                  80

Asp Gly Ile Ile Ala Asp Lys Ala Ala Pro Lys Thr Gln Gln Ala Thr
                85                  90                  95

Ile Leu Gln Thr Gly Asn Gly Ile Pro Gln Val Asn Ile Gln Thr Pro
            100                 105                 110

Thr Ser Ala Gly Val Ser Val Asn Gln Tyr Ala Gln Phe Asp Val Gly
        115                 120                 125

Asn Arg Gly Ala Ile Leu Asn Asn Ser Arg Ser Asn Thr Gln Thr Gln
    130                 135                 140

Leu Gly Gly Trp Ile Gln Gly Asn Pro Trp Leu Ala Arg Gly Glu Ala
145                 150                 155                 160

Arg Val Val Val Asn Gln Ile Asn Ser Ser His Ser Ser Gln Met Asn
                165                 170                 175

Gly Tyr Ile Glu Val Gly Gly Arg Arg Ala Glu Val Val Ile Ala Asn
            180                 185                 190

Pro Ala Gly Ile Ala Val Asn Gly Gly Gly Phe Ile Asn Ala Ser Arg
        195                 200                 205

Ala Thr Leu Thr Thr Gly Gln Pro Gln Tyr Gln Ala Gly Asp Leu Ser
    210                 215                 220

Gly Phe Lys Ile Arg Gln Gly Asn Val Val Ile Ala Gly His Gly Leu
225                 230                 235                 240

Asp Ala Arg Asp Thr Asp Phe Thr Arg Ile Leu Ser Tyr His Ser Lys
                245                 250                 255

Ile Asp Ala Pro Val Trp Gly Gln Asp Val Arg Val Val Ala Gly Gln
            260                 265                 270

Asn Asp Val Val Ala Thr Gly Asn Ala His Ser Pro Ile Leu Asn Asn
        275                 280                 285

Ala Ala Ala Asn Thr Ser Asn Asn Thr Ala Asn Asn Gly Thr His Ile
    290                 295                 300

Pro Leu Phe Ala Ile Asp Thr Gly Lys Leu Gly Gly Met Tyr Ala Asn
305                 310                 315                 320

Lys Ile Thr Leu Ile Ser Thr Ala Glu Gln Ala Gly Ile Arg Asn Gln

-continued

```
                325                 330                 335
Gly Gln Leu Phe Ala Ser Ser Gly Asn Val Ala Ile Asp Ala Asn Gly
                340                 345                 350
Arg Leu Val Asn Ser Gly Thr Met Ala Ala Asn Ala Lys Asp Thr
                355                 360                 365
Asp Asn Thr Ala Glu His Lys Val Asn Ile Arg Ser Gln Gly Val Glu
    370                 375                 380
Asn Ser Gly Thr Ala Val Ser Gln Gln Gly Thr Gln Ile His Ser Gln
385                 390                 395                 400
Ser Ile Gln Asn Thr Gly Thr Leu Leu Ser Ser Gly Glu Ile Leu Ile
                405                 410                 415
His Asn Ser Gly Ser Leu Lys Asn Glu Thr Ser Gly Thr Ile Glu Ala
                420                 425                 430
Ala Arg Leu Ala Ile Asp Thr Asp Thr Leu Asn Asn Gln Gly Lys Leu
                435                 440                 445
Ser Gln Thr Gly Ser Gln Lys Leu His Ile Asp Ala Gln Gly Lys Met
            450                 455                 460
Asp Asn Arg Gly Arg Met Gly Leu Gln Asp Thr Ala Pro Thr Ala Ser
465                 470                 475                 480
Asn Gly Ser Ser Asn Gln Thr Gly Asn Ser Tyr Asn Ala Ser Phe His
                485                 490                 495
Ser Ser Thr Thr Pro Thr Thr Ala Thr Gly Thr Gly Thr Ala Thr
            500                 505                 510
Val Ser Ile Ser Asn Ile Thr Ala Pro Thr Phe Ala Asp Gly Thr Ile
            515                 520                 525
Arg Thr His Gly Ala Leu Asp Asn Ser Gly Ser Ile Ile Ala Asn Gly
            530                 535                 540
Gln Thr Asp Val Ser Ala Gln Gln Gly Leu Asn Asn Ala Gly Gln Ile
545                 550                 555                 560
Asp Ile His Gln Leu Asn Ala Lys Gly Ser Ala Phe Asp Asn His Asn
                565                 570                 575
Gly Thr Ile Ile Ser Asp Ala Val His Ile Gln Ala Gly Ser Leu Asn
            580                 585                 590
Asn Gln Asn Gly Asn Ile Thr Thr Arg Gln Gln Leu Glu Ile Glu Thr
        595                 600                 605
Asp Gln Leu Asp Asn Ala His Gly Lys Leu Leu Ser Ala Glu Ile Ala
        610                 615                 620
Asp Leu Ala Val Ser Gly Ser Leu Asn Asn Gln Asn Gly Glu Ile Ala
625                 630                 635                 640
Thr Asn Gln Gln Leu Ile Ile His Asp Gly Gln Gln Ser Thr Ala Val
                645                 650                 655
Ile Asp Asn Thr Asn Gly Thr Ile Gln Ser Gly Arg Asp Val Ala Ile
            660                 665                 670
Gln Ala Lys Ser Leu Ser Asn Asn Gly Thr Leu Ala Ala Asp Asn Lys
            675                 680                 685
Leu Asp Ile Ala Leu Gln Asp Asp Phe Tyr Val Glu Arg Asn Ile Val
        690                 695                 700
Ala Gly Asn Glu Leu Ser Leu Ser Thr Arg Gly Ser Leu Lys Asn Ser
705                 710                 715                 720
His Thr Leu Gln Ala Gly Lys Arg Ile Arg Ile Lys Ala Asn Asn Leu
                725                 730                 735
Asp Asn Ala Ala Gln Gly Asn Ile Gln Ser Gly Gly Thr Thr Asp Ile
                740                 745                 750
```

```
Gly Thr Gln His Asn Leu Thr Asn Arg Gly Leu Ile Asp Gly Gln Gln
        755                 760                 765

Thr Lys Ile Gln Ala Gly Gln Met Asn Asn Ile Gly Thr Gly Arg Ile
    770                 775                 780

Tyr Gly Asp Asn Ile Ala Ile Ala Ala Thr Arg Leu Asp Asn Gln Asp
785                 790                 795                 800

Glu Asn Gly Thr Gly Ala Ala Ile Ala Ala Arg Glu Asn Leu Asn Leu
                805                 810                 815

Gly Ile Gly Gln Leu Asn Asn Arg Glu Asn Ser Leu Ile Tyr Ser Gly
            820                 825                 830

Asn Asp Met Ala Val Gly Gly Ala Leu Asp Thr Asn Gly Gln Ala Thr
        835                 840                 845

Gly Lys Ala Gln Arg Ile His Asn Ala Gly Ala Thr Ile Glu Ala Ala
    850                 855                 860

Gly Lys Met Arg Leu Gly Val Glu Lys Leu His Asn Thr Asn Glu His
865                 870                 875                 880

Leu Lys Thr Gln Leu Val Glu Thr Gly Arg Glu His Ile Val Asp Tyr
                885                 890                 895

Glu Ala Phe Gly Arg His Glu Leu Leu Arg Glu Gly Thr Gln His Glu
            900                 905                 910

Leu Gly Trp Ser Val Tyr Asn Asp Glu Ser Asp His Leu Arg Thr Pro
        915                 920                 925

Asp Gly Ala Ala His Glu Asn Trp His Lys Tyr Asp Tyr Glu Lys Val
    930                 935                 940

Thr Gln Lys Thr Gln Val Thr Gln Thr Ala Pro Ala Lys Ile Ile Ser
945                 950                 955                 960

Gly Asn Asp Leu Thr Ile Asp Gly Lys Glu Val Phe Asn Thr Asp Ser
                965                 970                 975

Gln Ile Ile Ala Gly Gly Asn Leu Ile Val Gln Thr Glu Lys Asp Gly
            980                 985                 990

Leu His Asn Glu Gln Thr Phe Gly Glu Lys Lys Val Phe Ser Glu Asn
        995                 1000                1005

Gly Lys Leu His Ser Tyr Trp Arg Glu Lys His Lys Gly Arg Asp
    1010                1015                1020

Ser Thr Gly His Ser Glu Gln Asn Tyr Thr Leu Pro Glu Glu Ile
    1025                1030                1035

Thr Arg Asn Ile Ser Leu Gly Ser Phe Ala Tyr Glu Ser His Arg
    1040                1045                1050

Lys Ala Leu Ser His His Ala Pro Ser Gln Gly Thr Glu Leu Pro
    1055                1060                1065

Gln Ser Asn Gly Ile Ser Leu Pro Tyr Thr Ser Asn Ser Phe Thr
    1070                1075                1080

Pro Leu Pro Ser Ser Ser Leu Tyr Ile Ile Asn Pro Val Asn Lys
    1085                1090                1095

Gly Tyr Leu Val Glu Thr Asp Pro Arg Phe Ala Asn Tyr Arg Gln
    1100                1105                1110

Trp Leu Gly Ser Asp Tyr Met Leu Asp Ser Leu Lys Leu Asp Pro
    1115                1120                1125

Asn Asn Leu His Lys Arg Leu Gly Asp Gly Tyr Tyr Glu Gln Arg
    1130                1135                1140

Leu Ile Asn Glu Gln Ile Ala Glu Leu Thr Gly His Arg Arg Leu
    1145                1150                1155
```

```
Asp Gly Tyr Gln Asn Asp Glu Gln Phe Lys Ala Leu Met Asp
    1160                1165                1170

Asn Gly Ala Thr Ala Ala Arg Ser Met Asn Leu Ser Val Gly Ile
    1175                1180                1185

Ala Leu Ser Ala Glu Gln Val Ala Gln Leu Thr Ser Asp Ile Val
    1190                1195                1200

Trp Leu Val Gln Lys Glu Val Lys Leu Pro Asp Gly Gly Thr Gln
    1205                1210                1215

Thr Val Leu Val Pro Gln Val Tyr Val Arg Val Lys Asn Gly Asp
    1220                1225                1230

Ile Asp Gly Lys Gly Ala Leu Leu Ser Gly Ser Asn Thr Gln Ile
    1235                1240                1245

Asn Val Ser Gly Ser Leu Lys Asn Ser Gly Thr Ile Ala Gly Arg
    1250                1255                1260

Asn Ala Leu Ile Ile Asn Thr Asp Thr Leu Asp Asn Ile Gly Gly
    1265                1270                1275

Arg Ile His Ala Gln Lys Ser Ala Val Thr Ala Thr Gln Asp Ile
    1280                1285                1290

Asn Asn Ile Gly Gly Met Leu Ser Ala Glu Gln Thr Leu Leu Leu
    1295                1300                1305

Asn Ala Gly Asn Asn Ile Asn Ser Gln Ser Thr Thr Ala Ser Ser
    1310                1315                1320

Gln Asn Thr Gln Gly Ser Ser Thr Tyr Leu Asp Arg Met Ala Gly
    1325                1330                1335

Ile Tyr Ile Thr Gly Lys Glu Lys Gly Val Leu Ala Ala Gln Ala
    1340                1345                1350

Gly Lys Asp Ile Asn Ile Ile Ala Gly Gln Ile Ser Asn Gln Ser
    1355                1360                1365

Glu Gln Gly Gln Thr Arg Leu Gln Ala Gly Arg Asp Ile Asn Leu
    1370                1375                1380

Asp Thr Val Gln Thr Ser Lys His Gln Ala Thr His Phe Asp Ala
    1385                1390                1395

Asp Asn His Val Ile Arg Gly Ser Thr Asn Glu Val Gly Ser Ser
    1400                1405                1410

Ile Gln Thr Lys Gly Asp Val Thr Leu Leu Ser Gly Asn Asn Leu
    1415                1420                1425

Asn Ala Lys Ala Ala Glu Val Ser Ser Ala Asn Gly Thr Leu Ala
    1430                1435                1440

Val Ser Ala Lys Asn Asp Ile Asn Ile Ser Ala Gly Ile Asn Thr
    1445                1450                1455

Thr His Val Asp Asp Ala Ser Lys His Thr Gly Arg Ser Gly Gly
    1460                1465                1470

Gly Asn Lys Leu Val Ile Thr Asp Lys Ala Gln Ser His His Glu
    1475                1480                1485

Thr Ala Gln Ser Ser Thr Phe Glu Gly Lys Gln Val Val Leu Gln
    1490                1495                1500

Ala Gly Asn Asp Ala Asn Ile Leu Gly Ser Asn Val Ile Ser Asp
    1505                1510                1515

Asn Gly Thr Gln Ile Gln Ala Gly Asn His Val Arg Ile Gly Thr
    1520                1525                1530

Thr Gln Thr Gln Ser Gln Ser Glu Thr Tyr His Gln Thr Gln Lys
    1535                1540                1545

Ser Gly Leu Met Ser Ala Gly Ile Gly Phe Thr Ile Gly Ser Lys
```

```
                1550                1555                1560

Thr Asn Thr Gln Glu Asn Gln Ser Gln Ser Asn Glu His Thr Gly
    1565                1570                1575

Ser Thr Val Gly Ser Leu Lys Gly Asp Thr Thr Ile Val Ala Gly
    1580                1585                1590

Lys His Tyr Glu Gln Ile Gly Ser Thr Val Ser Ser Pro Glu Gly
    1595                1600                1605

Asn Asn Thr Ile Tyr Ala Gln Ser Ile Asp Ile Gln Ala Ala His
    1610                1615                1620

Asn Lys Leu Asn Ser Asn Thr Thr Gln Thr Tyr Glu Gln Lys Gly
    1625                1630                1635

Leu Thr Val Ala Phe Ser Ser Pro Val Thr Asp Leu Ala Gln Gln
    1640                1645                1650

Ala Ile Ala Val Ala Gln Ser Ser Lys Gln Val Gly Gln Ser Lys
    1655                1660                1665

Asn Asp Arg Val Asn Ala Met Ala Ala Ala Asn Ala Gly Trp Gln
    1670                1675                1680

Ala Tyr Gln Thr Gly Lys Ser Ala Gln Asn Leu Ala Asn Gly Thr
    1685                1690                1695

Thr Asn Ala Lys Gln Val Ser Ile Ser Ile Thr Tyr Gly Glu Gln
    1700                1705                1710

Gln Asn Arg Gln Thr Thr Gln Val Gln Ala Asn Gln Ala Gln Ala
    1715                1720                1725

Ser Gln Ile Gln Ala Gly Gly Lys Thr Thr Leu Ile Ala Thr Gly
    1730                1735                1740

Ala Ala Glu Gln Ser Asn Ile Asn Ile Ala Gly Ser Asp Val Ala
    1745                1750                1755

Gly Lys Ala Gly Thr Ile Leu Ile Ala Asp Asn Asp Ile Thr Leu
    1760                1765                1770

Gln Ser Ala Glu Gln Ser Asn Thr Glu Arg Gly Gln Asn Lys Ser
    1775                1780                1785

Ala Gly Trp Asn Ala Gly Ala Ala Val Ser Phe Gly Gln Gly Gly
    1790                1795                1800

Trp Ser Leu Gly Val Thr Ala Gly Gly Asn Val Gly Lys Gly Tyr
    1805                1810                1815

Gly Asn Gly Asp Ser Ile Thr His Arg His Ser His Ile Gly Asp
    1820                1825                1830

Lys Gly Ser Gln Thr Leu Ile Gln Ser Gly Gly Asp Thr Thr Ile
    1835                1840                1845

Lys Gly Ala Gln Val Arg Gly Lys Gly Val Gln Val Asn Ala Lys
    1850                1855                1860

Asn Leu Ser Ile Gln Ser Val Gln Asp Arg Glu Thr Tyr Gln Ser
    1865                1870                1875

Lys Gln Gln Asn Ala Ser Ala Gln Val Thr Val Gly Tyr Gly Phe
    1880                1885                1890

Ser Ala Gly Gly Asp Tyr Ser Gln Ser Lys Ile Arg Ala Asp His
    1895                1900                1905

Val Ser Val Thr Glu Gln Ser Gly Ile Tyr Ala Gly Glu Asp Gly
    1910                1915                1920

Tyr Gln Ile Lys Val Gly Asn His Thr Asp Leu Lys Gly Gly Ile
    1925                1930                1935

Ile Thr Ser Thr Gln Ser Ala Glu Asp Lys Gly Lys Asn Arg Phe
    1940                1945                1950
```

```
Gln Thr Ala Thr Leu Thr His Ser Asp Ile Lys Asn His Ser Gln
    1955            1960            1965

Tyr Lys Gly Glu Ser Phe Gly Leu Gly Ala Ser Ala Ser Ile Ser
    1970            1975            1980

Gly Lys Thr Leu Gly Gln Gly Ala Gln Asn Lys Pro Gln Asn Lys
    1985            1990            1995

His Leu Thr Ser Val Ala Asp Lys Asn Ser Ala Ser Ser Ser Val
    2000            2005            2010

Gly Tyr Gly Ser Asp Ser Asp Ser Gln Ser Ser Ile Thr Lys Ser
    2015            2020            2025

Gly Ile Asn Thr Arg Asn Ile Gln Ile Thr Asp Glu Ala Ala Gln
    2030            2035            2040

Ile Arg Leu Thr Gly Lys Thr Ala Ala Gln Thr Lys Ala Asp Ile
    2045            2050            2055

Asp Thr Asn Val Thr Thr Asp Thr Ala Glu Arg His Ser Gly Ser
    2060            2065            2070

Leu Lys Asn Thr Phe Asn Lys Glu Ala Val Gln Ser Glu Leu Asp
    2075            2080            2085

Leu Gln Arg Thr Val Ser Gln Asp Phe Ser Lys Asn Val Gln Gln
    2090            2095            2100

Ala Asn Thr Glu Ile Asn Gln His Leu Asp Lys Leu Lys Ala Asp
    2105            2110            2115

Lys Glu Ala Ala Glu Thr Ala Ala Ala Glu Ala Leu Ala Asn Gly
    2120            2125            2130

Asp Met Glu Thr Ala Lys Arg Lys Ala His Glu Ala Gln Asp Ala
    2135            2140            2145

Ala Ala Lys Ala Asp Asn Trp Gln Gln Gly Lys Val Ile Leu Asn
    2150            2155            2160

Met Leu Ala Ser Gly Leu Ala Ala Pro Thr Gln Ser Gly Ala Gly
    2165            2170            2175

Ile Ala Ala Ala Thr Ala Ser Pro Ala Val Ser Tyr Ala Ile Gly
    2180            2185            2190

Gln His Phe Lys Asp Leu Ala Gly Gln Asn Ala Asn Gly Lys Leu
    2195            2200            2205

Thr Ala Ser Gln Glu Thr Ala His Val Leu Ala His Ala Val Leu
    2210            2215            2220

Gly Ala Ala Val Ala Ala Val Gly Asp Asn Asn Ala Leu Ala Gly
    2225            2230            2235

Ala Leu Ser Ala Gly Gly Ser Glu Ala Ala Pro Tyr Ile Ser
    2240            2245            2250

Lys Trp Leu Tyr Gly Lys Glu Lys Gly Ser Asp Leu Thr Ala Glu
    2255            2260            2265

Glu Lys Glu Thr Val Thr Ala Ile Thr Asn Val Leu Gly Thr Ala
    2270            2275            2280

Thr Gly Ala Ala Val Gly Asn Ser Ala Thr Asp Ala Ala Gln Gly
    2285            2290            2295

Ser Leu Asn Ala Gln Ser Ala Val Glu Asn Asn Asp Thr Val Glu
    2300            2305            2310

Gln Val Lys Phe Ala Leu Arg His Pro Arg Ile Ala Ile Ala Ile
    2315            2320            2325

Gly Ser Val His Lys Asp Pro Gly Ser Thr Leu Glu Pro Asn Ile
    2330            2335            2340
```

-continued

```
Ser Thr Ile Ala Ser Thr Phe Gln Leu Asn Leu Phe Pro Asn Ser
    2345                2350                2355
Glu Phe Gly Gly Glu Gly Val Gly Asn Ala Phe Arg His Val
    2360                2365                2370
Leu Trp Gln Ala Thr Ile Thr Arg Glu Phe Gly Lys Asp Ile Ala
    2375                2380                2385
Val Lys Val Gly Asn Ser His Glu Ser Gly Glu Lys Ile Asn Tyr
    2390                2395                2400
Ser Ile Arg Arg Asn Leu Ser Leu Asp Lys Ala Asp Glu Met Ile
    2405                2410                2415
Asp Gln Leu Asn Asn Glu Ile Gly Arg Glu Ile Ala Leu Asn Thr
    2420                2425                2430
Asn Arg Leu Asn Thr Lys Glu Leu Val Gly Leu Ile Leu Glu Thr
    2435                2440                2445
Tyr Lys Asn Asn Gly Phe Tyr Gln Ala Glu Arg Asn Ser Asn Gly
    2450                2455                2460
Asn Tyr Asp Val Val Arg Lys Arg Leu Ser Glu Lys Asp Tyr Gln
    2465                2470                2475
Asn Thr Ser Asn Ile Leu Ile His Leu Asp Asn Thr Gly Ala Gly
    2480                2485                2490
Phe Lys Ile Gln Gln Arg Arg Lys Gln Ile Arg Ala Gln Ile Ser
    2495                2500                2505
Ala Arg Gln Trp Arg Arg
    2510

<210> SEQ ID NO 41
<211> LENGTH: 1275
<212> TYPE: DNA
<213> ORGANISM: Neisseria meningitidis
<220> FEATURE:
<221> NAME/KEY: CDS
<222> LOCATION: (1)..(1275)
<223> OTHER INFORMATION: NMB0115

<400> SEQUENCE: 41 atg cgt agc agc gat att tta att gta gac gac gaa atc ggc atc cgc      48
Met Arg Ser Ser Asp Ile Leu Ile Val Asp Asp Glu Ile Gly Ile Arg
1               5                   10                  15 gac ctg ctg tcg gaa atc ctg cag gac gaa ggt tat tcg gtc gca ttg      96
Asp Leu Leu Ser Glu Ile Leu Gln Asp Glu Gly Tyr Ser Val Ala Leu
            20                  25                  30 gcg gaa aac gcc gaa gag gcg cgc aag ctg cgc cat cag gcg cgc ccc     144
Ala Glu Asn Ala Glu Glu Ala Arg Lys Leu Arg His Gln Ala Arg Pro
        35                  40                  45 gcg atg gtg ctg ctg gat att tgg atg cct gat tgc gac ggc atc acc     192
Ala Met Val Leu Leu Asp Ile Trp Met Pro Asp Cys Asp Gly Ile Thr
    50                  55                  60 ctt ttg aag gag tgg gcg aaa aac ggg cag ctc aat atg ccg gtg gtg     240
Leu Leu Lys Glu Trp Ala Lys Asn Gly Gln Leu Asn Met Pro Val Val
65                  70                  75                  80 atg atg agc ggg cat gcc agc atc gat acc gcc gtg gaa gcc acc aaa     288
Met Met Ser Gly His Ala Ser Ile Asp Thr Ala Val Glu Ala Thr Lys
                85                  90                  95 atc ggc gcg atc gat ttt ttg gaa aaa ccg att tcc ctg caa aag ctg     336
Ile Gly Ala Ile Asp Phe Leu Glu Lys Pro Ile Ser Leu Gln Lys Leu
            100                 105                 110 ctg tct gcc gtc gaa aac gcg ttg aag tac ggt gcg gcg caa acc gaa     384
Leu Ser Ala Val Glu Asn Ala Leu Lys Tyr Gly Ala Ala Gln Thr Glu
        115                 120                 125
```

```
acg ggg cct gta ttc gac aag ctg ggc aac agt gcg gcg att cag gaa      432
Thr Gly Pro Val Phe Asp Lys Leu Gly Asn Ser Ala Ala Ile Gln Glu
    130             135                 140 atg aac cgt gag gta ggg gct gcg gtg aaa tgt gcc tct ccc gta ctt      480
Met Asn Arg Glu Val Gly Ala Ala Val Lys Cys Ala Ser Pro Val Leu
145                 150                 155                 160 ttg acg ggc gag gcg ggt tcg ccg ttt gaa acg gtg gca cgc tat ttc      528
Leu Thr Gly Glu Ala Gly Ser Pro Phe Glu Thr Val Ala Arg Tyr Phe
                165                 170                 175 cat aaa aac ggt acg ccg tgg gtc agc ccg gca agg gtc gaa tat ctg      576
His Lys Asn Gly Thr Pro Trp Val Ser Pro Ala Arg Val Glu Tyr Leu
            180                 185                 190 atc gat atg ccg atg gaa ctg ttg cag aag gcg gag ggc ggc gtt ttg      624
Ile Asp Met Pro Met Glu Leu Leu Gln Lys Ala Glu Gly Gly Val Leu
        195                 200                 205 tat gtc ggc gac atc gcc cag tac agc cgc aac atc caa gcc ggt att      672
Tyr Val Gly Asp Ile Ala Gln Tyr Ser Arg Asn Ile Gln Ala Gly Ile
    210                 215                 220 gcc ttt att gtc gga aag gcg gaa cac cgc cgc gtc agg gtg gtc gca      720
Ala Phe Ile Val Gly Lys Ala Glu His Arg Arg Val Arg Val Val Ala
225                 230                 235                 240 tcg ggc agc agg gcg gca ggt tca gac ggc att gcc tgc gag gaa aag      768
Ser Gly Ser Arg Ala Ala Gly Ser Asp Gly Ile Ala Cys Glu Glu Lys
                245                 250                 255 ctg gcg gaa ctg ctg tcg gaa tcg gtc gtc cgt att ccg ccg ctg cgt      816
Leu Ala Glu Leu Leu Ser Glu Ser Val Val Arg Ile Pro Pro Leu Arg
            260                 265                 270 atg cag cat gaa gac att ccc ttc ctg ata cag ggg att gcc tgc aat      864
Met Gln His Glu Asp Ile Pro Phe Leu Ile Gln Gly Ile Ala Cys Asn
        275                 280                 285 gtg gcg gaa agc caa aag att gcg cct gcc tca ttc agt gaa gag gca      912
Val Ala Glu Ser Gln Lys Ile Ala Pro Ala Ser Phe Ser Glu Glu Ala
    290                 295                 300 ctt gcc gca ttg acc cgt tac gac tgg ccg gga aat ttc gac caa ctg      960
Leu Ala Ala Leu Thr Arg Tyr Asp Trp Pro Gly Asn Phe Asp Gln Leu
305                 310                 315                 320 caa agc gtc gtt gca acg ctg ttg ttg gag gcg gac gga cag gaa atc     1008
Gln Ser Val Val Ala Thr Leu Leu Leu Glu Ala Asp Gly Gln Glu Ile
                325                 330                 335 ggc gca ggg gcg gtt tct tcc ctt ttg ggg cag aat gtg cct gcc gag     1056
Gly Ala Gly Ala Val Ser Ser Leu Leu Gly Gln Asn Val Pro Ala Glu
            340                 345                 350 ggg gcg gaa gat atg gtg ggc ggg ttt aat ttc aac ctg ccc ctg cgc     1104
Gly Ala Glu Asp Met Val Gly Gly Phe Asn Phe Asn Leu Pro Leu Arg
        355                 360                 365 gaa ttg agg gag gag gtg gag cgg cgt tat ttc gag tac cac atc gcc     1152
Glu Leu Arg Glu Glu Val Glu Arg Arg Tyr Phe Glu Tyr His Ile Ala
    370                 375                 380 caa gaa ggt cag aat atg agc caa gtg gcg cag aaa gtt ggt ttg gaa     1200
Gln Glu Gly Gln Asn Met Ser Gln Val Ala Gln Lys Val Gly Leu Glu
385                 390                 395                 400 cgc acg cac ctt tac cgc aaa ctc aaa cag ctc ggc atc ggc gtt tcg     1248
Arg Thr His Leu Tyr Arg Lys Leu Lys Gln Leu Gly Ile Gly Val Ser
                405                 410                 415 cgc cgg gcg ggg gaa aaa acc gaa gaa                                 1275
Arg Arg Ala Gly Glu Lys Thr Glu Glu
            420                 425

<210> SEQ ID NO 42
```

```
<211> LENGTH: 425
<212> TYPE: PRT
<213> ORGANISM: Neisseria meningitidis

<400> SEQUENCE: 42

Met Arg Ser Ser Asp Ile Leu Ile Val Asp Asp Glu Ile Gly Ile Arg
1               5                   10                  15

Asp Leu Leu Ser Glu Ile Leu Gln Asp Glu Gly Tyr Ser Val Ala Leu
            20                  25                  30

Ala Glu Asn Ala Glu Glu Ala Arg Lys Leu Arg His Gln Ala Arg Pro
        35                  40                  45

Ala Met Val Leu Leu Asp Ile Trp Met Pro Asp Cys Asp Gly Ile Thr
    50                  55                  60

Leu Leu Lys Glu Trp Ala Lys Asn Gly Gln Leu Asn Met Pro Val Val
65                  70                  75                  80

Met Met Ser Gly His Ala Ser Ile Asp Thr Ala Val Glu Ala Thr Lys
                85                  90                  95

Ile Gly Ala Ile Asp Phe Leu Glu Lys Pro Ile Ser Leu Gln Lys Leu
            100                 105                 110

Leu Ser Ala Val Glu Asn Ala Leu Lys Tyr Gly Ala Ala Gln Thr Glu
        115                 120                 125

Thr Gly Pro Val Phe Asp Lys Leu Gly Asn Ser Ala Ala Ile Gln Glu
    130                 135                 140

Met Asn Arg Glu Val Gly Ala Ala Val Lys Cys Ala Ser Pro Val Leu
145                 150                 155                 160

Leu Thr Gly Glu Ala Gly Ser Pro Phe Glu Thr Val Ala Arg Tyr Phe
                165                 170                 175

His Lys Asn Gly Thr Pro Trp Val Ser Pro Ala Arg Val Glu Tyr Leu
            180                 185                 190

Ile Asp Met Pro Met Glu Leu Leu Gln Lys Ala Glu Gly Gly Val Leu
        195                 200                 205

Tyr Val Gly Asp Ile Ala Gln Tyr Ser Arg Asn Ile Gln Ala Gly Ile
    210                 215                 220

Ala Phe Ile Val Gly Lys Ala Glu His Arg Arg Val Arg Val Val Ala
225                 230                 235                 240

Ser Gly Ser Arg Ala Ala Gly Ser Asp Gly Ile Ala Cys Glu Glu Lys
                245                 250                 255

Leu Ala Glu Leu Leu Ser Glu Ser Val Val Arg Ile Pro Pro Leu Arg
            260                 265                 270

Met Gln His Glu Asp Ile Pro Phe Leu Ile Gln Gly Ile Ala Cys Asn
        275                 280                 285

Val Ala Glu Ser Gln Lys Ile Ala Pro Ala Ser Phe Ser Glu Glu Ala
    290                 295                 300

Leu Ala Ala Leu Thr Arg Tyr Asp Trp Pro Gly Asn Phe Asp Gln Leu
305                 310                 315                 320

Gln Ser Val Val Ala Thr Leu Leu Glu Ala Asp Gly Gln Glu Ile
                325                 330                 335

Gly Ala Gly Ala Val Ser Ser Leu Leu Gly Gln Asn Val Pro Ala Glu
            340                 345                 350

Gly Ala Glu Asp Met Val Gly Phe Asn Phe Asn Leu Pro Leu Arg
        355                 360                 365

Glu Leu Arg Glu Glu Val Glu Arg Arg Tyr Phe Glu Tyr His Ile Ala
    370                 375                 380

Gln Glu Gly Gln Asn Met Ser Gln Val Ala Gln Lys Val Gly Leu Glu
```

```
                385                 390                 395                 400
Arg Thr His Leu Tyr Arg Lys Leu Lys Gln Leu Gly Ile Gly Val Ser
                    405                 410                 415

Arg Arg Ala Gly Glu Lys Thr Glu Glu
                420                 425

<210> SEQ ID NO 43
<211> LENGTH: 1191
<212> TYPE: DNA
<213> ORGANISM: Neisseria meningitidis
<220> FEATURE:
<221> NAME/KEY: CDS
<222> LOCATION: (1)..(1191)
<223> OTHER INFORMATION: NMB0116

<400> SEQUENCE: 43 atg aca gag gac gaa cgt ttc gcg tgg ctg caa ttg gcg ttt acg ccc        48
Met Thr Glu Asp Glu Arg Phe Ala Trp Leu Gln Leu Ala Phe Thr Pro
1               5                   10                  15 tat atc ggc gcg gaa agt ttc ctg ctg ctg atg cgc cgt ttc ggc agc        96
Tyr Ile Gly Ala Glu Ser Phe Leu Leu Leu Met Arg Arg Phe Gly Ser
            20                  25                  30 gcg caa aat gcc ctg tcc gca ccg gcg gaa cag gtg gcg gca ctg ata       144
Ala Gln Asn Ala Leu Ser Ala Pro Ala Glu Gln Val Ala Ala Leu Ile
        35                  40                  45 cgg cac aaa cag gcg ctt gag gct tgg cgc aat gcg gaa aaa cgc gct       192
Arg His Lys Gln Ala Leu Glu Ala Trp Arg Asn Ala Glu Lys Arg Ala
    50                  55                  60 ctg gcg cgg cag gcg gca gaa gcg gca ttg gaa tgg gaa atg cgg gac       240
Leu Ala Arg Gln Ala Ala Glu Ala Ala Leu Glu Trp Glu Met Arg Asp
65                  70                  75                  80 gga tgc cgc ctg atg ctg ctt cag gat gaa gat ttt ccc gaa atg ctg       288
Gly Cys Arg Leu Met Leu Leu Gln Asp Glu Asp Phe Pro Glu Met Leu
                85                  90                  95 acg cag ggg ctg acc gcg cca ccg gtt ttg ttt ttg cgc ggc aac gtg       336
Thr Gln Gly Leu Thr Ala Pro Pro Val Leu Phe Leu Arg Gly Asn Val
            100                 105                 110 caa ctg ctg cac aaa cct tcc gcc gcc atc gtc ggc agc cgt cat gcc       384
Gln Leu Leu His Lys Pro Ser Ala Ala Ile Val Gly Ser Arg His Ala
        115                 120                 125 acg ccg cag gcg atg cgg att gcc aaa gat ttc ggc aag tcg ttg ggt       432
Thr Pro Gln Ala Met Arg Ile Ala Lys Asp Phe Gly Lys Ser Leu Gly
    130                 135                 140 ggg aaa ggc att ccc gtt gtg tcg ggt atg gct tcg ggc atc gat acc       480
Gly Lys Gly Ile Pro Val Val Ser Gly Met Ala Ser Gly Ile Asp Thr
145                 150                 155                 160 gcc gcc cat cag ggt gcg ttg cag gca gaa ggc ggc acc atc gcc gtg       528
Ala Ala His Gln Gly Ala Leu Gln Ala Glu Gly Gly Thr Ile Ala Val
                165                 170                 175 tgg ggg acg ggc ata gac cgc att tat ccg ccg gtc aac aaa aac ctt       576
Trp Gly Thr Gly Ile Asp Arg Ile Tyr Pro Pro Val Asn Lys Asn Leu
            180                 185                 190 gcc tat gaa atc gcc gaa aaa gga ttg att gtc agc gag ttc ccc atc       624
Ala Tyr Glu Ile Ala Glu Lys Gly Leu Ile Val Ser Glu Phe Pro Ile
        195                 200                 205 ggc acg cgg ccg tat gcc ggc aat ttt ccg cgc cgc aac cgc ctg att       672
Gly Thr Arg Pro Tyr Ala Gly Asn Phe Pro Arg Arg Asn Arg Leu Ile
    210                 215                 220 gcc gcc ctg tcg caa gta acg ctg gtg gtt gaa gcc gcg ttg gaa tcc       720
Ala Ala Leu Ser Gln Val Thr Leu Val Val Glu Ala Ala Leu Glu Ser
225                 230                 235                 240
```

```
ggt tcg ctg att act gcc aga ttg gcg gcg gag atg ggg cgc gaa gtg      768
Gly Ser Leu Ile Thr Ala Arg Leu Ala Ala Glu Met Gly Arg Glu Val
            245                 250                 255 atg gcg gta ccc ggc tcg ata gac aat cca cac agt aaa ggc tgc cac      816
Met Ala Val Pro Gly Ser Ile Asp Asn Pro His Ser Lys Gly Cys His
        260                 265                 270 aaa ctg att aaa gac ggc gca aaa ttg gtg gaa tgc ctg gac gac atc      864
Lys Leu Ile Lys Asp Gly Ala Lys Leu Val Glu Cys Leu Asp Asp Ile
    275                 280                 285 ctg aac gaa tgc ccg ggg cta ttg caa aat acg ggt gct tca tca tat      912
Leu Asn Glu Cys Pro Gly Leu Leu Gln Asn Thr Gly Ala Ser Ser Tyr
290                 295                 300 tct ata aat aag gga ata cct gaa aag cgc atc act gcc gtt cag acg      960
Ser Ile Asn Lys Gly Ile Pro Glu Lys Arg Ile Thr Ala Val Gln Thr
305                 310                 315                 320 gca tcc gac cag ctg tct ctg cct gaa ggc aaa atg ccg tct gaa aag     1008
Ala Ser Asp Gln Leu Ser Leu Pro Glu Gly Lys Met Pro Ser Glu Lys
                325                 330                 335 acg gag aac cga ccc gtc ggc ggc agt atc ttg gac agg atg ggt ttc     1056
Thr Glu Asn Arg Pro Val Gly Gly Ser Ile Leu Asp Arg Met Gly Phe
            340                 345                 350 gac cca gtt cat ccc gac gtg ctt gcc gga cag ttg gct atg cct gcc     1104
Asp Pro Val His Pro Asp Val Leu Ala Gly Gln Leu Ala Met Pro Ala
        355                 360                 365 gca gat ttg tat gcc gca ctg ttg gaa ttg gaa ttg gac ggc agc gtt     1152
Ala Asp Leu Tyr Ala Ala Leu Leu Glu Leu Glu Leu Asp Gly Ser Val
    370                 375                 380 gcc gca atg ccc ggc ggc aga tac cag cgt atc cga act                 1191
Ala Ala Met Pro Gly Gly Arg Tyr Gln Arg Ile Arg Thr
385                 390                 395

<210> SEQ ID NO 44
<211> LENGTH: 397
<212> TYPE: PRT
<213> ORGANISM: Neisseria meningitidis

<400> SEQUENCE: 44

Met Thr Glu Asp Glu Arg Phe Ala Trp Leu Gln Leu Ala Phe Thr Pro
1               5                   10                  15

Tyr Ile Gly Ala Glu Ser Phe Leu Leu Leu Met Arg Arg Phe Gly Ser
            20                  25                  30

Ala Gln Asn Ala Leu Ser Ala Pro Ala Glu Gln Val Ala Ala Leu Ile
        35                  40                  45

Arg His Lys Gln Ala Leu Glu Ala Trp Arg Asn Ala Glu Lys Arg Ala
    50                  55                  60

Leu Ala Arg Gln Ala Ala Glu Ala Ala Leu Glu Trp Glu Met Arg Asp
65                  70                  75                  80

Gly Cys Arg Leu Met Leu Leu Gln Asp Glu Asp Phe Pro Glu Met Leu
                85                  90                  95

Thr Gln Gly Leu Thr Ala Pro Pro Val Leu Phe Leu Arg Gly Asn Val
            100                 105                 110

Gln Leu Leu His Lys Pro Ser Ala Ala Ile Val Gly Ser Arg His Ala
        115                 120                 125

Thr Pro Gln Ala Met Arg Ile Ala Lys Asp Phe Gly Lys Ser Leu Gly
    130                 135                 140

Gly Lys Gly Ile Pro Val Val Ser Gly Met Ala Ser Gly Ile Asp Thr
145                 150                 155                 160
```

```
Ala Ala His Gln Gly Ala Leu Gln Ala Glu Gly Gly Thr Ile Ala Val
            165                 170                 175

Trp Gly Thr Gly Ile Asp Arg Ile Tyr Pro Pro Val Asn Lys Asn Leu
            180                 185                 190

Ala Tyr Glu Ile Ala Glu Lys Gly Leu Ile Val Ser Glu Phe Pro Ile
            195                 200                 205

Gly Thr Arg Pro Tyr Ala Gly Asn Phe Pro Arg Arg Asn Arg Leu Ile
            210                 215                 220

Ala Ala Leu Ser Gln Val Thr Leu Val Val Glu Ala Ala Leu Glu Ser
225                 230                 235                 240

Gly Ser Leu Ile Thr Ala Arg Leu Ala Ala Glu Met Gly Arg Glu Val
            245                 250                 255

Met Ala Val Pro Gly Ser Ile Asp Asn Pro His Ser Lys Gly Cys His
            260                 265                 270

Lys Leu Ile Lys Asp Gly Ala Lys Leu Val Glu Cys Leu Asp Asp Ile
            275                 280                 285

Leu Asn Glu Cys Pro Gly Leu Leu Gln Asn Thr Gly Ala Ser Ser Tyr
            290                 295                 300

Ser Ile Asn Lys Gly Ile Pro Glu Lys Arg Ile Thr Ala Val Gln Thr
305                 310                 315                 320

Ala Ser Asp Gln Leu Ser Leu Pro Glu Gly Lys Met Pro Ser Glu Lys
            325                 330                 335

Thr Glu Asn Arg Pro Val Gly Gly Ser Ile Leu Asp Arg Met Gly Phe
            340                 345                 350

Asp Pro Val His Pro Asp Val Leu Ala Gly Gln Leu Ala Met Pro Ala
            355                 360                 365

Ala Asp Leu Tyr Ala Ala Leu Leu Glu Leu Glu Leu Asp Gly Ser Val
            370                 375                 380

Ala Ala Met Pro Gly Gly Arg Tyr Gln Arg Ile Arg Thr
385                 390                 395

<210> SEQ ID NO 45
<211> LENGTH: 459
<212> TYPE: DNA
<213> ORGANISM: Neisseria meningitidis
<220> FEATURE:
<221> NAME/KEY: CDS
<222> LOCATION: (1)..(459)
<223> OTHER INFORMATION: NMB0117

<400> SEQUENCE: 45 atg acc gaa gtc atc gcc tac ctc atc gaa cat ttc caa gat ttc gat     48
Met Thr Glu Val Ile Ala Tyr Leu Ile Glu His Phe Gln Asp Phe Asp
1               5                   10                  15 acc tgc ccg ccg ccc gaa gac ttg ggt atg ctg ctt gaa gaa gcg ggt     96
Thr Cys Pro Pro Pro Glu Asp Leu Gly Met Leu Leu Glu Glu Ala Gly
                20                  25                  30 ttc gat acg atg gaa atc ggc aac acc ctg atg atg atg gaa gta ttg    144
Phe Asp Thr Met Glu Ile Gly Asn Thr Leu Met Met Met Glu Val Leu
            35                  40                  45 ctc aac agc tcc gaa ttt tcc gcc gaa ccc gcc gac agc ggc gca ttg    192
Leu Asn Ser Ser Glu Phe Ser Ala Glu Pro Ala Asp Ser Gly Ala Leu
        50                  55                  60 cgc gtg tac agc aaa gaa gaa acc gac aac ctg ccg cag gaa gtg atg    240
Arg Val Tyr Ser Lys Glu Glu Thr Asp Asn Leu Pro Gln Glu Val Met
65                  70                  75                  80 ggg ctg atg cag tat ctg att gaa gaa aaa gcc gtc agc tgc gaa cag    288
Gly Leu Met Gln Tyr Leu Ile Glu Glu Lys Ala Val Ser Cys Glu Gln
```

-continued

```
                  85                  90                  95
cgg gaa atc atc atc cac gcg ctc atg cac att ccg ggc gac gaa att       336
Arg Glu Ile Ile Ile His Ala Leu Met His Ile Pro Gly Asp Glu Ile
            100                 105                 110 acc gta gat acc gcc aaa gtg ctg acc ctg ctg ctt tta tgg gca aac       384
Thr Val Asp Thr Ala Lys Val Leu Thr Leu Leu Leu Leu Trp Ala Asn
        115                 120                 125 aag agc gag ctg ccc gtg ttg gtc ggc gac gag ctg atg agc gcg ctt       432
Lys Ser Glu Leu Pro Val Leu Val Gly Asp Glu Leu Met Ser Ala Leu
    130                 135                 140 tta ctc gac aac aaa ccc acg atg aac                                   459
Leu Leu Asp Asn Lys Pro Thr Met Asn
145                 150

<210> SEQ ID NO 46
<211> LENGTH: 153
<212> TYPE: PRT
<213> ORGANISM: Neisseria meningitidis

<400> SEQUENCE: 46

Met Thr Glu Val Ile Ala Tyr Leu Ile Glu His Phe Gln Asp Phe Asp
1               5                   10                  15

Thr Cys Pro Pro Pro Glu Asp Leu Gly Met Leu Leu Glu Glu Ala Gly
            20                  25                  30

Phe Asp Thr Met Glu Ile Gly Asn Thr Leu Met Met Met Glu Val Leu
        35                  40                  45

Leu Asn Ser Ser Glu Phe Ser Ala Glu Pro Ala Asp Ser Gly Ala Leu
    50                  55                  60

Arg Val Tyr Ser Lys Glu Glu Thr Asp Asn Leu Pro Gln Glu Val Met
65                  70                  75                  80

Gly Leu Met Gln Tyr Leu Ile Glu Glu Lys Ala Val Ser Cys Glu Gln
                85                  90                  95

Arg Glu Ile Ile Ile His Ala Leu Met His Ile Pro Gly Asp Glu Ile
            100                 105                 110

Thr Val Asp Thr Ala Lys Val Leu Thr Leu Leu Leu Leu Trp Ala Asn
        115                 120                 125

Lys Ser Glu Leu Pro Val Leu Val Gly Asp Glu Leu Met Ser Ala Leu
    130                 135                 140

Leu Leu Asp Asn Lys Pro Thr Met Asn
145                 150

<210> SEQ ID NO 47
<211> LENGTH: 1776
<212> TYPE: DNA
<213> ORGANISM: Neisseria meningitidis
<220> FEATURE:
<221> NAME/KEY: CDS
<222> LOCATION: (1)..(1776)
<223> OTHER INFORMATION: NMB2075

<400> SEQUENCE: 47 atg acg gtt ttg aag ctt tcg cac tgg cgg gtg ttg gcg gag ctt gcc       48
Met Thr Val Leu Lys Leu Ser His Trp Arg Val Leu Ala Glu Leu Ala
1               5                   10                  15 gac ggt ttg ccg caa cac gtc tcg caa ctg gcg cgt atg gcg gat atg       96
Asp Gly Leu Pro Gln His Val Ser Gln Leu Ala Arg Met Ala Asp Met
            20                  25                  30 aag ccg cag cag ctc aac ggt ttt tgg cag cag atg ccg gcg cac ata       144
Lys Pro Gln Gln Leu Asn Gly Phe Trp Gln Gln Met Pro Ala His Ile
        35                  40                  45
```

| | | |
|---|---|---|
| cgc ggg ctg ttg cgc caa cac gac ggc tat tgg cgg ctg gtg cgc cca<br>Arg Gly Leu Leu Arg Gln His Asp Gly Tyr Trp Arg Leu Val Arg Pro<br>50 55 60 | 192 | |
| ttg gcg gtt ttc gat gcc gaa ggt ttg cgc gag ctg ggg gaa agg tcg<br>Leu Ala Val Phe Asp Ala Glu Gly Leu Arg Glu Leu Gly Glu Arg Ser<br>65 70 75 80 | 240 | |
| ggt ttt cag acg gca ttg aag cac gag tgc gcg tcc agc aac gac gag<br>Gly Phe Gln Thr Ala Leu Lys His Glu Cys Ala Ser Ser Asn Asp Glu<br>85 90 95 | 288 | |
| ata ctg gaa ttg gcg cgg att gcg ccg gac aag gcg cac aaa acc ata<br>Ile Leu Glu Leu Ala Arg Ile Ala Pro Asp Lys Ala His Lys Thr Ile<br>100 105 110 | 336 | |
| tgc gtg acc cac ctg caa agt aag ggc agg ggg cgc cag ggg cgg aag<br>Cys Val Thr His Leu Gln Ser Lys Gly Arg Gly Arg Gln Gly Arg Lys<br>115 120 125 | 384 | |
| tcg cac cgt ttg ggc gag tgt ctg atg ttc agt ttt ggc tgg gtg<br>Trp Ser His Arg Leu Gly Glu Cys Leu Met Phe Ser Phe Gly Trp Val<br>130 135 140 | 432 | |
| ttt gac cgg ccg cag tat gag ttg ggt tcg ctg tcg cct gtt gcg gca<br>Phe Asp Arg Pro Gln Tyr Glu Leu Gly Ser Leu Ser Pro Val Ala Ala<br>145 150 155 160 | 480 | |
| gtg gcg tgt cgg cgc gcc ttg tcg cgt tta ggt ttg gat gtg cag att<br>Val Ala Cys Arg Arg Ala Leu Ser Arg Leu Gly Leu Asp Val Gln Ile<br>165 170 175 | 528 | |
| aag tgg ccc aat gat ttg gtt gtc gga cgc gac aaa ttg ggc ggc att<br>Lys Trp Pro Asn Asp Leu Val Val Gly Arg Asp Lys Leu Gly Gly Ile<br>180 185 190 | 576 | |
| ctg att gaa acg gtc agg acg ggc ggc aaa acg gtt gcc gtg gtc ggt<br>Leu Ile Glu Thr Val Arg Thr Gly Gly Lys Thr Val Ala Val Val Gly<br>195 200 205 | 624 | |
| atc ggc atc aat ttt gtc ctg ccc aag gaa gta gaa aat gcc gct tcc<br>Ile Gly Ile Asn Phe Val Leu Pro Lys Glu Val Glu Asn Ala Ala Ser<br>210 215 220 | 672 | |
| gtg caa tcg ctg ttt cag acg gca tcg cgg cgg ggc aat gcc gat gcc<br>Val Gln Ser Leu Phe Gln Thr Ala Ser Arg Arg Gly Asn Ala Asp Ala<br>225 230 235 240 | 720 | |
| gcc gtg ctg ctg gaa acg ctg ttg gtg gaa ctg gac gcg gtg ttg ttg<br>Ala Val Leu Leu Glu Thr Leu Leu Val Glu Leu Asp Ala Val Leu Leu<br>245 250 255 | 768 | |
| caa tat gcg cgg gac gga ttt gcg cct ttt gtg gcg gaa tat cag gct<br>Gln Tyr Ala Arg Asp Gly Phe Ala Pro Phe Val Ala Glu Tyr Gln Ala<br>260 265 270 | 816 | |
| gcc aac cgc gac cac ggc aag gcg gta ttg ctg ttg cgc gac ggc gaa<br>Ala Asn Arg Asp His Gly Lys Ala Val Leu Leu Leu Arg Asp Gly Glu<br>275 280 285 | 864 | |
| acc gtg ttc gaa ggc acg gtt aaa ggc gtg gac gga caa ggc gtt ttg<br>Thr Val Phe Glu Gly Thr Val Lys Gly Val Asp Gly Gln Gly Val Leu<br>290 295 300 | 912 | |
| cac ttg gaa acg gca gag ggc aaa cag acg gtc gtc agc ggc gaa atc<br>His Leu Glu Thr Ala Glu Gly Lys Gln Thr Val Val Ser Gly Glu Ile<br>305 310 315 320 | 960 | |
| agc ctg cgg tcc gac gac agg ccg gtt tcc gtg ccg aag cgg cgg gat<br>Ser Leu Arg Ser Asp Asp Arg Pro Val Ser Val Pro Lys Arg Arg Asp<br>325 330 335 | 1008 | |
| tcg gaa cgt ttt ctg ctg ttg gac ggc ggc aac agc cgg ctc aag tgg<br>Ser Glu Arg Phe Leu Leu Leu Asp Gly Gly Asn Ser Arg Leu Lys Trp<br>340 345 350 | 1056 | |
| gcg tgg gtg gaa aac ggc acg ttc gca acc gtc ggt agc gcg ccg tac<br>Ala Trp Val Glu Asn Gly Thr Phe Ala Thr Val Gly Ser Ala Pro Tyr | 1104 | |

```
                355                 360                 365
cgc gat ttg tcg cct ttg ggc gcg gag tgg gcg gaa aag gcg gat gga    1152
Arg Asp Leu Ser Pro Leu Gly Ala Glu Trp Ala Glu Lys Ala Asp Gly
370                 375                 380 aat gtc cgc atc gtc ggt tgc gct gtg tgc gga gaa ttc aaa aag gca    1200
Asn Val Arg Ile Val Gly Cys Ala Val Cys Gly Glu Phe Lys Lys Ala
385                 390                 395                 400 caa gtg cag gaa cag ctc gcc cga aaa atc gag tgg ctg ccg tct tcc    1248
Gln Val Gln Glu Gln Leu Ala Arg Lys Ile Glu Trp Leu Pro Ser Ser
                405                 410                 415 gca cag gct ttg ggc ata cgc aac cac tac cgc cac ccc gaa gaa cac    1296
Ala Gln Ala Leu Gly Ile Arg Asn His Tyr Arg His Pro Glu Glu His
            420                 425                 430 ggt tcc gac cgc tgg ttc aac gcc ttg ggc agc cgc cgc ttc agc cgc    1344
Gly Ser Asp Arg Trp Phe Asn Ala Leu Gly Ser Arg Arg Phe Ser Arg
        435                 440                 445 aac gcc tgc gtc gtc gtc agt tgc ggc acg gcg gta acg gtt gac gcg    1392
Asn Ala Cys Val Val Val Ser Cys Gly Thr Ala Val Thr Val Asp Ala
450                 455                 460 ctc acc gat gac gga cat tat ctc ggg gga acc atc atg ccc ggt ttc    1440
Leu Thr Asp Asp Gly His Tyr Leu Gly Gly Thr Ile Met Pro Gly Phe
465                 470                 475                 480 cac ctg atg aaa gaa tcg ctc gcc gtc cga acc gcc aac ctc aac cgg    1488
His Leu Met Lys Glu Ser Leu Ala Val Arg Thr Ala Asn Leu Asn Arg
                485                 490                 495 cac gcc ggt aag cgt tat cct ttc ccg acc aca acg ggc aat gcc gtc    1536
His Ala Gly Lys Arg Tyr Pro Phe Pro Thr Thr Thr Gly Asn Ala Val
            500                 505                 510 gcc agc ggc atg atg gat gcg gtt tgc ggc tcg gtt atg atg atg cac    1584
Ala Ser Gly Met Met Asp Ala Val Cys Gly Ser Val Met Met Met His
        515                 520                 525 ggg cgt ttg aaa gaa aaa acc ggg gcg ggc aag cct gtc gat gtc atc    1632
Gly Arg Leu Lys Glu Lys Thr Gly Ala Gly Lys Pro Val Asp Val Ile
530                 535                 540 att acc ggc ggc ggc gcg gca aaa gtt gcc gaa gcc ctg ccg cct gca    1680
Ile Thr Gly Gly Gly Ala Ala Lys Val Ala Glu Ala Leu Pro Pro Ala
545                 550                 555                 560 ttt ttg gcg gaa aat acc gtg cgc gtg gcg gac aac ctc gtc att tac    1728
Phe Leu Ala Glu Asn Thr Val Arg Val Ala Asp Asn Leu Val Ile Tyr
                565                 570                 575 ggg ttg ttg aac atg att gcc gcc gaa ggc agg gaa tat gaa cat att    1776
Gly Leu Leu Asn Met Ile Ala Ala Glu Gly Arg Glu Tyr Glu His Ile
            580                 585                 590

<210> SEQ ID NO 48
<211> LENGTH: 592
<212> TYPE: PRT
<213> ORGANISM: Neisseria meningitidis

<400> SEQUENCE: 48

Met Thr Val Leu Lys Leu Ser His Trp Arg Val Leu Ala Glu Leu Ala
1               5                   10                  15

Asp Gly Leu Pro Gln His Val Ser Gln Leu Ala Arg Met Ala Asp Met
                20                  25                  30

Lys Pro Gln Gln Leu Asn Gly Phe Trp Gln Met Pro Ala His Ile
            35                  40                  45

Arg Gly Leu Leu Arg Gln His Asp Gly Tyr Trp Arg Leu Val Arg Pro
        50                  55                  60

Leu Ala Val Phe Asp Ala Glu Gly Leu Arg Glu Leu Gly Glu Arg Ser
```

```
            65                  70                  75                  80
Gly Phe Gln Thr Ala Leu Lys His Glu Cys Ala Ser Ser Asn Asp Glu
                85                  90                  95

Ile Leu Glu Leu Ala Arg Ile Ala Pro Asp Lys Ala His Lys Thr Ile
               100                 105                 110

Cys Val Thr His Leu Gln Ser Lys Gly Arg Gly Arg Gln Gly Arg Lys
               115                 120                 125

Trp Ser His Arg Leu Gly Glu Cys Leu Met Phe Ser Phe Gly Trp Val
               130                 135                 140

Phe Asp Arg Pro Gln Tyr Glu Leu Gly Ser Leu Ser Pro Val Ala Ala
145                150                 155                 160

Val Ala Cys Arg Arg Ala Leu Ser Arg Leu Gly Leu Asp Val Gln Ile
                   165                 170                 175

Lys Trp Pro Asn Asp Leu Val Val Gly Arg Asp Lys Leu Gly Gly Ile
               180                 185                 190

Leu Ile Glu Thr Val Arg Thr Gly Gly Lys Thr Val Ala Val Val Gly
               195                 200                 205

Ile Gly Ile Asn Phe Val Leu Pro Lys Glu Val Glu Asn Ala Ala Ser
           210                 215                 220

Val Gln Ser Leu Phe Gln Thr Ala Ser Arg Arg Gly Asn Ala Asp Ala
225                230                 235                 240

Ala Val Leu Leu Glu Thr Leu Leu Val Glu Leu Asp Ala Val Leu Leu
                   245                 250                 255

Gln Tyr Ala Arg Asp Gly Phe Ala Pro Phe Val Ala Glu Tyr Gln Ala
                   260                 265                 270

Ala Asn Arg Asp His Gly Lys Ala Val Leu Leu Arg Asp Gly Glu
               275                 280                 285

Thr Val Phe Glu Gly Thr Val Lys Gly Val Asp Gly Gln Gly Val Leu
               290                 295                 300

His Leu Glu Thr Ala Glu Gly Lys Gln Thr Val Val Ser Gly Glu Ile
305                310                 315                 320

Ser Leu Arg Ser Asp Asp Arg Pro Val Ser Val Pro Lys Arg Arg Asp
                   325                 330                 335

Ser Glu Arg Phe Leu Leu Leu Asp Gly Gly Asn Ser Arg Leu Lys Trp
               340                 345                 350

Ala Trp Val Glu Asn Gly Thr Phe Ala Thr Val Gly Ser Ala Pro Tyr
               355                 360                 365

Arg Asp Leu Ser Pro Leu Gly Ala Glu Trp Ala Glu Lys Ala Asp Gly
370                375                 380

Asn Val Arg Ile Val Gly Cys Ala Val Cys Gly Glu Phe Lys Lys Ala
385                390                 395                 400

Gln Val Gln Glu Gln Leu Ala Arg Lys Ile Glu Trp Leu Pro Ser Ser
                   405                 410                 415

Ala Gln Ala Leu Gly Ile Arg Asn His Tyr Arg His Pro Glu Glu His
                   420                 425                 430

Gly Ser Asp Arg Trp Phe Asn Ala Leu Gly Ser Arg Arg Phe Ser Arg
               435                 440                 445

Asn Ala Cys Val Val Ser Cys Gly Thr Ala Val Thr Val Asp Ala
               450                 455                 460

Leu Thr Asp Asp Gly His Tyr Leu Gly Gly Thr Ile Met Pro Gly Phe
465                470                 475                 480

His Leu Met Lys Glu Ser Leu Ala Val Arg Thr Ala Asn Leu Asn Arg
               485                 490                 495
```

```
His Ala Gly Lys Arg Tyr Pro Phe Pro Thr Thr Thr Gly Asn Ala Val
            500                 505                 510

Ala Ser Gly Met Met Asp Ala Val Cys Gly Ser Val Met Met Met His
        515                 520                 525

Gly Arg Leu Lys Glu Lys Thr Gly Ala Gly Lys Pro Val Asp Val Ile
    530                 535                 540

Ile Thr Gly Gly Gly Ala Ala Lys Val Ala Glu Ala Leu Pro Pro Ala
545                 550                 555                 560

Phe Leu Ala Glu Asn Thr Val Arg Val Ala Asp Asn Leu Val Ile Tyr
                565                 570                 575

Gly Leu Leu Asn Met Ile Ala Ala Glu Gly Arg Glu Tyr Glu His Ile
            580                 585                 590

<210> SEQ ID NO 49
<211> LENGTH: 864
<212> TYPE: DNA
<213> ORGANISM: Neisseria meningitidis
<220> FEATURE:
<221> NAME/KEY: CDS
<222> LOCATION: (1)..(864)
<223> OTHER INFORMATION: NMB2074

<400> SEQUENCE: 49
```

| | |
|---|---:|
| atg aaa tgg cta ttt atc ctt ttg gtt gcg att aat att gcc gta ttc<br>Met Lys Trp Leu Phe Ile Leu Leu Val Ala Ile Asn Ile Ala Val Phe<br>1               5                   10                  15 | 48 |
| ggc ggt acg gta ggt tac aaa ctg aca ctg aaa cag gcc ggc aga ata<br>Gly Gly Thr Val Gly Tyr Lys Leu Thr Leu Lys Gln Ala Gly Arg Ile<br>            20                  25                  30 | 96 |
| ccg gag gca cag aat gcc gca aac aat ttg cag gtt caa cca gtt gcc<br>Pro Glu Ala Gln Asn Ala Ala Asn Asn Leu Gln Val Gln Pro Val Ala<br>        35                  40                  45 | 144 |
| cca act atg ccg gtt gtt cgg aat att cca gca tcc ggt cct gtc gtt<br>Pro Thr Met Pro Val Val Arg Asn Ile Pro Ala Ser Gly Pro Val Val<br>    50                  55                  60 | 192 |
| cag gcg gca tct gaa tcg gat aca ggc gca ctg ctc aaa cag ggc gac<br>Gln Ala Ala Ser Glu Ser Asp Thr Gly Ala Leu Leu Lys Gln Gly Asp<br>65                  70                  75                  80 | 240 |
| att ctg agc gaa gaa cag gcg gag cag ttg cgc ttg aaa aaa gaa gcg<br>Ile Leu Ser Glu Glu Gln Ala Glu Gln Leu Arg Leu Lys Lys Glu Ala<br>                85                  90                  95 | 288 |
| gaa cag aaa aaa ctg aaa gag aaa aaa cag cgt gaa gaa aaa gcc cgc<br>Glu Gln Lys Lys Leu Lys Glu Lys Lys Gln Arg Glu Glu Lys Ala Arg<br>            100                 105                 110 | 336 |
| cgc gaa aaa ctc gcc gcc gaa aag gcg cag gcg gaa cgc gaa aac ggc<br>Arg Glu Lys Leu Ala Ala Glu Lys Ala Gln Ala Glu Arg Glu Asn Gly<br>        115                 120                 125 | 384 |
| gcg gcg gat gcc tta tgc gcc gcg cag gca agc ctc acg atg gac gaa<br>Ala Ala Asp Ala Leu Cys Ala Ala Gln Ala Ser Leu Thr Met Asp Glu<br>    130                 135                 140 | 432 |
| gat gac tac cac cgc atc aaa gga ctt ttg ggc aaa tgg tcg cac gtt<br>Asp Asp Tyr His Arg Ile Lys Gly Leu Leu Gly Lys Trp Ser His Val<br>145                 150                 155                 160 | 480 |
| gcc agc agg agc gtc gaa aaa cgc acc gcc caa gcc aaa cct gcc gac<br>Ala Ser Arg Ser Val Glu Lys Arg Thr Ala Gln Ala Lys Pro Ala Asp<br>                165                 170                 175 | 528 |
| aaa acc tac cgc gtc gtc ctg ccc gtt tcc gcc gat gcc gaa aat cag<br>Lys Thr Tyr Arg Val Val Leu Pro Val Ser Ala Asp Ala Glu Asn Gln<br>            180                 185                 190 | 576 |

```
gcg gcg gag ctg tct gcc aaa ggt ttc aac ccc ata ccg ttt gac ggc    624
Ala Ala Glu Leu Ser Ala Lys Gly Phe Asn Pro Ile Pro Phe Asp Gly
            195                 200                 205 gca ttg agt ttg ggt gtc ggc aac agc cgg gaa aac gcc caa gcc ctg    672
Ala Leu Ser Leu Gly Val Gly Asn Ser Arg Glu Asn Ala Gln Ala Leu
        210                 215                 220 caa aac cgg ctt gcc ggc gcc gga ttc ggc ggg gcg cat att gtc gaa    720
Gln Asn Arg Leu Ala Gly Ala Gly Phe Gly Gly Ala His Ile Val Glu
225                 230                 235                 240 cac ttt gcc gaa gcc gac agg cag gac gat tct ttg agc gtg tcg cgt    768
His Phe Ala Glu Ala Asp Arg Gln Asp Asp Ser Leu Ser Val Ser Arg
                245                 250                 255 atg acg gtt ttg ttt acc ggc gtg aat gcc gcc gat gcg gac gaa att    816
Met Thr Val Leu Phe Thr Gly Val Asn Ala Ala Asp Ala Asp Glu Ile
            260                 265                 270 cgt aaa atc acg tcc cta tac ggc aaa ctg aac ctc aag tct tgc aaa    864
Arg Lys Ile Thr Ser Leu Tyr Gly Lys Leu Asn Leu Lys Ser Cys Lys
        275                 280                 285

<210> SEQ ID NO 50
<211> LENGTH: 288
<212> TYPE: PRT
<213> ORGANISM: Neisseria meningitidis

<400> SEQUENCE: 50

Met Lys Trp Leu Phe Ile Leu Leu Val Ala Ile Asn Ile Ala Val Phe
1               5                   10                  15

Gly Gly Thr Val Gly Tyr Lys Leu Thr Leu Lys Gln Ala Gly Arg Ile
            20                  25                  30

Pro Glu Ala Gln Asn Ala Ala Asn Asn Leu Gln Val Gln Pro Val Ala
        35                  40                  45

Pro Thr Met Pro Val Val Arg Asn Ile Pro Ala Ser Gly Pro Val Val
    50                  55                  60

Gln Ala Ala Ser Glu Ser Asp Thr Gly Ala Leu Leu Lys Gln Gly Asp
65                  70                  75                  80

Ile Leu Ser Glu Glu Gln Ala Glu Gln Leu Arg Leu Lys Lys Glu Ala
                85                  90                  95

Glu Gln Lys Lys Leu Lys Glu Lys Gln Arg Glu Glu Lys Ala Arg
            100                 105                 110

Arg Glu Lys Leu Ala Ala Glu Lys Ala Gln Ala Glu Arg Glu Asn Gly
        115                 120                 125

Ala Ala Asp Ala Leu Cys Ala Ala Gln Ala Ser Leu Thr Met Asp Glu
    130                 135                 140

Asp Asp Tyr His Arg Ile Lys Gly Leu Leu Gly Lys Trp Ser His Val
145                 150                 155                 160

Ala Ser Arg Ser Val Glu Lys Arg Thr Ala Gln Ala Lys Pro Ala Asp
                165                 170                 175

Lys Thr Tyr Arg Val Val Leu Pro Val Ser Ala Asp Ala Glu Asn Gln
            180                 185                 190

Ala Ala Glu Leu Ser Ala Lys Gly Phe Asn Pro Ile Pro Phe Asp Gly
        195                 200                 205

Ala Leu Ser Leu Gly Val Gly Asn Ser Arg Glu Asn Ala Gln Ala Leu
    210                 215                 220

Gln Asn Arg Leu Ala Gly Ala Gly Phe Gly Gly Ala His Ile Val Glu
225                 230                 235                 240

His Phe Ala Glu Ala Asp Arg Gln Asp Asp Ser Leu Ser Val Ser Arg
                245                 250                 255
```

```
Met Thr Val Leu Phe Thr Gly Val Asn Ala Ala Asp Ala Asp Glu Ile
            260                 265                 270
Arg Lys Ile Thr Ser Leu Tyr Gly Lys Leu Asn Leu Lys Ser Cys Lys
            275                 280                 285

<210> SEQ ID NO 51
<211> LENGTH: 786
<212> TYPE: DNA
<213> ORGANISM: Neisseria meningitidis
<220> FEATURE:
<221> NAME/KEY: CDS
<222> LOCATION: (1)..(786)
<223> OTHER INFORMATION: NMA 0385

<400> SEQUENCE: 51 atg aaa caa gct atg aaa aat tgg ttt gct gcc ttg ctg ttg gca gta      48
Met Lys Gln Ala Met Lys Asn Trp Phe Ala Ala Leu Leu Leu Ala Val
1               5                   10                  15 ccc atg ggt gcg gca ttt gct tcg ggc ggt cat gca cac tat gag aaa      96
Pro Met Gly Ala Ala Phe Ala Ser Gly Gly His Ala His Tyr Glu Lys
            20                  25                  30 gtc gat atc gat ttg cgc gac caa gtc agc ctg cag cgc ggc gca caa     144
Val Asp Ile Asp Leu Arg Asp Gln Val Ser Leu Gln Arg Gly Ala Gln
        35                  40                  45 atc ttt acc aac tat tgc ctg tcc tgc cac tcg gca agc ggt atg cgt     192
Ile Phe Thr Asn Tyr Cys Leu Ser Cys His Ser Ala Ser Gly Met Arg
    50                  55                  60 ttc aac cgt ttg aaa gac atc ggt ttg act gac gaa gaa atc aag aaa     240
Phe Asn Arg Leu Lys Asp Ile Gly Leu Thr Asp Glu Glu Ile Lys Lys
65                  70                  75                  80 aac ctg atg ttt acc acc gat aat gtc ggc gat gtc atg cat tcg gcg     288
Asn Leu Met Phe Thr Thr Asp Asn Val Gly Asp Val Met His Ser Ala
                85                  90                  95 atg aac ccg aaa gat gcg gca aaa tgg ttt ggt gct gct ccg ccc gat     336
Met Asn Pro Lys Asp Ala Ala Lys Trp Phe Gly Ala Ala Pro Pro Asp
            100                 105                 110 ttg aca ttg att gcg cgt tcc aaa ggt gca gac tac ctt tac gct tat     384
Leu Thr Leu Ile Ala Arg Ser Lys Gly Ala Asp Tyr Leu Tyr Ala Tyr
        115                 120                 125 atg cgc ggc ttc tat aaa gat ccg acc cgt ccg agc ggc tgg aac aat     432
Met Arg Gly Phe Tyr Lys Asp Pro Thr Arg Pro Ser Gly Trp Asn Asn
    130                 135                 140 act gta ttc gat aaa gtc ggt atg ccc cac ccg ttg tgg gaa cag caa     480
Thr Val Phe Asp Lys Val Gly Met Pro His Pro Leu Trp Glu Gln Gln
145                 150                 155                 160 ggc gtt caa gcc gtt gag ttg gat gcc aaa ggt cag ccg gtt atg gta     528
Gly Val Gln Ala Val Glu Leu Asp Ala Lys Gly Gln Pro Val Met Val
                165                 170                 175 aaa gac gaa cac ggc gag atg aag cct aag ctg tat tgg gaa tct acc     576
Lys Asp Glu His Gly Glu Met Lys Pro Lys Leu Tyr Trp Glu Ser Thr
            180                 185                 190 ggt ttg cac agc cgc cgt ctg cct aac ggc aaa gtg atc caa aaa gag     624
Gly Leu His Ser Arg Arg Leu Pro Asn Gly Lys Val Ile Gln Lys Glu
        195                 200                 205 tac gac gca tat gta cgc gat ttg gtc aat tac ctt gtg tac atg ggc     672
Tyr Asp Ala Tyr Val Arg Asp Leu Val Asn Tyr Leu Val Tyr Met Gly
    210                 215                 220 gaa cct gca caa ctg caa cgc aaa cgt ata ggc tat gtc gtg atg att     720
Glu Pro Ala Gln Leu Gln Arg Lys Arg Ile Gly Tyr Val Val Met Ile
225                 230                 235                 240
```

```
ttc cta ttt gcg gtt atg ctg cct ttg gcg tat ttc ctg aaa aaa gaa      768
Phe Leu Phe Ala Val Met Leu Pro Leu Ala Tyr Phe Leu Lys Lys Glu
                245                 250                 255 tat tgg aaa gac gta cac                                               786
Tyr Trp Lys Asp Val His
                260
```

<210> SEQ ID NO 52
<211> LENGTH: 262
<212> TYPE: PRT
<213> ORGANISM: Neisseria meningitidis

<400> SEQUENCE: 52

```
Met Lys Gln Ala Met Lys Asn Trp Phe Ala Ala Leu Leu Leu Ala Val
1               5                   10                  15

Pro Met Gly Ala Ala Phe Ala Ser Gly Gly His Ala His Tyr Glu Lys
                20                  25                  30

Val Asp Ile Asp Leu Arg Asp Gln Val Ser Leu Gln Arg Gly Ala Gln
            35                  40                  45

Ile Phe Thr Asn Tyr Cys Leu Ser Cys His Ser Ala Ser Gly Met Arg
        50                  55                  60

Phe Asn Arg Leu Lys Asp Ile Gly Leu Thr Asp Glu Glu Ile Lys Lys
65                  70                  75                  80

Asn Leu Met Phe Thr Thr Asp Asn Val Gly Asp Val Met His Ser Ala
                85                  90                  95

Met Asn Pro Lys Asp Ala Ala Lys Trp Phe Gly Ala Ala Pro Pro Asp
                100                 105                 110

Leu Thr Leu Ile Ala Arg Ser Lys Gly Ala Asp Tyr Leu Tyr Ala Tyr
            115                 120                 125

Met Arg Gly Phe Tyr Lys Asp Pro Thr Arg Pro Ser Gly Trp Asn Asn
        130                 135                 140

Thr Val Phe Asp Lys Val Gly Met Pro His Pro Leu Trp Glu Gln Gln
145                 150                 155                 160

Gly Val Gln Ala Val Glu Leu Asp Ala Lys Gly Gln Pro Val Met Val
                165                 170                 175

Lys Asp Glu His Gly Glu Met Lys Pro Lys Leu Tyr Trp Glu Ser Thr
                180                 185                 190

Gly Leu His Ser Arg Arg Leu Pro Asn Gly Lys Val Ile Gln Lys Glu
            195                 200                 205

Tyr Asp Ala Tyr Val Arg Asp Leu Val Asn Tyr Leu Val Tyr Met Gly
        210                 215                 220

Glu Pro Ala Gln Leu Gln Arg Lys Arg Ile Gly Tyr Val Val Met Ile
225                 230                 235                 240

Phe Leu Phe Ala Val Met Leu Pro Leu Ala Tyr Phe Leu Lys Lys Glu
                245                 250                 255

Tyr Trp Lys Asp Val His
                260
```

<210> SEQ ID NO 53
<211> LENGTH: 1782
<212> TYPE: DNA
<213> ORGANISM: Neisseria meningitidis
<220> FEATURE:
<221> NAME/KEY: CDS
<222> LOCATION: (1)..(1782)
<223> OTHER INFORMATION: NMB2050

<400> SEQUENCE: 53

-continued

```
atg gaa ctg atg act gtt ttg ctg cct ttg gcg gcg ttg gtg tcg ggc      48
Met Glu Leu Met Thr Val Leu Leu Pro Leu Ala Ala Leu Val Ser Gly
 1               5                  10                  15 gtg ttg ttt aca tgg ttg ctg atg aag ggc cgg ttt cag ggc gag ttt      96
Val Leu Phe Thr Trp Leu Leu Met Lys Gly Arg Phe Gln Gly Glu Phe
             20                  25                  30 gcc ggt ttg aac gcg cac ctg gcg gaa aag gcg gca aga tgt gat ttt     144
Ala Gly Leu Asn Ala His Leu Ala Glu Lys Ala Ala Arg Cys Asp Phe
         35                  40                  45 gtc gaa cag gca cac ggc aaa acc gtg tcg gaa ttg gcg gtg ttg gac     192
Val Glu Gln Ala His Gly Lys Thr Val Ser Glu Leu Ala Val Leu Asp
     50                  55                  60 ggg aaa tac cgg cat ttg cag gac gaa aat tat gct ttg ggc aac cgt     240
Gly Lys Tyr Arg His Leu Gln Asp Glu Asn Tyr Ala Leu Gly Asn Arg
 65                  70                  75                  80 ttt tcc gca gcc gaa aag cag att gcc cat ttg cag gaa aaa gag gcg     288
Phe Ser Ala Ala Glu Lys Gln Ile Ala His Leu Gln Glu Lys Glu Ala
                 85                  90                  95 gag tcg gcg cgg ctg aag cag tcg tat atc gag ttg cag gaa aag gca     336
Glu Ser Ala Arg Leu Lys Gln Ser Tyr Ile Glu Leu Gln Glu Lys Ala
            100                 105                 110 cag ggt ttg gcg gtt gaa aac gaa cgt ttg gca acg cag ctc gga cag     384
Gln Gly Leu Ala Val Glu Asn Glu Arg Leu Ala Thr Gln Leu Gly Gln
        115                 120                 125 gaa cgg aag gcg ttt gcc gac caa tat gcc ttg gaa cgc caa atc cgc     432
Glu Arg Lys Ala Phe Ala Asp Gln Tyr Ala Leu Glu Arg Gln Ile Arg
    130                 135                 140 caa aga atc gaa acc gat ttg gaa gaa agc cgc caa act gtc cgc gac     480
Gln Arg Ile Glu Thr Asp Leu Glu Glu Ser Arg Gln Thr Val Arg Asp
145                 150                 155                 160 gtg caa aac gac ctt tcc gat gtc ggc aac cgt ttt gcc gca gcc gaa     528
Val Gln Asn Asp Leu Ser Asp Val Gly Asn Arg Phe Ala Ala Ala Glu
                165                 170                 175 aaa cag att gcc cat ttg cag gaa aaa gag gcg gaa gcg gag cgg ttg     576
Lys Gln Ile Ala His Leu Gln Glu Lys Glu Ala Glu Ala Glu Arg Leu
            180                 185                 190 agg cag tcg cat acc gag ttg cag gaa aag gca cag ggt ttg gcg gtt     624
Arg Gln Ser His Thr Glu Leu Gln Glu Lys Ala Gln Gly Leu Ala Val
        195                 200                 205 gaa aac gaa cgt ttg gca acg caa atc gaa cag gaa cgc ctt gct tct     672
Glu Asn Glu Arg Leu Ala Thr Gln Ile Glu Gln Glu Arg Leu Ala Ser
    210                 215                 220 gaa gag aag ctg tcc ttg ctg ggc gag gcg cgc aaa agt ttg agc gat     720
Glu Glu Lys Leu Ser Leu Leu Gly Glu Ala Arg Lys Ser Leu Ser Asp
225                 230                 235                 240 cag ttt caa aat ctt gcc aac acg att ttg gaa gaa aaa agc cgc cgt     768
Gln Phe Gln Asn Leu Ala Asn Thr Ile Leu Glu Glu Lys Ser Arg Arg
                245                 250                 255 ttt acc gag cag aac cgc gag cag ctc cat cag gtt ttg aac ccg cta     816
Phe Thr Glu Gln Asn Arg Glu Gln Leu His Gln Val Leu Asn Pro Leu
            260                 265                 270 aac gaa cgc atc cac ggt ttc ggc gag ttg gtc aag caa acc tat gat     864
Asn Glu Arg Ile His Gly Phe Gly Glu Leu Val Lys Gln Thr Tyr Asp
        275                 280                 285 aaa gaa tcg cgc gag cgg ctg acg ttg gaa aac gaa ttg aaa cgg ctt     912
Lys Glu Ser Arg Glu Arg Leu Thr Leu Glu Asn Glu Leu Lys Arg Leu
    290                 295                 300 cag ggg ttg aac gcg cag ctg cac agc gag gca aag gcc ctg acc aac     960
Gln Gly Leu Asn Ala Gln Leu His Ser Glu Ala Lys Ala Leu Thr Asn
305                 310                 315                 320
```

```
gcg ctg acc ggt acg cag aat aag gtt cag ggc aat tgg ggc gag atg      1008
Ala Leu Thr Gly Thr Gln Asn Lys Val Gln Gly Asn Trp Gly Glu Met
            325                 330                 335 att ctg gaa acg gtt ttg gaa aat tcc ggc ctt cag aaa ggg cgg gaa      1056
Ile Leu Glu Thr Val Leu Glu Asn Ser Gly Leu Gln Lys Gly Arg Glu
        340                 345                 350 tat gtg gtt cag gcg gca tcc gtc cga aaa gag gaa gac ggc ggc acg      1104
Tyr Val Val Gln Ala Ala Ser Val Arg Lys Glu Glu Asp Gly Gly Thr
    355                 360                 365 cgc cgc ctc cag ccc gac gtt ttg gtc aac ctg ccc gac aac aag cag      1152
Arg Arg Leu Gln Pro Asp Val Leu Val Asn Leu Pro Asp Asn Lys Gln
370                 375                 380 att gtg att gat tcc aag gtc tcg ctg aca gct tat gtg cgc tac acg      1200
Ile Val Ile Asp Ser Lys Val Ser Leu Thr Ala Tyr Val Arg Tyr Thr
385                 390                 395                 400 cag gcg gcg gat gcg gat acg gcg gca cgc gaa ctg gcg gca cac gtt      1248
Gln Ala Ala Asp Ala Asp Thr Ala Ala Arg Glu Leu Ala Ala His Val
                405                 410                 415 gcc agc atc cgt gca cac atg aaa ggc ttg tcg ctg aag gat tac acc      1296
Ala Ser Ile Arg Ala His Met Lys Gly Leu Ser Leu Lys Asp Tyr Thr
            420                 425                 430 gat ttg gaa ggt gtg aac aca ttg gat ttc gtc ttt atg ttt atc cct      1344
Asp Leu Glu Gly Val Asn Thr Leu Asp Phe Val Phe Met Phe Ile Pro
        435                 440                 445 gtc gaa ccg gcc tac ctg ttg gcg ttg cag aat gac gcg ggc ttg ttc      1392
Val Glu Pro Ala Tyr Leu Leu Ala Leu Gln Asn Asp Ala Gly Leu Phe
    450                 455                 460 caa gag tgt ttc gac aaa cgg att atg ctg gtc ggc ccc agt acg ctg      1440
Gln Glu Cys Phe Asp Lys Arg Ile Met Leu Val Gly Pro Ser Thr Leu
465                 470                 475                 480 ctg gcg act ttg agg acg gtg gcg aat att tgg cgc aac gaa cag caa      1488
Leu Ala Thr Leu Arg Thr Val Ala Asn Ile Trp Arg Asn Glu Gln Gln
                485                 490                 495 aat cag aac gca ctg gcg att gcg gac gaa ggc ggc aag ctg tac gac      1536
Asn Gln Asn Ala Leu Ala Ile Ala Asp Glu Gly Gly Lys Leu Tyr Asp
            500                 505                 510 aag ttt gtc ggc ttc gta cag acg ctc gaa agc gtc ggc aaa ggc atc      1584
Lys Phe Val Gly Phe Val Gln Thr Leu Glu Ser Val Gly Lys Gly Ile
        515                 520                 525 gat cag gcg caa agc agt ttt cag acg gca ttc aag caa ctt gcc gaa      1632
Asp Gln Ala Gln Ser Ser Phe Gln Thr Ala Phe Lys Gln Leu Ala Glu
    530                 535                 540 ggg cgc ggg aat ctg gtc gga cgc gcc gag aaa ctg cgt ctg ttg ggc      1680
Gly Arg Gly Asn Leu Val Gly Arg Ala Glu Lys Leu Arg Leu Leu Gly
545                 550                 555                 560 gtg aag gca ggc aaa caa ctt caa cgg gat ttg gtc gag cgt tcc aat      1728
Val Lys Ala Gly Lys Gln Leu Gln Arg Asp Leu Val Glu Arg Ser Asn
                565                 570                 575 gaa aca acg gcg ttg tcg gaa tct ttg gaa tac gcg gca gaa gat gaa      1776
Glu Thr Thr Ala Leu Ser Glu Ser Leu Glu Tyr Ala Ala Glu Asp Glu
            580                 585                 590 gca gtc                                                              1782
Ala Val <210> SEQ ID NO 54
<211> LENGTH: 594
<212> TYPE: PRT
<213> ORGANISM: Neisseria meningitidis

<400> SEQUENCE: 54
```

-continued

```
Met Glu Leu Met Thr Val Leu Leu Pro Leu Ala Ala Leu Val Ser Gly
1               5                   10                  15

Val Leu Phe Thr Trp Leu Leu Met Lys Gly Arg Phe Gln Gly Glu Phe
            20                  25                  30

Ala Gly Leu Asn Ala His Leu Ala Glu Lys Ala Ala Arg Cys Asp Phe
            35                  40                  45

Val Glu Gln Ala His Gly Lys Thr Val Ser Glu Leu Ala Val Leu Asp
        50                  55                  60

Gly Lys Tyr Arg His Leu Gln Asp Glu Asn Tyr Ala Leu Gly Asn Arg
65                  70                  75                  80

Phe Ser Ala Ala Glu Lys Gln Ile Ala His Leu Gln Glu Lys Glu Ala
                85                  90                  95

Glu Ser Ala Arg Leu Lys Gln Ser Tyr Ile Glu Leu Gln Glu Lys Ala
                100                 105                 110

Gln Gly Leu Ala Val Glu Asn Glu Arg Leu Ala Thr Gln Leu Gly Gln
            115                 120                 125

Glu Arg Lys Ala Phe Ala Asp Gln Tyr Ala Leu Glu Arg Gln Ile Arg
130                 135                 140

Gln Arg Ile Glu Thr Asp Leu Glu Glu Ser Arg Gln Thr Val Arg Asp
145                 150                 155                 160

Val Gln Asn Asp Leu Ser Asp Val Gly Asn Arg Phe Ala Ala Ala Glu
                165                 170                 175

Lys Gln Ile Ala His Leu Gln Glu Lys Glu Ala Glu Ala Glu Arg Leu
                180                 185                 190

Arg Gln Ser His Thr Glu Leu Gln Glu Lys Ala Gln Gly Leu Ala Val
                195                 200                 205

Glu Asn Glu Arg Leu Ala Thr Gln Ile Glu Gln Glu Arg Leu Ala Ser
210                 215                 220

Glu Glu Lys Leu Ser Leu Leu Gly Glu Ala Arg Lys Ser Leu Ser Asp
225                 230                 235                 240

Gln Phe Gln Asn Leu Ala Asn Thr Ile Leu Glu Glu Lys Ser Arg Arg
                245                 250                 255

Phe Thr Glu Gln Asn Arg Glu Gln Leu His Gln Val Leu Asn Pro Leu
                260                 265                 270

Asn Glu Arg Ile His Gly Phe Gly Glu Leu Val Lys Gln Thr Tyr Asp
                275                 280                 285

Lys Glu Ser Arg Glu Arg Leu Thr Leu Glu Asn Glu Leu Lys Arg Leu
                290                 295                 300

Gln Gly Leu Asn Ala Gln Leu His Ser Glu Ala Lys Ala Leu Thr Asn
305                 310                 315                 320

Ala Leu Thr Gly Thr Gln Asn Lys Val Gln Gly Asn Trp Gly Glu Met
                325                 330                 335

Ile Leu Glu Thr Val Leu Glu Asn Ser Gly Leu Gln Lys Gly Arg Glu
                340                 345                 350

Tyr Val Val Gln Ala Ala Ser Val Arg Lys Glu Glu Asp Gly Gly Thr
                355                 360                 365

Arg Arg Leu Gln Pro Asp Val Leu Val Asn Leu Pro Asp Asn Lys Gln
370                 375                 380

Ile Val Ile Asp Ser Lys Val Ser Leu Thr Ala Tyr Val Arg Tyr Thr
385                 390                 395                 400

Gln Ala Ala Asp Ala Asp Thr Ala Ala Arg Glu Leu Ala Ala His Val
                405                 410                 415
```

```
Ala Ser Ile Arg Ala His Met Lys Gly Leu Ser Leu Lys Asp Tyr Thr
            420                 425                 430

Asp Leu Glu Gly Val Asn Thr Leu Asp Phe Val Phe Met Phe Ile Pro
            435                 440                 445

Val Glu Pro Ala Tyr Leu Leu Ala Leu Gln Asn Asp Ala Gly Leu Phe
            450                 455                 460

Gln Glu Cys Phe Asp Lys Arg Ile Met Leu Val Gly Pro Ser Thr Leu
465                 470                 475                 480

Leu Ala Thr Leu Arg Thr Val Ala Asn Ile Trp Arg Asn Glu Gln Gln
                485                 490                 495

Asn Gln Asn Ala Leu Ala Ile Ala Asp Glu Gly Gly Lys Leu Tyr Asp
            500                 505                 510

Lys Phe Val Gly Phe Val Gln Thr Leu Glu Ser Val Gly Lys Gly Ile
            515                 520                 525

Asp Gln Ala Gln Ser Ser Phe Gln Thr Ala Phe Lys Gln Leu Ala Glu
            530                 535                 540

Gly Arg Gly Asn Leu Val Gly Arg Ala Glu Lys Leu Arg Leu Leu Gly
545                 550                 555                 560

Val Lys Ala Gly Lys Gln Leu Gln Arg Asp Leu Val Glu Arg Ser Asn
                565                 570                 575

Glu Thr Thr Ala Leu Ser Glu Ser Leu Glu Tyr Ala Ala Glu Asp Glu
            580                 585                 590

Ala Val
```

<210> SEQ ID NO 55
<211> LENGTH: 819
<212> TYPE: DNA
<213> ORGANISM: Neisseria meningitidis
<220> FEATURE:
<221> NAME/KEY: CDS
<222> LOCATION: (1)..(819)
<223> OTHER INFORMATION: HemK

<400> SEQUENCE: 55

```
atg acg ttt gat aaa tgg ttg ggc ttg tca aaa ctg cct aaa aat gaa      48
Met Thr Phe Asp Lys Trp Leu Gly Leu Ser Lys Leu Pro Lys Asn Glu
1               5                   10                  15 gca aga atg ctg ctg caa tat gtt tcg gaa tat acg cgc gtg cag ttg      96
Ala Arg Met Leu Leu Gln Tyr Val Ser Glu Tyr Thr Arg Val Gln Leu
            20                  25                  30 ttg acg cgg ggc ggg gaa gaa atg ccg gac gaa gtc cga cag cgg gcg     144
Leu Thr Arg Gly Gly Glu Glu Met Pro Asp Glu Val Arg Gln Arg Ala
        35                  40                  45 gac agg ctg gcg caa cgc cgt ctg aac ggc gag ccg gtt gcc tat att     192
Asp Arg Leu Ala Gln Arg Arg Leu Asn Gly Glu Pro Val Ala Tyr Ile
    50                  55                  60 tta ggt gcg cgc gaa ttt tat ggc aga cgc ttt aca gtc aac ccg agc     240
Leu Gly Ala Arg Glu Phe Tyr Gly Arg Arg Phe Thr Val Asn Pro Ser
65                  70                  75                  80 gtg ctg att ccg cgc ccc gaa acc gaa cat ttg gtc gaa gcc gta ttg     288
Val Leu Ile Pro Arg Pro Glu Thr Glu His Leu Val Glu Ala Val Leu
                85                  90                  95 gcg cgc ctg ccg gaa aac ggg cgc gtg tgg gat ttg ggg acg ggc agc     336
Ala Arg Leu Pro Glu Asn Gly Arg Val Trp Asp Leu Gly Thr Gly Ser
            100                 105                 110 gga gcg gtt gcc gta acc gtc gcg ctc gaa cgc ccc gat gcg ttt gta     384
Gly Ala Val Ala Val Thr Val Ala Leu Glu Arg Pro Asp Ala Phe Val
        115                 120                 125
```

```
cgc gca tcc gac atc agc ccg ccc gcc ctt gaa acg gcg cgg aaa aat       432
Arg Ala Ser Asp Ile Ser Pro Pro Ala Leu Glu Thr Ala Arg Lys Asn
    130                 135                 140 gcg gca gat ttg ggc gcg cgg gtc gaa ttt gca tac ggt tcg tgg ttc       480
Ala Ala Asp Leu Gly Ala Arg Val Glu Phe Ala Tyr Gly Ser Trp Phe
145                 150                 155                 160 gac acc gat atg ccg tct gaa ggg aaa tgg gac atc atc gtg tcc aac       528
Asp Thr Asp Met Pro Ser Glu Gly Lys Trp Asp Ile Ile Val Ser Asn
                165                 170                 175 ccg ccc tat atc gaa aac ggc gat aaa cat ttg tcg caa ggc gat ttg       576
Pro Pro Tyr Ile Glu Asn Gly Asp Lys His Leu Ser Gln Gly Asp Leu
            180                 185                 190 cgg ttt gag ccg caa atc gcg ctg acc gac ttt tca gac ggc cta agc       624
Arg Phe Glu Pro Gln Ile Ala Leu Thr Asp Phe Ser Asp Gly Leu Ser
        195                 200                 205 tgc atc cgc acc ttg gcg caa ggc gcg ccc gac cgt ttg gcg gag ggc       672
Cys Ile Arg Thr Leu Ala Gln Gly Ala Pro Asp Arg Leu Ala Glu Gly
210                 215                 220 ggt ttt tta ttg ctg gaa cac ggt ttc gat cag ggc gcg gcg gtg cgc       720
Gly Phe Leu Leu Leu Glu His Gly Phe Asp Gln Gly Ala Ala Val Arg
225                 230                 235                 240 ggc gtg ttg gcg gag aat ggt ttt tca gga gtg gaa acc ctg ccg gat       768
Gly Val Leu Ala Glu Asn Gly Phe Ser Gly Val Glu Thr Leu Pro Asp
                245                 250                 255 ttg gcg ggt ttg gac agg gtt acg ctg ggg aag tat atg aag cat ttg       816
Leu Ala Gly Leu Asp Arg Val Thr Leu Gly Lys Tyr Met Lys His Leu
            260                 265                 270 aaa                                                                   819
Lys

<210> SEQ ID NO 56
<211> LENGTH: 273
<212> TYPE: PRT
<213> ORGANISM: Neisseria meningitidis

<400> SEQUENCE: 56

Met Thr Phe Asp Lys Trp Leu Gly Leu Ser Lys Leu Pro Lys Asn Glu
1               5                   10                  15

Ala Arg Met Leu Leu Gln Tyr Val Ser Glu Tyr Thr Arg Val Gln Leu
            20                  25                  30

Leu Thr Arg Gly Gly Glu Glu Met Pro Asp Glu Val Arg Gln Arg Ala
        35                  40                  45

Asp Arg Leu Ala Gln Arg Arg Leu Asn Gly Glu Pro Val Ala Tyr Ile
    50                  55                  60

Leu Gly Ala Arg Glu Phe Tyr Gly Arg Arg Phe Thr Val Asn Pro Ser
65                  70                  75                  80

Val Leu Ile Pro Arg Pro Glu Thr Glu His Leu Val Glu Ala Val Leu
                85                  90                  95

Ala Arg Leu Pro Glu Asn Gly Arg Val Trp Asp Leu Gly Thr Gly Ser
            100                 105                 110

Gly Ala Val Ala Val Thr Val Ala Leu Glu Arg Pro Asp Ala Phe Val
        115                 120                 125

Arg Ala Ser Asp Ile Ser Pro Pro Ala Leu Glu Thr Ala Arg Lys Asn
    130                 135                 140

Ala Ala Asp Leu Gly Ala Arg Val Glu Phe Ala Tyr Gly Ser Trp Phe
145                 150                 155                 160

Asp Thr Asp Met Pro Ser Glu Gly Lys Trp Asp Ile Ile Val Ser Asn
                165                 170                 175
```

```
Pro Pro Tyr Ile Glu Asn Gly Asp Lys His Leu Ser Gln Gly Asp Leu
            180                 185                 190

Arg Phe Glu Pro Gln Ile Ala Leu Thr Asp Phe Ser Asp Gly Leu Ser
        195                 200                 205

Cys Ile Arg Thr Leu Ala Gln Gly Ala Pro Asp Arg Leu Ala Glu Gly
    210                 215                 220

Gly Phe Leu Leu Glu His Gly Phe Asp Gln Gly Ala Ala Val Arg
225                 230                 235                 240

Gly Val Leu Ala Glu Asn Gly Phe Ser Gly Val Glu Thr Leu Pro Asp
            245                 250                 255

Leu Ala Gly Leu Asp Arg Val Thr Leu Gly Lys Tyr Met Lys His Leu
            260                 265                 270

Lys

<210> SEQ ID NO 57
<211> LENGTH: 2148
<212> TYPE: DNA
<213> ORGANISM: Neisseria meningitidis
<220> FEATURE:
<221> NAME/KEY: CDS
<222> LOCATION: (1)..(2148)
<223> OTHER INFORMATION: NMB0287

<400> SEQUENCE: 57
```

| | | | | | | | | | | | | | | | | |
|---|---|---|---|---|---|---|---|---|---|---|---|---|---|---|---|---|
| atg | ctc | acc | gat | tta | gaa | aaa | aac | gcc | atc | cgc | gac | cat | tac | caa | aac | 48 |
| Met | Leu | Thr | Asp | Leu | Glu | Lys | Asn | Ala | Ile | Arg | Asp | His | Tyr | Gln | Asn | |
| 1 | | | | 5 | | | | | 10 | | | | | 15 | | |
| atc | ggc | aaa | aac | ctg | ccc | ggt | ttc | cgt | ccg | cgt | gct | tcg | cag | cgg | gaa | 96 |
| Ile | Gly | Lys | Asn | Leu | Pro | Gly | Phe | Arg | Pro | Arg | Ala | Ser | Gln | Arg | Glu | |
| | | | 20 | | | | | 25 | | | | | 30 | | | |
| atg | att | gcg | gcg | gtt | gcc | aac | gct | ttt | tcg | cgg | acg | ttg | gcg | cgc | gaa | 144 |
| Met | Ile | Ala | Ala | Val | Ala | Asn | Ala | Phe | Ser | Arg | Thr | Leu | Ala | Arg | Glu | |
| | | 35 | | | | | 40 | | | | | 45 | | | | |
| gaa | ggc | ggc | gag | ccg | ccc | aag | cgc | gaa | ggc | gag | agc | att | gcc | gtg | atc | 192 |
| Glu | Gly | Gly | Glu | Pro | Pro | Lys | Arg | Glu | Gly | Glu | Ser | Ile | Ala | Val | Ile | |
| 50 | | | | | 55 | | | | | 60 | | | | | | |
| gaa | ggg | ccg | acc | ggc | gtg | ggc | aaa | tcg | ttg | gcc | tac | ctt | ttg | gcc | ggc | 240 |
| Glu | Gly | Pro | Thr | Gly | Val | Gly | Lys | Ser | Leu | Ala | Tyr | Leu | Leu | Ala | Gly | |
| 65 | | | | 70 | | | | | 75 | | | | | 80 | | |
| ggc | atc | atg | gcg | caa | aca | cgc | ggc | aag | cgg | ctg | att | gtg | agc | agc | gcg | 288 |
| Gly | Ile | Met | Ala | Gln | Thr | Arg | Gly | Lys | Arg | Leu | Ile | Val | Ser | Ser | Ala | |
| | | | 85 | | | | | 90 | | | | | 95 | | | |
| acg | gtt | gcc | ttg | cag | gag | cag | ttg | gta | gac | cgc | gac | ctg | ccg | ttt | ctg | 336 |
| Thr | Val | Ala | Leu | Gln | Glu | Gln | Leu | Val | Asp | Arg | Asp | Leu | Pro | Phe | Leu | |
| | | | | 100 | | | | | 105 | | | | | 110 | | |
| gtc | gaa | aaa | agc | ggt | ttg | gaa | ctg | acc | ttc | gca | ctt | gcc | aaa | ggg | cgc | 384 |
| Val | Glu | Lys | Ser | Gly | Leu | Glu | Leu | Thr | Phe | Ala | Leu | Ala | Lys | Gly | Arg | |
| | | | 115 | | | | | 120 | | | | | 125 | | | |
| ggc | cgc | tat | ctc | tgc | ccc | tac | aaa | ctc | tat | cga | ctg | acg | caa | agc | aat | 432 |
| Gly | Arg | Tyr | Leu | Cys | Pro | Tyr | Lys | Leu | Tyr | Arg | Leu | Thr | Gln | Ser | Asn | |
| | | 130 | | | | | 135 | | | | | 140 | | | | |
| gcc | cag | caa | aac | ctg | ctc | ggc | ttt | gaa | gcc | ccc | gcc | gtc | ttg | tgg | gac | 480 |
| Ala | Gln | Gln | Asn | Leu | Leu | Gly | Phe | Glu | Ala | Pro | Ala | Val | Leu | Trp | Asp | |
| 145 | | | | | 150 | | | | | 155 | | | | | 160 | |
| agc | aaa | ccc | aag | ccc | gaa | gaa | ttg | aag | ctg | ctg | cgc | gac | atc | gcc | gac | 528 |
| Ser | Lys | Pro | Lys | Pro | Glu | Glu | Leu | Lys | Leu | Leu | Arg | Asp | Ile | Ala | Asp | |
| | | | 165 | | | | | 170 | | | | | 175 | | | |
| gaa | ttt | tcc | gcc | cga | cgg | ttc | aac | ggc | gac | cgc | gac | act | tgg | ccg | gaa | 576 |
| Glu | Phe | Ser | Ala | Arg | Arg | Phe | Asn | Gly | Asp | Arg | Asp | Thr | Trp | Pro | Glu | |

|  |  |  |  |  |  |  |  |  |  |  |  |  |  |  |  |
|---|---|---|---|---|---|---|---|---|---|---|---|---|---|---|---|
|  |  |  | 180 |  |  |  | 185 |  |  |  | 190 |  |  |  |  |
| aaa | atc | gat | gac | gcg | att | tgg | ctc | aaa | gtg | acc | aac | gac | cgc | cac | ggc | 624 |
| Lys | Ile | Asp | Asp | Ala | Ile | Trp | Leu | Lys | Val | Thr | Asn | Asp | Arg | His | Gly |  |
|  |  | 195 |  |  |  | 200 |  |  |  | 205 |  |  |  |  |  |  |
| tgc | ctg | aaa | acc | gcc | tgt | ccc | aac | cgt | ccg | gaa | tgt | ccg | ttt | tac | cta | 672 |
| Cys | Leu | Lys | Thr | Ala | Cys | Pro | Asn | Arg | Pro | Glu | Cys | Pro | Phe | Tyr | Leu |  |
|  | 210 |  |  |  |  | 215 |  |  |  |  | 220 |  |  |  |  |  |
| gca | cgc | gat | gtc | ttg | gaa | acc | gtc | gat | gtc | gtc | gtt | gcc | aac | cac | gat | 720 |
| Ala | Arg | Asp | Val | Leu | Glu | Thr | Val | Asp | Val | Val | Val | Ala | Asn | His | Asp |  |
| 225 |  |  |  |  | 230 |  |  |  |  | 235 |  |  |  |  | 240 |  |
| ctt | ctg | ctt | gcc | gac | atc | agt | atg | ggc | ggc | ggc | gtg | att | ctg | cct | gcg | 768 |
| Leu | Leu | Leu | Ala | Asp | Ile | Ser | Met | Gly | Gly | Gly | Val | Ile | Leu | Pro | Ala |  |
|  |  |  |  | 245 |  |  |  |  | 250 |  |  |  |  | 255 |  |  |
| ccc | gaa | aac | agt | ttc | tat | tgc | atc | gac | gaa | gcg | cac | cac | ctg | ccc | aaa | 816 |
| Pro | Glu | Asn | Ser | Phe | Tyr | Cys | Ile | Asp | Glu | Ala | His | His | Leu | Pro | Lys |  |
|  |  |  | 260 |  |  |  | 265 |  |  |  | 270 |  |  |  |  |  |
| aaa | gcc | ctc | agc | cgt | ttt | gcc | gcc | gaa | cat | tca | tgg | aat | att | gcc | gtt | 864 |
| Lys | Ala | Leu | Ser | Arg | Phe | Ala | Ala | Glu | His | Ser | Trp | Asn | Ile | Ala | Val |  |
|  |  | 275 |  |  |  |  | 280 |  |  |  |  | 285 |  |  |  |  |
| tgg | acg | ctg | gaa | aaa | ctg | ccg | cag | ctg | acc | ggc | aaa | att | gcc | gcg | ctg | 912 |
| Trp | Thr | Leu | Glu | Lys | Leu | Pro | Gln | Leu | Thr | Gly | Lys | Ile | Ala | Ala | Leu |  |
|  | 290 |  |  |  |  | 295 |  |  |  |  | 300 |  |  |  |  |  |
| acc | gat | aaa | gcc | gaa | ctt | gcc | aac | cta | gcc | gac | gaa | gcc | gcc | gca | tcc | 960 |
| Thr | Asp | Lys | Ala | Glu | Leu | Ala | Asn | Leu | Ala | Asp | Glu | Ala | Ala | Ala | Ser |  |
| 305 |  |  |  |  | 310 |  |  |  |  | 315 |  |  |  |  | 320 |  |
| ttg | ctc | gac | agc | ctg | cat | gaa | tgg | caa | ttc | cat | ttg | gcg | gaa | gag | ccg | 1008 |
| Leu | Leu | Asp | Ser | Leu | His | Glu | Trp | Gln | Phe | His | Leu | Ala | Glu | Glu | Pro |  |
|  |  |  |  | 325 |  |  |  |  | 330 |  |  |  |  | 335 |  |  |
| tct | tta | agt | ctg | ggg | gtg | tct | gaa | aac | gac | aga | cga | acc | aac | agc | gaa | 1056 |
| Ser | Leu | Ser | Leu | Gly | Val | Ser | Glu | Asn | Asp | Arg | Arg | Thr | Asn | Ser | Glu |  |
|  |  |  | 340 |  |  |  | 345 |  |  |  | 350 |  |  |  |  |  |
| ccg | act | tgg | ctg | tgg | gaa | gac | ggc | aaa | atc | ccc | gaa | ggc | ctc | gaa | acc | 1104 |
| Pro | Thr | Trp | Leu | Trp | Glu | Asp | Gly | Lys | Ile | Pro | Glu | Gly | Leu | Glu | Thr |  |
|  |  | 355 |  |  |  |  | 360 |  |  |  |  | 365 |  |  |  |  |
| acc | gtt | tcc | aat | acg | gcc | att | gct | gcg | cgc | agc | ctg | ctc | aaa | cac | gtt | 1152 |
| Thr | Val | Ser | Asn | Thr | Ala | Ile | Ala | Ala | Arg | Ser | Leu | Leu | Lys | His | Val |  |
|  | 370 |  |  |  |  | 375 |  |  |  |  | 380 |  |  |  |  |  |
| atc | ggg | ctg | aac | gat | gcg | ctt | tct | gcc | gca | cgc | cgc | gaa | aaa | gaa | cag | 1200 |
| Ile | Gly | Leu | Asn | Asp | Ala | Leu | Ser | Ala | Ala | Arg | Arg | Glu | Lys | Glu | Gln |  |
| 385 |  |  |  |  | 390 |  |  |  |  | 395 |  |  |  |  | 400 |  |
| gac | ggc | gcg | ctc | ctc | gac | cgc | ctg | acc | agc | gag | ttc | ggt | ctt | ttt | atc | 1248 |
| Asp | Gly | Ala | Leu | Leu | Asp | Arg | Leu | Thr | Ser | Glu | Phe | Gly | Leu | Phe | Ile |  |
|  |  |  |  | 405 |  |  |  |  | 410 |  |  |  |  | 415 |  |  |
| gcc | cgt | atc | gaa | caa | atc | agc | gcg | gtt | tgg | gat | ttg | ctc | tcc | act | gtc | 1296 |
| Ala | Arg | Ile | Glu | Gln | Ile | Ser | Ala | Val | Trp | Asp | Leu | Leu | Ser | Thr | Val |  |
|  |  |  | 420 |  |  |  | 425 |  |  |  | 430 |  |  |  |  |  |
| ccc | ctc | gag | ggt | gaa | gaa | ccg | ttg | gcg | aaa | tgg | ata | acc | cgc | cgc | gcc | 1344 |
| Pro | Leu | Glu | Gly | Glu | Glu | Pro | Leu | Ala | Lys | Trp | Ile | Thr | Arg | Arg | Ala |  |
|  | 435 |  |  |  |  | 440 |  |  |  |  | 445 |  |  |  |  |  |
| gac | gac | aaa | aac | gac | tac | att | ttc | aac | gcc | agc | ccc | atc | agc | agc | gca | 1392 |
| Asp | Asp | Lys | Asn | Asp | Tyr | Ile | Phe | Asn | Ala | Ser | Pro | Ile | Ser | Ser | Ala |  |
|  | 450 |  |  |  |  | 455 |  |  |  |  | 460 |  |  |  |  |  |
| tcc | cac | ctt | gcc | aac | agc | ctg | tgg | cgg | cgt | gcg | gca | ggc | gcg | gta | ttg | 1440 |
| Ser | His | Leu | Ala | Asn | Ser | Leu | Trp | Arg | Arg | Ala | Ala | Gly | Ala | Val | Leu |  |
| 465 |  |  |  |  | 470 |  |  |  |  | 475 |  |  |  |  | 480 |  |
| act | tcc | gcc | acc | ctg | caa | tcc | ttg | ggc | aac | ttc | aac | ctg | atg | ctg | cgc | 1488 |
| Thr | Ser | Ala | Thr | Leu | Gln | Ser | Leu | Gly | Asn | Phe | Asn | Leu | Met | Leu | Arg |  |
|  |  |  |  | 485 |  |  |  |  | 490 |  |  |  |  | 495 |  |  |
| caa | acc | ggg | ctg | caa | tgg | ctg | ccc | gaa | acc | acc | acc | ctc | gcc | ctc | aaa | 1536 |

```
                Gln Thr Gly Leu Gln Trp Leu Pro Glu Thr Thr Thr Leu Ala Leu Lys
                                500                 505                 510 agc ccc ttt gac ttt gaa aaa cag ggc gaa ctc tac atc ccc ccc ata            1584
Ser Pro Phe Asp Phe Glu Lys Gln Gly Glu Leu Tyr Ile Pro Pro Ile
            515                 520                 525 tac gcc agc ccc aaa gac ccc gaa gcc cac acc gcc gcc gtc atc gaa            1632
Tyr Ala Ser Pro Lys Asp Pro Glu Ala His Thr Ala Ala Val Ile Glu
530                 535                 540 tgg ctg ccc aag ctt att tcg ccc acc gaa gcc atc ggc acg ctc gtc            1680
Trp Leu Pro Lys Leu Ile Ser Pro Thr Glu Ala Ile Gly Thr Leu Val
545                 550                 555                 560 ttg ttt tcc tcg cgc aaa caa atg cag gat gtc gcc ctg cgc ctg ccc            1728
Leu Phe Ser Ser Arg Lys Gln Met Gln Asp Val Ala Leu Arg Leu Pro
                565                 570                 575 gga gac tac ctg ccg ctc ttg ctc gta caa ggc gaa tta ccc aaa gcc            1776
Gly Asp Tyr Leu Pro Leu Leu Val Gln Gly Glu Leu Pro Lys Ala
            580                 585                 590 gtc ctc ctg caa aaa cac cac cgg gcc ata gaa gaa ggc aaa gcc agc            1824
Val Leu Leu Gln Lys His His Arg Ala Ile Glu Glu Gly Lys Ala Ser
            595                 600                 605 atc atc ttc gga ctc gac agc ttt gcc gaa gga ctc gac ctg ccc ggc            1872
Ile Ile Phe Gly Leu Asp Ser Phe Ala Glu Gly Leu Asp Leu Pro Gly
610                 615                 620 acc gcc tgc gtg caa gtc atc atc gcc aaa ctt ccc ttc gcc atg ccc            1920
Thr Ala Cys Val Gln Val Ile Ile Ala Lys Leu Pro Phe Ala Met Pro
625                 630                 635                 640 gac aac ccc atc gaa aaa acc caa aac cgc tgg ata gaa cag cgc ggc            1968
Asp Asn Pro Ile Glu Lys Thr Gln Asn Arg Trp Ile Glu Gln Arg Gly
                645                 650                 655 ggc aac ccc ttc atc gaa atc acc gtc ccc gaa gcc ggc atc aaa ctc            2016
Gly Asn Pro Phe Ile Glu Ile Thr Val Pro Glu Ala Gly Ile Lys Leu
            660                 665                 670 atc cag gcc gtc ggc cgc ctc atc cgc acc gaa caa gac tac ggc cgc            2064
Ile Gln Ala Val Gly Arg Leu Ile Arg Thr Glu Gln Asp Tyr Gly Arg
            675                 680                 685 gta acc atc ctc gac aac cgc atc aaa aca cag cgg tac ggc caa caa            2112
Val Thr Ile Leu Asp Asn Arg Ile Lys Thr Gln Arg Tyr Gly Gln Gln
690                 695                 700 tta ttg gcc ggc ctg ccg ccg ttt aaa agg ata ggg                            2148
Leu Leu Ala Gly Leu Pro Pro Phe Lys Arg Ile Gly
705                 710                 715

<210> SEQ ID NO 58
<211> LENGTH: 716
<212> TYPE: PRT
<213> ORGANISM: Neisseria meningitidis

<400> SEQUENCE: 58

Met Leu Thr Asp Leu Glu Lys Asn Ala Ile Arg Asp His Tyr Gln Asn
1               5                   10                  15

Ile Gly Lys Asn Leu Pro Gly Phe Arg Pro Arg Ala Ser Gln Arg Glu
                20                  25                  30

Met Ile Ala Ala Val Ala Asn Ala Phe Ser Arg Thr Leu Ala Arg Glu
            35                  40                  45

Glu Gly Gly Glu Pro Pro Lys Arg Glu Gly Ser Ile Ala Val Ile
        50                  55                  60

Glu Gly Pro Thr Gly Val Gly Lys Ser Leu Ala Tyr Leu Leu Ala Gly
65                  70                  75                  80

Gly Ile Met Ala Gln Thr Arg Gly Lys Arg Leu Ile Val Ser Ser Ala
```

```
            85                  90                  95
Thr Val Ala Leu Gln Glu Gln Leu Val Asp Arg Asp Leu Pro Phe Leu
            100                 105                 110

Val Glu Lys Ser Gly Leu Glu Leu Thr Phe Ala Leu Ala Lys Gly Arg
            115                 120                 125

Gly Arg Tyr Leu Cys Pro Tyr Lys Leu Tyr Arg Leu Thr Gln Ser Asn
            130                 135                 140

Ala Gln Gln Asn Leu Leu Gly Phe Glu Ala Pro Ala Val Leu Trp Asp
145                 150                 155                 160

Ser Lys Pro Lys Pro Glu Glu Leu Lys Leu Leu Arg Asp Ile Ala Asp
                165                 170                 175

Glu Phe Ser Ala Arg Arg Phe Asn Gly Asp Arg Asp Thr Trp Pro Glu
            180                 185                 190

Lys Ile Asp Asp Ala Ile Trp Leu Lys Val Thr Asn Asp Arg His Gly
            195                 200                 205

Cys Leu Lys Thr Ala Cys Pro Asn Arg Pro Glu Cys Pro Phe Tyr Leu
            210                 215                 220

Ala Arg Asp Val Leu Glu Thr Val Asp Val Val Ala Asn His Asp
225                 230                 235                 240

Leu Leu Leu Ala Asp Ile Ser Met Gly Gly Gly Val Ile Leu Pro Ala
                245                 250                 255

Pro Glu Asn Ser Phe Tyr Cys Ile Asp Glu Ala His His Leu Pro Lys
            260                 265                 270

Lys Ala Leu Ser Arg Phe Ala Ala Glu His Ser Trp Asn Ile Ala Val
            275                 280                 285

Trp Thr Leu Glu Lys Leu Pro Gln Leu Thr Gly Lys Ile Ala Ala Leu
            290                 295                 300

Thr Asp Lys Ala Glu Leu Ala Asn Leu Ala Asp Glu Ala Ala Ser
305                 310                 315                 320

Leu Leu Asp Ser Leu His Glu Trp Gln Phe His Leu Ala Glu Glu Pro
                325                 330                 335

Ser Leu Ser Leu Gly Val Ser Glu Asn Asp Arg Arg Thr Asn Ser Glu
            340                 345                 350

Pro Thr Trp Leu Trp Glu Asp Gly Lys Ile Pro Glu Gly Leu Glu Thr
            355                 360                 365

Thr Val Ser Asn Thr Ala Ile Ala Ala Arg Ser Leu Leu Lys His Val
            370                 375                 380

Ile Gly Leu Asn Asp Ala Leu Ser Ala Ala Arg Arg Glu Lys Glu Gln
385                 390                 395                 400

Asp Gly Ala Leu Leu Asp Arg Leu Thr Ser Glu Phe Gly Leu Phe Ile
                405                 410                 415

Ala Arg Ile Glu Gln Ile Ser Ala Val Trp Asp Leu Leu Ser Thr Val
            420                 425                 430

Pro Leu Glu Gly Glu Glu Pro Leu Ala Lys Trp Ile Thr Arg Arg Ala
            435                 440                 445

Asp Asp Lys Asn Asp Tyr Ile Phe Asn Ala Ser Pro Ile Ser Ser Ala
            450                 455                 460

Ser His Leu Ala Asn Ser Leu Trp Arg Ala Ala Gly Ala Val Leu
465                 470                 475                 480

Thr Ser Ala Thr Leu Gln Ser Leu Gly Asn Phe Asn Leu Met Leu Arg
                485                 490                 495

Gln Thr Gly Leu Gln Trp Leu Pro Glu Thr Thr Leu Ala Leu Lys
            500                 505                 510
```

```
Ser Pro Phe Asp Phe Glu Lys Gln Gly Glu Leu Tyr Ile Pro Pro Ile
        515                 520                 525

Tyr Ala Ser Pro Lys Asp Pro Glu Ala His Thr Ala Ala Val Ile Glu
        530                 535                 540

Trp Leu Pro Lys Leu Ile Ser Pro Thr Glu Ala Ile Gly Thr Leu Val
545                 550                 555                 560

Leu Phe Ser Ser Arg Lys Gln Met Gln Asp Val Ala Leu Arg Leu Pro
                565                 570                 575

Gly Asp Tyr Leu Pro Leu Leu Val Gln Gly Glu Leu Pro Lys Ala
                580                 585                 590

Val Leu Leu Gln Lys His His Arg Ala Ile Glu Glu Gly Lys Ala Ser
        595                 600                 605

Ile Ile Phe Gly Leu Asp Ser Phe Ala Glu Gly Leu Asp Leu Pro Gly
        610                 615                 620

Thr Ala Cys Val Gln Val Ile Ala Lys Leu Pro Phe Ala Met Pro
625                 630                 635                 640

Asp Asn Pro Ile Glu Lys Thr Gln Asn Arg Trp Ile Glu Arg Gly
                645                 650                 655

Gly Asn Pro Phe Ile Glu Ile Thr Val Pro Glu Ala Gly Ile Lys Leu
                660                 665                 670

Ile Gln Ala Val Gly Arg Leu Ile Arg Thr Glu Gln Asp Tyr Gly Arg
        675                 680                 685

Val Thr Ile Leu Asp Asn Arg Ile Lys Thr Gln Arg Tyr Gly Gln Gln
        690                 695                 700

Leu Leu Ala Gly Leu Pro Pro Phe Lys Arg Ile Gly
705                 710                 715

<210> SEQ ID NO 59
<211> LENGTH: 558
<212> TYPE: DNA
<213> ORGANISM: Neisseria meningitidis
<220> FEATURE:
<221> NAME/KEY: CDS
<222> LOCATION: (1)..(558)
<223> OTHER INFORMATION: sodC CDS

<400> SEQUENCE: 59 atg aat atg aaa acc tta tta gca cta gcg gtt agt gca gta tgt tca    48
Met Asn Met Lys Thr Leu Leu Ala Leu Ala Val Ser Ala Val Cys Ser
1               5                   10                  15 gtt ggt gtt gcg caa gca cac gag cat aat acg ata cct aaa ggt gct    96
Val Gly Val Ala Gln Ala His Glu His Asn Thr Ile Pro Lys Gly Ala
            20                  25                  30 tct att gaa gtg aaa gtg caa caa ctt gat cca gta aac ggt aac aaa   144
Ser Ile Glu Val Lys Val Gln Gln Leu Asp Pro Val Asn Gly Asn Lys
        35                  40                  45 gat gtg ggt aca gtg act att act gaa tct aac tat ggt ctt gtg ttt   192
Asp Val Gly Thr Val Thr Ile Thr Glu Ser Asn Tyr Gly Leu Val Phe
    50                  55                  60 acc cct gat tta caa gga tta agc gaa ggc tta cat ggt ttc cac atc   240
Thr Pro Asp Leu Gln Gly Leu Ser Glu Gly Leu His Gly Phe His Ile
65                  70                  75                  80 cat gaa aac cca agc tgt gag cca aaa gaa aaa gaa ggt aaa ttg aca   288
His Glu Asn Pro Ser Cys Glu Pro Lys Glu Lys Glu Gly Lys Leu Thr
                85                  90                  95 gct ggt tta ggc gca ggc ggt cac tgg gat cct aaa ggt gca aaa caa   336
Ala Gly Leu Gly Ala Gly Gly His Trp Asp Pro Lys Gly Ala Lys Gln
            100                 105                 110
```

```
cat ggt tac cca tgg caa gat gat gca cac tta ggt gat tta cct gca        384
His Gly Tyr Pro Trp Gln Asp Asp Ala His Leu Gly Asp Leu Pro Ala
            115                 120                 125 tta act gta ttg cat gat ggc aca gca aca aat cct gtt tta gca cca        432
Leu Thr Val Leu His Asp Gly Thr Ala Thr Asn Pro Val Leu Ala Pro
130                 135                 140 cgt ctt aaa cat tta gat gat gtt cgc ggt cac tct att atg atc cac        480
Arg Leu Lys His Leu Asp Asp Val Arg Gly His Ser Ile Met Ile His
145                 150                 155                 160 acg ggt ggt gat aat cac tcc gat cat cca gct cca ctt ggc ggt ggc        528
Thr Gly Gly Asp Asn His Ser Asp His Pro Ala Pro Leu Gly Gly Gly
                165                 170                 175 ggc cca cgt atg gca tgt ggc gtg att aaa                                558
Gly Pro Arg Met Ala Cys Gly Val Ile Lys
            180                 185

<210> SEQ ID NO 60
<211> LENGTH: 186
<212> TYPE: PRT
<213> ORGANISM: Neisseria meningitidis

<400> SEQUENCE: 60

Met Asn Met Lys Thr Leu Leu Ala Leu Ala Val Ser Ala Val Cys Ser
1               5                   10                  15

Val Gly Val Ala Gln Ala His Glu His Asn Thr Ile Pro Lys Gly Ala
            20                  25                  30

Ser Ile Glu Val Lys Val Gln Gln Leu Asp Pro Val Asn Gly Asn Lys
        35                  40                  45

Asp Val Gly Thr Val Thr Ile Thr Glu Ser Asn Tyr Gly Leu Val Phe
    50                  55                  60

Thr Pro Asp Leu Gln Gly Leu Ser Glu Gly Leu His Gly Phe His Ile
65                  70                  75                  80

His Glu Asn Pro Ser Cys Glu Pro Lys Glu Lys Glu Gly Lys Leu Thr
                85                  90                  95

Ala Gly Leu Gly Ala Gly Gly His Trp Asp Pro Lys Gly Ala Lys Gln
            100                 105                 110

His Gly Tyr Pro Trp Gln Asp Asp Ala His Leu Gly Asp Leu Pro Ala
        115                 120                 125

Leu Thr Val Leu His Asp Gly Thr Ala Thr Asn Pro Val Leu Ala Pro
    130                 135                 140

Arg Leu Lys His Leu Asp Asp Val Arg Gly His Ser Ile Met Ile His
145                 150                 155                 160

Thr Gly Gly Asp Asn His Ser Asp His Pro Ala Pro Leu Gly Gly Gly
                165                 170                 175

Gly Pro Arg Met Ala Cys Gly Val Ile Lys
            180                 185

<210> SEQ ID NO 61
<211> LENGTH: 1290
<212> TYPE: DNA
<213> ORGANISM: Neisseria meningitidis
<220> FEATURE:
<221> NAME/KEY: CDS
<222> LOCATION: (1)..(1290)
<223> OTHER INFORMATION: NMB0315

<400> SEQUENCE: 61 atg gct gtc ttc cca ctt tcg gca aaa cat cgg aaa tac gcg ctg cgt         48
Met Ala Val Phe Pro Leu Ser Ala Lys His Arg Lys Tyr Ala Leu Arg
```

-continued

```
1               5                   10                  15
gcg ctt gcc gtt tcg att att ttg gtg tcg gcg gca tac att gct tcg      96
Ala Leu Ala Val Ser Ile Ile Leu Val Ser Ala Ala Tyr Ile Ala Ser
            20                  25                  30 aca gag agg acg gag cgc gtc aga ccg cag cgc gtg gaa caa aat ctg      144
Thr Glu Arg Thr Glu Arg Val Arg Pro Gln Arg Val Glu Gln Asn Leu
        35                  40                  45 ccg ccg ctg tct tgg ggc ggc agc ggc gtt cag acg gca tat tgg gtg      192
Pro Pro Leu Ser Trp Gly Gly Ser Gly Val Gln Thr Ala Tyr Trp Val
    50                  55                  60 cag gag gcg gtg cag ccg ggc gac tcg ctg gcg gac gtg ctg gcg cgt      240
Gln Glu Ala Val Gln Pro Gly Asp Ser Leu Ala Asp Val Leu Ala Arg
65                  70                  75                  80 tcg ggt atg gcg cgg gac gag att gcc cga atc acg gaa aaa tat ggc      288
Ser Gly Met Ala Arg Asp Glu Ile Ala Arg Ile Thr Glu Lys Tyr Gly
                85                  90                  95 ggc gaa gcc gat ttg cgg cat ttg cgt gcc gac cag tcg gtt cat gtt      336
Gly Glu Ala Asp Leu Arg His Leu Arg Ala Asp Gln Ser Val His Val
            100                 105                 110 ttg gtc ggc ggc gac ggc ggc gcg cgc gaa gtg cag ttt ttt acc gac      384
Leu Val Gly Gly Asp Gly Gly Ala Arg Glu Val Gln Phe Phe Thr Asp
        115                 120                 125 gaa gac ggc gag cgc aat ctg gtc gct ttg gaa aag aaa ggc ggc ata      432
Glu Asp Gly Glu Arg Asn Leu Val Ala Leu Glu Lys Lys Gly Gly Ile
    130                 135                 140 tgg cgg cgg tcg gct tct gag gcg gat atg aag gtt ttg ccg acg ctg      480
Trp Arg Arg Ser Ala Ser Glu Ala Asp Met Lys Val Leu Pro Thr Leu
145                 150                 155                 160 cgt tcg gtc gtg gtc aaa acg tcg gcg cgc ggt tcg ctg gcg cgg gcg      528
Arg Ser Val Val Val Lys Thr Ser Ala Arg Gly Ser Leu Ala Arg Ala
                165                 170                 175 gaa gtg ccc gtc gaa atc cgc gaa tcc tta agc ggg att ttc gcc ggc      576
Glu Val Pro Val Glu Ile Arg Glu Ser Leu Ser Gly Ile Phe Ala Gly
            180                 185                 190 cgc ttc agc ctt gac ggt ttg aag gaa ggc gat gcc gtg cgc ctg atg      624
Arg Phe Ser Leu Asp Gly Leu Lys Glu Gly Asp Ala Val Arg Leu Met
        195                 200                 205 tac gac agc ctg tat ttc cac ggg cag cag gtg gcg gcg ggc gat att      672
Tyr Asp Ser Leu Tyr Phe His Gly Gln Gln Val Ala Ala Gly Asp Ile
    210                 215                 220 ttg gcg gct gaa gtc gtt aag ggc ggc aca agg cat cag gcg ttc tat      720
Leu Ala Ala Glu Val Val Lys Gly Gly Thr Arg His Gln Ala Phe Tyr
225                 230                 235                 240 tac cgt tcg gac aag gaa ggc gga ggg ggc ggc aat tat tat gat gaa      768
Tyr Arg Ser Asp Lys Glu Gly Gly Gly Gly Gly Asn Tyr Tyr Asp Glu
                245                 250                 255 gac ggc aag gtg ttg cag gaa aaa ggc ggc ttc aac atc gag ccg ctg      816
Asp Gly Lys Val Leu Gln Glu Lys Gly Gly Phe Asn Ile Glu Pro Leu
            260                 265                 270 gtc tat acg cgc att tct tcg ccg ttc ggc tac cgt atg cac ccc atc      864
Val Tyr Thr Arg Ile Ser Ser Pro Phe Gly Tyr Arg Met His Pro Ile
        275                 280                 285 ctg cac aca tgg cgg ctg cac acg ggc atc gat tat gcc gca ccg cag      912
Leu His Thr Trp Arg Leu His Thr Gly Ile Asp Tyr Ala Ala Pro Gln
    290                 295                 300 gga acg ccg gtc agg gct tcc gcc gac ggc gtg att acc ttt aaa ggc      960
Gly Thr Pro Val Arg Ala Ser Ala Asp Gly Val Ile Thr Phe Lys Gly
305                 310                 315                 320 cgg aag ggc gga tac ggc aac gcg gtg atg ata cgc cac gcc aac ggt      1008
```

```
Arg Lys Gly Gly Tyr Gly Asn Ala Val Met Ile Arg His Ala Asn Gly
                325                 330                 335 gtg gaa acg ctg tac gcg cac ttg agc gcg ttt tcg cag gcg gaa ggc       1056
Val Glu Thr Leu Tyr Ala His Leu Ser Ala Phe Ser Gln Ala Glu Gly
            340                 345                 350 aat gtg cgc ggc ggc gag gtc atc ggt ttt gtc ggt tcg acc ggg cgt       1104
Asn Val Arg Gly Gly Glu Val Ile Gly Phe Val Gly Ser Thr Gly Arg
        355                 360                 365 tcg acc ggg ccg cac ctg cat tac gag gcg cgc atc aac ggg cag ccc       1152
Ser Thr Gly Pro His Leu His Tyr Glu Ala Arg Ile Asn Gly Gln Pro
    370                 375                 380 gtc aat cct gtt tcg gtc gca ttg ccg aca ccg gaa ttg acg cag gcg       1200
Val Asn Pro Val Ser Val Ala Leu Pro Thr Pro Glu Leu Thr Gln Ala
385                 390                 395                 400 gac aag gcg gcg ttt gcc gcg cag aaa cag aag gcg gac gcg ctg ctt       1248
Asp Lys Ala Ala Phe Ala Ala Gln Lys Gln Lys Ala Asp Ala Leu Leu
                405                 410                 415 gcg cgc ttg cgc ggc ata ccg gtt acc gtg tcg caa tcg gat               1290
Ala Arg Leu Arg Gly Ile Pro Val Thr Val Ser Gln Ser Asp
            420                 425                 430
```

<210> SEQ ID NO 62
<211> LENGTH: 430
<212> TYPE: PRT
<213> ORGANISM: Neisseria meningitidis

<400> SEQUENCE: 62

```
Met Ala Val Phe Pro Leu Ser Ala Lys His Arg Lys Tyr Ala Leu Arg
1               5                   10                  15

Ala Leu Ala Val Ser Ile Ile Leu Val Ser Ala Ala Tyr Ile Ala Ser
            20                  25                  30

Thr Glu Arg Thr Glu Arg Val Arg Pro Gln Arg Val Glu Gln Asn Leu
        35                  40                  45

Pro Pro Leu Ser Trp Gly Gly Ser Gly Val Gln Thr Ala Tyr Trp Val
    50                  55                  60

Gln Glu Ala Val Gln Pro Gly Asp Ser Leu Ala Asp Val Leu Ala Arg
65                  70                  75                  80

Ser Gly Met Ala Arg Asp Glu Ile Ala Arg Ile Thr Glu Lys Tyr Gly
                85                  90                  95

Gly Glu Ala Asp Leu Arg His Leu Arg Ala Asp Gln Ser Val His Val
            100                 105                 110

Leu Val Gly Gly Asp Gly Gly Ala Arg Glu Val Gln Phe Phe Thr Asp
        115                 120                 125

Glu Asp Gly Glu Arg Asn Leu Val Ala Leu Glu Lys Lys Gly Gly Ile
    130                 135                 140

Trp Arg Arg Ser Ala Ser Glu Ala Asp Met Lys Val Leu Pro Thr Leu
145                 150                 155                 160

Arg Ser Val Val Lys Thr Ser Ala Arg Gly Ser Leu Ala Arg Ala
                165                 170                 175

Glu Val Pro Val Glu Ile Arg Glu Ser Leu Ser Gly Ile Phe Ala Gly
            180                 185                 190

Arg Phe Ser Leu Asp Gly Leu Lys Glu Gly Asp Ala Val Arg Leu Met
        195                 200                 205

Tyr Asp Ser Leu Tyr Phe His Gly Gln Gln Val Ala Ala Gly Asp Ile
    210                 215                 220

Leu Ala Ala Glu Val Val Lys Gly Gly Thr Arg His Gln Ala Phe Tyr
225                 230                 235                 240
```

```
Tyr Arg Ser Asp Lys Glu Gly Gly Gly Gly Asn Tyr Tyr Asp Glu
            245                 250                 255

Asp Gly Lys Val Leu Gln Glu Lys Gly Gly Phe Asn Ile Glu Pro Leu
        260                 265                 270

Val Tyr Thr Arg Ile Ser Ser Pro Phe Gly Tyr Arg Met His Pro Ile
        275                 280                 285

Leu His Thr Trp Arg Leu His Thr Gly Ile Asp Tyr Ala Ala Pro Gln
        290                 295                 300

Gly Thr Pro Val Arg Ala Ser Ala Asp Gly Val Ile Thr Phe Lys Gly
305                 310                 315                 320

Arg Lys Gly Gly Tyr Gly Asn Ala Val Met Ile Arg His Ala Asn Gly
                325                 330                 335

Val Glu Thr Leu Tyr Ala His Leu Ser Ala Phe Ser Gln Ala Glu Gly
                340                 345                 350

Asn Val Arg Gly Gly Glu Val Ile Gly Phe Val Gly Ser Thr Gly Arg
                355                 360                 365

Ser Thr Gly Pro His Leu His Tyr Glu Ala Arg Ile Asn Gly Gln Pro
        370                 375                 380

Val Asn Pro Val Ser Val Ala Leu Pro Thr Pro Glu Leu Thr Gln Ala
385                 390                 395                 400

Asp Lys Ala Ala Phe Ala Ala Gln Lys Gln Lys Ala Asp Ala Leu Leu
                405                 410                 415

Ala Arg Leu Arg Gly Ile Pro Val Thr Val Ser Gln Ser Asp
                420                 425                 430

<210> SEQ ID NO 63
<211> LENGTH: 603
<212> TYPE: DNA
<213> ORGANISM: Neisseria meningitidis
<220> FEATURE:
<221> NAME/KEY: CDS
<222> LOCATION: (1)..(603)
<223> OTHER INFORMATION: NMB1119

<400> SEQUENCE: 63 atg acc atc tat ttc aaa aac ggc ttt tac gac gac aca ttg ggc ggc      48
Met Thr Ile Tyr Phe Lys Asn Gly Phe Tyr Asp Asp Thr Leu Gly Gly
1               5                   10                  15 atc ccc gaa ggc gcg gtt gcc gtc cgc gcc gaa gaa tac gcc gcc ctt      96
Ile Pro Glu Gly Ala Val Ala Val Arg Ala Glu Glu Tyr Ala Ala Leu
                20                  25                  30 ttg gca gga cag gcg cag ggc ggg cag att gcc gca gat tcc gac ggc     144
Leu Ala Gly Gln Ala Gln Gly Gly Gln Ile Ala Ala Asp Ser Asp Gly
            35                  40                  45 cgc ccc gtt tta acc ccg ccg cgc ccg tcc gat tac cac gaa tgg gac     192
Arg Pro Val Leu Thr Pro Pro Arg Pro Ser Asp Tyr His Glu Trp Asp
        50                  55                  60 ggc aaa aaa tgg aaa atc agc aaa gcc gcc gcc gcc gcc cgt ttc gcc     240
Gly Lys Lys Trp Lys Ile Ser Lys Ala Ala Ala Ala Ala Arg Phe Ala
65                  70                  75                  80 aaa caa aaa acc gcc ttg gca ttc cgc ctc gcg gaa aag gcg gac gaa     288
Lys Gln Lys Thr Ala Leu Ala Phe Arg Leu Ala Glu Lys Ala Asp Glu
                85                  90                  95 ctc aaa aac agc ctc ttg gcg ggc tat ccc caa gtg gaa atc gac agc     336
Leu Lys Asn Ser Leu Leu Ala Gly Tyr Pro Gln Val Glu Ile Asp Ser
            100                 105                 110 ttt tac agg cag gaa aaa gaa gcc ctc gcg cgg cag gcg gac aac aac     384
Phe Tyr Arg Gln Glu Lys Glu Ala Leu Ala Arg Gln Ala Asp Asn Asn
```

|  |  |  |  |  |  |  |  |  |  |  |  |  |  |  |  |
|---|---|---|---|---|---|---|---|---|---|---|---|---|---|---|---|
|  |  | 115 |  |  |  | 120 |  |  |  | 125 |  |  |  |  |  |
| gcc | ccg | acc | ccg | atg | ctg | gcg | caa | atc | gcc | gcc | gca | agg | ggc | gtg | gaa | 432 |
| Ala | Pro | Thr | Pro | Met | Leu | Ala | Gln | Ile | Ala | Ala | Ala | Arg | Gly | Val | Glu |
|  | 130 |  |  |  |  | 135 |  |  |  |  | 140 |  |  |  |  |
| ttg | gac | gtt | ttg | att | gaa | aaa | gtt | atc | gaa | aaa | tcc | gcc | cgc | ctg | gct | 480 |
| Leu | Asp | Val | Leu | Ile | Glu | Lys | Val | Ile | Glu | Lys | Ser | Ala | Arg | Leu | Ala |
| 145 |  |  |  |  | 150 |  |  |  |  | 155 |  |  |  |  | 160 |
| gtt | gcc | gcc | ggc | gcg | att | atc | gga | aag | cgt | cag | cag | ctc | gaa | gac | aaa | 528 |
| Val | Ala | Ala | Gly | Ala | Ile | Ile | Gly | Lys | Arg | Gln | Gln | Leu | Glu | Asp | Lys |
|  |  |  |  | 165 |  |  |  |  |  | 170 |  |  |  |  | 175 |
| ttg | aac | acc | atc | gaa | acc | gcg | ccc | gga | ttg | gac | gcg | ctg | gaa | aag | gaa | 576 |
| Leu | Asn | Thr | Ile | Glu | Thr | Ala | Pro | Gly | Leu | Asp | Ala | Leu | Glu | Lys | Glu |
|  |  |  | 180 |  |  |  |  | 185 |  |  |  |  | 190 |  |  |
| atc | gaa | gaa | tgg | acg | cta | aac | atc | ggc |  |  |  |  |  |  |  | 603 |
| Ile | Glu | Glu | Trp | Thr | Leu | Asn | Ile | Gly |
|  |  |  | 195 |  |  |  |  | 200 |

<210> SEQ ID NO 64
<211> LENGTH: 201
<212> TYPE: PRT
<213> ORGANISM: Neisseria meningitidis

<400> SEQUENCE: 64

Met Thr Ile Tyr Phe Lys Asn Gly Phe Tyr Asp Asp Thr Leu Gly Gly
1               5                   10                  15

Ile Pro Glu Gly Ala Val Ala Val Arg Ala Glu Tyr Ala Ala Leu
            20                  25                  30

Leu Ala Gly Gln Ala Gln Gly Gly Gln Ile Ala Ala Asp Ser Asp Gly
        35                  40                  45

Arg Pro Val Leu Thr Pro Pro Arg Pro Ser Asp Tyr His Glu Trp Asp
    50                  55                  60

Gly Lys Lys Trp Lys Ile Ser Lys Ala Ala Ala Ala Arg Phe Ala
65                  70                  75                  80

Lys Gln Lys Thr Ala Leu Ala Phe Arg Leu Ala Glu Lys Ala Asp Glu
                85                  90                  95

Leu Lys Asn Ser Leu Leu Ala Gly Tyr Pro Gln Val Glu Ile Asp Ser
            100                 105                 110

Phe Tyr Arg Gln Glu Lys Glu Ala Leu Ala Arg Gln Ala Asp Asn Asn
        115                 120                 125

Ala Pro Thr Pro Met Leu Ala Gln Ile Ala Ala Arg Gly Val Glu
    130                 135                 140

Leu Asp Val Leu Ile Glu Lys Val Ile Glu Lys Ser Ala Arg Leu Ala
145                 150                 155                 160

Val Ala Ala Gly Ala Ile Ile Gly Lys Arg Gln Gln Leu Glu Asp Lys
                165                 170                 175

Leu Asn Thr Ile Glu Thr Ala Pro Gly Leu Asp Ala Leu Glu Lys Glu
            180                 185                 190

Ile Glu Glu Trp Thr Leu Asn Ile Gly
        195                 200

<210> SEQ ID NO 65
<211> LENGTH: 681
<212> TYPE: DNA
<213> ORGANISM: Neisseria meningitidis
<220> FEATURE:
<221> NAME/KEY: CDS
<222> LOCATION: (1)..(681)
<223> OTHER INFORMATION: NMB1119

```
<400> SEQUENCE: 65 atg ccg tct gaa aaa tgt tca gac ggc att tct tat aac ctt ttg ttt    48
Met Pro Ser Glu Lys Cys Ser Asp Gly Ile Ser Tyr Asn Leu Leu Phe
1               5                   10                  15 gca gca cat aac caa tca gtc ttt cct att ccg ttc cga aat gca tac    96
Ala Ala His Asn Gln Ser Val Phe Pro Ile Pro Phe Arg Asn Ala Tyr
            20                  25                  30 cat gcg ccc gta ccc aat att tgc gaa caa gga aag aaa atg gca cgt   144
His Ala Pro Val Pro Asn Ile Cys Glu Gln Gly Lys Lys Met Ala Arg
        35                  40                  45 tta acc gta cac acc ctc gaa acc gcc ccc gaa gcc gcc aaa gcg cgc   192
Leu Thr Val His Thr Leu Glu Thr Ala Pro Glu Ala Ala Lys Ala Arg
50                  55                  60 gtc gag gcg gta ctt caa aac aac ggc ttt atc ccc aac ctt atc ggc   240
Val Glu Ala Val Leu Gln Asn Asn Gly Phe Ile Pro Asn Leu Ile Gly
65                  70                  75                  80 gta tta tca aac gcc ccc gaa gcc ttg gcg ttt tac caa gaa gtc ggc   288
Val Leu Ser Asn Ala Pro Glu Ala Leu Ala Phe Tyr Gln Glu Val Gly
                85                  90                  95 aag ctc aac gcc gcc aac agc ctg acc gcc ggc gaa gtc gaa gtc atc   336
Lys Leu Asn Ala Ala Asn Ser Leu Thr Ala Gly Glu Val Glu Val Ile
            100                 105                 110 cag atc atc gcc gcc cgt acc aac caa tgc ggt ttt tgc gtg gca ggg   384
Gln Ile Ile Ala Ala Arg Thr Asn Gln Cys Gly Phe Cys Val Ala Gly
        115                 120                 125 cac acc aaa ctc gca acc ctg aaa aaa ctc ctg tcc gaa caa tcc gtc   432
His Thr Lys Leu Ala Thr Leu Lys Lys Leu Leu Ser Glu Gln Ser Val
    130                 135                 140 aaa gcc gcg cgc gct ttg gca gca ggc gaa ttt gac gat gcc aaa ctc   480
Lys Ala Ala Arg Ala Leu Ala Ala Gly Glu Phe Asp Asp Ala Lys Leu
145                 150                 155                 160 ggc gcg ctc gcc gcc ttc acc caa gcc gta atg gcg aaa aaa ggc gcg   528
Gly Ala Leu Ala Ala Phe Thr Gln Ala Val Met Ala Lys Lys Gly Ala
                165                 170                 175 gta tcc gac gag gaa ctc aaa gca ttt ttc gat gcg ggc tac aac cag   576
Val Ser Asp Glu Glu Leu Lys Ala Phe Phe Asp Ala Gly Tyr Asn Gln
            180                 185                 190 cag cag gca gtc gaa gtc gtg atg ggc gta gcc ttg gca acc ctg tgc   624
Gln Gln Ala Val Glu Val Val Met Gly Val Ala Leu Ala Thr Leu Cys
        195                 200                 205 aac tac gtc aac aac ctc gga caa acc gaa atc aac ccc gaa ttg cag   672
Asn Tyr Val Asn Asn Leu Gly Gln Thr Glu Ile Asn Pro Glu Leu Gln
    210                 215                 220 gct tac gcc                                                        681
Ala Tyr Ala
225

<210> SEQ ID NO 66
<211> LENGTH: 227
<212> TYPE: PRT
<213> ORGANISM: Neisseria meningitidis

<400> SEQUENCE: 66

Met Pro Ser Glu Lys Cys Ser Asp Gly Ile Ser Tyr Asn Leu Leu Phe
1               5                   10                  15

Ala Ala His Asn Gln Ser Val Phe Pro Ile Pro Phe Arg Asn Ala Tyr
            20                  25                  30

His Ala Pro Val Pro Asn Ile Cys Glu Gln Gly Lys Lys Met Ala Arg
        35                  40                  45
```

```
Leu Thr Val His Thr Leu Glu Thr Ala Pro Glu Ala Ala Lys Ala Arg
    50                  55                  60

Val Glu Ala Val Leu Gln Asn Asn Gly Phe Ile Pro Asn Leu Ile Gly
 65                  70                  75                  80

Val Leu Ser Asn Ala Pro Glu Ala Leu Ala Phe Tyr Gln Glu Val Gly
                 85                  90                  95

Lys Leu Asn Ala Ala Asn Ser Leu Thr Ala Gly Glu Val Glu Val Ile
            100                 105                 110

Gln Ile Ile Ala Ala Arg Thr Asn Gln Cys Gly Phe Cys Val Ala Gly
            115                 120                 125

His Thr Lys Leu Ala Thr Leu Lys Lys Leu Leu Ser Glu Gln Ser Val
    130                 135                 140

Lys Ala Ala Arg Ala Leu Ala Ala Gly Glu Phe Asp Asp Ala Lys Leu
145                 150                 155                 160

Gly Ala Leu Ala Ala Phe Thr Gln Ala Val Met Ala Lys Lys Gly Ala
                165                 170                 175

Val Ser Asp Glu Glu Leu Lys Ala Phe Phe Asp Ala Gly Tyr Asn Gln
            180                 185                 190

Gln Gln Ala Val Glu Val Val Met Gly Val Ala Leu Ala Thr Leu Cys
        195                 200                 205

Asn Tyr Val Asn Asn Leu Gly Gln Thr Glu Ile Asn Pro Glu Leu Gln
    210                 215                 220

Ala Tyr Ala
225

<210> SEQ ID NO 67
<211> LENGTH: 681
<212> TYPE: DNA
<213> ORGANISM: Neisseria meningitidis
<220> FEATURE:
<221> NAME/KEY: CDS
<222> LOCATION: (1)..(681)
<223> OTHER INFORMATION: NMB0995  macrophage infectivity potentiator-
      related protein

<400> SEQUENCE: 67 atg ccg tct gaa aaa tgt tca gac ggc att tct tat aac ctt ttg ttt       48
Met Pro Ser Glu Lys Cys Ser Asp Gly Ile Ser Tyr Asn Leu Leu Phe
1               5                   10                  15 gca gca cat aac caa tca gtc ttt cct att ccg ttc cga aat gca tac       96
Ala Ala His Asn Gln Ser Val Phe Pro Ile Pro Phe Arg Asn Ala Tyr
                20                  25                  30 cat gcg ccc gta ccc aat att tgc gaa caa gga aag aaa atg gca cgt      144
His Ala Pro Val Pro Asn Ile Cys Glu Gln Gly Lys Lys Met Ala Arg
            35                  40                  45 tta acc gta cac acc ctc gaa acc gcc ccc gaa gcc gcc aaa gcg cgc      192
Leu Thr Val His Thr Leu Glu Thr Ala Pro Glu Ala Ala Lys Ala Arg
    50                  55                  60 gtc gag gcg gta ctt caa aac aac ggc ttt atc ccc aac ctt atc ggc      240
Val Glu Ala Val Leu Gln Asn Asn Gly Phe Ile Pro Asn Leu Ile Gly
 65                  70                  75                  80 gta tta tca aac gcc ccc gaa gcc ttg gcg ttt tac caa gaa gtc ggc      288
Val Leu Ser Asn Ala Pro Glu Ala Leu Ala Phe Tyr Gln Glu Val Gly
                 85                  90                  95 aag ctc aac gcc gcc aac agc ctg acc gcc ggc gaa gtc gaa gtc atc      336
Lys Leu Asn Ala Ala Asn Ser Leu Thr Ala Gly Glu Val Glu Val Ile
            100                 105                 110 cag atc atc gcc gcc cgt acc aac caa tgc ggt ttt tgc gtg gca ggg      384
Gln Ile Ile Ala Ala Arg Thr Asn Gln Cys Gly Phe Cys Val Ala Gly
```

| | | | | | | | | | | | | | | |
|---|---|---|---|---|---|---|---|---|---|---|---|---|---|---|
| | | 115 | | | 120 | | | | 125 | | | | | |
| cac | acc | aaa | ctc | gca | acc | ctg | aaa | aaa | ctc | ctg | tcc | gaa | caa tcc gtc | 432 |
| His | Thr | Lys | Leu | Ala | Thr | Leu | Lys | Lys | Leu | Leu | Ser | Glu | Gln Ser Val | |
| | 130 | | | | 135 | | | | | 140 | | | | |
| aaa | gcg | gcg | cgc | gct | ttg | gca | gca | ggc | gaa | ttt | gac | gat | gcc aaa ctc | 480 |
| Lys | Ala | Ala | Arg | Ala | Leu | Ala | Ala | Gly | Glu | Phe | Asp | Asp | Ala Lys Leu | |
| 145 | | | | | 150 | | | | | 155 | | | 160 | |
| ggc | gcg | ctc | gcc | gcc | ttc | acc | caa | gcc | gta | atg | gcg | aaa | aaa ggc gcg | 528 |
| Gly | Ala | Leu | Ala | Ala | Phe | Thr | Gln | Ala | Val | Met | Ala | Lys | Lys Gly Ala | |
| | | | | 165 | | | | | 170 | | | | 175 | |
| gta | tcc | gac | gag | gaa | ctc | aaa | gca | ttt | ttc | gat | gcg | ggc | tac aac cag | 576 |
| Val | Ser | Asp | Glu | Glu | Leu | Lys | Ala | Phe | Phe | Asp | Ala | Gly | Tyr Asn Gln | |
| | | | 180 | | | | | 185 | | | | | 190 | |
| cag | cag | gca | gtc | gaa | gtc | gtg | atg | ggc | gta | gcc | ttg | gca | acc ctg tgc | 624 |
| Gln | Gln | Ala | Val | Glu | Val | Val | Met | Gly | Val | Ala | Leu | Ala | Thr Leu Cys | |
| | | 195 | | | | | 200 | | | | | 205 | | |
| aac | tac | gtc | aac | aac | ctc | gga | caa | acc | gaa | atc | aac | ccc | gaa ttg cag | 672 |
| Asn | Tyr | Val | Asn | Asn | Leu | Gly | Gln | Thr | Glu | Ile | Asn | Pro | Glu Leu Gln | |
| | 210 | | | | | 215 | | | | | 220 | | | |
| gct | tac | gcc | | | | | | | | | | | | 681 |
| Ala | Tyr | Ala | | | | | | | | | | | | |
| 225 | | | | | | | | | | | | | | |

<210> SEQ ID NO 68
<211> LENGTH: 227
<212> TYPE: PRT
<213> ORGANISM: Neisseria meningitidis

<400> SEQUENCE: 68

Met Pro Ser Glu Lys Cys Ser Asp Gly Ile Ser Tyr Asn Leu Leu Phe
1               5                   10                  15

Ala Ala His Asn Gln Ser Val Phe Pro Ile Pro Phe Arg Asn Ala Tyr
            20                  25                  30

His Ala Pro Val Pro Asn Ile Cys Glu Gln Gly Lys Lys Met Ala Arg
        35                  40                  45

Leu Thr Val His Thr Leu Glu Thr Ala Pro Glu Ala Ala Lys Ala Arg
    50                  55                  60

Val Glu Ala Val Leu Gln Asn Asn Gly Phe Ile Pro Asn Leu Ile Gly
65                  70                  75                  80

Val Leu Ser Asn Ala Pro Glu Ala Leu Ala Phe Tyr Gln Glu Val Gly
                85                  90                  95

Lys Leu Asn Ala Ala Asn Ser Leu Thr Ala Gly Glu Val Glu Val Ile
            100                 105                 110

Gln Ile Ile Ala Ala Arg Thr Asn Gln Cys Gly Phe Cys Val Ala Gly
        115                 120                 125

His Thr Lys Leu Ala Thr Leu Lys Lys Leu Leu Ser Glu Gln Ser Val
    130                 135                 140

Lys Ala Ala Arg Ala Leu Ala Ala Gly Glu Phe Asp Asp Ala Lys Leu
145                 150                 155                 160

Gly Ala Leu Ala Ala Phe Thr Gln Ala Val Met Ala Lys Lys Gly Ala
                165                 170                 175

Val Ser Asp Glu Glu Leu Lys Ala Phe Phe Asp Ala Gly Tyr Asn Gln
            180                 185                 190

Gln Gln Ala Val Glu Val Val Met Gly Val Ala Leu Ala Thr Leu Cys
        195                 200                 205

Asn Tyr Val Asn Asn Leu Gly Gln Thr Glu Ile Asn Pro Glu Leu Gln
    210                 215                 220

Ala Tyr Ala
225

<210> SEQ ID NO 69
<211> LENGTH: 939
<212> TYPE: DNA
<213> ORGANISM: Neisseria meningitidis
<220> FEATURE:
<221> NAME/KEY: CDS
<222> LOCATION: (1)..(939)
<223> OTHER INFORMATION: NMB0652 maf A

<400> SEQUENCE: 69

```
atg aaa acc ctg ctc ctc ctc atc ccc ctc gtc ctc aca gcc tgc ggc     48
Met Lys Thr Leu Leu Leu Leu Ile Pro Leu Val Leu Thr Ala Cys Gly
1               5                   10                  15 aca ctg acc ggc ata ccc gcc cac ggc ggc aaa cgc ttt gcc gtc         96
Thr Leu Thr Gly Ile Pro Ala His Gly Gly Lys Arg Phe Ala Val
            20                  25                  30 gaa caa gaa ctc gtc gcc gca tcg tcc cgc gcc gcc gtc aaa gaa atg    144
Glu Gln Glu Leu Val Ala Ala Ser Ser Arg Ala Ala Val Lys Glu Met
        35                  40                  45 gat ttg tcc gcc cta aaa gga cgc aaa gcc gcc ctt tac gtc tcc gtt    192
Asp Leu Ser Ala Leu Lys Gly Arg Lys Ala Ala Leu Tyr Val Ser Val
    50                  55                  60 atg ggc gac caa ggt tcg ggc aac ata agc ggc gga cgc tac tct atc    240
Met Gly Asp Gln Gly Ser Gly Asn Ile Ser Gly Gly Arg Tyr Ser Ile
65                  70                  75                  80 gac gca ctg ata cgc ggc ggc tac cac aac aac ccc gaa agt gcc acc    288
Asp Ala Leu Ile Arg Gly Gly Tyr His Asn Asn Pro Glu Ser Ala Thr
                85                  90                  95 caa tac agc tac ccc gcc tac gac act acc gcc acc acc aaa tcc gac    336
Gln Tyr Ser Tyr Pro Ala Tyr Asp Thr Thr Ala Thr Thr Lys Ser Asp
            100                 105                 110 gcg ctc tcc agc gta acc act tcc aca tcg ctt ttg aac gcc ccc gcc    384
Ala Leu Ser Ser Val Thr Thr Ser Thr Ser Leu Leu Asn Ala Pro Ala
        115                 120                 125 gcc gcc ctg acg aaa aac agc gga cgc aaa ggc gaa cgc tcc gcc gga    432
Ala Ala Leu Thr Lys Asn Ser Gly Arg Lys Gly Glu Arg Ser Ala Gly
    130                 135                 140 ctg tcc gtc aac ggc acg ggc gac tac cgc aac gaa acc ctg ctc gcc    480
Leu Ser Val Asn Gly Thr Gly Asp Tyr Arg Asn Glu Thr Leu Leu Ala
145                 150                 155                 160 aac ccc cgc gac gtt tcc ttc ctg acc aac ctc atc caa acc gtc ttc    528
Asn Pro Arg Asp Val Ser Phe Leu Thr Asn Leu Ile Gln Thr Val Phe
                165                 170                 175 tac ctg cgc ggc atc gaa gtc gta ccg ccc gaa tac gcc gac acc gac    576
Tyr Leu Arg Gly Ile Glu Val Val Pro Pro Glu Tyr Ala Asp Thr Asp
            180                 185                 190 gta ttc gta acc gtc gac gta ttc ggc acc gtc cgc agc cgt acc gaa    624
Val Phe Val Thr Val Asp Val Phe Gly Thr Val Arg Ser Arg Thr Glu
        195                 200                 205 ctg cac ctc tac aac gcc gaa acc ctt aaa gcc caa acc aag ctc gaa    672
Leu His Leu Tyr Asn Ala Glu Thr Leu Lys Ala Gln Thr Lys Leu Glu
    210                 215                 220 tat ttc gcc gtt gac cgc gac agc cgg aaa ctg ctg att acc cct aaa    720
Tyr Phe Ala Val Asp Arg Asp Ser Arg Lys Leu Leu Ile Thr Pro Lys
225                 230                 235                 240 acc gcc gcc tac gaa tcc caa tac caa gaa caa tac gcc ctt tgg acc    768
Thr Ala Ala Tyr Glu Ser Gln Tyr Gln Glu Gln Tyr Ala Leu Trp Thr
                245                 250                 255
```

```
ggc cct tac aaa gtc agc aaa acc gtc aaa gcc tca gac cgc ctg atg      816
Gly Pro Tyr Lys Val Ser Lys Thr Val Lys Ala Ser Asp Arg Leu Met
            260                 265                 270 gtc gat ttc tcc gac att acc ccc tac ggc gac aca acc gcc caa aac      864
Val Asp Phe Ser Asp Ile Thr Pro Tyr Gly Asp Thr Thr Ala Gln Asn
        275                 280                 285 cgt ccc gac ttc aaa caa aac aac ggt aaa aaa ccc gat gtc ggc aac      912
Arg Pro Asp Phe Lys Gln Asn Asn Gly Lys Lys Pro Asp Val Gly Asn
    290                 295                 300 gaa gtc atc cgc cgc cgc aaa gga gga                                  939
Glu Val Ile Arg Arg Arg Lys Gly Gly
305                 310

<210> SEQ ID NO 70
<211> LENGTH: 313
<212> TYPE: PRT
<213> ORGANISM: Neisseria meningitidis

<400> SEQUENCE: 70

Met Lys Thr Leu Leu Leu Ile Pro Leu Val Leu Thr Ala Cys Gly
1               5                   10                  15

Thr Leu Thr Gly Ile Pro Ala His Gly Gly Lys Arg Phe Ala Val
            20                  25                  30

Glu Gln Glu Leu Val Ala Ala Ser Arg Ala Ala Val Lys Glu Met
        35                  40                  45

Asp Leu Ser Ala Leu Lys Gly Arg Lys Ala Ala Leu Tyr Val Ser Val
    50                  55                  60

Met Gly Asp Gln Gly Gly Asn Ile Ser Gly Arg Tyr Ser Ile
65                  70                  75                  80

Asp Ala Leu Ile Arg Gly Gly Tyr His Asn Asn Pro Glu Ser Ala Thr
                85                  90                  95

Gln Tyr Ser Tyr Pro Ala Tyr Asp Thr Thr Ala Thr Thr Lys Ser Asp
            100                 105                 110

Ala Leu Ser Ser Val Thr Thr Ser Thr Ser Leu Leu Asn Ala Pro Ala
        115                 120                 125

Ala Ala Leu Thr Lys Asn Ser Gly Arg Lys Gly Glu Arg Ser Ala Gly
    130                 135                 140

Leu Ser Val Asn Gly Thr Gly Asp Tyr Arg Asn Glu Thr Leu Leu Ala
145                 150                 155                 160

Asn Pro Arg Asp Val Ser Phe Leu Thr Asn Leu Ile Gln Thr Val Phe
                165                 170                 175

Tyr Leu Arg Gly Ile Glu Val Val Pro Pro Glu Tyr Ala Asp Thr Asp
            180                 185                 190

Val Phe Val Thr Val Asp Val Phe Gly Thr Val Arg Ser Arg Thr Glu
        195                 200                 205

Leu His Leu Tyr Asn Ala Glu Thr Leu Lys Ala Gln Thr Lys Leu Glu
    210                 215                 220

Tyr Phe Ala Val Asp Arg Asp Ser Arg Lys Leu Leu Ile Thr Pro Lys
225                 230                 235                 240

Thr Ala Ala Tyr Glu Ser Gln Tyr Gln Glu Gln Tyr Ala Leu Trp Thr
                245                 250                 255

Gly Pro Tyr Lys Val Ser Lys Thr Val Lys Ala Ser Asp Arg Leu Met
            260                 265                 270

Val Asp Phe Ser Asp Ile Thr Pro Tyr Gly Asp Thr Thr Ala Gln Asn
        275                 280                 285
```

```
Arg Pro Asp Phe Lys Gln Asn Asn Gly Lys Lys Pro Asp Val Gly Asn
        290                 295                 300

Glu Val Ile Arg Arg Arg Lys Gly Gly
305                 310

<210> SEQ ID NO 71
<211> LENGTH: 1308
<212> TYPE: DNA
<213> ORGANISM: Neisseria meningitidis
<220> FEATURE:
<221> NAME/KEY: CDS
<222> LOCATION: (1)..(1308)
<223> OTHER INFORMATION: NMB1876  N-acetyl glutamate synthetase

<400> SEQUENCE: 71 atg agc gcg ccc gac ctc ttt gtc gcc cac ttc cgc gaa gcc gtc ccc       48
Met Ser Ala Pro Asp Leu Phe Val Ala His Phe Arg Glu Ala Val Pro
1               5                   10                  15 tac atc cgc caa atg cgc ggc aaa acg ctg gtc gcc ggc ata gac gac       96
Tyr Ile Arg Gln Met Arg Gly Lys Thr Leu Val Ala Gly Ile Asp Asp
                20                  25                  30 cgc ctg ctc gaa ggt gat acc tta aac aag ctc gcc gcc gac atc ggg      144
Arg Leu Leu Glu Gly Asp Thr Leu Asn Lys Leu Ala Ala Asp Ile Gly
            35                  40                  45 ctg ttg tcg caa ctg ggc atc agg ctc gtc ctc atc cac ggc gcg cgc      192
Leu Leu Ser Gln Leu Gly Ile Arg Leu Val Leu Ile His Gly Ala Arg
        50                  55                  60 cac ttc ctc gac cgc cac gcc gcc gct caa ggc cgc acg ccg cat tat      240
His Phe Leu Asp Arg His Ala Ala Ala Gln Gly Arg Thr Pro His Tyr
65                  70                  75                  80 tgc cgg ggc ttg cgc gtt acc gac gaa acc tcg ctc gaa cag gcg cag      288
Cys Arg Gly Leu Arg Val Thr Asp Glu Thr Ser Leu Glu Gln Ala Gln
                85                  90                  95 cag ttt gcc ggc acc gtc cgc agc cgt ttt gaa gcc gca ttg tgc ggc      336
Gln Phe Ala Gly Thr Val Arg Ser Arg Phe Glu Ala Ala Leu Cys Gly
                100                 105                 110 agc gtt tcc ggg ttc gcg cgc gcg cct tcc gtc ccg ctc gta tcg ggc      384
Ser Val Ser Gly Phe Ala Arg Ala Pro Ser Val Pro Leu Val Ser Gly
            115                 120                 125 aac ttc ctg acc gcc cgt ccg ata ggt gtg att gac gga acc gat atg      432
Asn Phe Leu Thr Ala Arg Pro Ile Gly Val Ile Asp Gly Thr Asp Met
        130                 135                 140 gaa tac gcg ggc gtt atc cgc aaa acc gac acc gcc gcc ctc cgt ttc      480
Glu Tyr Ala Gly Val Ile Arg Lys Thr Asp Thr Ala Ala Leu Arg Phe
145                 150                 155                 160 caa ctc gac gcg ggc aat atc gtc tgg ctg ccg ccg ctc gga cat tcc      528
Gln Leu Asp Ala Gly Asn Ile Val Trp Leu Pro Pro Leu Gly His Ser
                165                 170                 175 tac agc ggc aag acc ttc tat ctc gat atg ctt caa acc gcc gcc tcc      576
Tyr Ser Gly Lys Thr Phe Tyr Leu Asp Met Leu Gln Thr Ala Ala Ser
                180                 185                 190 gcc gcc gtc tcg ctt cag gcc gaa aaa ctc gtt tac ctg acc ctt tca      624
Ala Ala Val Ser Leu Gln Ala Glu Lys Leu Val Tyr Leu Thr Leu Ser
            195                 200                 205 gac ggc att tcc cgc ccc gac ggc acg ctc gcc gaa acc ctc tcg gca      672
Asp Gly Ile Ser Arg Pro Asp Gly Thr Leu Ala Glu Thr Leu Ser Ala
        210                 215                 220 cag gaa gcg caa tcg ctg gcg gaa cac gcc ggc ggc gaa acg cga cgg      720
Gln Glu Ala Gln Ser Leu Ala Glu His Ala Gly Gly Glu Thr Arg Arg
225                 230                 235                 240 ctg att tcg tcc gcc gtt gcc gcg ctc gaa ggc ggc gtg cat cgc gtc      768
```

```
Leu Ile Ser Ser Ala Val Ala Leu Glu Gly Gly Val His Arg Val
            245                 250                 255 caa atc ctc aac gga gcc gcc gac ggc agc ctg ctg caa gaa ctc ttc       816
Gln Ile Leu Asn Gly Ala Ala Asp Gly Ser Leu Leu Gln Glu Leu Phe
            260                 265                 270 acc cgc aac ggc atc ggc acg tcc att gcc aaa gaa gcc ttc gtc tcc       864
Thr Arg Asn Gly Ile Gly Thr Ser Ile Ala Lys Glu Ala Phe Val Ser
            275                 280                 285 atc cgg cag gcg cac agc ggc gac atc ccg cac atc gcc gcc ctc atc       912
Ile Arg Gln Ala His Ser Gly Asp Ile Pro His Ile Ala Ala Leu Ile
            290                 295                 300 cgc ccg ctg gaa gaa cag ggc atc ctg ctg cac cgc agc cgc gaa tac       960
Arg Pro Leu Glu Glu Gln Gly Ile Leu Leu His Arg Ser Arg Glu Tyr
305                 310                 315                 320 ctc gaa aac cac att tcc gaa ttt tcc atc ctc gaa cac gac ggc aac      1008
Leu Glu Asn His Ile Ser Glu Phe Ser Ile Leu Glu His Asp Gly Asn
                325                 330                 335 ctg tac ggt tgc gcc gcc ctg aaa acc ttt gcc gaa gcc gat tgc ggc      1056
Leu Tyr Gly Cys Ala Ala Leu Lys Thr Phe Ala Glu Ala Asp Cys Gly
                340                 345                 350 gaa atc gcc tgc ctt gcc gtc tcg ccg cag gca cag gac ggc ggc tac      1104
Glu Ile Ala Cys Leu Ala Val Ser Pro Gln Ala Gln Asp Gly Gly Tyr
            355                 360                 365 ggc gaa cgc ctg ctt gcc cac att atc gat aag gcg cgc ggc ata ggc      1152
Gly Glu Arg Leu Leu Ala His Ile Ile Asp Lys Ala Arg Gly Ile Gly
        370                 375                 380 ata agc agg ctg ttc gca ctg tcc aca aat acc ggc gaa tgg ttt gcc      1200
Ile Ser Arg Leu Phe Ala Leu Ser Thr Asn Thr Gly Glu Trp Phe Ala
385                 390                 395                 400 gaa cgc ggc ttt cag acg gca tcg gaa gac gag ttg ccc gaa acg cgg      1248
Glu Arg Gly Phe Gln Thr Ala Ser Glu Asp Glu Leu Pro Glu Thr Arg
                405                 410                 415 cgc aaa gac tac cgc agc aac gga cgg aac tcg cat att ctg gta cgt      1296
Arg Lys Asp Tyr Arg Ser Asn Gly Arg Asn Ser His Ile Leu Val Arg
            420                 425                 430 cgc ctg cac cgc                                                      1308
Arg Leu His Arg
            435

<210> SEQ ID NO 72
<211> LENGTH: 436
<212> TYPE: PRT
<213> ORGANISM: Neisseria meningitidis

<400> SEQUENCE: 72

Met Ser Ala Pro Asp Leu Phe Val Ala His Phe Arg Glu Ala Val Pro
1               5                   10                  15

Tyr Ile Arg Gln Met Arg Gly Lys Thr Leu Val Ala Gly Ile Asp Asp
                20                  25                  30

Arg Leu Leu Glu Gly Asp Thr Leu Asn Lys Leu Ala Ala Asp Ile Gly
            35                  40                  45

Leu Leu Ser Gln Leu Gly Ile Arg Leu Val Leu Ile His Gly Ala Arg
        50                  55                  60

His Phe Leu Asp Arg His Ala Ala Ala Gln Gly Arg Thr Pro His Tyr
65                  70                  75                  80

Cys Arg Gly Leu Arg Val Thr Asp Glu Thr Ser Leu Glu Gln Ala Gln
                85                  90                  95

Gln Phe Ala Gly Thr Val Arg Ser Arg Phe Glu Ala Ala Leu Cys Gly
            100                 105                 110
```

Ser Val Ser Gly Phe Ala Arg Ala Pro Ser Val Pro Leu Val Ser Gly
        115                 120                 125

Asn Phe Leu Thr Ala Arg Pro Ile Gly Val Ile Asp Gly Thr Asp Met
        130                 135                 140

Glu Tyr Ala Gly Val Ile Arg Lys Thr Asp Thr Ala Ala Leu Arg Phe
145                 150                 155                 160

Gln Leu Asp Ala Gly Asn Ile Val Trp Leu Pro Pro Leu Gly His Ser
                165                 170                 175

Tyr Ser Gly Lys Thr Phe Tyr Leu Asp Met Leu Gln Thr Ala Ala Ser
            180                 185                 190

Ala Ala Val Ser Leu Gln Ala Glu Lys Leu Val Tyr Leu Thr Leu Ser
        195                 200                 205

Asp Gly Ile Ser Arg Pro Asp Gly Thr Leu Ala Glu Thr Leu Ser Ala
        210                 215                 220

Gln Glu Ala Gln Ser Leu Ala Glu His Ala Gly Gly Glu Thr Arg Arg
225                 230                 235                 240

Leu Ile Ser Ser Ala Val Ala Leu Glu Gly Val His Arg Val
                245                 250                 255

Gln Ile Leu Asn Gly Ala Ala Asp Gly Ser Leu Leu Gln Glu Leu Phe
            260                 265                 270

Thr Arg Asn Gly Ile Gly Thr Ser Ile Ala Lys Glu Ala Phe Val Ser
        275                 280                 285

Ile Arg Gln Ala His Ser Gly Asp Ile Pro His Ile Ala Ala Leu Ile
        290                 295                 300

Arg Pro Leu Glu Glu Gln Gly Ile Leu Leu His Arg Ser Arg Glu Tyr
305                 310                 315                 320

Leu Glu Asn His Ile Ser Glu Phe Ser Ile Leu Glu His Asp Gly Asn
                325                 330                 335

Leu Tyr Gly Cys Ala Ala Leu Lys Thr Phe Ala Glu Ala Asp Cys Gly
            340                 345                 350

Glu Ile Ala Cys Leu Ala Val Ser Pro Gln Ala Gln Asp Gly Gly Tyr
        355                 360                 365

Gly Glu Arg Leu Leu Ala His Ile Ile Asp Lys Ala Arg Gly Ile Gly
        370                 375                 380

Ile Ser Arg Leu Phe Ala Leu Ser Thr Asn Thr Gly Glu Trp Phe Ala
385                 390                 395                 400

Glu Arg Gly Phe Gln Thr Ala Ser Glu Asp Glu Leu Pro Glu Thr Arg
                405                 410                 415

Arg Lys Asp Tyr Arg Ser Asn Gly Arg Asn Ser His Ile Leu Val Arg
            420                 425                 430

Arg Leu His Arg
        435

<210> SEQ ID NO 73
<211> LENGTH: 712
<212> TYPE: PRT
<213> ORGANISM: Neisseria meningitidis
<220> FEATURE:
<221> NAME/KEY: MISC_FEATURE
<223> OTHER INFORMATION: TbpB

<400> SEQUENCE: 73

Met Asn Asn Pro Leu Val Asn Gln Ala Ala Met Val Leu Pro Val Phe
1               5                   10                  15

Leu Leu Ser Ala Cys Leu Gly Gly Gly Gly Ser Phe Asp Leu Asp Ser

-continued

```
                20                  25                  30
Val Asp Thr Glu Ala Pro Arg Pro Ala Pro Lys Tyr Gln Asp Val Phe
             35                  40                  45
Ser Glu Lys Pro Gln Ala Gln Lys Asp Gln Gly Gly Tyr Gly Phe Ala
 50                  55                  60
Met Arg Leu Lys Arg Arg Asn Trp Tyr Pro Gln Ala Lys Glu Asp Glu
 65                  70                  75                  80
Val Lys Leu Asp Glu Ser Asp Trp Glu Ala Thr Gly Leu Pro Asp Glu
             85                  90                  95
Pro Lys Glu Leu Pro Lys Arg Gln Lys Ser Val Ile Glu Lys Val Glu
             100                 105                 110
Thr Asp Ser Asp Asn Asn Ile Tyr Ser Ser Pro Tyr Leu Lys Pro Ser
             115                 120                 125
Asn His Gln Asn Gly Asn Thr Gly Asn Gly Ile Asn Gln Pro Lys Asn
             130                 135                 140
Gln Ala Lys Asp Tyr Glu Asn Phe Lys Tyr Val Tyr Ser Gly Trp Phe
145                 150                 155                 160
Tyr Lys His Ala Lys Arg Glu Phe Asn Leu Lys Val Glu Pro Lys Ser
             165                 170                 175
Ala Lys Asn Gly Asp Asp Gly Tyr Ile Phe Tyr His Gly Lys Glu Pro
             180                 185                 190
Ser Arg Gln Leu Pro Ala Ser Gly Lys Ile Thr Tyr Lys Gly Val Trp
             195                 200                 205
His Phe Ala Thr Asp Thr Lys Lys Gly Gln Lys Phe Arg Glu Ile Ile
             210                 215                 220
Gln Pro Ser Lys Ser Gln Gly Asp Arg Tyr Ser Gly Phe Ser Gly Asp
225                 230                 235                 240
Asp Gly Glu Glu Tyr Ser Asn Lys Asn Lys Ser Thr Leu Thr Asp Gly
             245                 250                 255
Gln Glu Gly Tyr Gly Phe Thr Ser Asn Leu Glu Val Asp Phe His Asn
             260                 265                 270
Lys Lys Leu Thr Gly Lys Leu Ile Arg Asn Asn Ala Asn Thr Asp Asn
             275                 280                 285
Asn Gln Ala Thr Thr Thr Gln Tyr Tyr Ser Leu Glu Ala Gln Val Thr
             290                 295                 300
Gly Asn Arg Phe Asn Gly Lys Ala Thr Ala Thr Asp Lys Pro Gln Gln
305                 310                 315                 320
Asn Ser Glu Thr Lys Glu His Pro Phe Val Ser Asp Ser Ser Ser Leu
             325                 330                 335
Ser Gly Gly Phe Phe Gly Pro Gln Gly Glu Glu Leu Gly Phe Arg Phe
             340                 345                 350
Leu Ser Asp Asp Gln Lys Val Ala Val Val Gly Ser Ala Lys Thr Lys
             355                 360                 365
Asp Lys Pro Ala Asn Gly Asn Thr Ala Ala Ala Ser Gly Gly Thr Asp
             370                 375                 380
Ala Ala Ala Ser Asn Gly Ala Ala Gly Thr Ser Ser Glu Asn Gly Lys
385                 390                 395                 400
Leu Thr Thr Val Leu Asp Ala Val Glu Leu Lys Leu Gly Asp Lys Glu
             405                 410                 415
Val Gln Lys Leu Asp Asn Phe Ser Asn Ala Ala Gln Leu Val Val Asp
             420                 425                 430
Gly Ile Met Ile Pro Leu Leu Pro Glu Ala Ser Glu Ser Gly Asn Asn
             435                 440                 445
```

Gln Ala Asn Gln Gly Thr Asn Gly Gly Thr Ala Phe Thr Arg Lys Phe
    450                 455                 460

Asp His Thr Pro Glu Ser Asp Lys Lys Asp Ala Gln Ala Gly Thr Gln
465                 470                 475                 480

Thr Asn Gly Ala Gln Thr Ala Ser Asn Thr Ala Gly Asp Thr Asn Gly
                485                 490                 495

Lys Thr Lys Thr Tyr Glu Val Glu Val Cys Cys Ser Asn Leu Asn Tyr
            500                 505                 510

Leu Lys Tyr Gly Met Leu Thr Arg Lys Asn Ser Lys Ser Ala Met Gln
        515                 520                 525

Ala Gly Glu Ser Ser Gln Ala Asp Ala Lys Thr Glu Gln Val Glu
    530                 535                 540

Gln Ser Met Phe Leu Gln Gly Glu Arg Thr Asp Glu Lys Glu Ile Pro
545                 550                 555                 560

Ser Glu Gln Asn Ile Val Tyr Arg Gly Ser Trp Tyr Gly Tyr Ile Ala
                565                 570                 575

Asn Asp Lys Ser Thr Ser Trp Ser Gly Asn Ala Ser Asn Ala Thr Ser
            580                 585                 590

Gly Asn Arg Ala Glu Phe Thr Val Asn Phe Ala Asp Lys Lys Ile Thr
        595                 600                 605

Gly Thr Leu Thr Ala Asp Asn Arg Gln Glu Ala Thr Phe Thr Ile Asp
    610                 615                 620

Gly Asn Ile Lys Asp Asn Gly Phe Glu Gly Thr Ala Lys Thr Ala Glu
625                 630                 635                 640

Ser Gly Phe Asp Leu Asp Gln Ser Asn Thr Thr Arg Thr Pro Lys Ala
                645                 650                 655

Tyr Ile Thr Asp Ala Lys Val Gln Gly Gly Phe Tyr Gly Pro Lys Ala
            660                 665                 670

Glu Glu Leu Gly Gly Trp Phe Ala Tyr Pro Gly Asp Lys Gln Thr Lys
        675                 680                 685

Asn Ala Thr Asn Ala Ser Gly Asn Ser Ser Ala Thr Val Val Phe Gly
    690                 695                 700

Ala Lys Arg Gln Gln Pro Val Arg
705                 710

<210> SEQ ID NO 74
<211> LENGTH: 67
<212> TYPE: DNA
<213> ORGANISM: Neisseria meningitidis
<220> FEATURE:
<221> NAME/KEY: misc_feature
<223> OTHER INFORMATION: porA promoter sequence

<400> SEQUENCE: 74
ttgaagacgt atcgggtgtt tgcccgatgt ttttaggttt ttatcaaatt tacaaaagga    60
agccgat    67

<210> SEQ ID NO 75
<211> LENGTH: 253
<212> TYPE: PRT
<213> ORGANISM: unidentified
<220> FEATURE:
<221> NAME/KEY: MISC_FEATURE
<223> OTHER INFORMATION: kanamycin resistance

<400> SEQUENCE: 75

Met Asn Gly Pro Ile Ile Met Thr Arg Glu Glu Arg Met Lys Ile Val

```
              1               5              10              15

His Glu Ile Lys Glu Arg Ile Leu Asp Lys Tyr Gly Asp Asp Val Lys
                 20                      25                  30

Ala Ile Gly Val Tyr Gly Ser Leu Gly Arg Gln Thr Asp Gly Pro Tyr
                 35                  40              45

Ser Asp Ile Glu Met Met Cys Val Met Ser Thr Glu Glu Ala Glu Phe
        50              55                      60

Ser His Glu Trp Thr Thr Gly Glu Trp Lys Val Glu Val Asn Phe Asp
65                      70                  75                  80

Ser Glu Glu Ile Leu Leu Asp Tyr Ala Ser Gln Val Glu Ser Asp Trp
                 85                      90                  95

Pro Leu Thr His Gly Gln Phe Phe Ser Ile Leu Pro Ile Tyr Asp Ser
                100                     105             110

Gly Gly Tyr Leu Glu Lys Val Tyr Gln Thr Ala Lys Ser Val Glu Ala
                115                     120             125

Gln Thr Phe His Asp Ala Ile Cys Ala Leu Ile Val Glu Glu Leu Phe
                130             135                 140

Glu Tyr Ala Gly Lys Trp Arg Asn Ile Arg Val Gln Gly Pro Thr Thr
145                     150                 155                 160

Phe Leu Pro Ser Leu Thr Val Gln Val Ala Met Ala Gly Ala Met Leu
                165                     170                 175

Ile Gly Leu His His Arg Ile Cys Tyr Thr Thr Ser Ala Ser Val Leu
                180                     185             190

Thr Glu Ala Val Lys Gln Ser Asp Leu Pro Ser Gly Tyr Asp His Leu
            195                 200                 205

Cys Gln Phe Val Met Ser Gly Gln Leu Ser Asp Ser Glu Lys Leu Leu
    210                 215                 220

Glu Ser Leu Glu Asn Phe Trp Asn Gly Ile Gln Glu Trp Thr Glu Arg
225                 230                 235                 240

His Gly Tyr Ile Val Asp Val Ser Lys Arg Ile Pro Phe
                245                 250
```

MULTICOMPONENT MENINGOCOCCAL VACCINE

REFERENCE TO RELATED APPLICATIONS

This application is a Continuation-in-Part of U.S. application Ser. No. 12/289,098, filed Oct. 20, 2008, now abandoned, which is a continuation of application Ser. No. 10/320,800, filed Dec. 17, 2002, now abandoned, which is a Continuation-in-Part of U.S. application Ser. No. 09/830,854 filed on Aug. 29, 2001, now U.S. Pat. No. 6,821,521 B1, filed as application No. PCT/GB99/03626 on Nov. 2, 1999, the contents of each of these applications are fully incorporated herein by reference.

BACKGROUND

The present invention relates to a multicomponent vaccine and methods for preparing a multicomponent vaccine that confers protective immunity to a broad spectrum of infection by Gram negative pathogens. In particular the present invention relates to a multicomponent vaccine that provides both passive and active protective immunity to meningococcal disease.

Meningococcal meningitis is a major problem worldwide and in many countries incidence of infection is increasing. *Neisseria meningitidis* is the causative agent of the disease and is also responsible for meningococcal septicaemia, which is associated with rapid onset and high mortality, with around 22% of cases proving fatal.

At present, vaccines directed at providing protective immunity against meningococcal disease provide only limited protection because of the many different strains of *N. meningitidis*. Vaccines based upon the serogroup antigens, the capsular polysaccharides, offer only short lived protection against infection and do not protect against many strains commonly found in North America and Europe. A further drawback of these vaccines is that they provide low levels of protection for children under the age of 2 years, one of the most vulnerable groups that are commonly susceptible to infection.

The meningococcal transferrin receptor is made up of two types of component protein chain, Transferrin binding protein A (TbpA) and TbpB. The receptor complex is believed to be formed from a dimer of TbpA which associates with a single TbpB (Boulton et al. (1998)). Epitopes present in TbpA are known to be masked within the interior of the protein (Ala'Aldeen (1996)). Vaccines against meningococcal meningitis based on TbpB from one strain alone show some cross reactivity and there is evidence of a cross-reactive immune response in rabbits immunised with TbpB alone (Feirreros et al. (1998)).

It would be of advantage, nevertheless, to provide a vaccine that gives a broader range of protective immunity to infection from a wider spectrum of strains of *N. meningitidis*. It would be of further advantage to provide a vaccine that confers protective immunity to infants as well as adults and whose protection is long term. It would also be of advantage to provide a vaccine that protects against subclinical infection, i.e. where symptoms of meningococcal infection are not immediately apparent that the infected individual may act as a carrier of the pathogen.

It is an object of the present invention to provide compositions containing Tbps, and vaccines based thereon, that meet or at least ameliorate the disadvantages in the art. In particular, it is an object of the invention to provide a vaccine composition that consistently and reliably induces protective immunity to meningococcal infection.

Accordingly, a first aspect of the present invention provides a composition comprising both transferrin binding proteins A (TbpA) and B (TbpB), suitably in a molar ratio of about 2:1 (TbpA:TbpB). In a preferred embodiment of the present invention the molar ratio of TbpA to TbpB is 2:1.

The composition may be combined with a pharmaceutically acceptable carrier—for example the adjuvant alum although any carrier suitable for oral, intravenous, subcutaneous, intraperitoneal or any other route of administration is suitable—to produce a pharmaceutical composition for treatment of meningococcal disease.

The present invention thus provides for a vaccine comprising both TbpA+B proteins, preferably with a molar ratio of between 1.8 and 2.2 molecules of TbpA to one molecule of TbpB, more preferably 2 molecules of TbpA to one of TbpB. This particular combination of components, surprisingly, can provide higher protective immunity to meningococcal infection, compared to vaccination with TbpB alone. In a specific embodiment of the invention, described in more detail below, a 1:1 combination of A:B is more protective against challenge than B alone. This is surprising as TbpA has previously been considered to be non-protective. The present results differ from this established view with some experiments (described in more detail below) showing that, when administered as a vaccine, TbpA is also able to provide protective immunity to meningococcal infection. However, the present results most strikingly demonstrate the consistent performance of vaccines that comprise both Tbps A and B compared to those comprising Tbp A or B alone. It is this lack of variability between compositions and the consistently high level of protection to infection induced in response to vaccination with Tbp A+B, that enables the compositions of the invention to demonstrate significant advantage over the vaccines of the prior art.

Transferrin binding proteins are known to be located on the outer membranes of a number of Gram negative bacteria such as *N. meningitidis*. Formulations of the composition of the present invention with conventional carriers or adjuvants provide a composition for treatment of infection by these bacteria.

It is an advantage that following administration of a composition according to the present invention antibodies may be raised against epitopes that consist of sequences from TbpA and TbpB in juxtaposition. Thus, the immune response obtainable using such a composition may be improved compared with that from prior art vaccine compositions which comprise only one component of the Tbp complex and in which the full range of potential Tbp epitopes are unavailable. It is a further option in the present invention for one Tbp subunit component of the TbpA+B complex to be from a first strain of *N. meningitidis* and another from a second strain different from the first. For example, the TbpA dimer is taken from the first strain and the TbpB is from the second. The TbpA and TbpB proteins may be selected independently from strains K454, H44/76 and B16B6. In all aspects of the invention the Tbps can be directly isolated from the bacterial source or can be produced by recombinant methods commonly known in the art. Combinations of proteins from other strains are also envisaged, and the combining of components from different strains of bacteria offers the potential for providing an individual with a broader spectrum of protection against meningococcal infection. It is further optional for a composition or vaccine of the invention to contain a mixture of A proteins from different strains or a mixture of B proteins from different strains, broadening further the potential spectrum of protection conferred by the invention. A still further option is for Tbps to be obtained from or derived from other bacteria, including *N. gonorrhoeae, N. lactamica* and *Moraxella catarrhalis*.

In the present invention, the term "transferrin binding protein" or "Tbp" refers to a protein which either alone binds to transferrin or can be part of a complex of proteins that binds transferrin. The term also embraces fragments, variants and derivatives of such a protein provided that antibodies raised against the fragment, variant or derivative bind the protein. Thus, TbpA and TbpB either dissociated or associated into a complex are considered to be Tbp. Moreover, mutants, fusion proteins or fragments of either TbpA or B or other derivatives of the TbpA+B complex with a common antigenic identity are also considered to be represented by the term Tbp in the present invention.

A second aspect of the invention provides a composition comprising a complex of two TbpAs and one TbpB. The proteins are thus held together in the ratio seen in the native receptor. The individual proteins may be linked, for example, by hydrogen bonds or covalent bonds. In the latter case, each TbpA is covalently linked to the TbpA, either directly or indirectly. In a preferred embodiment, the complex of TbpA and TbpB assumes a native configuration.

A native TbpA+B complex may be isolated and purified from *N. meningitidis*. Alternatively, the invention also provides for synthesis of recombinant Tbp protein followed by assembly of the TbpA+B complex in vitro. The TbpA+B complex may be formed by admixture, or may be cross-linked by physical (e.g. UV radiation) or chemical methods known to the art, resulting in a combination of Tbps that will remain together and cannot dissociate from each other. In a further example, a single chain recombinant protein comprising two TbpA sequences, preferably in the form of the TbpA dimer, is then covalently linked with TbpB protein to form a complete TbpA+B complex in vitro. Another example of the invention in use provides that TbpA and B are mutated so as to introduce cysteine residues that facilitate the formation of disulphide bridges between the TbpA and TbpB subunits, so as to obtain a covalently bound complex.

In preparation of a recombinant protein TbpA and TbpB genes may also be truncated so that only those domains known to contribute to the antigenicity of the protein are incorporated in the Tbp complex.

In some compositions of the invention the TbpA+B complex is able to act as a transferrin receptor and binds to human transferrin. In other compositions of the invention the TbpA+B complex is non-functional in the sense that it does not bind transferrin, but it nevertheless provides an antigenic component that elicits an appropriate immune response.

A third aspect of the invention provides for a composition comprising a Tbp and *N. meningitidis* outer membrane vesicles. An advantage of this composition is that when administered to a vaccinee or patient it presents a different combination of *N. meningitidis* antigens, and particularly antigens that are in a formation substantially as present on the membrane of live infecting organisms. The combination offers the potential for a more effective protection against infection or a broader spectrum of protection than existing vaccines. Known methods of outer membrane vesicle isolation, such as by desoxycholate treatment, are suitable for preparation of compositions of the invention. In various preferred embodiments the Tbp is Tbp A, Tbp B or TbpA+B either in a native complex or in dissociated form.

The outer membrane vesicles may further be pretreated in vitro with Tbp so as to enrich the vesicle membrane with Tbp. By "enrich" and like terms, we refer to an outer membrane vesicle to which has been added Tbps so as to increase the concentration or density of Tbps in that vesicle. Preferably, the enrichment results in an outer membrane vesicle having an increased number of transferrin receptors located in the membrane, due to an increased concentration of TbpA and TbpB following their addition to the vesicle and their association into receptors or receptor-like structures. A particular advantage of such embodiments of the invention is that the Tbps, regarded as key antigenic components of the vaccine, are presented in a highly antigenic environment that closely mimics the environment in which transferrin receptors are presented on live, infecting bacteria.

As mentioned previously, the Tbp components of the composition need not be wild-type Tbps. They can be made recombinantly, and in so doing sequence alterations may be introduced. In one typical example of the invention, recombinant TbpB is modified so as to comprise a membrane binding domain. A preferred membrane spanning domain is a hydrophobic alpha helical region added to either the N or C terminus of the Tbp B protein. However, a membrane anchoring region need not only be an alpha helix, addition of a fatty acid or lipid chain would also facilitate membrane anchoring. In fact, wild type TbpB is believed to anchored to the bacterial outer membrane via such a lipid chain anchor. In a further example of the invention in use, the outer membrane vesicles are pretreated in vitro with membrane binding recombinant TbpB so as to enrich the vesicle membrane with TbpB. OMVs enriched with Tbps are additionally generated by inducing high levels of Tbp expression in *N. meningitidis* and then isolating OMVs via one of the methods described previously. This latter method is typically achieved by transforming the *N. meningitidis* host with a suitable expression vector into which has been inserted a gene or genes encoding the Tbps of choice. Suitable expression vectors for use in neisserial species include the plasmid pMGC10 (Nassif et al. (1991)).

It is preferred that the composition of the present invention comprises outer membrane vesicles and TbpA+B complexes isolated from a range of different strains of *N. meningitidis*. Other preferred compositions of the invention comprise other *N. meningitidis* proteins including surface antigens, periplasmic proteins, superoxide dismutase and glycoproteins.

The composition of the third aspect of the invention may instead of or in addition to outer membrane vesicles comprise one or more liposomes, each liposome including TbpA and/or TbpB preferably including TbpA and TbpB associated into a receptor or into a receptor-like complex. Thus a further means of presenting the transferrin receptor antigens is provided.

In a further embodiment of the third aspect of the invention, the composition comprises 22 kD antigen (Neisserial surface protein A (NspA)) as well as or instead of outer membrane vesicles. NspA and its preparation are described by Martin et al, 1997.

A fourth aspect of the invention provides for a vaccine comprising a composition of the invention as described above. A vaccine of the invention may also comprise antibodies to Tbp and thus provide a level of passive immunity to bacterial infection.

A fifth aspect of the invention provides for a method of manufacturing a composition that comprises combining TbpA, TbpB and *N. meningitidis* outer membrane vesicles with a pharmaceutically acceptable carrier. It is preferred that the molar ratio of TbpA to TbpB is about 2:1. The outer membrane vesicles can be pretreated in vitro with native TbpA+B so as to enrich the vesicle membrane with Tbp complex. However, the outer membrane vesicles may also be pretreated with other protein components so as to enrich them for these antigenic components also. The outer membrane vesicles may also be pretreated with antigenic proteins and proteoglycans from several different strains of N. meningitidis.

A further aspect of the invention provides for a composition comprising a Tbp and a Cu,Zn-Superoxide dismutase (Cu,Zn-SOD).

Cu,Zn-Superoxide Dismutase (Cu,Zn-SOD) is an metalloenzyme found in many prokaryotic and eukaryotic organisms. It catalyses the reduction of the superoxide radical anion, $O_2^-$, to hydrogen peroxide and molecular oxygen, thus playing an important role in the removal of cytotoxic free radicals from the organism. In bacteria Cu,Zn-SODs have been identified in the periplasm of a number of Gram negative species including N. meningitidis. The enzyme can exist as a dimer or a monomer, and accordingly in a preferred embodiment the present invention provides for a composition comprising a Tbp and a Cu,Zn-SOD of the dimeric type.

As mentioned previously with regard to the use of the term "Tbp", the Cu,Zn-SOD of the present invention is also considered to encompass fragments, variants and derivatives of such a protein provided that antibodies raised against the fragment, variant or derivative bind the wild type Cu,Zn-SOD.

In examples of the invention in use, compositions are provided that comprise a Cu,Zn-SOD and either a TbpA, a TbpB or a TbpA+B complex. In the latter example it is preferred that the molar ratio of TbpA to Tbp B is between 1.8 and 2.2, with the most suitable compositions having a ratio of 2:1 (TbpA:TbpB). In further compositions of the invention the Tbps are from a different strain of N. meningitidis to that of the Cu,Zn-SOD, thus facilitating the formation of a broader spectrum of immune response to meningococcal infection.

The invention also provides for compositions wherein the Tbps and Cu,Zn-SOD are from different bacterial species, typically different Gram negative species. Such compositions thereby allow an even broader spectrum of immune response to be elicited when administered as a vaccine. Typical compositions comprise a neisserial TbpA+B complex as well as a monomeric Cu,Zn-SOD—from E. coli for example—and optionally a further dimeric Cu,Zn-SOD—for example from Haemophilus parainfluenzae.

Other aspects of the invention provide for methods of manufacturing compositions that provide protective immunity to Gram negative bacterial infection, comprising combining a covalently linked complex of TbpA and TbpB with either or both of N. meningitidis outer membrane vesicles and a Cu,Zn-SOD, plus a pharmaceutically acceptable carrier.

A further aspect provides for use of Tbps A and B in the manufacture of a medicament for human vaccination. It is preferred that such a medicament is suitable for vaccination against meningococcal infection, although some compositions of the invention provide broad spectrum protection to infection from a wider range of bacterial pathogens.

We have identified that combining Neisseria meningitidis outer membrane vesicles (OMVs) and an antigenic component isolated from Neisseria meningitidis increases the cross-protective capability of a meningococcal disease vaccine against a range of meningococcal strains.

The invention thus provides a composition comprising Neisseria meningitidis outer membrane vesicles (OMVs) and at least one antigenic component.

It is an option for the composition to comprise a plurality of antigenic components—for example, at least 2, 3, 4 or 5 antigenic components. Said plurality of antigenic components may be from different sources, for example, from different strains of Neisseria meningitidis.

We have also identified that enriching Neisseria meningitidis outer membrane vesicles (OMVs) with an antigenic component isolated from Neisseria meningitidis increases the cross-protective capability of a meningococcal disease vaccine against a range of meningococcal strains.

The invention thus provides Neisseria meningitidis outer membrane vesicles (OMVs) that are enriched with at least one antigenic component.

It is an option for the Neisseria meningitidis outer membrane vesicles to be enriched with a plurality of antigenic components—for example, at least 2, 3, 4 or 5 antigenic components. Said plurality of antigenic components may be from different sources, such as different strains of Neisseria meningitidis.

By "enrich" (and like terms), we refer to an outer membrane vesicle to which has been added at least one antigenic component, so as to increase the concentration or density of antigenic components in that vesicle. A particular advantage of this aspect of the invention is that the antigenic components are presented in a highly antigenic environment that closely mimics the environment in which these antigenic components are presented on live, infecting bacteria.

The antigenic component may, in one embodiment, comprise or consist of a N. meningitidis antigenic component, such as a N. meningitidis antigenic protein or an N. meningitidis antigenic proteoglycan.

In one embodiment, the antigenic component may comprise or consist of a N. meningitidis antigenic protein selected from the group consisting of TbpA, TbpB, NspA, PorA, OMP85, FrpB (now know as FetA), PilQ, Hsf, SodC, MafA. Thus, in one embodiment, the invention thus provides Neisseria meningitidis outer membrane vesicles (OMVs) that are enriched with at least one antigenic component selected from the group consisting of N. meningitidis TbpA, TbpB, Neisserial Surface Protein A (NspA), PorA, OMP85, FrpB (now known as FetA), PilQ, Hsf, SodC and MafA.

In one embodiment, said antigenic component comprises or consists of a peptide having a sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70 and 72, or a sequence having at least 90 or 95% sequence identity thereto.

In one embodiment, the antigenic component comprises or consists of an antigenic proteoglycan, such as a N. meningitidis antigenic proteoglycan selected from the group consisting of a surface antigen, a periplasmic protein, a superoxide dismutase and a glycoprotein.

The antigenic component need not be a wild-type antigenic component. In one embodiment, the antigenic component is made recombinantly and, in doing so, it is an option for sequence alterations (eg. insertions, deletions or substitutions) to be introduced.

In one embodiment, said outer membrane vesicles are from a first strain of Neisseria meningitidis and said antigenic component is from a second strain of Neisseria meningitidis, wherein said second strain is different from said first strain. By way of example, said first and second different strains of *Neisseria meningitidis* may be selected from strain NZ98/254 or strain 44/76.

The invention also provides a composition comprising *Neisseria meningitidis* outer membrane vesicles (OMVs) that are enriched with at least one antigenic component.

Said composition may comprise a plurality of said *Neisseria meningitidis* outer membrane vesicles, wherein said plurality of *Neisseria meningitidis* outer membrane vesicles are enriched with different antigenic components. Alternatively, or in addition, said composition may comprise a plurality of said *Neisseria meningitidis* outer membrane vesicles that are from different strains *Neisseria meningitidis*.

The compositions of the invention may comprise a pharmaceutically acceptable carrier (any carrier suitable for oral, intravenous, subcutaneous, intraperitoneal or any other route of administration is suitable).

The compositions of the invention may, in one embodiment, be vaccine compositions.

Thus, in one embodiment, the invention provides a vaccine composition comprising *Neisseria meningitidis* outer membrane vesicles (OMVs) and at least one antigenic component.

In one embodiment, the invention provides a vaccine composition comprising *Neisseria meningitidis* outer membrane vesicles (OMVs) that are enriched with at least one antigenic component.

A vaccine composition may optionally comprise one or more conventional excipients, adjuvants, immunostimulatory compounds, antibodies, or anti-*Neisseria* drugs.

The invention also provides a method of manufacture of a composition, comprising combining *Neisseria meningitidis* outer membrane vesicles and an antigenic component (such as a *Neisseria meningitidis* antigenic component).

In one embodiment, said method comprises:
(a) extracting an antigenic component from an outer membrane of a bacteria, such as *Neisseria meningitidis*, and preparing an aqueous solution of said antigenic component;
(b) extracting outer membrane vesicles (OMVs) from a culture of *Neisseria meningitidis*, and preparing an aqueous solution of said OMVs; and
(c) admixing the solution prepared in (a) and the solution prepared in (b).

Step (a) of said method optionally comprises the initial step of recombinantly expressing a DNA that encodes the antigenic component in the bacteria (eg. *Neisseria meningitidis*), prior to extracting said antigenic component from the outer membrane of said bacterium, and preparing the aqueous solution of said antigenic component.

In one embodiment, the method further comprises combining the OMVs and antigenic component with a pharmaceutically acceptable carrier.

The invention also provides a method of manufacture of a composition comprising *Neisseria meningitidis* outer membrane vesicles that are enriched with at least one antigenic component (such as a *Neisseria meningitidis* antigenic component). In one embodiment, said method comprises:
(a) recombinantly expressing a DNA that encodes the antigenic component in the *Neisseria meningitidis* bacteria; and
(b) extracting outer membrane vesicles (OMVs) enriched with said antigenic component from a culture of said recombinant *Neisseria meningitidis*, and preparing an aqueous solution of said OMVs.

In one embodiment, the method further comprises combining the OMVs with a pharmaceutically acceptable carrier.

In one embodiment of said methods, the antigenic component is selected from any of the antigenic components (eg. *Neisseria meningitidis* antigenic components) described above. In one embodiment of said methods, the outer membrane vesicles and/or the antigenic components are obtained from different strains of *Neisseria meningitidis*.

Known methods of isolating OMVs, such as by desoxycholate treatment, are suitable for preparing compositions of the invention.

The invention also provides a method of stimulating an immune response in a subject, comprising administering to the subject a composition of the invention, which may optionally further comprise a pharmaceutically acceptable carrier. In one embodiment, said composition comprises *Neisseria meningitidis* outer membrane vesicles (OMVs) and at least one antigenic component. In one embodiment, said composition comprises *Neisseria meningitidis* outer membrane vesicles (OMVs) that are enriched with at least one antigenic component.

The invention also provides a method of preventing *Neisseria meningitidis* infection in a subject, comprising administering to the subject a composition as described above, which may optionally further comprise a pharmaceutically acceptable carrier. In one embodiment, said composition comprises *Neisseria meningitidis* outer membrane vesicles (OMVs) and at least one antigenic component. In one embodiment, said composition comprises *Neisseria meningitidis* outer membrane vesicles (OMVs) that are enriched with at least one antigenic component.

Said subject is typically a mammal such as a human.

BRIEF DESCRIPTION OF THE DRAWINGS

The embodiments of the invention are discussed in more detail by means of the Example described below. The results referred to in the Example are illustrated by the accompanying drawings, in which:

FIGS. 4A and 4B show protection of mice against meningococcal infection following immunisation with either neisserial TbpA+B, TbpB or TbpA (nTbps) or recombinant Tbps (rTbps);

FIGS. 5A and 5B show protection of mice against challenges of $10^6$ and $10^7$ organisms/mouse of *N. meningitidis* strain K454 respectively, following immunisation with recombinant TbpA+B, TbpB or TbpA;

FIG. 10 illustrates IgG surface labelling of *N. meningitidis* strains NZ98/254 and M01-240149. Total IgG binding to both strains NZ98/254 and M01-240149 was increased when mice were vaccinated with OMV+PorA, as compared to vaccination with OMVs alone. The symbol ** indicates a greater than 95% certainty of a significant difference between these values, determined using a z-test; and FIG. 11 illustrates the OPA response against *N. meningitidis* strains NZ98/24 and M01-240149. Mice immunised with OMV+PorA elicited a greater OPA response against strains NZ98/254 and M01-240149, as compared to the OPA response to immunisation with OMVs alone. The symbol ** indicates a greater than 95% certainty of a significant difference between these values, determined using a z-test.

DETAILED DESCRIPTION

The invention is further illustrated by the following non-limiting examples.

EXAMPLES

Example 1

Mouse Protective Data

Figure 1:
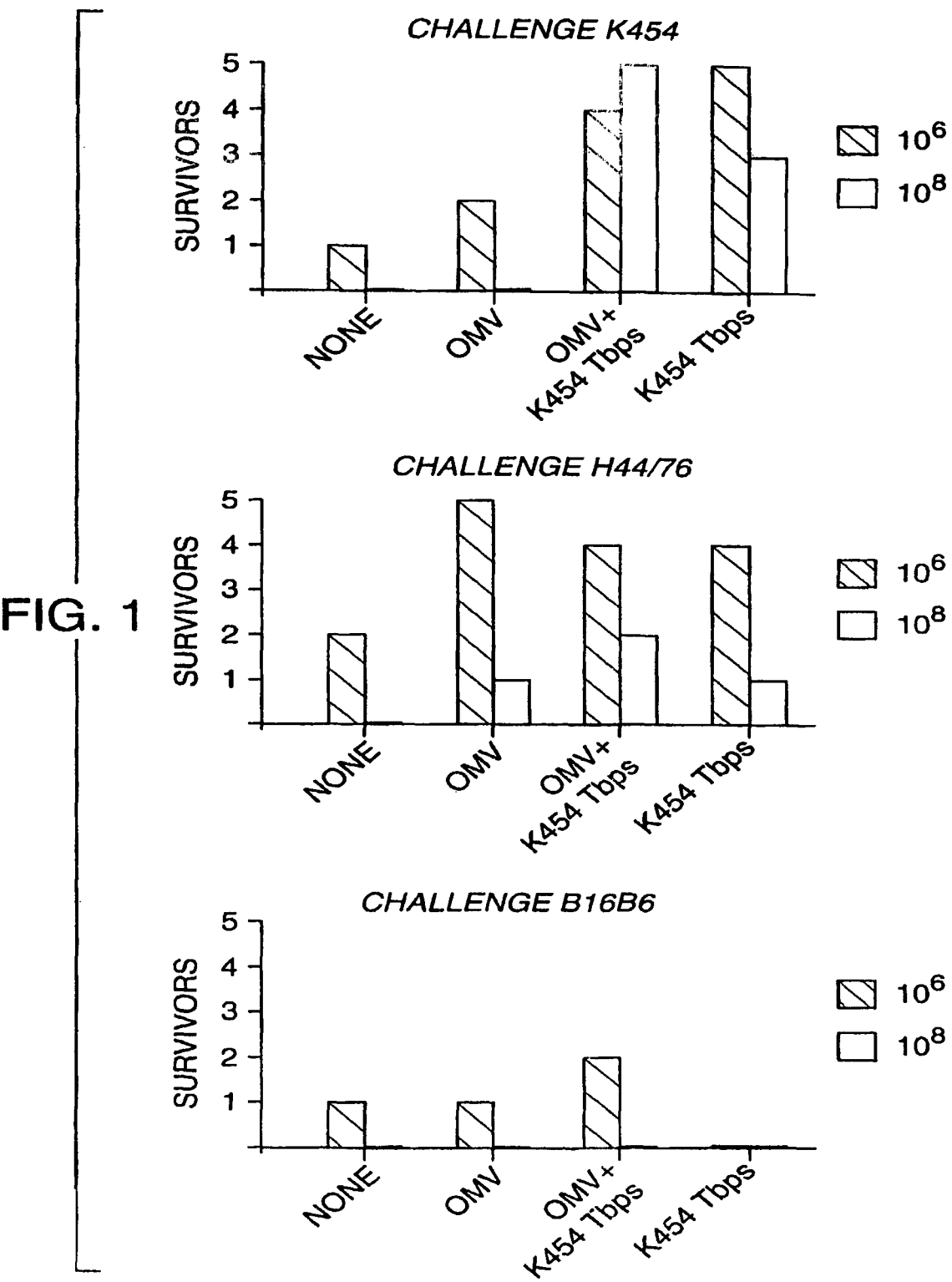
FIG. 1 shows immunisation of mice with TbpA+B and outer membrane vesicles.
Figure 2:
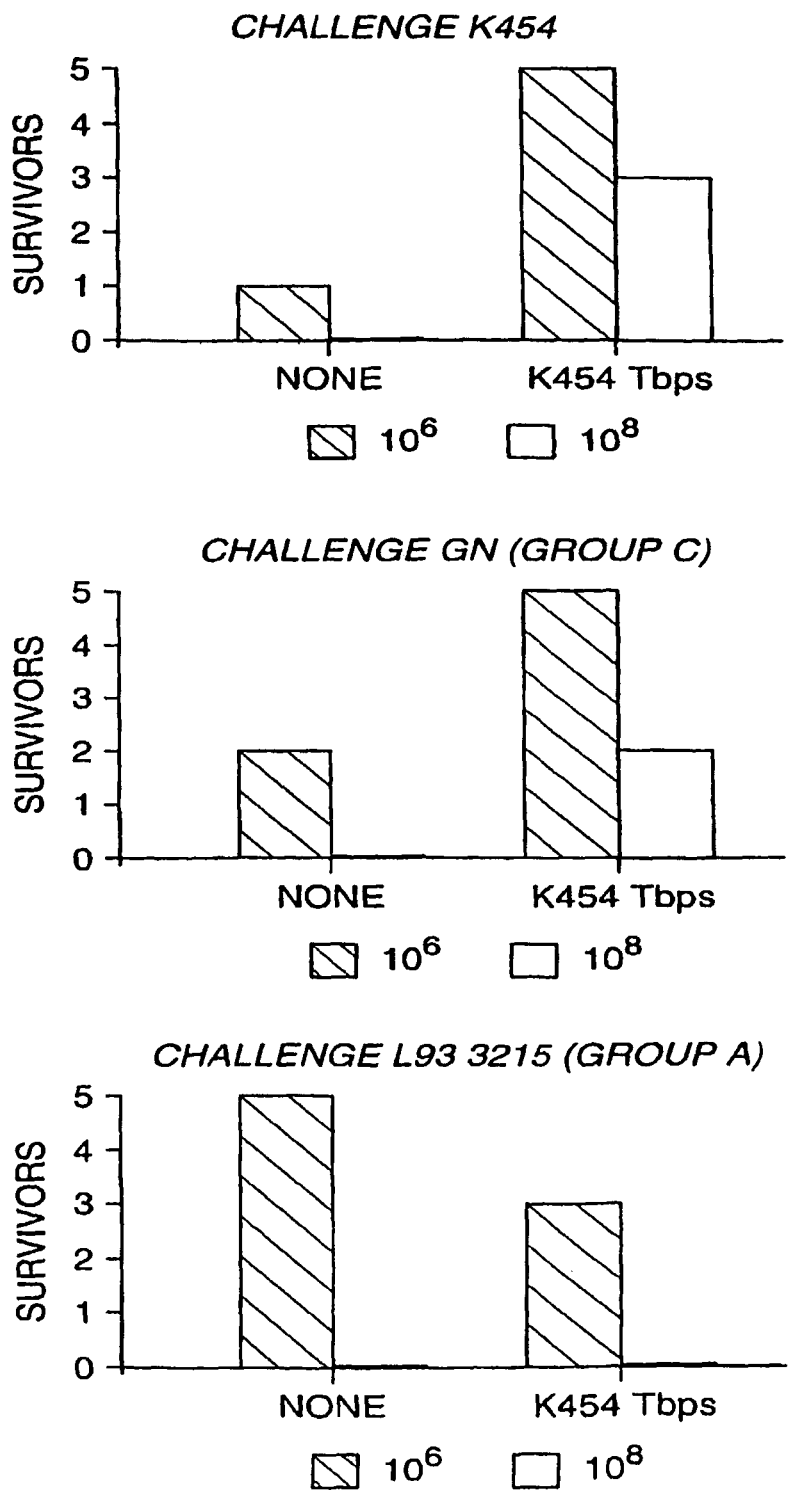
FIG. 2 shows immunisation of mice with TbpA+B.

Mice (CAMR-NIH) were immunised with Tbps and/or outer membrane vesicles and challenged with either the homologous or a heterologous meningococcal strain. Survivors per group of mice immunised with Tbps from strain K454 and the outer membrane vesicle vaccine following challenge by strain K454 are shown in FIG. 1. Compared to Tbps, the outer membrane vesicle vaccine gave reduced protection but this may be because it is produced from a different group B strain (H44/76). Animals immunised with TbpA+B isolated from strain K454 were also protected against challenge with other serogroup B organisms (FIG. 1), with greater protection seen with the homologous strain and strains expressing a TbpB with a similar molecular weight. Little or no protection was observed against challenge with meningococci possessing TbpB with a very different molecular weight (strain B16B6). With the heterologous challenge strains, there is a slightly greater number survivors in the groups vaccinated with the combination of Tbps+outer membrane vesicles. However, the numbers involved are small and no definite conclusions can be reached. It is interesting to observe that mice immunised with TbpA+B from strain K454 were also protected against infection with a serogroup C but not a serogroup A strain (FIG. 2).

Figure 3:
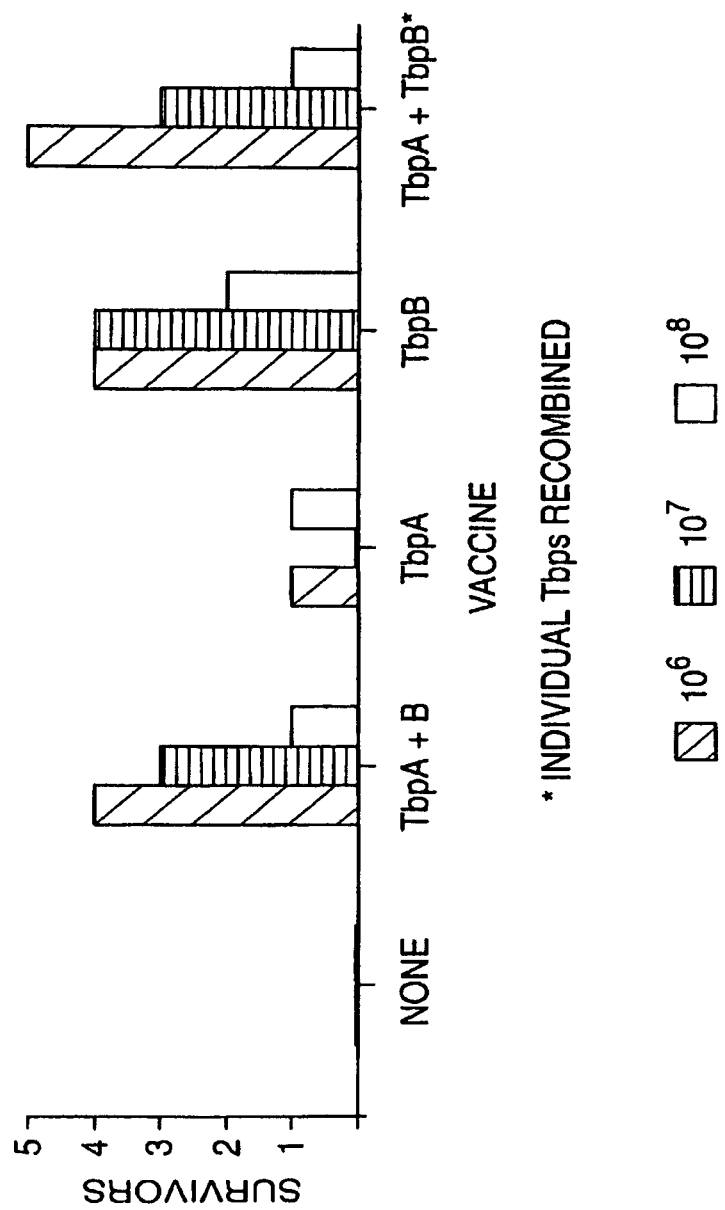
FIG. 3 shows protection of mice against IP infection after immunisation with TbpA+B, isolated TbpA or isolated TbpB.

Protection against challenge with strain K454 with mice immunised with co-purified TbpA+B and isolated TbpA and TbpB is shown in FIG. 3. It can be seen that TbpB is the predominant antigen responsible for protection, with little protection afforded by TbpA alone.

Recombinant TbpA and TbpB

TbpA and TbpB from *N. meningitidis* strain K454 were cloned and overexpressed in *E. coli*. The proteins were purified using affinity chromatography and used to determine their protective potency in a mouse model of meningococcal disease. Recombinant Tbps showed equivalent protection to that provided by Tbps isolated from iron-stressed *N. meningitidis* (FIGS. 4A and 4B). These recombinant Tbps were also utilised in two further larger IP challenge experiments (FIGS. 5A-B).

The strong and consistent protective potency of Tbps against mouse I.P. infection with *N. meningitidis* is probably the most compelling evidence for their vaccine potential.

Interestingly, the results shown in FIGS. 4B and 5A-B, although arising from experiments of similar design, show the surprising variability associated with vaccine compositions that depend solely upon either TbpA or TbpB alone. In FIG. 4B the recombinant TbpA composition displayed low levels of protection compared to TbpB or TbpA+B. However, in FIGS. 5A and 5B the recombinant TbpA vaccine composition that showed high levels of protection comparable to the TbpA+B complex and the TbpB alone composition demonstrated poor protection to infection. This latter result is completely contrary to the teaching of the prior art.

Human Immune Response to TbpA and TbpB in Convalescent Sera

We have undertaken a number of studies looking at the antibody response in humans to TbpA and TbpB following meningococcal disease. The general conclusions are that both TbpA and TbpB are expressed during meningococcal disease and that an immune response is raised against them. The response is functional (opsonic) and is more cross-reactive between different meningococcal strains than is the response induced by immunisation of animals with Tbps. The immune response to TbpA appears to be stronger and more cross-reactive than that to TbpB, confirming the importance of the vaccine potential of TbpA.

TbpA and TbpB Form a Transferrin Receptor

Our structural studies indicate that the transferrin receptor on the meningococcal surface consists of two TbpA molecules and one TbpB molecule that act together.

Effect of a Vaccine Containing A+B Tbps

Figure 6:
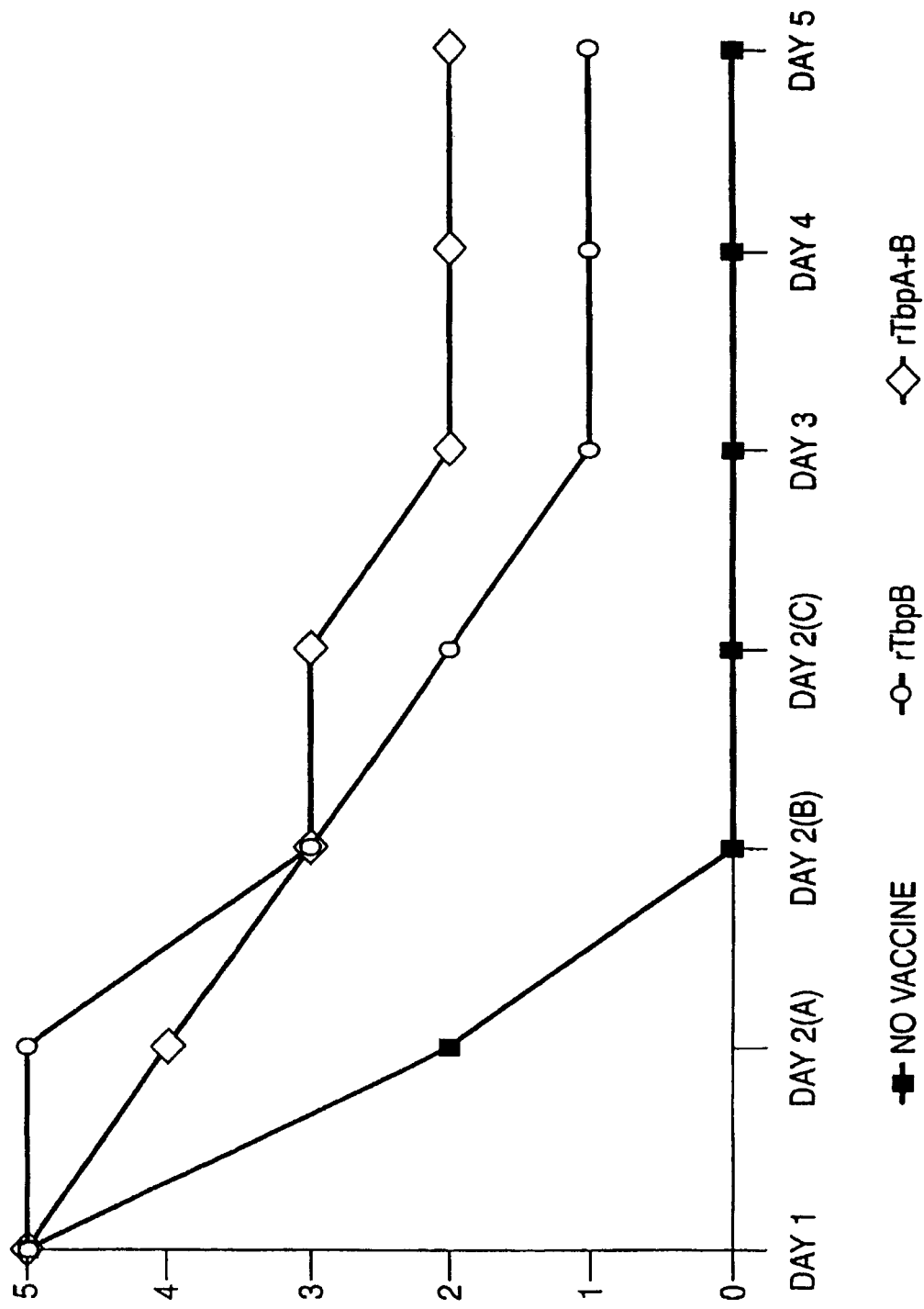
FIG. 6 shows protection against challenge with heterologous serogroup.
Figure 7:
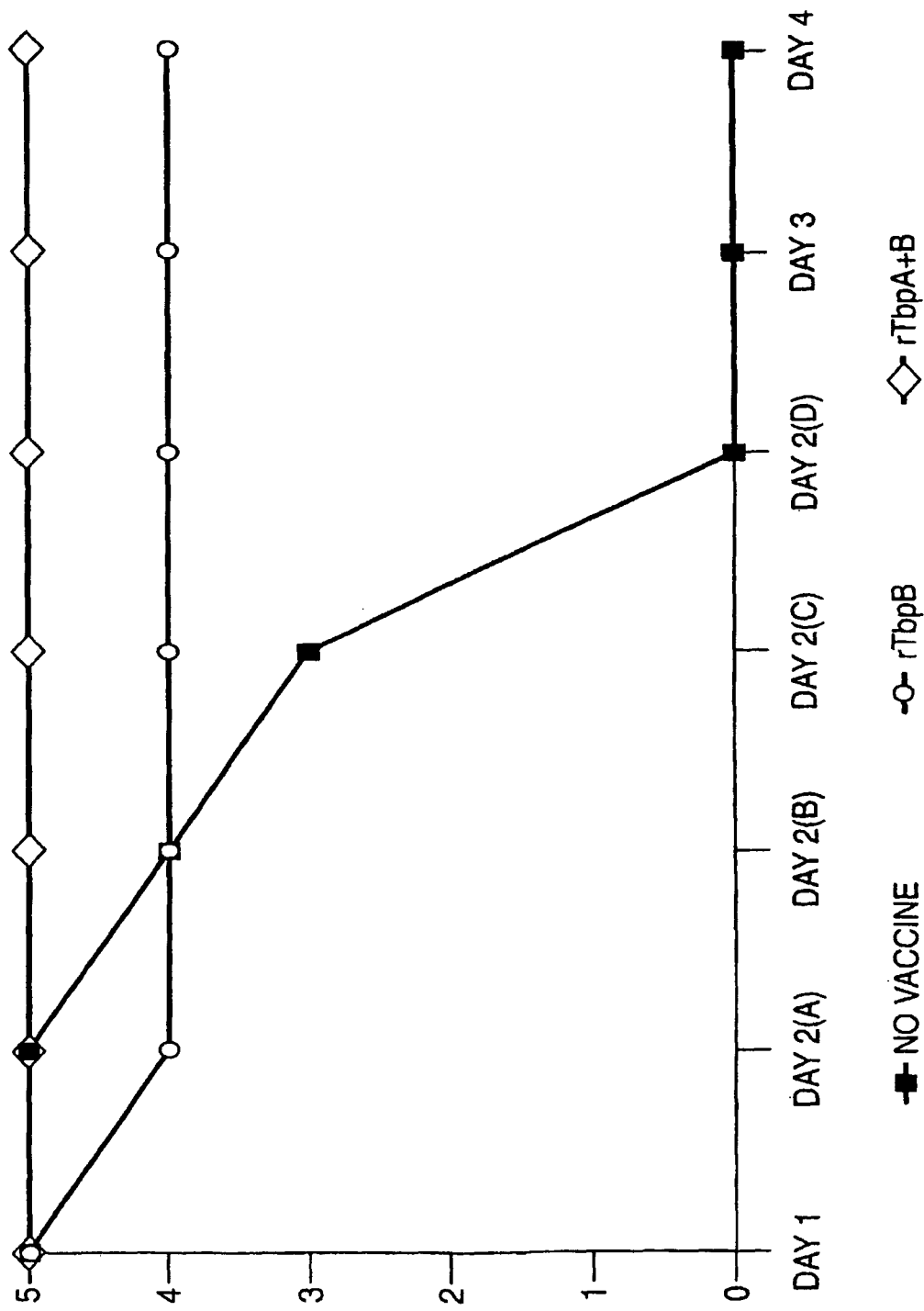
FIG. 7 shows protection against challenge with B16B6.

We carried out further tests of the efficacy of recombinant TbpB versus recombinant TbpA+B containing vaccine formulations against challenge from *N. meningitidis* strains L91 705 and B16B6, the results of which are illustrated in FIGS. 6 and 7 respectively. In both cases some improved protection was conferred by A+B compared to B alone.

Example 2

Up Regulation of Genes in Meningococcal Species

Figure 8:
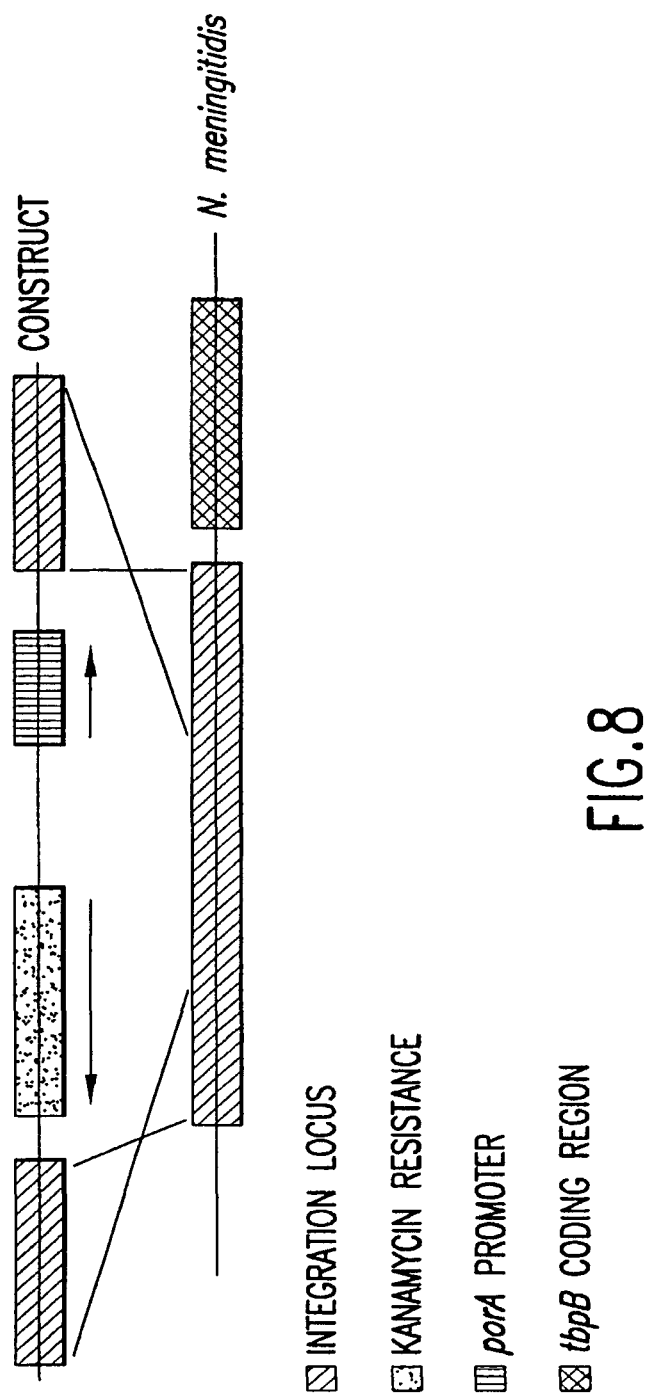
FIG. 8 shows insertion of a promoter construct into the *N. meningitidis* genome for up regulation of endogenous TbpB in *N. meningitidis* by homologous recombination.
Figure 9:
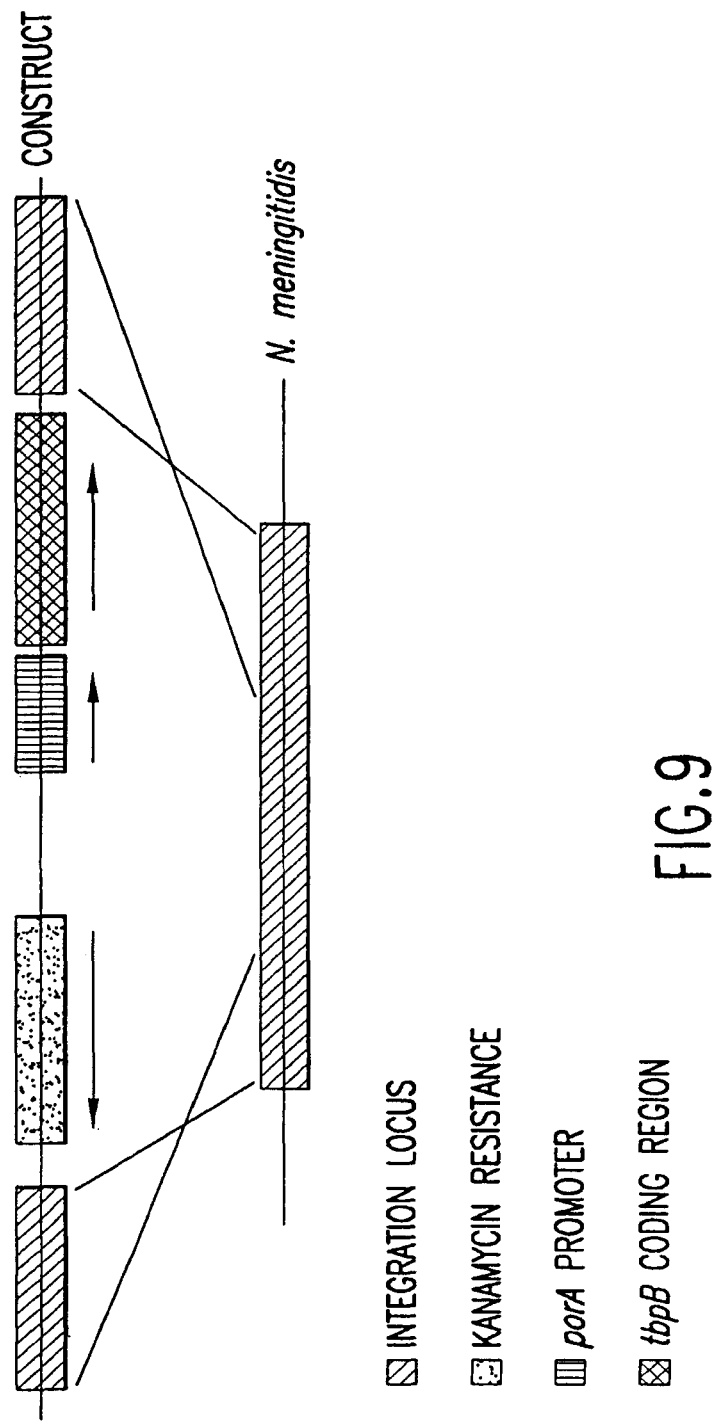
FIG. 9. shows insertion of an expression cassette into the *N. meningitidis* genome by homologous recombination.

These methods can be used to enhance expression of TbpB but can equally be applied to other meningococcal outer membrane proteins with known sequence such as NspA (Martin et al., 1997), OMP85 (Manning et al., 1998) or FrpB (Pettersson et al., 1995). Any of the antigenic component sequences disclosed herein (SEQ ID NOS: 1; 3; 5; 7; 9; 11; 13; 15; 17; 19; 21; 23; 25; 27; 29; 31; 33; 35; 37; 39; 41; 43; 45; 47; 49; 51; 53; 55; 57; 59; 61; 63; 65; 67; 69; and 71) would also be suitable for over expression in this system as would any immunogenic meningococcal sequence.

In the following methods primers are designed using the primer select program from the >DNA star=software package (www.dnastar.com). Primers to flanking sequences are designed following sequencing from the known coding region.

Up Regulation of TbpB in *N. meningitidis* by Promoter Delivery

Using homologous recombination (Frosch et al., 1990, van der Ley et al., 1995) a strong promoter such as the porA promoter is inserted into the *N. meningitidis* genome upstream of the tbpB coding region (Legrain et al., 1993). A selectable marker, encoding resistance to kanamycin, is also included in the delivery cassette upstream from the promoter. The integration locus is selected by sequencing upstream from the tbpB coding region.

PCR primers are designed to the regions flanking the porA promoter and incorporate restriction endonuclease sites for ligation into this amplified sequence. This is then inserted into the multiple cloning site of a vector containing the kanamycin resistance gene. Also inserted through PCR produced products are integration loci that complement a region directly before the coding region for tbpB in the *N. meningitidis* genome. Through homologous recombination the construct shown in FIG. 8 will be produced.

From the published sequence of porA (McGuinnes et al. 1990) (SEQ ID NO: 1) a primer is constructed at the N-terminal region in order to sequence up steam of the coding region. This sequence data yields the promoter region of the highly expressed porA gene. Primers are designed to this sequence so as to amplify any conserved hexamers centred around −35 and −10 the consensus sequences of TTGACA and TATAAT with a 16-18 bp gap between them and up to 67 bp upstream of the start of transcription (ATG). The designed primers have restriction endonuclease sites incorporated in order to insert the amplified region into a suitable vector.

In order to identify a suitable integration locus in front of the tbpB coding region a primer is designed to the start of the tbpB coding region, using the published sequence (Legrain et al. 1993), running up stream into the tbpB promoter region. The promoter region itself as well as some sequence upstream is suitable as the integration locus. This section is amplified in two halves using 4 primers and restriction endonucleases are incorporated in order to ligate the sections into a suitable vector.

The vector used already contains an antibiotic resistance marker (such as kanamycin) and this is suitably positioned between the integration loci but upstream from the incorporated porA promoter, as illustrated in FIG. 8. This means that the vector used has cloning sites either side of the selectable marker.

Up Regulation of TbpB in *N. meningitidis* by Gene Delivery

A construct is produced containing a selectable marker, such as kanamycin resistance, up stream from a strong promoter (porA) which is in turn upstream from the coding region for tbpB. Using homologous recombination (Frosch et al., 1990, van der Ley et al., 1995), the cassette is inserted into the *N. meningitidis* genome. The integration locus is selected by sequencing upstream from a known sequenced area that is also known to actively expressed.

PCR is used to amplify the tbpB coding region and porA promoter region with suitable restriction endonucleases incorporated so they can be inserted in series, into a vector containing kanamycin resistance. Also inserted into the construct are two flanking integration loci complementing a region of the *N. meningitidis* genome (see FIG. 9).

From the published sequence of porA (McGuinness et al. 1990) (SEQ ID NO: 1) a primer can be constructed to complement the N-terminal region in order to sequence up steam of the coding region. This sequence data yields the promoter region of the highly expressed porA gene. Primers are designed to this sequence so as to amplify any conserved hexamers centred around −35 and −10 the consensus sequences of TTGACA and TATAAT with a 16-18 bp gap between them and up to 67 bp upstream of the start of transcription (ATG). The reverse primer is designed to be as close as possible to the start of the coding region, but does not actually include any of it. This ensures that when it is positioned in series with any inserted DNA it acts as an efficient promoter. The designed primers have restriction endonuclease sites incorporated in order to insert the amplified region into a suitable vector.

From the published sequence of tbpB (Legrain et al. 1993) primers are constructed to complement the C-terminal and N-terminal regions in order to sequence the flanking regions of the gene. From this sequence primers are constructed which amplify the entire gene. The forward primer incorporates the first coding triplet (ATG) of the gene and does not include the full native promoter region. The reverse is as close to the end of the coding region as possible while still being a good partner to the forward primer. It is accepted that this means the reverse primer may be some distance downstream of the gene of interest.

Example 3

A combination of outer membrane vesicles (OMV)+PorA extends the cross-reactivity of the antibody response.

We have demonstrated that the addition of recombinant PorA from strain NZ98/254 (PorA serosubtype P1.7-2, 4) to OMVs isolated from strain 44/76 (PorA serosubtype P1.7, 16) broadens the protective response elicited by OMVs from strain 44/76.

Serum bactericidal antibody (SBA) is a correlate of protection (Frasch et al., Vaccine, 2009; 27 Suppl 2:B112-6).

We have shown that the SBA titre against strain NZ98/254 in serum from mice vaccinated with 44/76 OMVs alone was 16 (Table 1). However, the SBA titre obtained against this strain with OMV+PorA was 256.

TABLE 1

SBA titres:

| Vaccine | SBA titre against strain NZ98/254 |
|---|---|
| OMVs from 44/76 | 16 |
| PorA from NZ98/254 | 4 |
| OMVs from 44/76 + PorA from NZ98/254 | 256 |

Binding of IgG antibody to the surface of intact *N. meningitidis* can be determined by flow cytometry. Antibody binding to the organism is essential for bactericidal activity and also opsonophagocytic activity. FIG. 10 shows that the total IgG binding to both strains NZ98/254 and M01-240149 was increased when mice were vaccinated with OMV+PorA, as compared to vaccination with OMVs alone.

Opsonophagocytosis (OPA) is also important for protection against meningococcal disease (Granoff, Vaccine, 2009; 27 Suppl 2:B117-25). FIG. 11 shows that mice immunised with OMV+PorA elicited a greater OPA response against strains NZ98/254 and M01-240149, as compared to the OPA response to immunisation with OMVs alone.

In summary, the SBA, SLA and OPA assays all confirm that the OMV+PorA vaccine elicits greater cross-strain protection than OMV alone.

Methods:

Animal Vaccination

NIH mice (six to eight weeks old, Harlan, UK) were immunized on days 0, 21, and 28 by subcutaneous injection (0.2 ml), with:

MPL adjuvant only;

MPL and 10 μg *Neisseria meningitidis* 44/76-SL OMVs;

MPL and 10 μg PorA (P1.7-2,4); or

MPL with 10 μg *Neisseria meningitidis* 44/76-SL and 10 μg PorA (P1.7-2,4)

On Day 35 terminal sera were collected from mice.

Serum bactericidal assay (SBA):

SBA assays were performed using a standardized assay with a starting dilution of 1:2. Briefly, human serum, at 25%, was used as an exogenous source of human complement, with titers expressed as the reciprocal of the final dilution giving ≥50% SBA killing at 60 min compared with the level for the control (inactive complement and no test serum). Single determinations were made using each serum sample, the human complement used had previously been screened for lack of intrinsic bactericidal activity.

Surface Labelling and Opsonophagocytosis Assays

Bacteria: Bacteria used were killed using a protocol designed to minimise chemical alteration of surface epitopes. Briefly, live meningococci were incubated with 0.2% (w/v) sodium azide and 17 μg·ml$^{-1}$ phenylmethylsulphonyl fluoride for 48 hours at 37° C. Bacteria used in the opsonophagocytosis assay were first stained for 1 hour with 20 μM of 1,1'-dioctadecyl-3,3,3',3'-tetramethylindodicarbocyanine-5,5'-disulfonic acid (DiIC$_{18}$(5)-DS) (Invitrogen, UK).

Complement: Human plasma was used as a complement source and was IgG depleted using a protein G Sepharose column immediately before use. Briefly, the column was equilibrated with three column volumes of hanks buffered saline solution before one column volume of plasma was added. This was incubated for 5 minutes at 4° C. before one column volume of hanks buffered saline solution was used to displace the complement.

Opsonophagocytosis assay (OPA): Opsonophagocytosis (OP) of meningococci by HL-60 cells (American Type Culture Collection, Rockville Md., USA) differentiated to granulocytes with 0.8% N,N dimethyleformamide (Sigma, UK) for 5 days, was measured using a flow cytometric assay performed in U-bottom 96-well microtitre plates (Sterilin, UK). 20 μl of each test serum diluted 1:10 in OP buffer (Hanks balanced salts solution (Sigma, UK) containing 2% skimmed milk powder (Marvel, Premier International Foods, UK), 1.2 mM CaCl$_2$, and 1 mM MgSO$_4$ (Sigma, UK)) was added to 10 μl of target bacteria at 6.25×10$^8$ ml$^{-1}$ in OP buffer, followed by 10 μl of IgG depleted Human plasma as a complement source, and then incubated for 7.5 min with shaking (900 rpm) at 37.0° C.

Differentiated HL60 cells at 2.5×10$^7$ ml$^{-1}$ in OP buffer (50 μl) were added and incubation continued, with shaking, at 37.0° C. for 7.5 min. Opsonophagocytosis was stopped by addition of 80 μl of ice-cold Dulbecco phosphate-buffered saline (PBS; Sigma, UK) containing 0.02% EDTA (Sigma, UK).

Horizontal gates in the DiIC$_{18}$(5)-DS channel of a flow cytometer (Beckman Coulter FC500) were set against a complement-only, no-antibody control to include approximately 10% of the population. For each sample, 7,500 live HL60 cells were measured, and the percentage of cells showing DiIC$_{18}$(5)-DS fluorescence in the appropriate gate (% gated) was multiplied by the mean fluorescence of the gated population (X-mean) to calculate a fluorescence index (FI). The FI of each test was subtracted from the FI of the complement-only no antibody control to give FI minus complement control (FI-C').

Total antibody binding assay (SLA): IgG binding to the surface of meningococci was measured using a flow cytometric assay performed in U-bottom 96-well microtitre plates (Sterilin, UK).

For the assay, 2 μl of each test serum was added to 198 μl of target bacteria at an O.D$^{600}$0.1 in a blocking buffer of 1% bovine serum albumin (BSA) in PBS and the mixture incubated for 30 min with shaking (900 rpm) at 25.0° C. This was then centrifuged at 3050 g for 5 minutes and the supernatant removed and the pellet was then washed with 200 μl of blocking buffer. The process was repeated twice before the addition of 200 μl FITC-labelled goat anti-human IgG (Biodesign, UK) at 1:500 in blocking buffer, followed by incubation for 20 minutes at 4° C., before being washed twice more with blocking buffer.

Horizontal gates in the FITC channel of a flow cytometer (Beckman Coulter FC500) were set against a conjugate-only, no-antibody control to include approximately 10% of the population. For each sample, 7,500 bacteria were measured, and the percentage of cells showing FITC fluorescence in the appropriate gate (% gated) was multiplied by the mean fluorescence of the gated population (X-mean) to calculate a fluorescence index (FI).; the FI of the conjugate only control was subtracted from the FI of each test sera to give FI minus complement control (FI-Conj).

From the Foregoing, it will be appreciated that although specific embodiments of the invention have been described herein for purposes of illustration, various modifications may be made without deviating from the spirit and scope of the invention. Accordingly, the invention is not limited except as by the appended claims.

What is claimed is:

1. A composition comprising:
   (i) isolated *N. meningitidis* outer membrane vesicles;
   (ii) at least one isolated *N. meningitidis* antigenic protein, wherein said at least one isolated *N. meningitidis* antigenic protein
      (a) has been extracted from an outer membrane of an *N. meningitidis* bacterium; or
      (b) is a recombinant *N. meningitidis* antigenic protein; and
   (iii) alum in an amount effective as an adjuvant;
   wherein said isolated *N. meningitidis* outer membrane vesicles are from a first strain of *N. meningitidis* and said at least one isolated *N. meningitidis* antigenic protein is from a second strain of *N. meningitidis* different from the first,
   said at least one isolated *N. meningitidis* antigenic protein is not transferrin binding protein A (TbpA) nor transferrin binding protein B (TbpB), and
   the *N. meningitidis* outer membrane vesicles are isolated by desoxycholate treatment.

2. The composition of claim 1, wherein said composition comprises a plurality of isolated *N. meningitidis* antigenic proteins from different strains of *N. meningitidis*.

3. The composition of claim 1, wherein said at least one isolated *N. meningitidis* antigenic protein is an isolated *N. meningitidis* antigenic proteoglycan.

4. The composition of claim 1, wherein said at least one isolated *N. meningitidis* antigenic protein is an isolated *N. meningitidis* protein selected from the group consisting of a surface antigen, a periplasmic protein, a superoxide dismutase, and a glycoprotein.

5. The composition of claim 1, further comprising a pharmaceutically acceptable carrier.

6. The composition of claim 1, wherein the composition is obtained by a process comprising:
   (i) obtaining the isolated *N. meningitidis* outer membrane vesicles from a first strain of *N. meningitidis*;
   (ii) obtaining the at least one isolated *N. meningitidis* antigenic protein from a second strain of *N. meningitidis* different from the first; and
   (iii) combining the at least one isolated *N. meningitidis* antigenic protein with the isolated *N. meningitidis* outer membrane vesicles.

7. A vaccine composition comprising:
   (i) outer membrane vesicles from a first strain of *N. meningitidis*;
   (ii) an isolated antigenic protein from a second strain of *N. meningitidis* different from the first, wherein said isolated antigenic protein
      (a) has been extracted from an outer membrane of an *N. meningitidis* bacterium; or (b) is a recombinant *N. meningitidis* antigenic protein; and (iii) a pharmaceutically acceptable carrier comprising alum in an amount effective as an adjuvant, wherein said isolated antigenic protein is not transferrin binding protein A (TbpA) nor transferrin binding protein B (TbpB), and the *N. meningitidis* outer membrane vesicles are isolated by desoxycholate treatment.

8. The vaccine composition of claim 7, wherein said isolated antigenic protein is an *N. meningitidis* protein selected from the group consisting of a surface antigen, a periplasmic protein, a superoxide dismutase, and a glycoprotein.

9. The composition of claim 1, wherein said at least one isolated *N. meningitidis* antigenic protein comprises a surface antigen.

10. The composition of claim 2, wherein said at least one isolated *N. meningitidis* antigenic protein comprises a surface antigen.

11. The composition of claim 5, wherein said at least one isolated *N. meningitidis* antigenic protein comprises a surface antigen.

12. The composition of claim 6, wherein said at least one isolated *N. meningitidis* antigenic protein comprises a surface antigen.

13. The composition of claim 7, wherein said isolated *N. meningitidis* antigenic protein comprises a surface antigen.

14. The vaccine composition of claim 7, wherein said vaccine composition comprises a plurality of isolated *N. meningitidis* antigenic proteins from different strains of *N. meningitidis*.

15. A vaccine composition comprising:

(i) outer membrane vesicles from a first strain of *N. meningitidis;*

(ii) an isolated antigenic protein from a second strain of *N. meningitidis* different from the first, wherein said isolated antigenic protein (a) has been extracted from an outer membrane of an *N. meningitidis* bacterium; or (b) is a recombinant *N. meningitidis* antigenic protein; and (iii) a pharmaceutically acceptable carrier comprising an adjuvant, wherein the adjuvant is alum adjuvant, wherein said isolated antigenic protein is not transferrin binding protein A (TbpA) nor transferrin binding protein B (TbpB), and the *N. meningitidis* outer membrane vesicles are isolated by desoxycholate treatment.

16. The vaccine composition of claim 15, wherein said isolated antigenic protein is an *N. meningitidis* protein selected from the group consisting of a surface antigen, a periplasmic protein, a superoxide dismutase, and a glycoprotein.

17. The composition of claim 15, wherein said isolated *N. meningitidis* antigenic protein comprises a surface antigen.

18. The vaccine composition of claim 15, wherein said vaccine composition comprises a plurality of isolated *N. meningitidis* antigenic proteins from different strains of *N. meningitidis*.

* * * * *

UNITED STATES PATENT AND TRADEMARK OFFICE
CERTIFICATE OF CORRECTION

Page 1 of 1

PATENT NO. : 10,967,045 B2
APPLICATION NO. : 12/758315
DATED : April 6, 2021
INVENTOR(S) : Andrew Robinson et al.

It is certified that error appears in the above-identified patent and that said Letters Patent is hereby corrected as shown below:

On the Title Page

Under Foreign Application Priority Data, please correct the application number to read --9823978.3--

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*